(12) United States Patent
Olmstead et al.

(10) Patent No.: US 8,815,916 B2
(45) Date of Patent: Aug. 26, 2014

(54) PHARMACEUTICAL FORMULATIONS USEFUL FOR INHIBITING ACID SECRETION AND METHODS FOR MAKING AND USING THEM

(75) Inventors: Kay Olmstead, San Diego, CA (US); Warren Hall, Del Mar, CA (US); Gerald T. Proehl, San Diego, CA (US)

(73) Assignee: Santarus, Inc., Raleigh, NC (US)

(*) Notice: Subject to any disclaimer, the term of this patent is extended or adjusted under 35 U.S.C. 154(b) by 876 days.

(21) Appl. No.: 11/287,888

(22) Filed: Nov. 28, 2005

(65) Prior Publication Data

US 2006/0147522 A1 Jul. 6, 2006

Related U.S. Application Data

(63) Continuation-in-part of application No. 11/138,763, filed on May 25, 2005.

(60) Provisional application No. 60/574,646, filed on May 25, 2004, provisional application No. 60/574,663, filed on May 25, 2004.

(51) Int. Cl.
*A61K 31/4439* (2006.01)
*A61K 9/48* (2006.01)
*A61K 33/10* (2006.01)

(52) U.S. Cl.
USPC ........... 514/338; 514/819; 514/962; 424/452; 424/717

(58) Field of Classification Search
None
See application file for complete search history.

(56) References Cited

U.S. PATENT DOCUMENTS

| | | | |
|---|---|---|---|
| 4,045,564 A | 8/1977 | Berntsson et al. |
| 4,182,766 A | 1/1980 | Krasso et al. |
| 4,255,431 A | 3/1981 | Junggren et al. |
| 4,337,257 A | 6/1982 | Junggren et al. |
| 4,359,465 A | 11/1982 | Ruwart |
| 4,414,216 A | 11/1983 | Kawakita et al. |
| 4,472,409 A | 9/1984 | Senn-Bilfinger |
| 4,508,905 A | 4/1985 | Junggren et al. |
| 4,544,750 A | 10/1985 | Brandstrom et al. |
| 4,620,008 A | 10/1986 | Brandstrom et al. |
| 4,628,098 A | 12/1986 | Nohara et al. |
| 4,636,499 A | 1/1987 | Brandstrom et al. |
| 4,689,333 A | 8/1987 | Nohara et al. |
| 4,725,691 A | 2/1988 | Brandstrom et al. |
| 4,738,974 A | 4/1988 | Brandstrom |
| 4,786,505 A | 11/1988 | Lovgren et al. |
| 4,808,596 A | 2/1989 | Matsuishi et al. |
| 4,853,230 A | 8/1989 | Lovgren et al. |
| 4,965,351 A | 10/1990 | Caruso et al. |
| 4,985,548 A | 1/1991 | Caruso et al. |
| 5,008,278 A | 4/1991 | Brandstrom et al. |
| 5,013,743 A | 5/1991 | Iwahi et al. |
| 5,019,584 A | 5/1991 | Brandstrom et al. |
| 5,025,024 A | 6/1991 | Brandstrom et al. |
| 5,026,560 A | 6/1991 | Makino et al. |
| 5,039,806 A | 8/1991 | Brandstrom et al. |
| 5,045,321 A | 9/1991 | Makino et al. |
| 5,075,323 A | 12/1991 | Fain et al. |
| 5,093,132 A | 3/1992 | Makino et al. |
| 5,093,342 A | 3/1992 | Tomoi et al. |
| 5,106,862 A | 4/1992 | Briving et al. |
| 5,124,158 A | 6/1992 | Ruwart et al. |
| 5,215,974 A | 6/1993 | Alminger et al. |
| 5,219,870 A | 6/1993 | Kim |
| 5,232,706 A | 8/1993 | Palomo Coll |
| 5,244,670 A | 9/1993 | Upson et al. |
| 5,246,714 A | 9/1993 | Dahlinder et al. |
| 5,288,506 A | 2/1994 | Spickett et al. |
| 5,374,730 A | 12/1994 | Slemon et al. |
| 5,385,739 A | 1/1995 | Debregeas et al. |
| 5,386,032 A | 1/1995 | Brandstrom |
| 5,391,752 A | 2/1995 | Hoermer et al. |
| 5,395,323 A | 3/1995 | Berglund |
| 5,399,700 A | 3/1995 | Min et al. |
| 5,417,980 A | 5/1995 | Goldman et al. |
| 5,430,042 A | 7/1995 | Lindberg et al. |
| 5,433,959 A | 7/1995 | Makino et al. |

(Continued)

FOREIGN PATENT DOCUMENTS

| | | |
|---|---|---|
| CA | 1234118 | 3/1988 |
| DE | 19752843 C2 | 1/2003 |

(Continued)

OTHER PUBLICATIONS

Adams, S.P. et al., "Comments of the Report of "Association" of Omeprazole with DNA by Phillips et al.," Mutagenesis, 1992, pp. 395-396, vol. 7, No. 5, Oxford University Press.
Al-Assi, M.T. et al., "Treatment of Helicobacter Pylori Infection with Omeprazole-Amoxicillin Combination Therapy Versus Rantidine/Sodium Bicarbonate-Amoxicillin," Am J. of Gastroenterology, 1995, pp. 1411-1414, vol. 90, No. 9.
Andersson, T. et al., "Pharmacokinetics of (14C) Omeprazole in Patients with Liver Cirrhosis," Clinical Pharmacokinetics, 1993, pp. 71-78, vol. 24, No. 1.

(Continued)

*Primary Examiner* — Savitha Rao
*Assistant Examiner* — Gregg Polansky
(74) *Attorney, Agent, or Firm* — Novak Druce Connolly Bove + Quigg LLP; Janelle D. Waack

(57) ABSTRACT

The present invention relates to pharmaceutical formulations comprising at least one acid-labile proton pump inhibiting agent and at least one antacid, which have improved bioavailability, chemical stability, physical stability, dissolution profiles, disintegration times, safety, as well as other improved pharmacokinetic, pharmacodynamic, chemical and/or physical properties. The present invention is directed to methods, kits, combinations, and compositions for treating, preventing or reducing the risk of developing a gastrointestinal disorder or disease, or the symptoms associated with, or related to, a gastrointestinal disorder or disease in a subject in need thereof.

11 Claims, 24 Drawing Sheets

(56) References Cited

U.S. PATENT DOCUMENTS

| | | | |
|---|---|---|---|
| 5,447,918 A | 9/1995 | McCullouch | |
| 5,447,923 A | 9/1995 | Catrenich et al. | |
| 5,464,632 A | 11/1995 | Cousin et al. | |
| 5,470,983 A | 11/1995 | Slemon et al. | |
| 5,504,082 A | 4/1996 | Kawakita et al. | |
| 5,536,735 A | 7/1996 | Takechi et al. | |
| 5,589,491 A | 12/1996 | Nakanishi et al. | |
| 5,599,794 A | 2/1997 | Eek et al. | |
| 5,629,305 A | 5/1997 | Eek et al. | |
| 5,633,244 A | 5/1997 | Eek et al. | |
| 5,635,520 A | 6/1997 | Uda | |
| 5,639,478 A | 6/1997 | Makino et al. | |
| 5,690,960 A | 11/1997 | Bengtsson et al. | |
| 5,693,818 A | 12/1997 | Von Unge | |
| 5,714,504 A | 2/1998 | Lindberg et al. | |
| 5,714,505 A | 2/1998 | Hasselkus | |
| 5,731,002 A | 3/1998 | Olovson et al. | |
| 5,753,265 A | 5/1998 | Bergstrand et al. | |
| 5,766,765 A | 6/1998 | Nelson | |
| 5,798,120 A | 8/1998 | Tomohisa et al. | |
| 5,814,338 A | 9/1998 | Veronesi | |
| 5,817,338 A | 10/1998 | Bergstrand et al. | |
| 5,824,339 A | 10/1998 | Shimizu et al. | |
| 5,840,737 A | 11/1998 | Phillips | |
| 5,846,562 A | 12/1998 | Yanai et al. | |
| 5,876,759 A | 3/1999 | Gowan, Jr. | |
| 5,877,192 A | 3/1999 | Lindberg et al. | |
| 5,879,708 A | 3/1999 | Makino et al. | |
| 5,883,102 A | 3/1999 | Hamley et al. | |
| 5,885,594 A | 3/1999 | Nilsen et al. | |
| 5,900,424 A | 5/1999 | Kallstrom et al. | |
| 5,929,244 A | 7/1999 | Von Unge | |
| 5,935,600 A | 8/1999 | Cherukuri et al. | |
| 5,939,091 A | 8/1999 | Eoga et al. | |
| 5,948,773 A | 9/1999 | Akiyama et al. | |
| 5,948,789 A | 9/1999 | Larsson et al. | |
| 5,955,107 A | 9/1999 | Augello et al. | |
| 5,958,955 A | 9/1999 | Gustavsson et al. | |
| 5,962,022 A | 10/1999 | Bolt et al. | |
| 5,965,162 A | 10/1999 | Fuisz et al. | |
| 5,972,389 A | 10/1999 | Shell et al. | |
| 5,979,515 A | 11/1999 | Olsson | |
| 5,997,903 A | 12/1999 | Dietrich et al. | |
| 6,013,281 A | 1/2000 | Lundberg et al. | |
| 6,017,560 A | 1/2000 | Makino et al. | |
| 6,030,988 A | 2/2000 | Gillis et al. | |
| 6,047,829 A | 4/2000 | Johnstone et al. | |
| 6,090,827 A | 7/2000 | Erickson et al. | |
| 6,110,493 A * | 8/2000 | Guentensberger et al. | |
| 6,123,962 A | 9/2000 | Makino et al. | |
| 6,124,464 A | 9/2000 | Hogberg et al. | |
| 6,132,770 A | 10/2000 | Lundberg | |
| 6,132,771 A | 10/2000 | Depui et al. | |
| 6,136,344 A | 10/2000 | Depui et al. | |
| 6,143,771 A | 11/2000 | Lindberg et al. | |
| 6,147,103 A | 11/2000 | Anousis et al. | |
| 6,150,380 A | 11/2000 | Lovqvist et al. | |
| 6,162,816 A | 12/2000 | Bohlin et al. | |
| 6,166,213 A | 12/2000 | Anousis et al. | |
| 6,169,102 B1 | 1/2001 | Kanamaru et al. | |
| 6,183,776 B1 | 2/2001 | Depui et al. | |
| 6,235,311 B1 | 5/2001 | Ullah et al. | |
| 6,248,363 B1 | 6/2001 | Patel et al. | |
| 6,262,085 B1 | 7/2001 | Whittle et al. | |
| 6,262,086 B1 | 7/2001 | Whittle et al. | |
| 6,268,385 B1 | 7/2001 | Whittle et al. | |
| 6,274,173 B1 | 8/2001 | Sachs et al. | |
| 6,284,271 B1 | 9/2001 | Lundberg et al. | |
| 6,294,192 B1 | 9/2001 | Patel et al. | |
| 6,299,904 B1 | 10/2001 | Shimizu et al. | |
| 6,319,513 B1 | 11/2001 | Dobrozsi | |
| 6,319,904 B1 | 11/2001 | Akiyama et al. | |
| 6,328,993 B1 | 12/2001 | Linder et al. | |
| 6,328,994 B1 | 12/2001 | Shimuzu et al. | |
| 6,365,180 B1 | 4/2002 | Meyer et al. | |
| 6,432,381 B2 | 8/2002 | Liversidge et al. | |
| 6,444,689 B1 | 9/2002 | Whittle et al. | |
| 6,462,058 B1 | 10/2002 | Fujishima et al. | |
| 6,489,346 B1 | 12/2002 | Phillips | |
| 6,500,459 B1 | 12/2002 | Chhabra et al. | |
| 6,551,621 B1 | 4/2003 | Debregeas et al. | |
| 6,555,139 B2 | 4/2003 | Sharma | |
| 6,569,453 B2 | 5/2003 | Linder et al. | |
| 6,569,463 B2 | 5/2003 | Patel et al. | |
| 6,572,900 B1 | 6/2003 | Zyck et al. | |
| 6,586,004 B2 | 7/2003 | Shimizu et al. | |
| 6,608,092 B1 | 8/2003 | Fujishima et al. | |
| 6,645,988 B2 | 11/2003 | Phillips | |
| 6,664,276 B2 | 12/2003 | Fujishima et al. | |
| 6,699,885 B2 | 3/2004 | Phillips | |
| 6,740,339 B1 | 5/2004 | Ohkouchi et al. | |
| 2001/0009678 A1 | 7/2001 | Toshihiro et al. | |
| 2001/0010825 A1 | 8/2001 | Shimizu et al. | |
| 2001/0027192 A1 | 10/2001 | Akiyama et al. | |
| 2001/0048946 A1 | 12/2001 | Ghebre-Sellassie | |
| 2002/0012680 A1 | 1/2002 | Patel et al. | |
| 2002/0025342 A1 | 2/2002 | Linder et al. | |
| 2002/0039597 A1 | 4/2002 | Ukai et al. | |
| 2002/0044960 A1 | 4/2002 | Cherukuri | |
| 2002/0044962 A1 | 4/2002 | Cherukuri et al. | |
| 2002/0068088 A1 | 6/2002 | Gruber | |
| 2002/0142034 A1 | 10/2002 | Shimizu et al. | |
| 2002/0146451 A1 | 10/2002 | Sharma et al. | |
| 2002/0160046 A1 | 10/2002 | Robinson et al. | |
| 2002/0192299 A1 | 12/2002 | Taneja et al. | |
| 2003/0045724 A1 | 3/2003 | Fujishima et al. | |
| 2003/0050620 A1 | 3/2003 | Odidi et al. | |
| 2003/0088106 A1 | 5/2003 | Whittall et al. | |
| 2003/0091630 A1 | 5/2003 | Louie-Helm et al. | |
| 2003/0091643 A1 | 5/2003 | Friesen et al. | |
| 2003/0096012 A1 | 5/2003 | Besse et al. | |
| 2003/0096845 A1 | 5/2003 | Whittle et al. | |
| 2003/0144306 A1 | 7/2003 | Phillips | |
| 2003/0181487 A1 | 9/2003 | Kamiyama et al. | |
| 2003/0191159 A1 | 10/2003 | Phillips | |
| 2003/0215527 A1 | 11/2003 | Phillips | |
| 2003/0235628 A1 | 12/2003 | Taneja et al. | |
| 2004/0005362 A1 | 1/2004 | Taneja | |
| 2004/0006109 A1 | 1/2004 | Taneja | |
| 2004/0018239 A1 | 1/2004 | Ishida et al. | |
| 2004/0039027 A1 | 2/2004 | Kamiyama et al. | |
| 2004/0048896 A1 | 3/2004 | Phillips | |
| 2004/0048898 A1 | 3/2004 | Fujishima et al. | |
| 2004/0049045 A1 | 3/2004 | Hashimoto et al. | |
| 2004/0052854 A1 | 3/2004 | Yoshinari et al. | |
| 2004/0058018 A1 | 3/2004 | Phillips | |
| 2004/0081671 A1 | 4/2004 | Taneja | |
| 2004/0081700 A1 | 4/2004 | Taneja | |
| 2004/0082618 A1 | 4/2004 | Taneja | |
| 2004/0082791 A1 | 4/2004 | Fujishima et al. | |
| 2004/0097539 A1 | 5/2004 | Terashita et al. | |
| 2004/0097555 A1 | 5/2004 | Ohkawa et al. | |
| 2004/0121004 A1 | 6/2004 | Taneja | |
| 2004/0131675 A1 | 7/2004 | Yamamoto et al. | |
| 2004/0131676 A1 | 7/2004 | Taneja | |
| 2004/0146559 A1 | 7/2004 | Sowden et al. | |
| 2004/0170750 A1 | 9/2004 | Bunick et al. | |
| 2004/0248942 A1 | 12/2004 | Hepburn et al. | |
| 2005/0037070 A1 | 2/2005 | Hall et al. | |
| 2005/0054682 A1 | 3/2005 | Phillips | |
| 2005/0112193 A1 | 5/2005 | Phillips et al. | |
| 2005/0266071 A1 | 12/2005 | Olmstead et al. | |

FOREIGN PATENT DOCUMENTS

| | | | |
|---|---|---|---|
| EP | 0005129 A1 | 10/1979 | |
| EP | 0005129 B1 | 4/1981 | |
| EP | 0040639 A1 | 12/1981 | |
| EP | 0040639 B1 | 5/1984 | |
| EP | 0244380 A2 | 11/1987 | |
| EP | 0247983 A2 | 12/1987 | |
| EP | 0248634 A2 | 12/1987 | |
| EP | 0308515 A1 | 3/1989 | |
| EP | 0315964 A1 | 5/1989 | |

(56) References Cited

FOREIGN PATENT DOCUMENTS

| | | |
|---|---|---|
| EP | 0394471 A1 | 10/1990 |
| EP | 0452697 A1 | 10/1991 |
| EP | 0465254 A1 | 1/1992 |
| EP | 0502556 B1 | 6/1992 |
| EP | 0237200 B1 | 7/1992 |
| EP | 0496437 A2 | 7/1992 |
| EP | 0496437 B1 | 7/1992 |
| EP | 0502556 A1 | 9/1992 |
| EP | 0244380 B1 | 1/1993 |
| EP | 0247983 B1 | 1/1993 |
| EP | 0315964 B1 | 1/1993 |
| EP | 0338861 B1 | 1/1993 |
| EP | 0248634 B1 | 7/1993 |
| EP | 0414847 B1 | 9/1993 |
| EP | 0565210 A2 | 10/1993 |
| EP | 0567201 A2 | 10/1993 |
| EP | 0567643 A1 | 11/1993 |
| EP | 0308515 B1 | 1/1994 |
| EP | 0436620 B1 | 8/1994 |
| EP | 0654471 A1 | 5/1995 |
| EP | 0565210 A3 | 6/1995 |
| EP | 0567201 A3 | 7/1995 |
| EP | 0452697 B1 | 12/1995 |
| EP | 0496437 A3 | 7/1996 |
| EP | 0652751 B1 | 10/1996 |
| EP | 0587659 B1 | 5/1997 |
| EP | 0654471 B1 | 7/1998 |
| EP | 0567201 B1 | 9/1999 |
| EP | 0565210 B1 | 11/1999 |
| EP | 1004305 A1 | 5/2000 |
| EP | 0636364 B1 | 9/2000 |
| EP | 0696921 B1 | 2/2001 |
| ES | 2024993 A6 | 3/1992 |
| GB | 2189698 A | 11/1987 |
| JP | 45-039541 A | 12/1970 |
| JP | 45-039543 A | 12/1970 |
| JP | 46-009580 A | 3/1971 |
| JP | 46-009581 A | 3/1971 |
| JP | 48-103567 A | 12/1973 |
| JP | 49-005967 A | 1/1974 |
| JP | 49-013172 A | 2/1974 |
| JP | 49-020173 A | 2/1974 |
| JP | 49-020174 A | 2/1974 |
| JP | 49-041198 A | 4/1974 |
| JP | 49-093537 A | 9/1974 |
| JP | 49-095997 A | 9/1974 |
| JP | 50-052065 A | 5/1975 |
| JP | 50-112373 A | 9/1975 |
| JP | 50-142565 A | 11/1975 |
| JP | 51-016669 A | 2/1976 |
| JP | 51-131875 A | 11/1976 |
| JP | 52-005769 A | 1/1977 |
| JP | 51-017268 A | 2/1977 |
| JP | 52-014776 A | 2/1977 |
| JP | 52-097978 A | 8/1977 |
| JP | 52-102416 A | 8/1977 |
| JP | 53-059675 A | 5/1978 |
| JP | 55-019211 A | 2/1980 |
| JP | 56-061311 A | 5/1981 |
| JP | 59-095997 A | 6/1984 |
| JP | 61-221117 A | 10/1986 |
| JP | 62-145083 A | 6/1987 |
| JP | 62-258316 A | 11/1987 |
| JP | 62-258320 A | 11/1987 |
| JP | 62-277322 A | 12/1987 |
| JP | 62-283964 A | 12/1987 |
| JP | 02-22225 A | 1/1990 |
| JP | 03-34967 A | 2/1991 |
| JP | 03-48680 A | 3/1991 |
| JP | 03-52887 A | 3/1991 |
| JP | 03-163018 A | 7/1991 |
| JP | 05-117268 A | 5/1993 |
| JP | 05-104225 A | 8/1993 |
| JP | 05-194224 A | 8/1993 |
| JP | 05-194225 A | 8/1993 |
| JP | 05-255088 A | 10/1993 |
| JP | 05-294831 A | 11/1993 |
| JP | 06-092853 A | 4/1994 |
| JP | 06-100449 A | 4/1994 |
| JP | 07-033659 A | 2/1995 |
| JP | 09-087110 A | 3/1997 |
| JP | 10017470 A | 1/1998 |
| JP | 10017471 A | 1/1998 |
| JP | 11-139960 | 5/1999 |
| JP | 2000-026282 | 1/2000 |
| JP | 2000-212180 A | 8/2000 |
| JP | 2000-355540 A | 12/2000 |
| JP | 2001-000406 | 1/2001 |
| JP | 2001040006 | 2/2001 |
| KR | 1996-0003605 B1 | 3/1996 |
| KR | 1996-0011238 B1 | 8/1996 |
| KR | 1996-0011390 B1 | 8/1996 |
| RO | 88351 | 4/1996 |
| WO | WO-89-00566 A1 | 1/1989 |
| WO | WO-92-04898 A1 | 4/1992 |
| WO | WO-92-08716 A1 | 5/1992 |
| WO | WO-95-07913 A1 | 3/1993 |
| WO | WO-93-05770 A1 | 4/1993 |
| WO | WO-94-00112 A1 | 1/1994 |
| WO | WO-94-02140 A1 | 2/1994 |
| WO | WO-94-02141 A1 | 2/1994 |
| WO | WO-95-01783 A1 | 1/1995 |
| WO | WO-95-15962 A1 | 6/1995 |
| WO | WO-95-23594 A1 | 9/1995 |
| WO | WO-95-32957 A1 | 12/1995 |
| WO | WO-95-32959 A1 | 12/1995 |
| WO | WO-96-01612 A1 | 1/1996 |
| WO | WO-96-01622 A1 | 1/1996 |
| WO | WO-96-01623 A1 | 1/1996 |
| WO | WO-96-01624 A1 | 1/1996 |
| WO | WO-96-01625 A1 | 1/1996 |
| WO | WO-96-02236 A1 | 2/1996 |
| WO | WO-96-16959 A1 | 6/1996 |
| WO | WO-96-24338 A1 | 8/1996 |
| WO | WO-96-24375 A1 | 8/1996 |
| WO | WO-96-38175 A1 | 12/1996 |
| WO | WO-97-02020 A1 | 12/1996 |
| WO | WO-97-02021 A1 | 1/1997 |
| WO | WO-97-09964 A1 | 3/1997 |
| WO | WO-97-25064 A1 | 7/1997 |
| WO | WO-97-25065 A1 | 7/1997 |
| WO | WO 97/25066 | 7/1997 |
| WO | WO-97-41114 A1 | 11/1997 |
| WO | WO-97-48380 A1 | 12/1997 |
| WO | WO-98-00114 A2 | 1/1998 |
| WO | WO-98-02368 A1 | 1/1998 |
| WO | WO-98-16228 A1 | 4/1998 |
| WO | WO-98-28284 A1 | 7/1998 |
| WO | WO-98-40054 A1 | 9/1998 |
| WO | WO-98-50019 A1 | 11/1998 |
| WO | WO-98-53803 A1 | 12/1998 |
| WO | WO-98-54171 A1 | 12/1998 |
| WO | WO-99-00380 A1 | 1/1999 |
| WO | WO-99-08500 A2 | 2/1999 |
| WO | WO-99-25323 A1 | 5/1999 |
| WO | WO-99-25711 A1 | 5/1999 |
| WO | WO-99-27917 A1 | 6/1999 |
| WO | WO-99-29320 A1 | 6/1999 |
| WO | WO-99-29299 A1 | 7/1999 |
| WO | WO-99-32091 A1 | 7/1999 |
| WO | WO-99-32093 A1 | 7/1999 |
| WO | WO-99-45004 A1 | 9/1999 |
| WO | WO-99-53918 A1 | 10/1999 |
| WO | WO-99-55705 A1 | 11/1999 |
| WO | WO-99-55706 A1 | 11/1999 |
| WO | WO-00-01372 A2 | 1/2000 |
| WO | WO-00-09092 A1 | 2/2000 |
| WO | WO-00-10999 A2 | 3/2000 |
| WO | WO-00-10999 A3 | 3/2000 |
| WO | WO-00-15195 A1 | 3/2000 |
| WO | WO-00-26185 A2 | 5/2000 |
| WO | WO-00-27366 A1 | 5/2000 |
| WO | WO-00-28975 A2 | 5/2000 |
| WO | WO-00-28975 A3 | 5/2000 |

(56) References Cited

FOREIGN PATENT DOCUMENTS

| WO | WO-0026185 A3 | 5/2000 |
|---|---|---|
| WO | WO-00-30612 A1 | 6/2000 |
| WO | WO-00-35448 A1 | 6/2000 |
| WO | WO-00-44744 A1 | 8/2000 |
| WO | WO-00-45817 A1 | 8/2000 |
| WO | WO-00-50038 A1 | 8/2000 |
| WO | WO 00-69438 A1 | 11/2000 |
| WO | WO-00-78293 A1 | 12/2000 |
| WO | WO-01-03707 A1 | 1/2001 |
| WO | WO-01-24780 A2 | 4/2001 |
| WO | WO 01/28559 A1 | 4/2001 |
| WO | WO-01-34573 A1 | 5/2001 |
| WO | WO-01-51050 A1 | 7/2001 |
| WO | WO 02/053097 | 7/2002 |
| WO | WO 02/085889 A1 | 10/2002 |
| WO | WO-02-098352 A2 | 12/2002 |
| WO | WO-03-009846 A1 | 2/2003 |
| WO | WO-03-017980 A1 | 3/2003 |
| WO | WO-03-061584 A1 | 7/2003 |
| WO | WO-2005-007115 A2 | 1/2005 |
| WO | PCT/US04/23044 | 4/2005 |
| WO | WO-2005-076987 A2 | 8/2005 |
| WO | WO-2005-117870 A2 | 12/2005 |

OTHER PUBLICATIONS

Andersson, T. et al., "Pharmacokinetics of Various Single Intravenous and Oral Doses of Omeprazole," Eur. J. of Clin. Pharma., 1990, p9. 195-197, vol. 39, No. 2.

Andersson, T. et al., "Pharmacokinetics and Bioavailability of Omeprazole After Single and Repeated Oral Administration in Healthy Subjects," British J. of Clin. Pharma., 1990, pp. 557-563, vol. 29, No. 5.

Andersson, T., "Pharmacokinetics, Metabolism and Interactions of Acid Pump Inhibitors: Focus on Omeprazole, Lansoprazole and Pantoprazole," Clin. Pharacokinetics, 1996, pp. 9-28, vol. 31, No. 1.

Andersson, T. et al., "Pharmacokietic Studies with Esomeprazole, the (S)-Isomer of Omeprazole," Clin. Pharmacokinetics, 2001, pp. 411-426, vol. 40, No. 6.

Arvidsson, T. et al., "Peak Distortion in the Column Liquid Chromatographic Determination of Omeprazole Dissolved in Borax Buffer,"J. of Chromatography, 1991, pp. 271-278, vol. 586, Part 2.

Balaban, D. et al., "Nasogastric Omeprazole: Effects on Gastric pH in Critically Ill Patients," Am. J. of Gastroenterology, 1997, pp. 79-83, vol. 92, No. 1.

Ballard, E. et al., "Bioequivalence Between Lansoprazole Sachet for Suspension and Intact Capsule," Gastroenterology, 2001, pp. A-245, vol. 120, No. 5, Supp. 1, Abstract 1276.

Arturo Ballesteros, M. et al., "Bolus or Intravenous Infusion of Ranitidine: Effects on Gastric pH and Acid Secretion," Annals of Internal Medicine, 1990, pp. 334-339, Vo. 112.

Barie, P.S. and Hariri, R.J., "Therapeutic Use of Omeprazole for Refractory Stress-Induced Gastric Mucosal Hemorrage," Critical Care Medicine, 1992, pp. 899-901, vol. 20, No. 6.

Beekman, S.M., "Preparation and Properties of New Gastric Antacids I: Aluminum Hydroxide-Magnesium Carbonate Dried Gels," J. of the Am. Pharmaceutical Association, 1960, pp. 191-200, vol. 49.

Bennett, D.R. and Dickson, B.D. (eds.), "Gastrointestinal Drugs," Am Med. Assoc. Drug Eval., AMA, Chicago 1973, pp. 773-827, 2$^{nd}$ ed., Publishing Sciences Group, Acton, MASS USA.

Blum, A.L., "Therapeutic Approach to Ulcer Healing," Am J. of Med., Aug. 1985, pp. 8-14, vol. 79, Supp. 2C.

Bone, R.C., "Let's Agree on Terminology: Definition of Sepsis," Critical Care Med., 1991, p. 27, vol. 19, No. 7.

Borrero, E. et al., "Antacids vs. Sucralfate in Preventing Acute Gastrointestinal Tract Bleeding in Abdominal Aortic Surgery," Archives of Surgery, 1986, pp. 810-812, vol. 121.

Brunton, L.L., "Agents for Control of Gastric Activity and Treatment of Peptic Ulcers," The Pharmacologic Basis of Therapeutics, 1990, NY, p. 907.

Cantu, T.G. and Korek, J.S., "Central Nervous System Reactions to Histamine-2 Receptor Blockers," Annals of Int. Med., 1991, pp. 1027-1034, vol. 114.

Caos, A. et al., "Rabeprazole for the Prevention of Pathologic and Symptomatic Relapse of Erosive or Ulcerative Gastroesophageal Reflux Disease," Am. J. of Gastroenterolgy, 2000, pp. 3081-3088, vol. 95, No. 11.

Carroll et al., "Nasogastric Administration of Omeprazole for Control of Gastric pH," 10 World Congresses of Gastroenterolgy, 1994, Abstract 22P, vol. 2.

Cederberg, C. et al., "Omeprazole: Pharmacokinetics and Metabolism in Man," Scandinavian J. of Gastroenterology, 1989, pp. 33-40, vol. 24, Supp. 166.

Cederberg, C. et al., "Effect of Once Daily Intravenous and Oral Omeprazole on24-Hour Intragastric Acidity in Healthy Subjects," Scandinavian J. of Gastroenterology, 1993, pp. 179-184, vol. 28, No. 2.

Ching, C. and Lam, S., "Antacids-Indications and Limitations," Drugs, pp. 305-317, vol. 47, No. 2.

Cioffi, W.G. et al., "Comparison of Acid Neutralizing and Non-Acid Neutralizing Stress Ulcer Prophylaxis in Thermally Injured Patients," J. of Trauma, 1994, pp. 541-547, vol. 36, No. 4.

Cook, D.J. et al., "Nosocomial Pneumonia and the Role of Gastric pH: A Meta-Analysis," Chest, 1991, pp. 7-13, vol. 100, No. 1.

Cook, D.J. et al., "Risk Factors for Gastrointestinal Bleeding in Critically Ill Patients," N. Engl. J. of Med., Feb. 1994, pp. 377-381, vol. 330, No. 6.

Cook, D.J. et al., "Stress Ulcer Prophlaxis in the Critically Ill: A Meta-Analysis," Am. J. of Med., 1991, pp. 519-527, vol. 91.

Crill, C.M. et al., "Upper Gastrointestinal Tract Bleeding in Critically Ill Pediatric Patients," Pharmacotherapy, 1999, pp. 162-180, vol. 19, No. 2.

Czaja, A.J. et al., "Acute Gastroduodenal Disease After Thermal Injury: an Endoscopic Evaluation of Incidence and Natural History," N. Engl. J. of Med., Oct. 1974, pp. 925-929, vol. 291, No. 18.

Deakin, M. and Temple, J.G., "Therapeutic Process-Review XXXIII: Are We Making Progress in the Drug Treatment of Oesophageal Disease?";J. of Clin. Pharmacy and Therapeutics, 1988, pp. 365-374, vol. 13, No. 6.

Di Iorio, B. et al., "Aluminum and Phosphorus Urinary Excretion After Modifying Gastric Acid Secretion in Normal Subjects," Trace Elements and Electrolytes, 1996, pp. 47-49, vol. 13, No. 1.

Digiacinto, J.L. et al., "Stability of Suspension Formulations of Lansoprazole and Omeprazole Stored in Amber-Colored Plastic Oral Syringes," Annals of Pharmacotherapy, 2000, pp. 600-605, vol. 34, No. 5.

Doan, T.T. et al., "Comparative Pharmacokinetics and Pharmacodynamics of Lansoprazole Oral Capsules and Suspension in Healthy Subjects," Am. J. of Health-System Pharmacists, Aug. 2001, pp. 1512-1519, vol. 58, No. 16.

Dobkin, E.D. et al., "Does pH Paper Accurately Reflect Gastric pH?", Critical Care Medicine, 1990, pp. 985-988, vol. 18, No. 9.

Driks, M.R. et al., "Nosocomial Pneumonia in Intubated Patients Given Sucralfate As Compared with Antacids or Histamine Type 2 Blockers. The Role of Gastric Colonization," N. Engl. J. of Med., 1987, pp. 1376-1382, vol. 317.

Eisenberg, P.C. et al., Prospective Trial Comparing a Combination pH Probe-Nasogastric Tube with Aspirated Gastric pH in Intensive Care Unit Patients, Critical Care Med., 1990, pp. 1092-1095, vol. 18.

Ekpe, A. and Jacobsen, T., "Effect of Various Salts on the Stability of Lansoprazole, Omeprazole, and Pantoprazole as Determined by High-Performance Liquid Chromatography," Drug Dev. and Industrial Pharmacy, 1999, pp. 1057-1065, vol. 25, No. 9.

Elliot, R., "Nasogastric Administration of Omeprazole," Australian J. of Hosp. Pharmacy, 1998, pp. 174-176, vol. 28, No. 3.

Fabian, T.C. et al., "Pneumonia and Stress Ulceration in Severely Injured Patients. A Prospective Evaluation of the Effects of Stress Ulcer Prophylaxis," Feb. 1993, Archives of Surgery, pp. 185-192, vol. 128.

Fellenius, E. et al., "Substituted Benzimidazoles Inhibit Gastric Acid Secretion by Blocking (H+ + K+)ATPase," Nature, Mar. 1981, pp. 159-162, vol. 290.

(56) References Cited

OTHER PUBLICATIONS

Fiddian-Green, R.G. et al., "Predictive Value of Intramural pH and Other Risk Factors for Massive Bleeding from Stress Ulceration," Gastroenterology, 1983, pp. 613-620, vol. 85.
Fryklund et al., "Function and Structure of Parietal Cells After H+ - K+-ATPase Blockade," Am. J. of Physiology, 1988, pp. G399-407, vol. 254, No. 3, Pt. 1.
Fuchs, C., "Antacids: Their Function, Formulation, and Evaluation," Drug and Cosmetic Industry, Jun. 1949, vol. 64, No. 6, pp. 692-773.
Gafter, U. et al., "Thrombocytopenia Associated With Hypersensitivity to Rantidine: Possible Cross-Reactivity with Cimetidine," Am. J. of Gastroenterology, 1989, pp. 560-562, vol. 84, No. 5.
Garner, J.S. et al., "CDC Definitions for Nosocomial Infections, 1988," Am J. of Infection Control, 1988, pp. 128-140, vol. 16.
Garnett, W.R., "Efficacy, Safety, and Cost Issues in Managing Patients with Gastroesophael Reflux Diseases," Am. J. of Hosp. Pharmacy, 1993, pp. 511-518, vol. 50, Supp.1.
Gray et al., "Influence of Insulin Antibodies on Pharmacokinetics and Bioavailability of Recombinant Human and Highly Purified Beef Insulins in Insulin Dependent Diabetes," Br. Med. J., Jun. 1985, pp. 1687-1690, vol. 290.
Hardy, P. et al., "Inhibition of Gastric Secretion by Omeprazole and Efficiency of Calcium Carbonate on the Control of Hyperphosphatemia in Patients on Chronic Hemodialysis," Art. Organs, 1998, pp. 569-573, vol. 22, No. 7.
Hatlebakk, J.G. et al., "Lansoprazole Capsules and Amoxicillin Oral Suspension in the Treatment of Peptic Ulcer Disease," Scandinavian J. of Gastroenterology, 1995, pp. 1053-1057, vol. 30, No. 11.
Heath et al., "Intragastric pH Measurement Using a Novel Disposable Sensor," Intensive Care Med., 1988, pp. 232-235, vol. 14.
Hixson et al., "Current Trends in the Pharmacotherapy for Gastroesophageal Reflux Disease," Arch. Intern. Med., 1992, pp. 117-723, vol. 152, No. 4.
Hixson et al., "Current Trends in the Pharmacotherapy for Peptic Ulcer Disease," Arch. Intern. Med., 1992, pp. 726-732, vol. 152, No. 4.
Holbert, J.M. et al., "A Study of Antacid Buffers: The Time Factor in Neutralization of Gastric Acidity," J. of Am Pharmaceut. Assoc. (Scientific Edition), 1947, pp. 149-151, vol. 36.
Holt, S. and Howden, C.W., "Omeprazole, Overview and Opinion," Dig. Diseases and Sciences, 1991, pp. 385-393, vol. 36. No. 4.
Horn, J., "The Proton-Pump Inhibitors: Similarities and Differences," Clinical Therapeutics, 2000, pp. 266-280, vol. 22, No. 3.
Howden, C.W. et al., "Oral Pharmacokinetics of Omeprazole," Eur. J. of Clin. Pharmacology, 1984, pp. 641-643, vol. 26.
Humphries, T.J. and Merritt, G.J., "Review Article: Drug Interactions with Agents Used to Treat Acid-Related Diseases," Alimentary Pharmacol. & Therapeutics, 1999, pp. 18-26, vol. 13, Supp 3.
Jungnickel, P.W., "Pantoprazole: A New Proton Pump Inhibitor," Clin. Therapeutics, 2000, pp. 1268-1293, vol. 22, No. 11.
Karol, M.D. et al., "Pharmacokinetics of Lansoprazole in Hemodialysis Patients," J. of Clin. Pharmacology, 1995, pp. 815-820, vol. 35.
Kihira, K. et al., "Endoscopic Topical Therapy for the Treatment of Helicobacter Pylori Infection," J. of Gastroenterology, 1996, pp. 66-68, vol. 31, Supp. IX.
Kiilerich, S. et al., "Effect of Intravenous Infusion of Omeprazole and Rantidine on Twenty-Four Hour Intragastric pH in Patients with Duodenal Ulcer," Digestion, 1995, pp. 25-30, vol. 56.
Korponay-Szabo, I.R. et al., "High Acid Buffering Capacity of Protein Hydrolysate Infant Forumulas," J. of Pediatric Gastroenterology & Nutrition, Aug. 2000, vol. 31, Supp.2, Abstract 956.
Kromer, W. et al., "Differences in pH-Dependent Activation Rate of Substituted Benzimidazoles and Biological in vitro Correlates," Pharmacol., 1998, pp. 57-70, vol. 56.
Kromer, W., "Similarities and Differences in the Properties of Substituted Benzimidazoles: A Comparison Between Pantoprzole and Related Compounds," Digestion, 1995, pp. 443-454, vol. 56, No. 6.

Laggner, A. N. et al., "Prevention of Upper Gastrointestinal Bleeding in Long Term Ventilated Patients," Am. J. of Med., 1989, pp. 81-84, vol. 86, Supp. 6A.
Landahl, S. et al., "Pharmacokinetic Study of Omeprazole in Elderly Healthy Volunteers," Clinical Pharmacokinetics, 1992, pp. 496-476, vol. 23, No. 6.
Larson, G.M. et al., "Gastric Response to Severe Head Injury," Am. J. of Surgery, 1984, pp. 97-105, vol. 147.
Larson, C. et al., "Bioavailability and Efficacy of Omeprazole Given Orally and by Nasogastric Tube," Digestive Diseases and Sciences, 1996, pp. 475-479, vol. 41, No. 3.
Larsson, H. et al., "Gastric Acid Antisecretory Effect of Two Different Dosage of Omeprazole During Prolonged Oral Treatment in the Gastric Fistula Dog,", Canadian J. of Gastroenterology, 1988, pp. 1013-1019, vol. 23, No. 8.
Lasky, M., "A Prospective Study of Omeprazole Suspension to Prevent Clinically Significant Gastrointestinal Bleeding from Stress Ulcers in Mechanically Ventilated Trauma Patients," J. of Trauma: Injury, Infection and Critical Care, 1998, pp. 527-533, vol. 44, No. 3.
Lin, M. et al., "Evaluation of Buffering Capacity and Acid Neutralizing pH Time Profile of Antacids," J. of Formosan Med. Assoc., 1998, pp. 704-710, vol. 97, No. 10.
Lind, C. et al., "Inhibition of Basal and Betazole-and-sham-feeding induced Acid Secretion by Omeprazole in Man," Scandinavian J. of Gastroenterology, 1986, pp. 1004-1010, vol. 21.
Lockhart, S.P. and Baxter, G., "A Lansoprazole Suspension Formulation as an Alternative to Capsules for Oral Administration," World Congresses of Gastroenterology, 1998, p. 226, vol. 59 Supp. 3, Abstract ExhA2074.
Londong, W. et al., "Dose-Response Study of Omeprazole on Meal-Stimulated Gastric Acid Secretion and Gastrin-Release," 1983, Gastroenterology, pp. 1373-1378, vol. 85, No. 6.
Maconi, G. et al., "Prolonging Proton Pump Inhibitor-Based Anti-Helicobacer Pylori Treatment from One to Two Weeks in Duodenal Ulcer: Is It Worthwhile?", Digest of Liver Disease, 2000, pp. 275-280, vol. 32.
Marrone, G.C. and Silen, W., "Pathogenesis, Diagnosis and Treatment of Acute Gastric Mucosal Lesions," 1984, Clinics in Gastroenterology, pp. 635-650, vol. 13, No. 2.
Martin, L.F. et al., "Continuous Intravenous Cimetidine Decreases Stress-Related Upper Gastrointestinal Hemorrage Without Promoting Pneumonia," Critical Care Med., 1993, pp. 19-39, vol. 21, No. 1.
Martin, L.F. et al., "Stress Ulcers and Organ Failure in Intubated Patients in Surgical Intensive Care Unites," Ann. of Surgery, 1992, pp. 332-337, vol. 215, No. 4.
Maxwell, S.L. et al., "Control of Gastric pH in a Critical Care Unit: Physician Behavior and Pharmacologic Effectiveness," Am. Rev. of Respiratory Disease, 1991, pp. A482, vol. 143, No. 4 (Part 2).
McAndrews, K.L. and Eastham, J.H., "Omeprazole and Lansoprazole Suspensions for Nasogastric Administration," Am. J. of Health-System Pharmacy, 1999, pp. 81, vol. 56.
McTavish, D. et al., "Omeprazole: An Updated Review of its Pharmacology and Therapeutic Use in Acid-Related Disorders," Drugs, 1991, pp. 138-170, vol. 41, No. 1.
Meiners, D. etal., "Evaluation of Various Techniques to Monitor Intragastric pH," Arch. of Surgery, 1982, pp. 288-291, vol. 117.
Mohiuddin, M.A. et al., "Effective Gastric Acid Suppression After Oral Administration of Enteric-Coated Omeprazole Granules," Digestive Diseases and Sciences, 1997, pp. 715-719, vol. 42, No. 4.
Nakagawa, A. et al., "Lansoprazole: Phase I Study of Lansoprazole(AB-1749) Antiulcer Agent," Abstract in English, Text in Japanese, 1991, pp. 33-34.
Nakamura, M. et al., "Effect of Combined Administration of Lansoprazole and Sofalcone on Microvascular and Connective Tissue Regeration after Ethanol-Induced Mucosal Damage," J. of Clin. Gastroenterology, 1998, pp. S170-S177, vol. 27, Supp. 1.
Naunton, M. et al., "Overuse of Proton Pump Inhibitors," J. of Clin. Pharmacy and Ther., 2000, pp. 333-340, vol. 25.
Oh, M.S. and Carroll, H.J., "Electrolyte and Acid-Base Disorders," The Pharmacologic Approach to the Critically III Patient, 1994, pp. 957-968, $3^{rd}$ Ed., Williams & Wilkins, Baltimore, MD, USA.

(56) References Cited

OTHER PUBLICATIONS

Oosterhuis, B. and Jonkman, J.H.G., "Omeprazole: Pharmacology, Pharmacokinetics and Interactions," Digestions, 1989, pp. 9-17, vol. 44, Supp. 1.

Osler, P. et al., "Effect of Omeprazole on the Phosphate-Binding Capacity of Calcium Carbonate," Nephron, 1995, pp. 89-90, vol. 69.

Ostro, M.J. et al., "Control of Gastric pH with Cimetidine: Boluses Versus Primed Infusions," Gastroenterology, 1985, pp. 532,537, vol. 89, No. 3.

Paul, J. et al., "Pantoprozole Bicarbonate Suspension (PBS) Provides Oral Bioavailability Comparable to Tablet," Critical Care Med. 2001, 30th Int'l Educational & Scientific Symposium, A563.

Peckman, H.J., "Alternative Method for Administering Proton-Pump Inhibitors Through Nasogastric Tubes," Am. J. of Health Systems Pharmacy, 1999, pp. 1020, vol. 56.

Peura, D.A. and Johnson, L.F., "Cimetidine for Prevention and Treatment of Gastroduodenal Mucosal Lesions in Patients in an Intensive Care Unit," Ann. of Int. Med., 1985, pp. 173-177, vol. 103, No. 2.

Phillips, J. and Metzler,M., "Simplified Omeprazole Solution for the Prophylaxis of Stress-Related Mucosal Damage in Critically Ill Patients," Critical Care Med. 1994, p. A53, vol. 22, No. 1.

Phillips, J.O. et al., "A Prospective Study of Simplified Omeprazole Suspension for the Prophylaxis of Stress-Related Mucosal Damage," Crictial Care Med. 1996, pp. 1793-1800, vol. 24, No. 11.

Phillips, D.H., "Interaction of Omeprazole with DNA in Rat Tissues," Mutagenesis, 1992, pp. 277-283, vol. 7, No. 4.

Phillips, J.O. et al., "The Stability of Simplified Omeprazole Suspension (SOS)," Critical Care Med., 1998, p. A101, vol. 26, No. 1 (Supp.), Abstract No. 221.

Phillips, J.O. et al., "A Multicenter, Prospective, Randomized Clinical Trial of Continuous Infusion I.V. Rantidine vs. Omeprazole Suspension in the Prophylaxid of Stress Ulcers," Crititcal Care Med., 1998, pp. A101, vol. 26, No. 1 (Supp.), Abstract No. 222.

Phillips, J.O., "The Stability of Simplified Lansoprazole Suspension (SLS)," Gastroenterology, Abstract G0382, vol. 116, No. 4.

Pickworth, K.K. et al., "Occurrence of Nasocomial Pneumonia in Mechanically Ventilated Trauma Patients: A Comparison of Sucralfate and Ranitidine," Critical Care Med., 1993, pp. 1856-1862, vol. 21, No. 12.

Pilbrant, A. and Cederberg, C. et al., "Development of an Oral Forumulation of Omeprazole," Scandinavian J. of Gastroenterology, 1985, pp. 113-120, vol. 20, Supp. 108.

Pilbrant, A., "Principles for Development of Antacids," Scandinavian J. of Gastroenterology, 1982, pp. 32-36, vol. 75.

Pipkin, G.A. and Mills, J.G., "Onset of Action of Antisecretory Drugs: Beneficial Effects of a Rapid Increasein Intragastric pH in Acid Reflux Disease," Scandinavian J. of Gastroenterology, 1999, pp. 3-8, Supp. 230.

Prichard, P.J. et al., Omeprazole: A Study of its Inhibition of Gastric pH andOral Pharmacokinetics After Morning or Evening Dosage,: Gastroenterology, 1985, pp. 64-69, vol. 88.

Priebe,H. and Skillman, J.J., "Methods of Prophylaxis in Stress Ulcer Disease," World J. of Surgery, 1981, pp. 223-233, vol. 5, No. 2.

Quercia, R.A. et al., "Stability of Omeprazole in an Extemporaneously Prepared Oral Liquid," Am. J. of Health System Pharmacy, 1997, pp. 1833-1836, vol. 54, No. 16.

Regardh, C.G. et al., "The Pharmacokinetics of Omeprazole inHumans—A Study of Single Intravenous and Oral Doses," Ther. Drug Monitoring, 1990, pp. 163-172, vol. 12, No. 2.

Regardh et al., "Pharmacokinetics and Metabolism of Omeprazole in Animals and Man—An Overview," Scandinavian J. of Gastroenterology, Supp., 1985, pp. 79-84, vol. 108.

Rodrigo, J.M. and Ponce, J., "Therapeutic Approach to Peptic Ulcer-Relapse," Methods and Findings in Experimental and Clinical Pharmacology, 1989, pp. 131-135, vol. 11, Supp. 1.

Roy, P.K. et al., "Zollinger-Ellison Syndrome-Clinical Presentation in 261 Patients," Medicine, 2000, pp. 379-411, vol. 79, No. 6.

Ryan, P. et al., "Nosocomial Pneumonia During Stress Ulcer Prophylaxis with Cimetidine and Sucralfate," 1993, Arch. of Surgery, pp. 1353-1357, vol. 128.

Sax, M.J., "Clinically Important Adverse Effects and Drug Interactions with H2-Receptor Antagonists: An Update," Pharmacotherapy, 1987, pp. 110S-115S, vol. 7., No. 6, Part 2.

Schepp, W., "Stress Ulcer Prophylaxis: Still a Valid Option in the 1990s?", Digestion, 1993, pp. 189-199, vol. 54.

Schmassmann, A. et al., "Antacid Provides Better Restoration of Glandular Structures Within the Gastric Ulcer Scar than Omeprazole," Gut, 1994, pp. 869-904, vol. 35, No. 7.

Schmassmann, A. et al., "Antacids in Experimental Gastric Ulcer Healing: Pharmacokinetics of Aluminum and Quality of Healing," Eur. J. of Gastroenterology & Hepatology, 1993, pp. S111-S116, vol. 5, Supp. 3.

Shuman, R.B. et al., "Prophylactic Therapy for.Acute Ulcer Bleeding: A Reappraisal,", Ann. of Int. Med., 1987, pp. 562-567, vol. 106.

Schuster, D.P., "Stress Ulcer Prophylaxis: In Whom? With What?," Critical Care Med, 1993, pp. 4-6, vol. 21.

Sechet, A. et al., "Role of the Time of Administration of Calcium Carbonate in the Control of Hyperphophemia in Patients on Maintenance Hemodialysis," Nephrologie, 1999, pp. 209-212, vol. 20, No. 4.

Sechet, A. et al., "Inhibition of Gastric Secretion by Omeprazole and Efficacy of Calcium Carbonate in the Control of Hyperphosphatemia in Patients on Maintenance Hemodialysis," Nephrologie, 1888, pp. 213-216, vol. 20, No. 4.

Sharma, V.K. et al., "The Effects on Intragastric Acidity of Per-Gastrostomy Administration of an Alkaline Suspension of Omeprazole," Alimentary Pharmacology & Therapeutics, 1999, pp. 1091-1095, vol. 13.

Sharma, V.K. et al., "Oral Pharmacokinetics of Omeprazole and Lansoprazole After Single and Repeated Doses as Intact Capsules or as Suspensions in Sodium Bicarbonate," Alimentary Pharmacology & Therapeutics, 2000, pp. 887-892, vol. 14, No. 7.

Sharma, V.K. et al., The Pharmacodynamics of Lansoprazole Administered via Gastrostomy as Intact, Non-Encapsulate Granules, Alimentary Pharmacology & Therapeutics, 1998, pp. 1171-1174, vol. 12.

Sharma, V.K. et al., Simplified Lansoprazole Suspension—A Liquid Formulation of Lansoprazole-Effectively Suppress Intragastric Acidity when Administered Through a Gastrostomy, Am. J. of Gastroenterology, 1999, pp. 1813-1817, vol. 94, No. 7.

Sharma, V.K., "Comparison of 24-Hour Intragastric pH Using Four Liquid Formulations of Lansoprazole and Omeprazole," Am J. of Health System Pharmacy, 1999, p. S180-S21, vol. 56, Supp. 4.

Sharma, V.K. et al., "Effect on 24-Hour Intragastric Acidity of Simplifie Omeprazole Solution (SOS) Administered via Gastrostomy," Am. J. of Gastroenterolgy, 1997, p. 1625, vol. 92, No. 9 Abstract #169.

Sharma, V.K., "Simplified Lansoprazole Suspension (SLS): A Proton Pump Inhibitor PPI) in a Liquid Formulation that Works," Am. J. of Gastroenterology, Sep. 1998, pp. 1647, Abstract #153.

Siepler, J.K. et al., Selecting Drug Therapy for Patients with Duodenal Ulcers, Clin. Pharmacy, 1990, pp. 463-467, vol. 9, No. 6.

Siepler, J:K., "A Dosage Alternative for H-2 Receptor Antagonists, Continuous-Infusion," Clin. Therapeutics, 1986, pp. 24-33, vol. 8, Supp. A.

Sih, J.C. et al., "Studies on (H(+)-K+)-ATPase Inhibitors of Gastric Acid Secretion, Prodrugs of 2-[(2-Pyridinlymethyl)sulfinyl] benzimidazole Proton-pump Inhibitors," J. of Med. Chem. 1991, pp. 1049-1062, vol. 34, No. 3.

Simms, H. et al., "Role of Gastric Colonization in the Development of Pneumonia in Critically Ill Trauma Patients: Results of a Prospective Randomized Trial," J. of Trauma, 1991, pp. 531-537, vol. 31, No. 4.

Skillman, J.J. et al., "Respiratory Failure, Hypotension, Sepsis and Jaundice: A Clinical Syndrom Associated with Lethal Hemorrhage from Acute Stress Ulceration of the Stomach," Am. J. of Surgery, 1969, pp. 523-530, vol. 117.

Skillman, J.J. et al., "The Gastric Mucosal Barrier: Clinical and Experimental Studies in Critically Ill and Normal Man, and in the Rabbit," Ann. of Surgery, 1970, 564-584, vol. 172,No. 4.

Smythe, M.A. and Zarowitz, B.J., "Changing Perspectives of Stress Gastritis Prophylaxis," Ann. of Pharmacotherapy, 1994, pp. 1073-1085, vol. 28.

(56) References Cited

OTHER PUBLICATIONS

Spencer, C.M. and Faulds, D., "Esomeprazole," Drugs, Aug. 2000, pp. 321-329, vol. 60, No. 2.
Spychal, R.T. and Wickman, N.W.R., "Thrombocytopenia Associated with Rantidine," Br. Med. J., 1985, p. 1687, vol. 291.
Stratford, M.R. L. et al., "Nicotinamide Pharmacokinetics in Humans: Effect of Gastric Acid Inhibition, Comparison of Rectal vs. Oral Administration and the Use of Saliva for Drug Monitoring," Br. J. of Cancer, 1996, pp. 16-21, vol. 74, No. 1.
Tabata, T. et al., "Stabilization of a New Antiulcer Drug (Lansoprazole) in the Solid Dosage Forms," Drug Dev. & Industrial Pharmacy, 1992, pp. 1437-1447, vol. 18, No. 3.
Takeuchi, K. et al., "Effects o Pantoprazole, a novel H+/K+-ATPase Inhibitor, on Duodenal Ulcerogenic and Healing Responses in Rats: A Comparative Study with Omeprazole and Lansoprazole," J. of Gastroenterology & Hepatology, 1999, pp. 251-257, vol. 14, No. 3.
Tanaka, M. et al., "Differntial Stereoselective Pharmacokinetics of Pantoprazole, a Proton Pump Inhibitor in Extensive and Poor Metabolizers of Pantoprazole—A Preliminary Study," Chirality, 1997, pp. 17-21, vol. 9.
Tanaka, H. et al., "Pathogenesis of the Earliest Epithilial Cell Damage by Mepirizole and Cysteamine in the Rat Duodenum," Jap. J. of Pharmacology, 1989, pp. 509-519, vol. 51, No. 4.
Thomson, A.B.R., "Are the Orally Administered Proton Pump Inhibitors Equivalent? A Comparison of Lansoprazole, Omeprazole, Pantoprazole, and Rabeprazole," Curr. Gastroenterology Reports, 2000, pp. 482-492, vol. 2.
Tryba, M., "Risk of Acute Stress Bleeding and Nosocomial Pneumonia in Ventilated Intensive Care Patients, Sucralfate vs. Antacids," Am. J. of Med., 1987, pp. 117-124, vol. 87, Supp. 3B.
Tryba, M., "Stress Ulcer Prophylaxis-Quo Vadis?", Intensive Care Med., 1994, pp. 311-313, vol. 20.
Tytgat, G.N.J., "Drug Therapy of Reflux Oesophagitis: An Update," Scandinavian J. of Gastroentereology, 1989, pp. 38-49, vol. 24, Supp. 168.
Vial, T. et al., "Side Effects of Rantidine," Drug Safety, 1991, pp. 94-117, vol. 6, No. 2.
Vincent, J. et al., Concurrent Administration of Omeprazole and Antacid Does Not Alter the Pharmacokinetics of Doetilide in Healthy Subjects, Clin. Pharmacology & Therapeutics, 1996, p. 182, vol. 59, No. 2, Abstract P11-93.
Wade, L.G., Organic Chemistry, 1987, pp. 349-350, Prentice-Hall, Inc.,NJ, USA.
Walan, A, "Pharmacological Agents for Peptic Ulcer Disease," Scandinavian J. of Gastroenterology, Supp. 1984, p. 1, vol. 19, No. 98.
Wallmark, B. et al., "The Relationship Between Gastric Acid Secretion and Gastric H+/K+-ATPase Activity," J. of Biol. Chem., 1985, 13681-13684, vol. 260, No. 25.
Watanabe, K. et al., "Pharmocokinetic Evaluation of Omeprazole Suspension Following Oral Administration in Rats: Effect of Neutralization of Gastric Acid," Acta Medica Okayama, 1996, pp. 219-222, vol. 50, No. 4.
Wilder-Smith, C.H. and Merki, H.S., "Tolerance During Dosing with H2 Receptor Antagonists, An Overview," 1991, Scandinavian J. of Gastroenterology, pp. 14-19, vol. 27, Supp. 193.
Whipple, J. et al., "The Effect of Omeprazole/Sodium Bicarbonate Solution Administration on the Accuracy of Subsequent pH Measurements through the Nasogastric Tube," Critical Care Med., 1995, pp. A69, vol. 28, No. 1 (Supp.).
Yamakawa, T. et al., "Synthesis and Structure-Activity Relationships of Substituted 2-(2-Imidazolysufinyl)methyl) anilines as a New Class of Gastric H+/K(+)-ATPase Inhibitors. II.," Chem. and Pharmacuetical Bulletin, 1992, pp. 675-682, vol. 40, No. 3.
Yasuda, S. et al., "Antacids Have No Influence of the Pharmacokietics of Raberprazole, A New Proton Pump Inhibitor, in Healthy Volunteers," Intl. J. of Clin. Pharmacology & Therapeutics, 1999, pp. 249-253, vol. 37, No. 5.

Zinner, M.J. et al, "The Prevention of Gastro-Intestinal Tract Bleeding in Patients in an Intensive Care Unit," Surgery, Gynecology & Obstetrics, pp. 214-220, vol. 153.
"Agents for Control of Gastric Acidity and Treatement of Peptic Ulcers," Chapter 37, pp. 907-909.
"Buffered and Isotonic Solutions," Physical Pharmacy, pp. 169-189, Chapter 8.
Phillips, J.O. et al., "A Randomized, Pharmacokinetic and Pharmacodynamic, Cross-Over Study of Duodenal or Jejunal Administration Compared to Nasogastric Administration of Omeprazole Suspension in Patients at Risk for Stress Ulcers," American Journal of Gastroenterology (2001),vol. 96, No. 2, pp. 367-372.
Farup et al., "The Impact of Nocturnal Symptoms Associated with Gastroesophageal Reflux Disease on Health-Related Quality of Life," Arch Intern Med. 161:45-52 (2001).
EP05755940 Search Report mailed Aug. 19, 2010.
EP 05755940.3 Examination Report dated Jul. 28, 2011.
"Pharmacotherapy Related Outcomes Group Researching Effective Stress Ulcer Strategies," Overview of Omeprazole Suspension 2000 Presentation, 14 pages.
"Stress Ulcer Prophylaxis in the $21^{st}$ Century," Overview of Omeprazole Suspension 2001 Presentation, 13 pages.
Dialog patent search re: omeprazole & specific coating, May 27, 2003, 154 pages.
Dialog patent search re: omeprazole & specific coating, May 29, 2003, 59 pages.
Dialog patent search re: omeprazole & specific coating, U.S. patents bibliographic—titles, claims, abstracts only, May 30, 2003, p. 1-211.
Dialog search re: omeprazole & specific coating, EP, PCT full text files, May 30, 2003, p. 212-804.
Metzler, M., "Advances in the Use of PPI's from Efficacy to Effectiveness," Presentation: Simplified Omeprazole Suspension, 1999, 4 pages.
Nerac search re: omeprazole and (opadry or HPMC), Question No. 1116119.016, May 2003, 47 pages.
Nerac search re: omeprazole and ethocel (ETC), Question No. 1116119.014, May 2003, 38 pages.
Nerac search re: omeprazole and ethocel, Question No. 1116119. 015, May 2003, 3 pages.
Nerac search re: omeprazole and kollicoat 1R, Question No. 1116119.011, May 2003, 2 pages.
Nerac search re: omeprazole and RD100, Question No. 1116119. 017, May 2003, 12 pages.
Nerac search re: omeprazole/microencapsulation/HP, Question No. 1116119.008, May 2003, 13 pages.
Nerac search re: Omeprazole or Proton Pump Inhibitor and Coating (negate enteric), Question No. 1116119.009, May 2003, 57 pages.
PCT/US07/80641 International Search Report dated Jul. 29, 2008.
Phillips, "Simplified Omeprazole Solution-(S.O.S.)-Pharmacokinetic/Pharmacodynamic Study in Patients at Risk for Stress Related Mucosal Damage (SRMD)," Project #5122, 1994, 6 pages.
Phillips, J., "Overview of Omeprazole Suspension—From Efficacy to Effectiveness Alternative Dosing of PPI's," 1998, Presentation, 5 pages.
Phillips, J., "Overview of Omeprazole Suspension-Prolbems with Administering Granules," 1999/2000 Presentation, 3 pages.
Phillips, J., "Simplified Omeprazole Suspension (SOS)," 1998, Presentation, 8 pages.
Phillips, J., "Stress-Related Mucosal Damage Optimizing Drug Therapy in the 1990's," Presentation at U. of MO. Surgical Society Scientific Program, 1994, 6 pages.
Phillips, J., "Stress-Related Mucosal Damage-Optimizing Drug Therapy," Presentation 1997, 5 pages.
Phillips, J., "Update on Acid-Related Disorders—Optimizing Pharmacotherapy for the 1990's," Presentation 1996, 6 pages.

* cited by examiner

Mg Hydroxide Particle Effect in PK

| ID | Buffer (mg) | | Total Buffer | Ac-Di-Sol Level % | Tmax | AUC (0-6h) (ng*h/mL) |
|---|---|---|---|---|---|---|
| | NaHCO$_3$ | Mg(OH)$_2$ | | | | |
| SAN-10A | 420 | 470/100mesh | 21 mEq | 3.1% | 46 min | 2400 |
| SAN-10B | 420 | 470/60mesh | 21 mEq | 3.1% | 73 min | 2392 |
| SAN-10E | 378 | 425/MS-95* | 19 mEq | 8.9% | 47 min | 2108 |
| Prilosec | 0 | 0 | 0 | NA | 83 min | 2198 |

* Spray Dried Grade (5% starch)

Confidential

PK Study Results of Hi/Lo Ac-Di-Sol

Figure 10

All Munich CTM Lots

| Code | Feature | ANC (mEq) | Purpose | Period |
|---|---|---|---|---|
| SAN-10A | <100µ MH | 21.0 | Best Case | 2 |
| SAN-10B | <60µ MH | 21.0 | Practicality | 4 |
| SAN-10BB | Single Buffer | 13.1 | Good Stability | 9 |
| SAN-10C | OE size, 20mg | 9.5 | 2 capsule dosing | ND |
| SAN-10D | <80µ MH | 21.0 | In between case | ND |
| SAN-10E | MS-95 | 19.1 | MS-95 v. MH | 6 |
| SAN-10G | MS-95 High Ac-di-Sol | 19.1 | Higher % of Disintegrant | ND |
| SAN-10H | <60µ MH High Ac-di-Sol | 17.9 | Bimodal delivery of SAN-10B | 8 |
| SAN-10K | 880mg SB | 10.5 | Range finding | 11 |

Confidential

Figure 11

SAN-10 Pilot PK Data Summary (40mg)

| | C_max (ng/mL) | T_max (min) | AUC_(0-t) (ng*h/mL) | AUC_(0-inf) (ng*h/mL) | ANC (mEq) |
|---|---|---|---|---|---|
| Prilosec | 1061 | 1h 23 min | 2198 | 2620 | 0 |
| SAN-10A | 1155 | 46 min | 2400 | 2747 | 21.1 |
| SAN-10B | 990 | 73 min* | 2391 | 2919 | 21.1 |
| SAN-10E | 1130 | 47 min | 2106 | 2403 | 19.1 |
| SAN-10H | 1128 | 47 min | 2263 | 2551 | 17.9 |
| SAN-10BB | 1364 | 33 min | 2504 | 2910 | 13.1 |
| SAN-10K | 1378 | 34 min | 2202 | 2558 | 10.5 |

All data listed are mean values

Confidential

Pivotal PK Data - 20 mg, Day 1

Pivotal PK Data - 40 mg, Day 1

Cmax vs. Tmax for ChewTab, Capsule, Powder and Prilosec® Day 1 Dosing

Pivotal PK Data - 20 mg, Day 7

Pivotal PK Data - 40 mg, Day 7

Cmax vs. Tmax for ChewTab, Capsule, Powder and Prilosec® Day 7 Dosing

PHARMACEUTICAL FORMULATIONS USEFUL FOR INHIBITING ACID SECRETION AND METHODS FOR MAKING AND USING THEM

This application is a continuation-in-part of U.S. patent application Ser. No. 11/138,763, filed on May 25, 2005, which in turn claims benefit under 35 U.S.C. §119(e) of U.S. Provisional Application No. 60/574,646, filed May 25, 2004 and U.S. Provisional Application No. 60/574,663, filed May 25, 2004, the contents of each of which are incorporated herein by reference in their entirety.

FIELD OF THE INVENTION

The present invention relates to pharmaceutical formulations in solid oral dosage form comprising at least one acid-labile proton pump inhibiting agent and at least one antacid, which have improved bioavailability, chemical stability, physical stability, dissolution profiles, disintegration times, safety, as well as other improved pharmacokinetic, pharmacodynamic, chemical and/or physical properties. Also described herein are pharmaceutical formulations comprising at least one proton pump inhibiting agent and about 5 mEq to about 11 mEq of antacid, which have similar bioavailability, chemical stability, physical stability, dissolution profiles, disintegration times, safety, as well as other improved pharmacokinetic, pharmacodynamic, chemical and/or physical properties to similar combinations comprising greater than 11 mEq of antacid.

The present invention is directed to methods, kits, combinations, and compositions for treating, preventing or reducing the risk of developing a gastrointestinal disorder or disease, or the symptoms associated with, or related to, a gastrointestinal disorder or disease in a subject in need thereof.

BACKGROUND OF THE INVENTION

Upon ingestion, most acid-labile pharmaceutical compounds must be protected from contact with acidic stomach secretions to maintain their pharmaceutical activity. To accomplish this, compositions with enteric-coatings have been designed to dissolve at a neutral pH to ensure that the drug is released in the proximal region of the small intestine (duodenum), rather than the acidic environment of the stomach. However, due to the pH-dependent attributes of these enteric-coated compositions and the uncertainty of gastric retention time, in-vivo performance as well as both inter- and intra-subject variability are all major set backs of using enteric-coated systems for the controlled release of a drug.

In addition, Phillips et al. has described non-enteric coated pharmaceutical compositions. These compositions, which allow for the immediate release of the pharmaceutically active ingredient into the stomach, involve the administration of one or more antacids with an acid labile pharmaceutical agent, such as a proton pump inhibitor. The antacid is thought to prevent substantial degradation of the acid labile pharmaceutical agent in the acidic environment of the stomach by raising the pH. See, e.g., U.S. Pat. Nos. 5,840,737 and 6,489,346.

A class of acid-labile pharmaceutical compounds that are administered as enteric-coated dosage forms are proton pump inhibiting agents. Exemplary proton pump inhibitors include: omeprazole (Prilosec®), lansoprazole (Prevacid®), esomeprazole (Nexium®), rabeprazole (Aciphex®), pantoprazole (Protonix®), pariprazole, tenatoprazole, and leminoprazole. The drugs of this class suppress gastrointestinal acid secretion by the specific inhibition of the $H^+/K^+$-ATPase enzyme system (proton pump) at the secretory surface of the gastrointestinal parietal cell. Most proton pump inhibitors are susceptible to acid degradation and, as such, are rapidly destroyed as pH falls to an acidic level. Therefore, if the enteric-coating of these formulated products is disrupted (e.g., trituration to compound a liquid, or chewing the capsule or tablet) or the antacid fails to sufficiently neutralize the gastrointestinal pH, the drug will be exposed to degradation by the gastrointestinal acid in the stomach.

Omeprazole is one example of a proton pump inhibitor which is a substituted bicyclic aryl-imidazole, 5-methoxy-2-[(4-methoxy-3,5-dimethyl-2-pyridinyl)methyl]sulfinyl]-1H-benzimidazole, that inhibits gastrointestinal acid secretion. U.S. Pat. No. 4,786,505 to Lovgren et al. teaches that a pharmaceutical oral solid dosage form of omeprazole must be protected from contact with acidic gastrointestinal juice by an enteric-coating to maintain its pharmaceutical activity and describes an enteric-coated omeprazole preparation containing one or more subcoats between the core material and the enteric-coating.

Proton pump inhibitors are typically prescribed for short-term treatment of active duodenal ulcers, gastrointestinal ulcers, gastro esophageal reflux disease (GERD), severe erosive esophagitis, poorly responsive symptomatic GERD, and pathological hypersecretory conditions such as Zollinger Ellison syndrome. These above-listed conditions commonly arise in healthy or critically ill patients of all ages, and may be accompanied by significant upper gastrointestinal bleeding.

It is believed that omeprazole, lansoprazole and other proton pump inhibiting agents reduce gastrointestinal acid production by inhibiting $H^+/K^+$-ATPase of the parietal cell the final common pathway for gastrointestinal acid secretion. See, e.g., Fellenius et al., Substituted Benzimidazoles Inhibit Gastrointestinal Acid Secretion by Blocking $H^+/K^+$-ATPase, *Nature*, 290: 159-161 (1981); Wallmark et al., The Relationship Between Gastrointestinal Acid Secretion and Gastrointestinal $H^+/K^+$-ATPase Activity, *J. Biol. Chem.*, 260: 13681-13684 (1985); and Fryklund et al., Function and Structure of Parietal Cells After $H^+/K^+$-ATPase Blockade, *Am. J. Physiol.*, 254 (1988).

Proton pump inhibitors have the ability to act as weak bases that reach parietal cells from the blood and diffuse into the secretory canaliculi. There, the drugs become protonated and thereby trapped. The protonated compound can then rearrange to form a sulfenamide, which can covalently interact with sulfhydryl groups at critical sites in the extra cellular (luminal) domain of the membrane-spanning $H^+/K^+$-ATPase. See, e.g., Hardman et al., *Goodman & Gilman's The Pharmacological Basis of Therapeutics*, 907 (9th ed. 1996). As such, proton pump inhibitors are prodrugs that must be activated to be effective. The specificity of the effects of proton pump inhibiting agents is also dependent upon: (a) the selective distribution of $H^+/K^+$-ATPase; (b) the requirement for acidic conditions to catalyze generation of the reactive inhibitor; and (c) the trapping of the protonated drug and the cationic sulfenamide within the acidic canaliculi and adjacent to the target enzyme. See, e.g., Hardman et al.

SUMMARY OF THE INVENTION

The present invention is directed to pharmaceutical formulations in a solid oral dosage form comprising (a) at least one acid-labile proton pump inhibitor, and (b) at least one antacid sufficient to increase gastric pH to a pH that prevents acid degradation of at least some of the proton pump inhibitor in the gastric fluid, wherein upon oral administration to a patient, a therapeutically effective amount of the proton pump inhibitor is delivered and $T_{max}$ of the proton pump inhibitor is obtained within about 75 minutes after administration. In alternative embodiments, $T_{max}$ of the proton pump inhibitor is obtained within about 60 minutes, or within about 45 minutes, or within about 30 minutes after administration. In some embodiments, the solid oral dosage form is a capsule. In other embodiments, the solid oral dosage form is a caplet.

In one embodiment, pharmaceutical formulations in a solid oral dosage form comprising (a) at least one acid-labile proton pump inhibitor; (b) a sufficient amount of sodium bicarbonate to increase gastric fluid pH to a pH that prevents acid degradation of at least some of the proton pump inhibitor in the gastric fluid; and (c) less than about 3% of disintegrant, wherein upon oral administration to a patient a therapeutically effective amount of the proton pump inhibitor is delivered and $T_{max}$ of the proton pump inhibitor is obtained within about 75 minutes after administration are described. In other embodiments, the pharmaceutical formulations comprise less than about 2% or less than about 1% of disintegrant. In alternative embodiments, $T_{max}$ of the proton pump inhibitor is obtained within about 60 minutes, or within about 45 minutes, or within about 30 minutes after administration. In some embodiments, the solid oral dosage form is a capsule. In other embodiments, the solid oral dosage form is a caplet.

Stable pharmaceutical formulations in a solid oral dosage form comprising (a) at least one acid-labile proton pump inhibitor, and (b) at least one antacid in an amount sufficient to increase gastric fluid pH to a pH that prevents acid degradation of at least some of the proton pump inhibitor in the gastric fluid, wherein the pharmaceutical formulation does not comprise a binder; and wherein upon oral administration to a patient: a therapeutically effective amount of the proton pump inhibitor is delivered and $T_{max}$ of the proton pump inhibitor is obtained within about 75 minutes after administration are also provided herein. In some embodiments, the antacid is present in an amount of greater than about 5 mEqs. In other embodiments, the antacid is present in an amount of about 5 mEq to about 30 mEq, or about 5 mEq to about 20 mEq, or about 8 mEq to about 15 mEq, or about 10 mEq to about 15 mEq. In still other embodiments, the antacid is present in an amount of about 5 mEq, or about 6 mEq, or about 7 mEq, or about 8 mEq, or about 9 mEq, or about 10 mEq, or about 11 mEq, or about 12 mEq, or about 13 mEq, or about 14 mEq, or about 15 mEq, or about 16 mEq, or about 17 mEq, or about 18 mEq, or about 19 mEq, or about 20 mEq, or about 22.5 mEq, or about 25 mEq, or about 27 mEq, or about 30 mEq, or about 35 mEq. In some embodiments, the solid oral dosage form is a capsule. In other embodiments, the solid oral dosage form is a caplet.

Stable pharmaceutical formulations in a solid oral dosage form comprising (a) at least one acid-labile proton pump inhibitor, (b) at least about 5 mEq of antacid, wherein the antacid is a combination of at least two different antacids, and (c) between about 3% to about 11% of a disintegrant, wherein upon oral administration to a patient a therapeutically effective amount of the proton pump inhibitor is delivered and $T_{max}$ of the proton pump inhibitor is obtained within about 75 minutes, are also provided herein. In some embodiments the pharmaceutical formulation comprises about 4% to about 8% disintegrant. In other embodiments, the pharmaceutical formulation comprises about 5% to about 7% disintegrant. In alternative embodiments, $T_{max}$ of the proton pump inhibitor is obtained within about 60 minutes, or within about 45 minutes, or within about 30 minutes after administration. In some embodiments, the solid oral dosage form is a capsule. In other embodiments, the solid oral dosage form is a caplet.

Also provided herein are stable pharmaceutical formulations in a single capsule dosage form comprising (a) at least one acid-labile proton pump inhibitor, (b) about 5 to about 15 mEq of sodium bicarbonate, and (c) less than about 3% of a disintegrant, wherein upon oral administration to a patient a therapeutically effective amount of the proton pump inhibitor is delivered and $T_{max}$ of the proton pump inhibitor is obtained within about 75 minutes. In some embodiments, the pharmaceutical formulation comprises about 8 mEq to about 15 mEq of sodium bicarbonate. In other embodiments, the pharmaceutical formulation comprises about 10 mEq to about 15 mEq of sodium bicarbonate. In yet other embodiments, the pharmaceutical formulation comprises about 13 mEq of sodium bicarbonate. In still other embodiments, $T_{max}$ of the proton pump inhibitor is obtained within about 60 minutes, or within about 45 minutes, or within about 30 minutes after administration.

Stable pharmaceutical formulations in a solid oral dosage form comprising (a) omeprazole or a salt, hydrate, ester, amide, enantiomer, isomer, tautomer, polymorph, or prodrug thereof, (b) at least about 5 mEq of sodium bicarbonate, and (c) less than about 3% of a disintegrant, wherein the pharmaceutical formulation does not comprise a binder; and wherein upon oral administration to a patient a therapeutically effective amount of the proton pump inhibitor is delivered and $T_{max}$ of the proton pump inhibitor is obtained within about 75 minutes after administration are also provided herein. In some embodiments, the pharmaceutical formulation comprises between about 5 mEq to about 20 mEq, or between about 5 mEq to about 15 mEq, or between about 10 mEq to about 15 mEq of sodium bicarbonate. In other embodiments, the pharmaceutical formulation comprises less than about 2% sodium bicarbonate. In yet other embodiments, $T_{max}$ of the proton pump inhibitor is obtained within about 60 minutes, or within about 45 minutes, or within about 30 minutes after administration. In some embodiments, the solid oral dosage form is a capsule. In other embodiments, the solid oral dosage form is a caplet.

Also provided herein are stable pharmaceutical formulations in single capsule dosage form comprising (a) at least one acid-labile proton pump inhibitor, and (b) about 5 to about 30 mEq of antacid wherein the antacid is selected from magnesium hydroxide, magnesium oxide, sodium carbonate, sodium bicarbonate, and calcium carbonate, wherein upon oral administration to a patient: a therapeutically effective amount of the proton pump inhibitor is delivered; and $T_{max}$ of the proton pump inhibitor is obtained within about 75 minutes. In other embodiments, $T_{max}$ of the proton pump inhibitor is obtained within about 60 minutes, or within about 45 minutes, or within about 30 minutes after administration.

Also provided herein are pharmaceutical compositions in solid oral dosage forms wherein the wt-% of disintegrant is at least as great as the wt-% of binder. In some embodiments, the pharmaceutical formulation is substantially free of a binder. In other embodiments, the solid oral dosage form is a tablet (such as a caplet) and the binder is present in an amount of less than about 20 wt %, or less than about 10 wt-%, or less than about 5 wt-%. In other embodiments, the solid oral dosage form is a capsule and the binder is present in an amount of about 0 wt-% to about 5 wt-%.

The present invention provides a pharmaceutical composition comprising a proton pump inhibiting agent and about 5 mEq to about 11 mEq of antacid for oral administration and ingestion by a subject.

Pharmaceutical formulations are included that comprise (a) at least one acid-labile proton pump inhibitor, and (b) between about 5 mEq to about 11 mEq of antacid, wherein upon oral administration to a subject, the oral bioavailability of the proton pump inhibitor is at least 25% and the maximum serum concentration of the proton pump inhibitor is obtained within about 75 minutes after administration. In other embodiments, the maximum serum concentration is obtained within about 60 minutes, or within about 50 minutes, or within about 40 minutes, or within about 30 minutes, or within about 20 minutes after administration of the pharmaceutical formulation. In still other embodiments, the oral bioavailability of the proton pump inhibitor is about 25% to about 60%, or about 30% to about 50%, or at least about 30%, or at least about 35%, or at least about 40%.

Pharmaceutical formulations that comprise (a) at least one acid-labile proton pump inhibitor, and (b) between about 5 mEq to about 11 mEq of antacid, wherein the pharmaceutical formulation is bioequivalent to a pharmaceutical formulation comprising (a) at least one acid-labile proton pump inhibitor, and (b) greater than 11 mEq of antacid. In some embodiments, the area under the serum concentration time curve for the proton pump inhibitor is within about ±15% of the area under the serum concentration time curve for the proton pump inhibitor when an administered with greater than 11 mEq of antacid. In other embodiments, the area under the serum concentration time curve for the proton pump inhibitor is within about ±10% of the area under the serum concentration time curve for the proton pump inhibitor when an administered with greater than 11 mEq of antacid. In still other embodiments, the area under the serum concentration time curve for the proton pump inhibitor is within about ±5% of the area under the serum concentration time curve for the proton pump inhibitor when administered with greater than 11 mEq of antacid.

Pharmaceutical formulations that comprise (a) at least one acid-labile proton pump inhibitor, and (b) between about 5 mEq to about 11 mEq of antacid, wherein the pharmaceutical formulation is bioequivalent to a pharmaceutical formulation comprising (a) at least one acid-labile proton pump inhibitor, and (b) greater than 15 mEq of antacid. In some embodiments, the area under the serum concentration time curve for the proton pump inhibitor is within about ±15%, or within about ±10%, or within about ±5% of the area under the serum concentration time curve for the proton pump inhibitor when an administered with greater than 15 mEq of antacid.

Pharmaceutical formulations that comprise (a) at least one acid-labile proton pump inhibitor, and (b) between about 5 mEq to about 11 mEq of antacid, wherein the pharmaceutical formulation is bioequivalent to a pharmaceutical formulation comprising (a) at least one acid-labile proton pump inhibitor, and (b) greater than 20 mEq of antacid. In some embodiments, the area under the serum concentration time curve for the proton pump inhibitor is within about ±15%, or within about ±10%, or within about ±5% of the area under the serum concentration time curve for the proton pump inhibitor when an administered with greater than 20 mEq of antacid.

Pharmaceutical formulations comprising (a) at least one acid-labile proton pump inhibitor, and (b) between about 5 mEq to about 11 mEq of antacid wherein the pharmaceutical formulation is bioequivalent to a proton pump inhibitor product. In some embodiments, the pharmaceutical formulation is bioequivalent to Priolosec®, Nexium®, Prevacid®, Protonic®, and Aciphex®. In other embodiments, the maximum concentration of the proton pump inhibitor for the pharmaceutical formulation is within about 80% and about 120% of the maximum concentration (Cmax) for the proton pump inhibitor product. In some embodiments, the maximum concentration of the proton pump inhibitor for the pharmaceutical formulation is within about 80% and about 120% of the maximum concentration (Cmax) for the proton pump inhibitor product when the pharmaceutical formulation and proton pump inhibitor product are administered to the same patient.

Pharmaceutical formulations comprising (a) at least one acid-labile proton pump inhibitor, and (b) between about 5 mEq to about 11 mEq of antacid are provided herein, wherein upon oral administration to a subject, the pharmaceutical composition has an area under the serum concentration time curve (AUC) for the proton pump inhibitor that is equivalent to an area under the serum concentration time curve (AUC) for the proton pump inhibitor when an enteric form of the proton pump inhibitor is delivered without antacid. In some embodiments, the area under the serum concentration time curve for the proton pump inhibitor is within about ±20% of the area under the serum concentration time curve for the proton pump inhibitor when an enteric form of the proton pump inhibitor is delivered without antacid. In still other embodiments, the area under the serum concentration time curve for the proton pump inhibitor is within about ±15%, or within about ±10%, or with about ±5% of the area under the serum concentration time curve for the proton pump inhibitor when an enteric form of the proton pump inhibitor is delivered without antacid.

Pharmaceutical formulations comprising (a) at least one acid-labile proton pump inhibitor, and (b) between about 5 mEq to about 11 mEq of antacid are provided herein, wherein a therapeutic dose of the proton pump inhibitor is delivered as a single capsule, tablet, or caplet.

A pharmaceutical formulations comprising (a) at least one acid-labile proton pump inhibitor, and (b) between about 5 mEq to about 11 mEq of antacid, wherein upon oral administration to a patient: a therapeutically effective amount of the proton pump inhibitor is delivered; the antacid increases the gastric pH to at least about 3.5 for no more than about 30 minutes measured by a simulated stomach model such as Fuchs kinetic in-vitro pH model; and the maximum concentration of the proton pump inhibitor is obtained within about 75 minutes are also provided herein. In some embodiments, the antacid increases the gastric pH to at least about 3.5 for less than about 30 minutes, or less than about 25 minutes, or less than about 20 minutes, or less than about 15 minutes, or less than about 10 minutes. In other embodiments, the maximum concentration of the proton pump inhibitor is obtained within about 60 minutes.

Pharmaceutical formulations comprising (a) at least one acid-labile proton pump inhibitor, and (b) between about 5 mEq to about 11 mEq of antacid are provided herein, wherein the formulation comprises about 5 mgs to about 200 mgs of the proton pump inhibitor. In other embodiments, the pharmaceutical formulation comprises about 10 mgs, or about 20 mgs, or about 30 mgs, or about 40 mgs, or about 50 mgs, or about 60 mgs, or about 80 mgs, or about 120 mgs of the proton pump inhibitor. In yet other embodiments, the pharmaceutical formulation comprises about 5 mEq, or about 6 mEq, or about 7 mEq, or about 8 mEq, or about 9 mEq, or about 10 mEq, or about 11 mEq of antacid.

Compositions are provided such that an initial serum concentration of the proton pump inhibitor is greater than about 100 ng/ml at any time within about 30 minutes after administering the formulation. Initial serum concentration of the proton pump inhibitor can be greater than about 100 ng/ml at any time within about 15 minutes. Initial serum concentration of the proton pump inhibitor can be greater than about 200 ng/ml at any time within about 1 hour after administration, greater than about 300 ng/ml at any time within about 45 minutes after administration.

Compositions are provided such that a serum concentration of greater than about 100 ng/ml can be maintained from at least about 30 minutes to about 1 hour after administration of the composition. Compositions are provided such that a serum concentration of proton pump inhibitor greater than about 100 ng/ml can be maintained from at least about 15 minutes to about 30 minutes after administration. Compositions are provided such that a serum concentration of greater than about 100 ng/ml can be maintained from at least about 30 minutes to about 45 minutes after administration. Compositions are provided such that a serum concentration of greater than about 250 ng/ml can be maintained from at least about 30 minutes to about 1 hour after administration. Compositions are provided such that a serum concentration of greater than about 250 ng/ml can be maintained from at least about 30 minutes to about 45 minutes after administration. Compositions are provided such that a serum concentration of greater than about 250 ng/ml can be maintained from at least about 15 minutes to about 30 minutes after administration.

Compositions of the invention can be administered in an amount to maintain a serum concentration of the proton pump inhibitor greater than about 150 ng/ml from about 15 minutes to about 1 hour after administration. Compositions of the invention can be administered in an amount to maintain a serum concentration of the proton pump inhibitor greater than about 150 ng/ml from about 15 minutes to about 1.5 hours after administration. Compositions of the invention can be administered in an amount to maintain a serum concentration of the proton pump inhibitor greater than about 100 ng/ml from about 15 minutes to about 1.5 hours after administration. Compositions of the invention can be administered in an amount to maintain a serum concentration of the proton pump inhibitor greater than about 150 ng/ml from about 15 minutes to about 30 minutes after administration.

Compositions of the invention can be administered in an amount to achieve an initial serum concentration of the proton pump inhibitor greater than about 150 ng/ml at any time from about 5 minutes to about 30 minutes after administration. Compositions of the invention can be administered in an amount to achieve an initial serum concentration of the proton pump inhibitor greater than about 150 ng/ml at any time within about 30 minutes after administration.

Compositions are provided wherein, upon oral administration to the subject, the composition provides a pharmacokinetic profile such that at least about 50% of total area under serum concentration time curve (AUC) for the proton pump inhibitor occurs within about 2 hours after administration of a single dose of the composition to the subject. Compositions are provided wherein, upon oral administration to the subject, the area under the serum concentration time curve (AUC) for the proton pump inhibitor in the first 2 hours is at least about 60% of the total area. Compositions are provided wherein the area under the serum concentration time curve (AUC) for the proton pump inhibitor in the first 2 hours is at least about 70% of the total area.

Compositions are provided wherein at least about 50% of total area under the serum concentration time curve (AUC) for the proton pump inhibitor occurs within about 1.75 hours after administration of a single dose of the composition to the subject. Compositions are provided wherein at least about 50% of total area under the serum concentration time curve (AUC) for the proton pump inhibitor occurs within about 1.5 hours after administration of a single dose of the composition to the subject. Compositions are provided wherein at least about 50% of total area under the serum concentration time curve (AUC) for the proton pump inhibitor occurs within about 1 hour after administration of a single dose of the composition to the subject.

Compositions and methods are provided wherein, upon oral administration to the subject, the composition provides a pharmacokinetic profile such that the proton pump inhibitor reaches a maximum serum concentration within about 75 minutes after administration of a single dose of the pharmaceutical formulation. In yet other embodiments the maximum serum concentration is reached within about 60 minutes after administration, or within about 45 minutes after administration of the pharmaceutical formulation. In still other embodiments, the maximum serum concentration is reached within about 30 minutes after administration of the pharmaceutical formulation.

Methods are provided for treating a gastric acid related disorder including, but not limited to duodenal ulcer disease, gastric ulcer disease, gastroesophageal reflux disease, erosive esophagitis, poorly responsive symptomatic gastroesophageal reflux disease, pathological gastrointestinal hypersecretory disease, Zollinger Ellison syndrome, heartburn, esophageal disorder, and acid dyspepsia. Method are provided wherein the proton pump inhibitor treats an episode of gastric acid related disorder.

In some embodiments, the proton pump inhibitor is a substituted bicyclic aryl-imidazole. In other embodiments, the proton pump inhibitor is selected from the group consisting of omeprazole, hydroxyomeprazole, esomeprazole, tenatoprazole, lansoprazole, pantoprazole, rabeprazole, dontoprazole, habeprazole, perprazole, ransoprazole, pariprazole, leminoprazole; or a free base, free acid, salt, hydrate, ester, amide, enantiomer, isomer, tautomer, polymorph, or prodrug thereof. In still other embodiments, the proton pump inhibitor is selected from lansoprazole, tenatoprazole, esomeprazole, rabeprazole and pantoprazole, or a free base, free acid, salt, hydrate, ester, amide, enantiomer, isomer, tautomer, polymorph, or prodrug thereof.

Pharmaceutical formulations of the present invention comprise, for example, about 5 mgs to about 200 mgs of a proton pump inhibitor. In various embodiments, the pharmaceutical formulation may comprise about 10 mgs, or about 15 mgs, or about 20 mgs, or about 40 mgs, or about 60 mgs, or about 120 mgs of the proton pump inhibitor.

In various embodiments of the present invention, the antacid is an alkaline metal salt or a Group IA metal selected from a bicarbonate salt of a Group IA metal, a carbonate salt of a Group IA metal. In other embodiments, the antacid can be, but is not limited to, an amino acid, an alkali metal salt of an amino acid, aluminum hydroxide, aluminum hydroxide/magnesium carbonate/calcium carbonate co-precipitate, aluminum magnesium hydroxide, aluminum hydroxide/magnesium hydroxide co-precipitate, aluminum hydroxide/sodium bicarbonate coprecipitate, aluminum glycinate, calcium acetate, calcium bicarbonate, calcium borate, calcium carbonate, calcium citrate, calcium gluconate, calcium glycerophosphate, calcium hydroxide, calcium lactate, calcium phthalate, calcium phosphate, calcium succinate, calcium tartrate, dibasic sodium phosphate, dipotassium hydrogen phosphate, dipotassium phosphate, disodium hydrogen phosphate, disodium succinate, dry aluminum hydroxide gel, L-arginine, magnesium acetate, magnesium aluminate, magnesium borate, magnesium bicarbonate, magnesium carbonate, magnesium citrate, magnesium gluconate, magnesium hydroxide, magnesium lactate, magnesium metasilicate aluminate, magnesium oxide, magnesium phthalate, magnesium phosphate, magnesium silicate, magnesium succinate, magnesium tartrate, potassium acetate, potassium carbonate, potassium bicarbonate, potassium borate, potassium citrate, potassium metaphosphate, potassium phthalate, potassium phosphate, potassium polyphosphate, potassium pyrophosphate, potassium succinate, potassium tartrate, sodium acetate, sodium bicarbonate, sodium borate, sodium carbonate, sodium citrate, sodium gluconate, sodium hydrogen phosphate, sodium hydroxide, sodium lactate, sodium phthalate, sodium phosphate, sodium polyphosphate, sodium pyrophosphate, sodium sesquicarbonate, sodium succinate, sodium tartrate, sodium tripolyphosphate, synthetic hydrotalcite, tetrapotassium pyrophosphate, tetrasodium pyrophosphate, tripotassium phosphate, trisodium phosphate, trometamol, Effersoda® (a mixture of sodium bicarbonate and sodium carbonate) and mixtures thereof. In yet other embodiments, the antacid can be sodium bicarbonate, sodium carbonate, Effersoda®, calcium carbonate, magnesium oxide, magnesium hydroxide, magnesium carbonate, aluminum hydroxide, and mixtures thereof. In some embodiments, the composition is substantially free of sucralfate. In other embodiments, the composition does not contain an amino acid buffer. In still other embodiments, the composition is a combination of two or more antacids, wherein at least two of the antacids are not amino acids.

Pharmaceutical formulations of the present invention may comprise varying amounts of antacid. For example, in some embodiments, the pharmaceutical formulation comprises about 100 to 3000 mg of antacid. In other embodiments, the pharmaceutical formulation comprises about 400 to about 1300 mg of antacid. In still other embodiments the pharmaceutical formulation comprises about 5 mEq to about 30 mEq, or about 8 mEq to about 20 mEq, or about 10 mEq to about 15 mEq of antacid. In further embodiments, the pharmaceutical formulations comprise about 13 mEq of antacid.

Pharmaceutical formulations of the present invention may be in the form of a tablet, (including a suspension tablet, a chewable tablet, a fast-melt tablet, a bite-disintegration tablet, a rapid-disintegration tablet, an effervescent tablet, or a caplet), a pill, a powder (including a sterile packaged powder, a dispensable powder, or an effervescent powder) a capsule (including both soft or hard capsules, e.g., capsules made from animal-derived gelatin or plant-derived HPMC) a lozenge, a sachet, a troche, pellets, granules, or an aerosol. In some embodiments, the pharmaceutical formulation is in the form of a powder for suspension. In other embodiments, the pharmaceutical formulation is in the form of a tablet, including but not limited to, a chewable tablet. Additionally, pharmaceutical formulations of the present invention may be administered as a single capsule or in multiple capsule dosage form. In some embodiments, the pharmaceutical formulation is administered in two, or three, or four, capsules.

In various embodiments of the present invention, the proton pump inhibitor may be microencapsulated with a material that enhances the shelf life of the pharmaceutical formulation. In some embodiments, the material that enhances the shelf life of the pharmaceutical formulation is selected from the group consisting of cellulose hydroxypropyl ethers; low-substituted hydroxypropyl ethers; cellulose hydroxypropyl methyl ethers; methylcellulose polymers; ethylcelluloses and mixtures thereof; polyvinyl alcohol; hydroxyethylcelluloses; carboxymethylcelluloses and salts of carboxymethylcelluloses; polyvinyl alcohol and polyethylene glycol co-polymers; monoglycerides; triglycerides; polyethylene glycols, modified food starch, acrylic polymers; mixtures of acrylic polymers with cellulose ethers; cellulose acetate phthalate; sepifilms, cyclodextrins; and mixtures thereof. In other embodiments, the material that enhances the shelf life of the pharmaceutical formulation further comprise an antioxidant, sodium bicarbonate, or a plasticizer.

In various embodiments, the pharmaceutical formulations of the present invention further comprise or more excipients selected from the group consisting of parietal cell activators, organic solvents, erosion facilitators, flavoring agents, sweetening agents, diffusion facilitators, antioxidants and carrier materials selected from binders, suspending agents, disintegration agents, filling agents, surfactants, solubilizers, stabilizers, lubricants, wetting agents, diluents, anti-adherents, and antifoaming agents.

DESCRIPTION OF THE FIGURES

FIG. 10 is a summary of exemplary formulations with the ANC present in the individual pharmaceutical formulations.

FIG. 11 is a summary of the pharmacokinetics of various formulations.

DETAILED DESCRIPTION OF THE INVENTION

Figure 1:
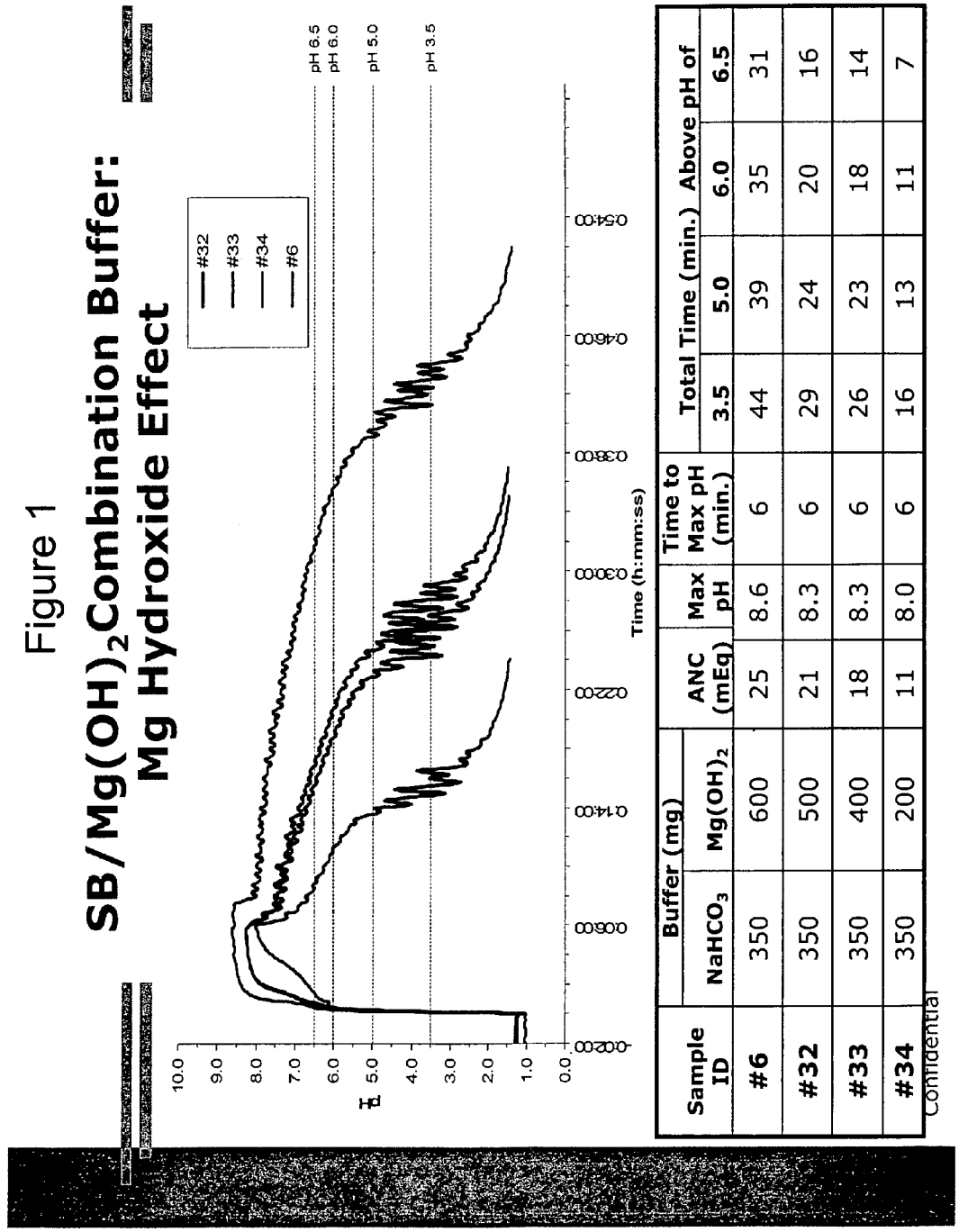
FIG. 1 shows a comparison of buffer systems comprising various mixtures of $NaHCO_3$ and $Mg(OH)_2$.
Figure 2:
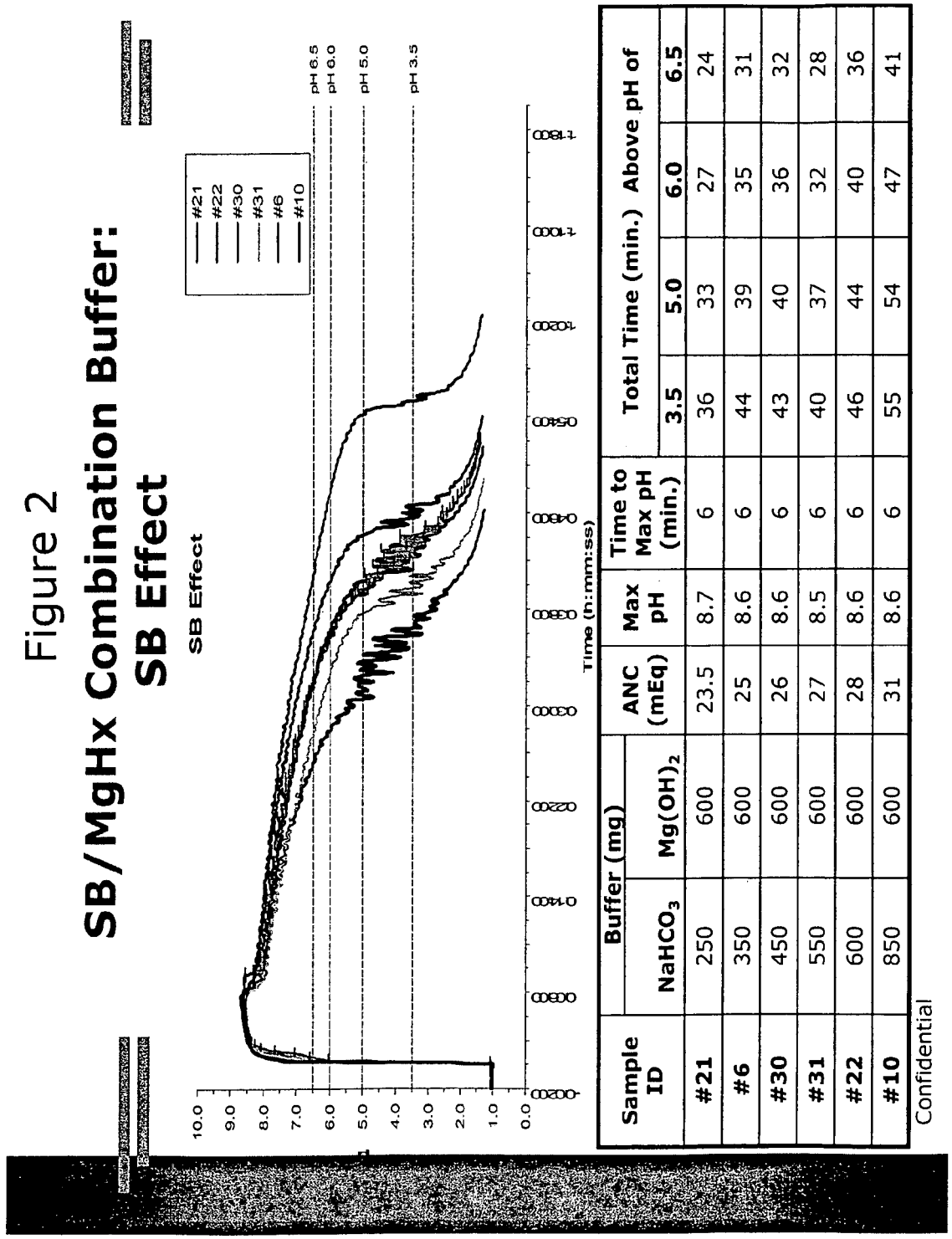
FIG. 2 shows a comparison of buffer systems comprising various mixtures of $NaHCO_3$ and $Mg(OH)_2$.
Figure 3:
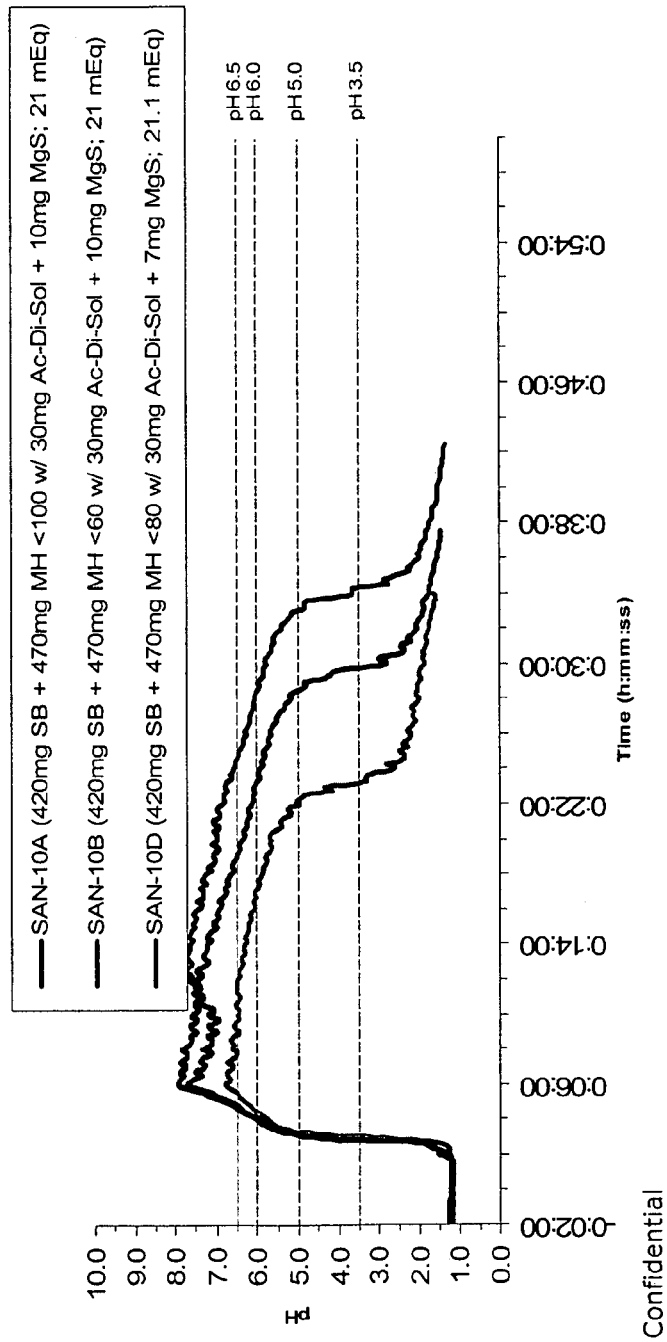
FIG. 3 shows the particle size effect of magnesium hydroxide on in-vitro/in-vivo neutralization for immediate release capsule formulations SAN-10A, SAN-10B and SAN-10D.
Figure 4:
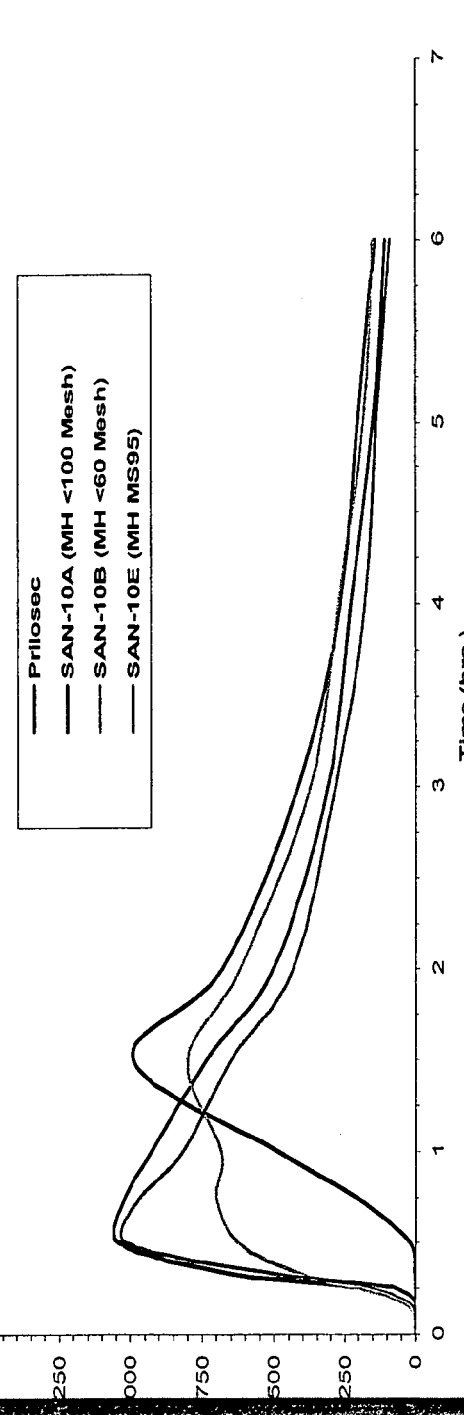
FIG. 4 shows the particle size effect of magnesium hydroxide on the pharmacokinetics of various formulations.
Figure 5:
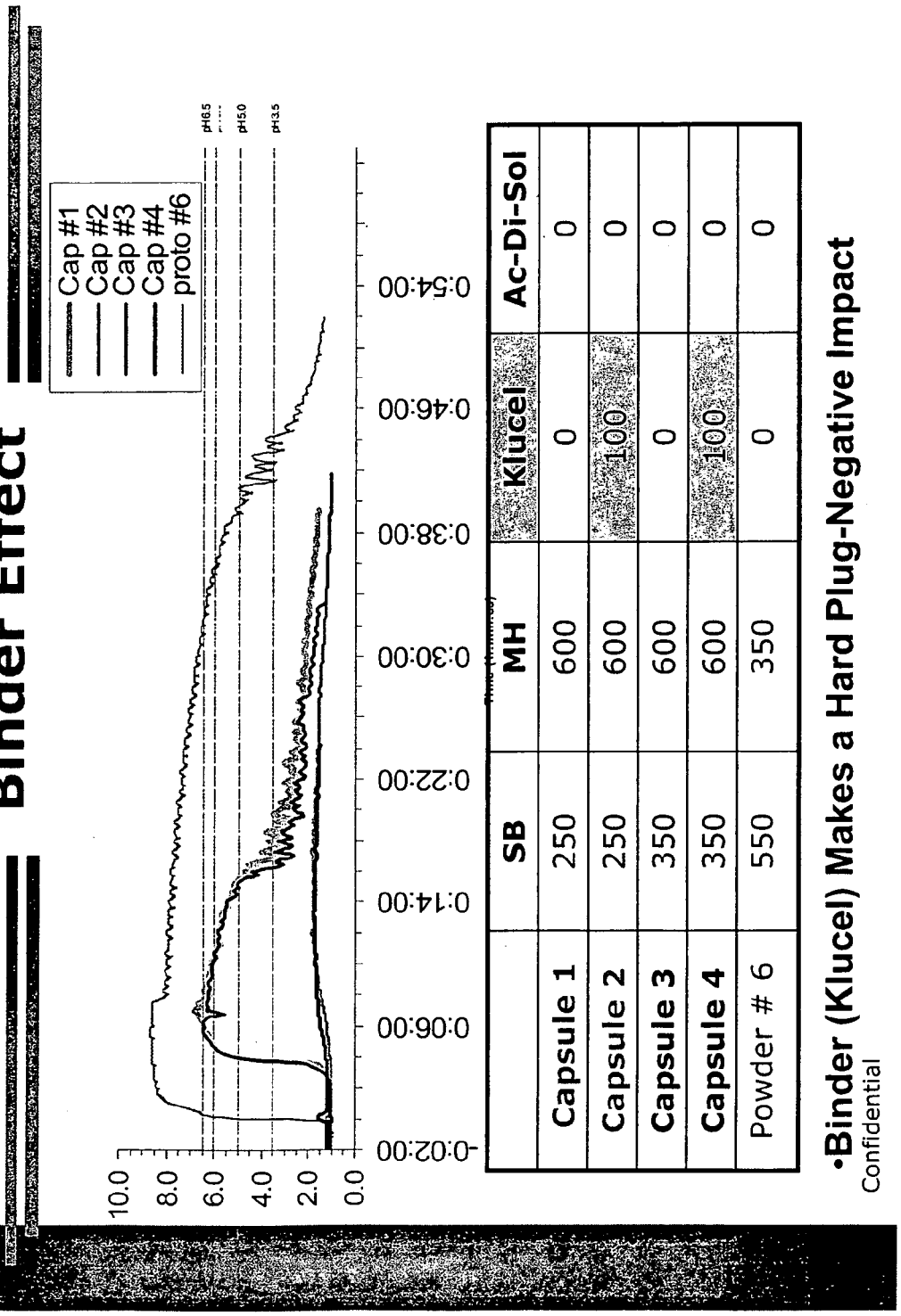
FIG. 5 shows the binder effect on various pharmaceutical formulations.
Figure 6:
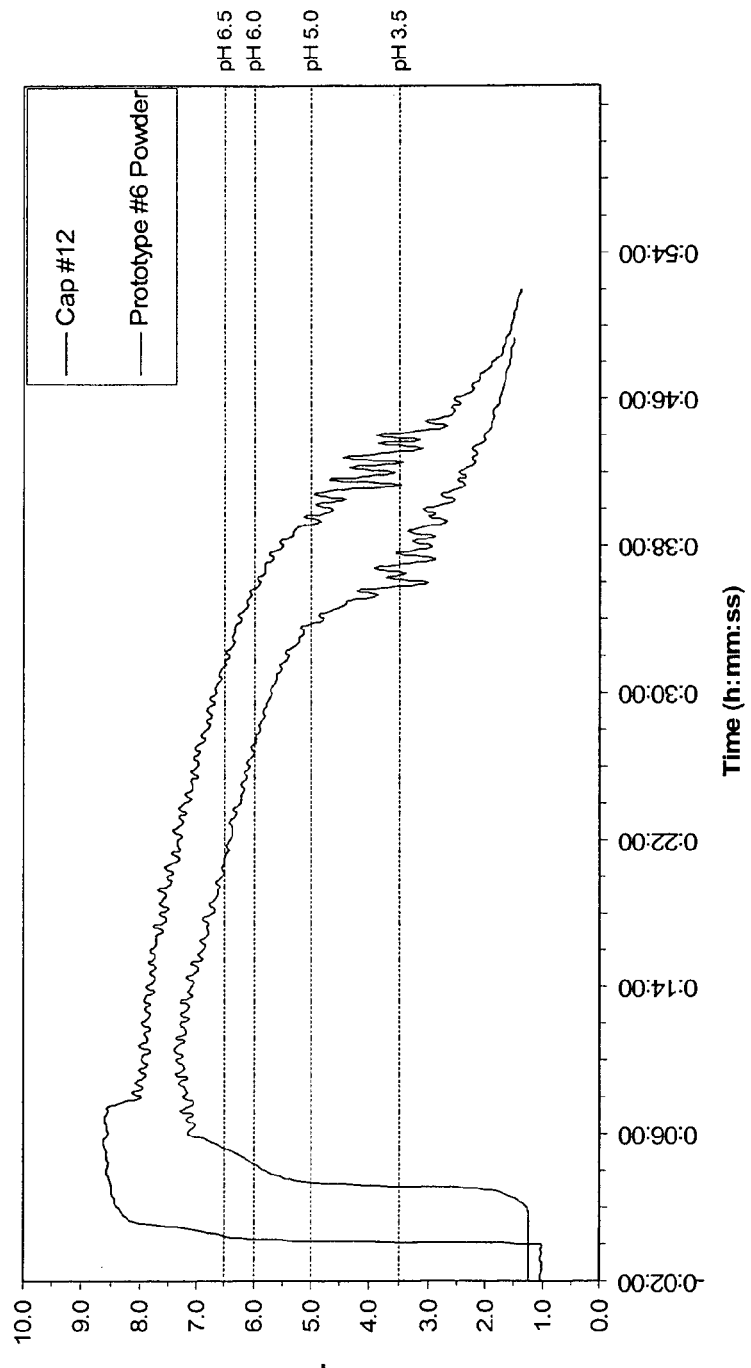
FIG. 6 shows the capsule dissolution effect with 5% binder as compared to a powder for suspension.
Figure 7:
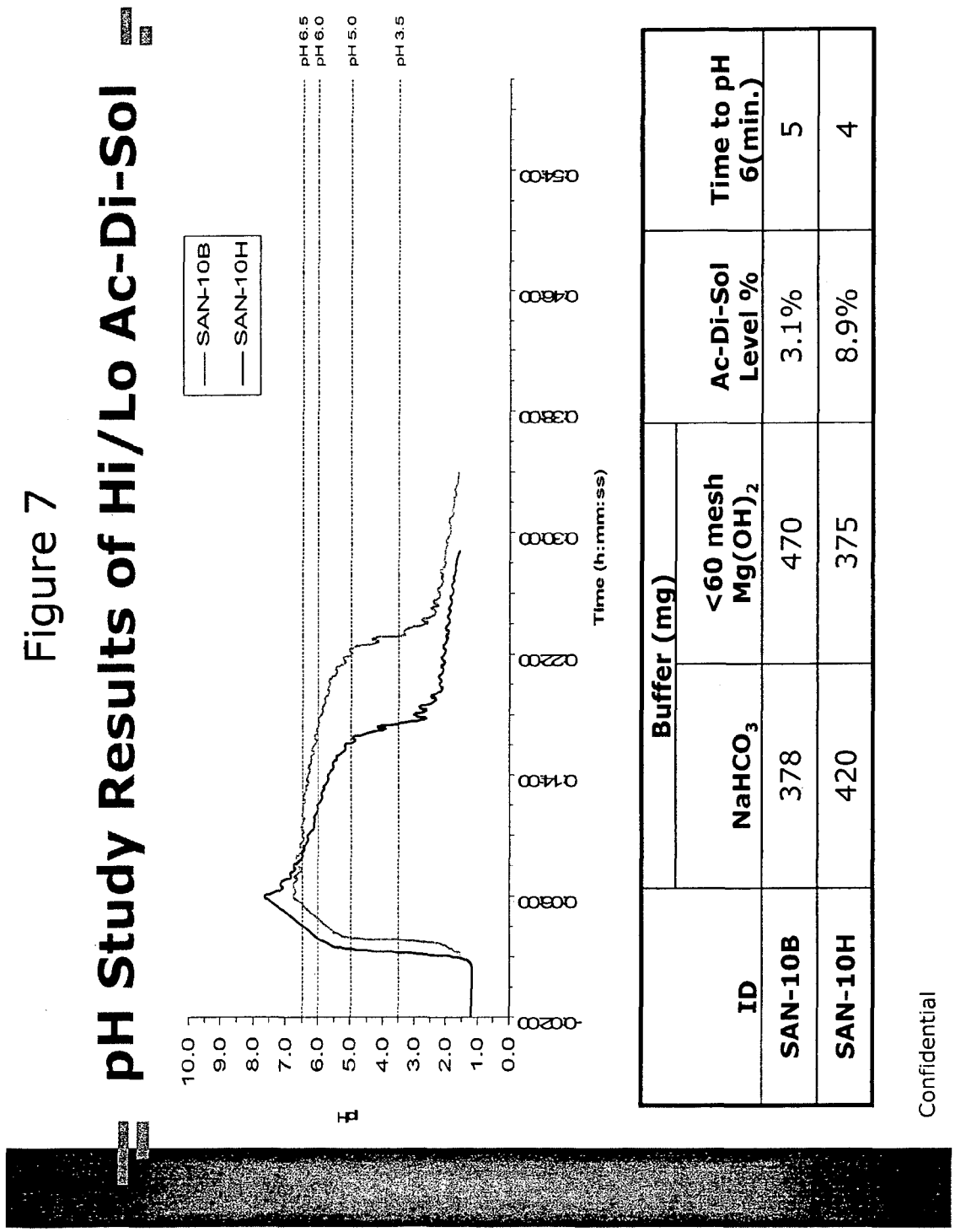
FIG. 7 shows the pH study results of high/low Ac-Di-Sol (disintegrant).
Figure 8:
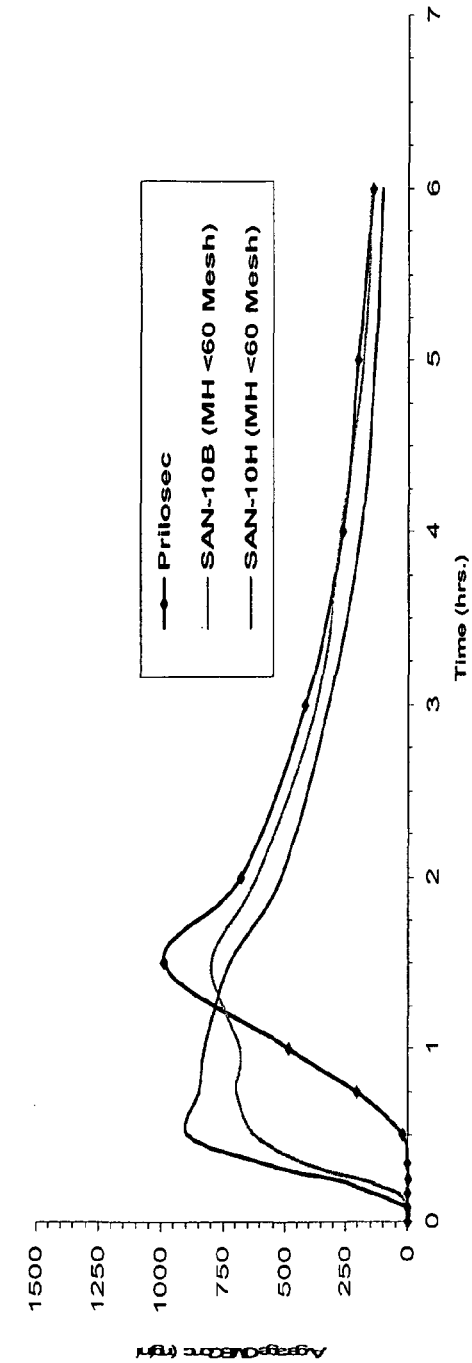
FIG. 8 shows the pharmacokinetic study results of high/low Ac-Di-Sol (disintegrant) as compared to Prilosec.
Figure 9:
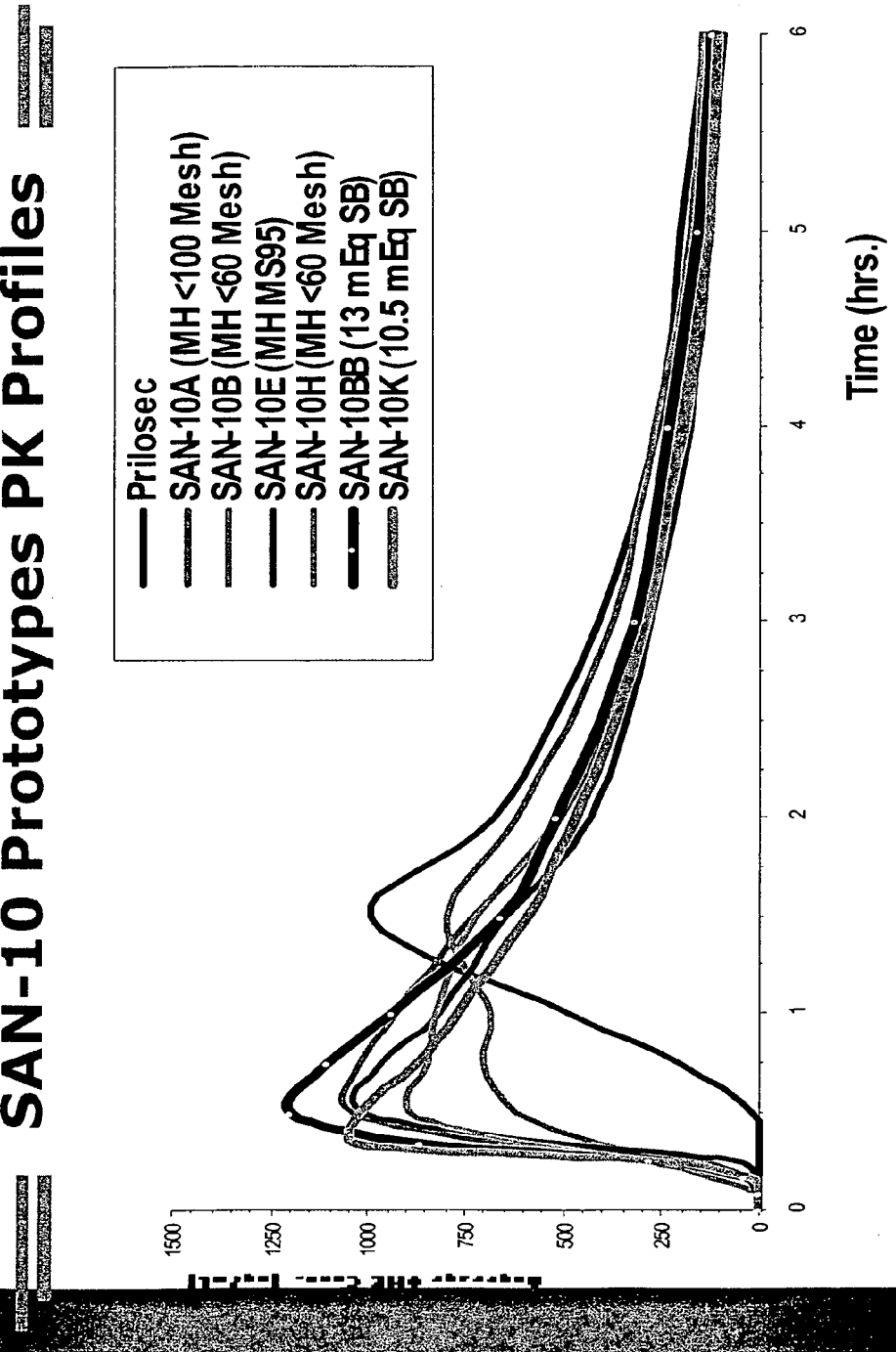
FIG. 9 shows the pharmacokinetic profiles for six different pharmaceutical formulations.
Figure 12:
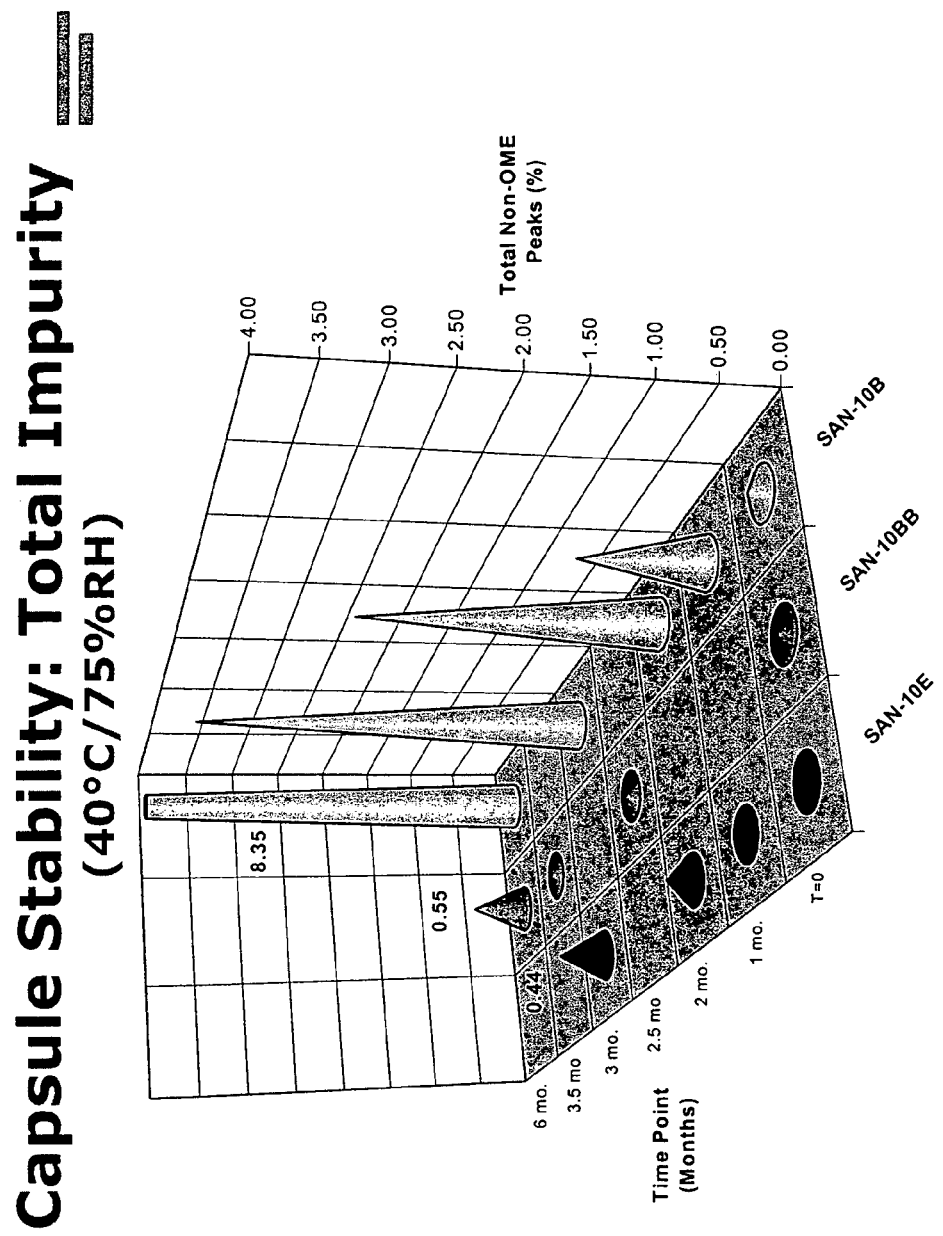
FIG. 12 shows the capsule stability of SAN-10E, SAN-10BB, and SAN-10B.
Figure 13:
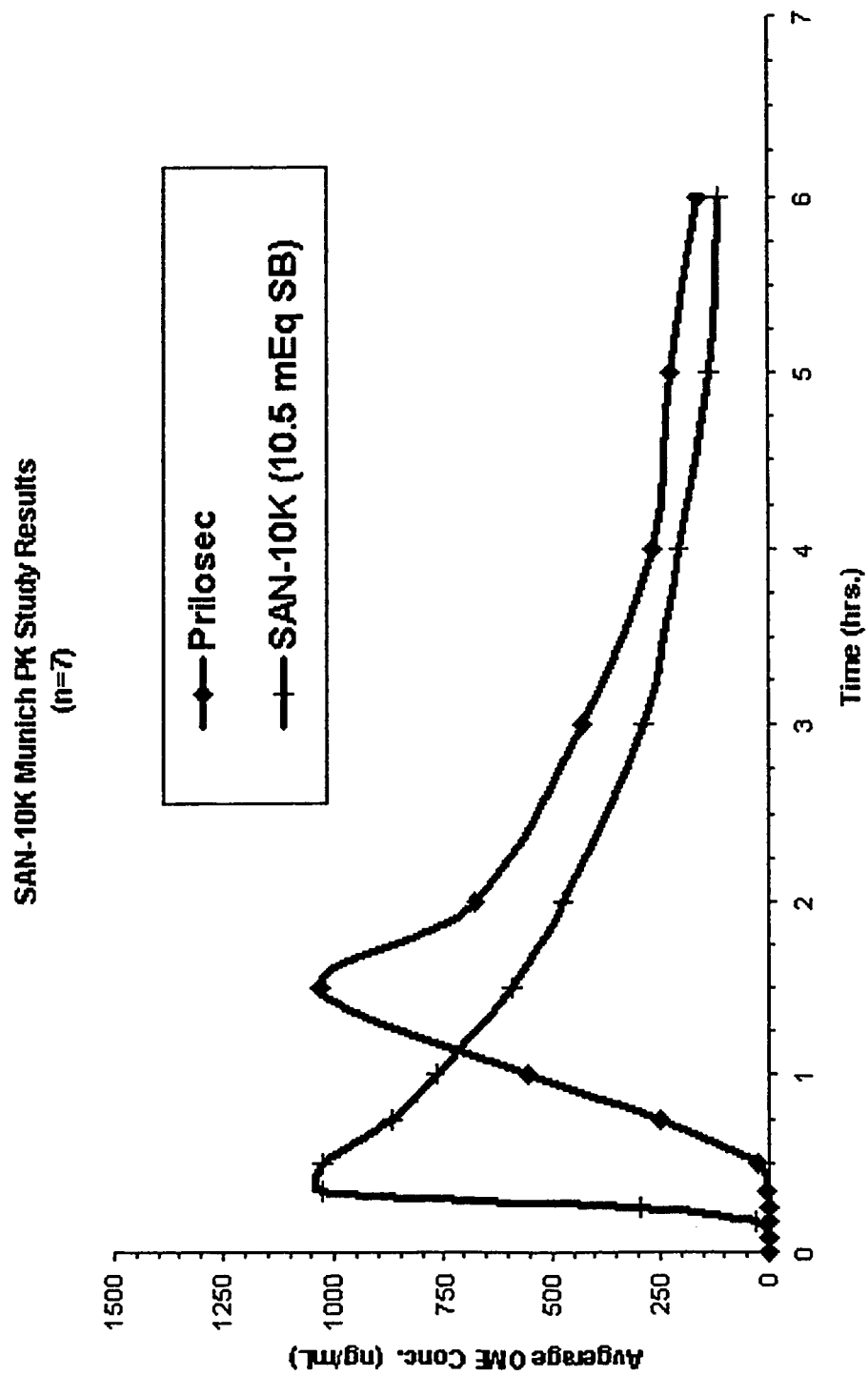
FIG. 13 compares the concentration/time curve for Prilosec® to the concentration/time curve of SAN-10K (10.5 mEq of Sodium Bicarbonate and 40 mg omeprazole).

The present invention is directed to methods, kits, combinations, and compositions for treating a condition or disorder where treatment with an acid labile proton pump inhibitor is indicated. Also provided are methods, kits, combinations, and compositions for treating, preventing or reducing the risk of developing a gastrointestinal disorder or disease, or the symptoms associated with, or related to a gastrointestinal disorder or disease in a subject in need thereof.

While the present invention may be embodied in many different forms, several specific embodiments are discussed herein with the understanding that the present disclosure is to be considered only as an exemplification of the principles of the invention, and it is not intended to limit the invention to the embodiments illustrated. For example, where the present invention is illustrated herein with particular reference to omeprazole, hydroxyomeprazole, esomeprazole, tenatoprazole, lansoprazole, pantoprazole, rabeprazole, dontoprazole, habeprazole, periprazole, ransoprazole, pariprazole, or leminoprazole, it will be understood that any other proton pump inhibiting agent, if desired, can be substituted in whole or in part for such agents in the methods, kits, combinations, and compositions herein described.

To more readily facilitate an understanding of the invention and its preferred embodiments, the meanings of terms used herein will become apparent from the context of this specification in view of common usage of various terms and the explicit definitions of other terms provided in the glossary below or in the ensuing description.

GLOSSARY

As used herein, the terms "comprising," "including," and "such as" are used in their open, non-limiting sense.

The term "about" is used synonymously with the term "approximately." As one of ordinary skill in the art would understand, the exact boundary of "about" will depend on the component of the composition. Illustratively, the use of the term "about" indicates that values slightly outside the cited values, i.e., plus or minus 0.1% to 10%, which are also effective and safe.

The phrase "acid-labile pharmaceutical agent" refers to any pharmacologically active drug subject to acid catalyzed degradation.

"Anti-adherents," "glidants," or "anti-adhesion" agents prevent components of the formulation from aggregating or sticking and improve flow characteristics of a material. Such compounds include, e.g., colloidal silicon dioxide such as Cab-o-Sil®; tribasic calcium phosphate, talc, corn starch, DL-leucine, sodium lauryl sulfate, magnesium stearate, calcium stearate, sodium stearate, kaolin, and micronized amorphous silicon dioxide (Syloid®) and the like.

"Antifoaming agents" reduce foaming during processing which can result in coagulation of aqueous dispersions, bubbles in the finished film, or generally impair processing. Exemplary anti-foaming agents include silicon emulsions or sorbitan sesquoleate.

"Antioxidants" include, e.g., butylated hydroxytoluene (BHT), sodium ascorbate, and tocopherol.

"Binders" impart cohesive qualities and include, e.g., alginic acid and salts thereof; cellulose derivatives such as carboxymethylcellulose, methylcellulose (e.g., Methocel®), hydroxypropylmethylcellulose, hydroxyethylcellulose, hydroxypropylcellulose (e.g., Klucel®), ethylcellulose (e.g., Ethocel®), and microcrystalline cellulose (e.g., Avicel®); microcrystalline dextrose; amylose; magnesium aluminum silicate; polysaccharide acids; bentonites; gelatin; polyvinylpyrrolidone/vinyl acetate copolymer; crospovidone; povidone; starch; pregelatinized starch; tragacanth, dextrin, a sugar, such as sucrose (e.g., Dipac®), glucose, dextrose, molasses, mannitol, sorbitol, xylitol (e.g., Xylitab®), and lactose; a natural or synthetic gum such as acacia, tragacanth, ghatti gum, mucilage of isapol husks, polyvinylpyrrolidone (e.g., Polyvidone® CL, Kollidon® CL, Polyplasdone® XL-10), larch arabogalactan, Veegum®, polyethylene glycol, waxes, sodium alginate, and the like.

"Bioavailability" refers to the extent to which an active moiety, e.g., drug, prodrug, or metabolite, is absorbed into the general circulation and becomes available at the site of drug action in the body. Thus, a proton pump inhibitor administered through IV is 100% bioavailable. "Oral bioavailability" refers to the extent to which the proton pump inhibitor (or other active moiety) is absorbed into the general circulation and becomes available at the site of drug action in the body when the pharmaceutical composition is taken orally.

"Bioequivalence" or "bioequivalent" means that the area under the serum concentration time curve (AUC) and the peak serum concentration ($C_{max}$) are each within 80% and 120%.

"Carrier materials" include any commonly used excipients in pharmaceutics and should be selected on the basis of compatibility with the proton pump inhibitor and the release profile properties of the desired dosage form. Exemplary carrier materials include, e.g., binders, suspending agents, disintegration agents, filling agents, surfactants, solubilizers, stabilizers, lubricants, wetting agents, diluents, and the like. "Pharmaceutically compatible carrier materials" may comprise, e.g., acacia, gelatin, colloidal silicon dioxide, calcium glycerophosphate, calcium lactate, maltodextrin, glycerine, magnesium silicate, sodium caseinate, soy lecithin, sodium chloride, tricalcium phosphate, dipotassium phosphate, sodium stearoyl lactylate, carrageenan, monoglyceride, diglyceride, pregelatinized starch, and the like. See, e.g., *Remington: The Science and Practice of Pharmacy*, Nineteenth Ed (Easton, Pa.: Mack Publishing Company, 1995); Hoover, John E., *Remington's Pharmaceutical Sciences*, Mack Publishing Co., Easton, Pa. 1975; Liberman, H. A. and Lachman, L., Eds., *Pharmaceutical Dosage Forms*, Marcel Decker, New York, N.Y., 1980; and *Pharmaceutical Dosage Forms and Drug Delivery Systems*, Seventh Ed. (Lippincott Williams & Wilkins 1999).

"Character notes" include, e.g., aromatics, basis tastes, and feeling factors. The intensity of the character note can be scaled from 0-none, 1-slight, 2-moderate, or 3-strong.

A "derivative" is a compound that is produced from another compound of similar structure by the replacement of substitution of an atom, molecule or group by another suitable atom, molecule or group. For example, one or more hydrogen atom of a compound may be substituted by one or more alkyl, acyl, amino, hydroxyl, halo, haloalkyl, aryl, heteroaryl, cycloalkyl, heterocycloalkyl, or heteroalkyl group to produce a derivative of that compound.

"Diffusion facilitators" and "dispersing agents" include materials that control the diffusion of an aqueous fluid through a coating. Exemplary diffusion facilitators/dispersing agents include, e.g., hydrophilic polymers, electrolytes, Tween® 60 or 80, PEG and the like. Combinations of one or more erosion facilitator with one or more diffusion facilitator can also be used in the present invention.

"Diluents" increase bulk of the composition to facilitate compression. Such compounds include e.g., lactose; starch; mannitol; sorbitol; dextrose; microcrystalline cellulose such as Avicel®; dibasic calcium phosphate; dicalcium phosphate dihydrate; tricalcium phosphate; calcium phosphate; anhydrous lactose; spray-dried lactose; pregelatinzed starch; compressible sugar, such as Di-Pac® (Amstar); mannitol; hydroxypropylmethylcellulose; sucrose-based diluents; confectioner's sugar; monobasic calcium sulfate monohydrate; calcium sulfate dihydrate; calcium lactate trihydrate; dextrates; hydrolyzed cereal solids; amylose; powdered cellulose; calcium carbonate; glycine; kaolin; mannitol; sodium chloride; inositol; bentonite; and the like.

The term "disintegrate" includes both the dissolution and dispersion of the dosage form when contacted with gastrointestinal fluid.

"Disintegration agents" facilitate the breakup or disintegration of a substance. Examples of disintegration agents include a starch, e.g., a natural starch such as corn starch or potato starch, a pregelatinized starch such as National 1551 or Amijel®, or sodium starch glycolate such as Promogel® or Explotab®; a cellulose such as a wood product, methylcrystalline cellulose, e.g., Avicel®, Avicel® PH101, Avicel® PH102, Avicel® PH105, Elcema® P100, Emcocel®, Vivacel®, Ming Tia®, and Solka-Floc®, methylcellulose, croscarmellose, or a cross-linked cellulose, such as cross-linked sodium carboxymethylcellulose (Ac-Di-Sol®), cross-linked carboxymethylcellulose, or cross-linked croscarmellose; a cross-linked starch such as sodium starch glycolate; a cross-linked polymer such as crospovidone; a cross-linked polyvinylpyrrolidone; alginate such as alginic acid or a salt of alginic acid such as sodium alginate; a clay such as Veegum® HV (magnesium aluminum silicate); a gum such as agar, guar, locust bean, Karaya, pectin, or tragacanth; sodium starch glycolate; bentonite; a natural sponge; a surfactant; a resin such as a cation-exchange resin; citrus pulp; sodium lauryl sulfate; sodium lauryl sulfate in combination starch; and the like.

"Drug absorption" or "absorption" refers to the process of movement from the site of administration of a drug toward the systemic circulation, e.g., into the bloodstream of a subject.

An "enteric coating" is a substance that remains substantially intact in the stomach but dissolves and releases the drug once the small intestine is reached. Generally, the enteric coating comprises a polymeric material that prevents release in the low pH environment of the stomach but that ionizes at a slightly higher pH, typically a pH of 4 or 5, and thus dissolves sufficiently in the small intestines to gradually release the active agent therein.

The "enteric form of the proton pump inhibitor" is intended to mean that some or most of the proton pump inhibitor has been enterically coated to ensure that at least some of the drug is released in the proximal region of the small intestine (duodenum), rather than the acidic environment of the stomach.

"Erosion facilitators" include materials that control the erosion of a particular material in gastrointestinal fluid. Erosion facilitators are generally known to those of ordinary skill in the art. Exemplary erosion facilitators include, e.g., hydrophilic polymers, electrolytes, proteins, peptides, and amino acids.

"Filling agents" include compounds such as lactose, calcium carbonate, calcium phosphate, dibasic calcium phosphate, calcium sulfate, microcrystalline cellulose, cellulose powder, dextrose; dextrates; dextran, starches, pregelatinized starch, sucrose, xylitol, lactitol, mannitol, sorbitol, sodium chloride, polyethylene glycol, and the like.

"Flavoring agents" or "sweeteners" useful in the pharmaceutical compositions of the present invention include, e.g., acacia syrup, acesulfame K, alitame, anise, apple, aspartame, banana, Bavarian cream, berry, black currant, butterscotch, calcium citrate, camphor, caramel, cherry, cherry cream, chocolate, cinnamon, bubble gum, citrus, citrus punch, citrus cream, cotton candy, cocoa, cola, cool cherry, cool citrus, cyclamate, cylamate, dextrose, eucalyptus, eugenol, fructose, fruit punch, ginger, glycyrrhetinate, glycyrrhiza (licorice) syrup, grape, grapefruit, honey, isomalt, lemon, lime, lemon cream, monoammonium glyrrhizinate (MagnaSweet®), maltol, mannitol, maple, marshmallow, menthol, mint cream, mixed berry, neohesperidine DC, neotame, orange, pear, peach, peppermint, peppermint cream, Prosweet® Powder, raspberry, root beer, rum, saccharin, safrole, sorbitol, spearmint, spearmint cream, strawberry, strawberry cream, stevia, sucralose, sucrose, sodium saccharin, saccharin, aspartame, acesulfame potassium, mannitol, talin, sylitol, sucralose, sorbitol, Swiss cream, tagatose, tangerine, thaumatin, tutti fruitti, vanilla, walnut, watermelon, wild cherry, wintergreen, xylitol, or any combination of these flavoring ingredients, e.g., anise-menthol, cherry-anise, cinnamon-orange, cherry-cinnamon, chocolate-mint, honey-lemon, lemon-lime, lemon-mint, menthol-eucalyptus, orange-cream, vanilla-mint, and mixtures thereof.

"Gastrointestinal fluid" is the fluid of stomach secretions of a subject or the saliva of a subject after oral administration of a composition of the present invention, or the equivalent thereof. An "equivalent of stomach secretion" includes, e.g., an in vitro fluid having similar content and/or pH as stomach secretions such as a 1% sodium dodecyl sulfate solution or 0.1N HCl solution in water.

"Half-life" refers to the time required for the plasma drug concentration or the amount in the body to decrease by 50% from its maximum concentration.

"Lubricants" are compounds that prevent, reduce or inhibit adhesion or friction of materials. Exemplary lubricants include, e.g., stearic acid; calcium hydroxide; talc; sodium stearyl fumerate; a hydrocarbon such as mineral oil, or hydrogenated vegetable oil such as hydrogenated soybean oil (Sterotex®); higher fatty acids and their alkali-metal and alkaline earth metal salts, such as aluminum, calcium, magnesium, zinc, stearic acid, sodium stearates, glycerol, talc, waxes, Stearowet®, boric acid, sodium benzoate, sodium acetate, sodium chloride, leucine, a polyethylene glycol or a methoxypolyethylene glycol such as Carbowax™, sodium oleate, glyceryl behenate, polyethylene glycol, magnesium or sodium lauryl sulfate, colloidal silica such as Syloid™, Carb-O-Sil®, a starch such as corn starch, silicone oil, a surfactant, and the like.

A "measurable serum concentration" or "measurable plasma concentration" describes the blood serum or blood plasma concentration, typically measured in mg, μg, or ng of therapeutic agent per ml, dl, or l of blood serum, of a therapeutic agent that is absorbed into the bloodstream after administration. One of ordinary skill in the art would be able to measure the serum concentration or plasma concentration of a proton pump inhibitor or a prokinetic agent. See, e.g., Gonzalez H. et al., *J. Chromatogr. B. Analyt. Technol. Biomed. Life Sci.*, vol. 780, pp 459-65, (Nov. 25, 2002).

"Parietal cell activators" or "activators" stimulate the parietal cells and enhance the pharmaceutical activity of the proton pump inhibitor. Parietal cell activators include, e.g., chocolate; alkaline substances such as sodium bicarbonate; calcium such as calcium carbonate, calcium gluconate, calcium hydroxide, calcium acetate and calcium glycerophosphate; peppermint oil; spearmint oil; coffee; tea and colas (even if decaffeinated); caffeine; theophylline; theobromine; amino acids (particularly aromatic amino acids such as phenylalanine and tryptophan); and combinations thereof.

"Pharmacodynamics" refers to the factors which determine the biologic response observed relative to the concentration of drug at a site of action.

"Pharmacokinetics" refers to the factors which determine the attainment and maintenance of the appropriate concentration of drug at a site of action.

"Plasma concentration" refers to the concentration of a substance in blood plasma or blood serum of a subject. It is understood that the plasma concentration of a therapeutic agent may vary many-fold between subjects, due to variability with respect to metabolism of therapeutic agents. In accordance with one aspect of the present invention, the plasma concentration of a proton pump inhibitors and/or prokinetic agent may vary from subject to subject. Likewise, values such as maximum plasma concentration ($C_{max}$) or time to reach maximum serum concentration ($T_{max}$), or area under the serum concentration time curve (AUC) may vary from subject to subject. Due to this variability, the amount necessary to constitute "a therapeutically effective amount" of proton pump inhibitor, prokinetic agent, or other therapeutic agent, may vary from subject to subject. It is understood that when mean plasma concentrations are disclosed for a population of subjects, these mean values may include substantial variation.

"Plasticizers" are compounds used to soften the microencapsulation material or film coatings to make them less brittle. Suitable plasticizers include, e.g., polyethylene glycols such as PEG 300, PEG 400, PEG 600, PEG 1450, PEG 3350, and PEG 800, stearic acid, propylene glycol, oleic acid, and triacetin.

"Prevent" or "prevention" when used in the context of a gastric acid related disorder means no gastrointestinal disorder or disease development if none had occurred, or no further gastrointestinal disorder or disease development if there had already been development of the gastrointestinal disorder or disease. Also considered is the ability of one to prevent some or all of the symptoms associated with the gastrointestinal disorder or disease.

A "prodrug" refers to a drug or compound in which the pharmacological action results from conversion by metabolic processes within the body. Prodrugs are generally drug precursors that, following administration to a subject and subsequent absorption, are converted to an active, or a more active species via some process, such as conversion by a metabolic pathway. Some prodrugs have a chemical group present on the prodrug which renders it less active and/or confers solubility or some other property to the drug. Once the chemical group has been cleaved and/or modified from the prodrug the active drug is generated. Prodrugs may be designed as reversible drug derivatives, for use as modifiers to enhance drug transport to site-specific tissues. The design of prodrugs to date has been to increase the effective water solubility of the therapeutic compound for targeting to regions where water is the principal solvent. See, e.g., Fedorak et al., *Am. J. Physiology*, 269:G210-218 (1995); McLoed et al., *Gastroenterol.*, 106:405-413 (1994); Hochhaus et al., *Biomed. Chrom.*, 6:283-286 (1992); J. Larsen and H. Bundgaard, *Int. J. Pharmaceutics*, 37, 87 (1987); J. Larsen et al., *Int. J. Pharmaceutics*, 47, 103 (1988); Sinkula et al., *J. Pharm. Sci.*, 64:181-210 (1975); T. Higuchi and V. Stella, *Pro-drugs as Novel Delivery Systems*, Vol. 14 of the A.C.S. Symposium Series; and Edward B. Roche, *Bioreversible Carriers in Drug Design*, American Pharmaceutical Association and Pergamon Press, 1987.

"Proton pump inhibitor product" refers to a product sold on the market. Proton pump inhibitor products include, for example, Priolosec®, Nexium®, Prevacid®, Protonic®, and Aciphex®.

"Serum concentration" refers to the concentration of a substance such as a therapeutic agent, in blood plasma or blood serum of a subject. It is understood that the serum concentration of a therapeutic agent may vary many-fold between subjects, due to variability with respect to metabolism of therapeutic agents. In accordance with one aspect of the present invention, the serum concentration of a proton pump inhibitors and/or prokinetic agent may vary from subject to subject. Likewise, values such as maximum serum concentration ($C_{max}$) or time to reach maximum serum concentration ($T_{max}$), or total area under the serum concentration time curve (AUC) may vary from subject to subject. Due to this variability, the amount necessary to constitute "a therapeutically effective amount" of proton pump inhibitor, prokinetic agent, or other therapeutic agent, may vary from subject to subject. It is understood that when mean serum concentrations are disclosed for a population of subjects, these mean values may include substantial variation.

"Solubilizers" include compounds such as citric acid, succinic acid, fumaric acid, malic acid, tartaric acid, maleic acid, glutaric acid, sodium bicarbonate, sodium carbonate and the like.

"Stabilizers" include compounds such as any antioxidation agents, buffers, acids, and the like.

"Suspending agents" or "thickening agents" include compounds such as polyvinylpyrrolidone, e.g., polyvinylpyrrolidone K12, polyvinylpyrrolidone K17, polyvinylpyrrolidone K25, or polyvinylpyrrolidone K30; polyethylene glycol, e.g., the polyethylene glycol can have a molecular weight of about 300 to about 6000, or about 3350 to about 4000, or about 7000 to about 5400; sodium carboxymethylcellulose; methylcellulose; hydroxy-propylmethylcellulose; polysorbate-80; hydroxyethylcellulose; sodium alginate; gums, such as, e.g., gum tragacanth and gum acacia; guar gum; xanthans, including xanthan gum; sugars; cellulosics, such as, e.g., sodium carboxymethylcellulose, methylcellulose, sodium carboxymethylcellulose, hydroxypropylmethylcellulose, hydroxyethylcellulose; polysorbate-80; sodium alginate; polyethoxylated sorbitan monolaurate; polyethoxylated sorbitan monolaurate; povidone and the like.

"Surfactants" include compounds such as sodium lauryl sulfate, sorbitan monooleate, polyoxyethylene sorbitan monooleate, polysorbates, polaxomers, bile salts, glyceryl monostearate, copolymers of ethylene oxide and propylene oxide, e.g., Pluronic® (BASF); and the like.

A "therapeutically effective amount" or "effective amount" is that amount of a pharmaceutical agent to achieve a pharmacological effect. The term "therapeutically effective amount" includes, for example, a prophylactically effective amount. An "effective amount" of a proton pump inhibitor is an amount effective to achieve a desired pharmacologic effect or therapeutic improvement without undue adverse side effects. For example, an effective amount of a proton pump inhibitor refers to an amount of proton pump inhibitor that reduces acid secretion, or raises gastrointestinal fluid pH, or reduces gastrointestinal bleeding, or reduces the need for blood transfusion, or improves survival rate, or provides for a more rapid recovery from a gastric acid related disorder. The effective amount of a pharmaceutical agent will be selected by those skilled in the art depending on the particular patient and the disease level. It is understood that "an effect amount" or "a therapeutically effective amount" can vary from subject to subject, due to variation in metabolism of therapeutic agents such as proton pump inhibitors and/or prokinetic agents, age, weight, general condition of the subject, the condition being treated, the severity of the condition being treated, and the judgment of the prescribing physician.

"Total intensity of aroma" is the overall immediate impression of the strength of the aroma and includes both aromatics and nose feel sensations.

"Total intensity of flavor" is the overall immediate impression of the strength of the flavor including aromatics, basic tastes and mouth feel sensations.

"Treat" or "treatment" as used in the context of a gastric acid related disorder refers to any treatment of a disorder or disease associated with a gastrointestinal disorder, such as preventing the disorder or disease from occurring in a subject which may be predisposed to the disorder or disease, but has not yet been diagnosed as having the disorder or disease; inhibiting the disorder or disease, e.g., arresting the development of the disorder or disease, relieving the disorder or disease, causing regression of the disorder or disease, relieving a condition caused by the disease or disorder, or stopping the symptoms of the disease or disorder. Thus, as used herein, the term "treat" is used synonymously with the term "prevent."

"Wetting agents" include compounds such as oleic acid, glyceryl monostearate, sorbitan monooleate, sorbitan monolaurate, triethanolamine oleate, polyoxyethylene sorbitan monooleate, polyoxyethylene sorbitan monolaurate, sodium oleate, sodium lauryl sulfate, and the like.

Proton Pump Inhibitors

The terms "proton pump inhibitor," "PPI," and "proton pump inhibiting agent" can be used interchangeably to describe any acid labile pharmaceutical agent possessing pharmacological activity as an inhibitor of H+/K+-ATPase. A proton pump inhibitor may, if desired, be in the form of free base, free acid, salt, ester, hydrate, anhydrate, amide, enantiomer, isomer, tautomer, prodrug, polymorph, derivative, or the like, provided that the free base, salt, ester, hydrate, amide, enantiomer, isomer, tautomer, prodrug, or any other pharmacologically suitable derivative is therapeutically active.

In various embodiments, the proton pump inhibitor can be a substituted bicyclic aryl-imidazole, wherein the aryl group can be, e.g., a pyridine, a phenyl, or a pyrimidine group and is attached to the 4- and 5-positions of the imidazole ring. Proton pump inhibitors comprising a substituted bicyclic aryl-imidazoles include, but are not limited to, omeprazole, hydroxyomeprazole, esomeprazole, lansoprazole, pantoprazole, rabeprazole, dontoprazole, habeprazole, perprazole, tenatoprazole, ransoprazole, pariprazole, leminoprazole, or a free base, free acid, salt, hydrate, ester, amide, enantiomer, isomer, tautomer, polymorph, prodrug, or derivative thereof. See, e.g., *The Merck Index*, Merck & Co. Rahway, N.J. (2001).

Other proton pump inhibitors include but are not limited to: soraprazan (Altana); ilaprazole (U.S. Pat. No. 5,703,097) (Il-Yang); AZD-0865 (AstraZeneca); YH-1885 (PCT Publication WO 96/05177) (SB-641257) (2-pyrimidinamine, 4-(3, 4-dihydro-1-methyl-2(1H)-isoquinolinyl)-N-(4-fluorophenyl)-5,6-dimethyl-monohydrochloride)(YuHan); BY-112 (Altana); SPI-447 (Imidazo(1,2-a)thieno(3,2-c)pyridin-3-amine,5-methyl-2-(2-methyl-3-thienyl) (Shinnippon); 3-hydroxymethyl-2-methyl-9-phenyl-7H-8,9-dihydro-pyrano(2, 3-c)-imidazo(1,2-a)pyridine (PCT Publication WO 95/27714) (AstraZeneca); Pharmaprojects No. 4950 (3-hydroxymethyl-2-methyl-9-phenyl-7H-8,9-dihydro-pyrano(2, 3-c)-imidazo(1,2-a)pyridine) (AstraZeneca, ceased) WO 95/27714; Pharmaprojects No. 4891 (EP 700899) (Aventis); Pharmaprojects No. 4697 (PCT Publication WO 95/32959) (AstraZeneca); H-335/25 (AstraZeneca); T-330 (Saitama 335) (Pharmacological Research Lab); Pharmaprojects No. 3177 (Roche); BY-574 (Altana); Pharmaprojects No. 2870 (Pfizer); AU-1421 (EP 264883) (Merck); AU-2064 (Merck); AY-28200 (Wyeth); Pharmaprojects No. 2126 (Aventis); WY-26769 (Wyeth); pumaprazole (PCT Publication WO 96/05199) (Altana); YH-1238 (YuHan); Pharmaprojects No. 5648 (PCT Publication WO 97/32854) (Dainippon); BY-686 (Altana); YM-020 (Yamanouchi); GYKI-34655 (Ivax); FPL-65372 (Aventis); Pharmaprojects No. 3264 (EP 509974) (AstraZeneca); nepaprazole (Toa Eiyo); HN-11203 (Nycomed Pharma); OPC-22575; pumilacidin A (BMS); saviprazole (EP 234485) (Aventis); SKandF-95601 (GSK, discontinued); Pharmaprojects No. 2522 (EP 204215) (Pfizer); S-3337 (Aventis); RS-13232A (Roche); AU-1363 (Merck); SKandF-96067 (EP 259174) (Altana); SUN 8176 (Daiichi Phama); Ro-18-5362 (Roche); ufiprazole (EP 74341) (AstraZeneca); and Bay-p-1455 (Bayer); or a free base, free acid, salt, hydrate, ester, amide, enantiomer, isomer, tautomer, polymorph, prodrug, or derivative of these compounds.

Still other proton pump inhibitors contemplated by the present invention include those described in the following U.S. Pat. Nos. 4,628,098; 4,689,333; 4,786,505; 4,853,230; 4,965,269; 5,021,433; 5,026,560; 5,045,321; 5,093,132; 5,430,042; 5,433,959; 5,576,025; 5,639,478; 5,703,110; 5,705,517; 5,708,017; 5,731,006; 5,824,339; 5,855,914; 5,879,708; 5,948,773; 6,017,560; 6,123,962; 6,187,340; 6,296,875; 6,319,904; 6,328,994; 4,255,431; 4,508,905; 4,636,499; 4,738,974; 5,690,960; 5,714,504; 5,753,265; 5,817,338; 6,093,734; 6,013,281; 6,136,344; 6,183,776; 6,328,994; 6,479,075; 6,559,167.

Other substituted bicyclic aryl-imidazole compounds as well as their salts, hydrates, esters, amides, enantiomers, isomers, tautomers, polymorphs, prodrugs, and derivatives may be prepared using standard procedures known to those skilled in the art of synthetic organic chemistry. See, e.g., March, *Advanced Organic Chemistry: Reactions, Mechanisms and Structure*, 4th Ed. (New York: Wiley-Interscience, 1992); Leonard et al., *Advanced Practical Organic Chemistry* (1992); Howarth et al., *Core Organic Chemistry* (1998); and Weisermel et al., *Industrial Organic Chemistry* (2002).

"Pharmaceutically acceptable salts," or "salts," include, e.g., the salt of a proton pump inhibitor prepared from formic, acetic, propionic, succinic, glycolic, gluconic, lactic, malic, tartaric, citric, ascorbic, glucuronic, maleic, fumaric, pyruvic, aspartic, glutamic, benzoic, anthranilic, mesylic, stearic, salicylic, p-hydroxybenzoic, phenylacetic, mandelic, embonic, methanesulfonic, ethanesulfonic, benzenesulfonic, pantothenic, toluenesulfonic, 2-hydroxyethanesulfonic, sulfanilic, cyclohexylaminosulfonic, algenic, β-hydroxybutyric, galactaric and galacturonic acids.

In one embodiment, acid addition salts are prepared from the free base using conventional methodology involving reaction of the free base with a suitable acid. Suitable acids for preparing acid addition salts include both organic acids, e.g., acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid, and the like, as well as inorganic acids, e.g., hydrochloric acid, hydrobromic acid, sulfuric acid, nitric acid, phosphoric acid, and the like.

In other embodiments, an acid addition salt is reconverted to the free base by treatment with a suitable base. In a further embodiment, the acid addition salts of the proton pump inhibitors are halide salts, which are prepared using hydrochloric or hydrobromic acids. In still other embodiments, the basic salts are alkali metal salts, e.g., sodium salt.

Salt forms of proton pump inhibiting agents include, but are not limited to: a sodium salt form such as esomeprazole sodium, omeprazole sodium, rabeprazole sodium, pantoprazole sodium; or a magnesium salt form such as esomeprazole magnesium or omeprazole magnesium, described in U.S. Pat. No. 5,900,424; a calcium salt form; or a potassium salt form such as the potassium salt of esomeprazole, described in U.S. Patent Application No. 02/0198239 and U.S. Pat. No. 6,511, 996. Other salts of esomeprazole are described in U.S. Pat. No. 4,738,974 and U.S. Pat. No. 6,369,085. Salt forms of pantoprazole and lansoprazole are discussed in U.S. Pat. Nos. 4,758,579 and 4,628,098, respectively.

In one embodiment, preparation of esters involves fictionalization of hydroxyl and/or carboxyl groups which may be present within the molecular structure of the drug. In one embodiment, the esters are acyl-substituted derivatives of free alcohol groups, e.g., moieties derived from carboxylic acids of the formula $RCOOR_1$ where $R_1$ is a lower alkyl group. Esters can be reconverted to the free acids, if desired, by using conventional procedures such as hydrogenolysis or hydrolysis.

"Amides" may be prepared using techniques known to those skilled in the art or described in the pertinent literature. For example, amides may be prepared from esters, using suitable amine reactants, or they may be prepared from an anhydride or an acid chloride by reaction with an amine group such, as ammonia or a lower alkyl amine.

"Tautomers" of substituted bicyclic aryl-imidazoles include, e.g., tautomers of omeprazole such as those described in U.S. Pat. Nos. 6,262,085; 6,262,086; 6,268,385; 6,312,723; 6,316,020; 6,326,384; 6,369,087; and 6,444,689; and U.S. Patent Publication No. 02/0156103.

An exemplary "isomer" of a substituted bicyclic aryl-imidazole is the isomer of omeprazole including but not limited to isomers described in: Oishi et al., Acta Cryst. (1989), C45, 1921-1923; U.S. Pat. No. 6,150,380; U.S. Patent Publication No. 02/0156284; and PCT Publication No. WO 02/085889.

Exemplary "polymorphs" include, but are not limited to, those described in PCT Publication No. WO 92/08716, and U.S. Pat. Nos. 4,045,563; 4,182,766; 4,508,905; 4,628,098; 4,636,499; 4,689,333; 4,758,579; 4,783,974; 4,786,505; 4,808,596; 4,853,230; 5,026,560; 5,013,743; 5,035,899; 5,045,321; 5,045,552; 5,093,132; 5,093,342; 5,433,959; 5,464,632; 5,536,735; 5,576,025; 5,599,794; 5,629,305; 5,639,478; 5,690,960; 5,703,110; 5,705,517; 5,714,504; 5,731,006; 5,879,708; 5,900,424; 5,948,773; 5,997,903; 6,017,560; 6,123,962; 6,147,103; 6,150,380; 6,166,213; 6,191,148; 5,187,340; 6,268,385; 6,262,086; 6,262,085; 6,296,875; 6,316,020; 6,328,994; 6,326,384; 6,369,085; 6,369,087; 6,380,234; 6,428,810; 6,444,689; and 6,462,0577.

Micronized Proton Pump Inhibitor

Particle size of the proton pump inhibitor can affect the solid dosage form in numerous ways. Since decreased particle size increases in surface area (S), the particle size reduction provides an increase in the rate of dissolution (dM/dt) as expressed in the Noyes-Whitney equation below:

$$dM/dt = dS/h(Cs-C)$$

M=mass of drug dissolved; t=time; D=diffusion coefficient of drug; S=effective surface area of drug particles; H=stationary layer thickness; Cs=concentration of solution at saturation; and C=concentration of solution at time t.

Because omeprazole, as well as other proton pump inhibitors, has poor water solubility, to aid the rapid absorption of the drug product, various embodiments of the present invention use micronized proton pump inhibitor is used in the drug product formulation.

In various embodiments of the present invention, the proton pump inhibitor is micronized. In some embodiments, the average particle size of at least about 90% the micronized proton pump inhibitor is less than about 40 μm, or less than about 35 μm, or less than about 30 μm, or less than about 25 μm, or less than about 20 μm, or less than about 15 μm, or less than about 10 μm. In other embodiments, at least 80% of the micronized proton pump inhibitor has an average particle size of less than about 40 μm, or less than about 35 μm, or less than about 30 μm, or less than about 25 μm, or less than about 20 μm, or less than about 15 μm, or less than about 10 μm. In still other embodiments, at least 70% of the micronized proton pump inhibitor has an average particle size of less than about 40 μm, or less than about 35 μm, or less than about 30 μm, or less than about 25 μm, or less than about 20 μm, or less than about 15 μm, or less than about 10 μm.

Compositions are provided wherein the micronized proton pump inhibitor is of a size which allows greater than 75% of the proton pump inhibitor to be released within about 1 hour, or within about 50 minutes, or within about 40 minutes, or within about 30 minutes, or within about 20 minutes, or within about 10 minutes, or within about 5 minutes of dissolution testing. In another embodiment of the invention, the micronized proton pump inhibitor is of a size which allows greater than 90% of the proton pump inhibitor to be released within about 1 hour, or within about 50 minutes, or within about 40 minutes, or within about 30 minutes, or within about 20 minutes, or within about 10 minutes, or within about 5 minutes of dissolution testing. See U.S. patent application Ser. No. 10/893,092, filed Jul. 16, 2004, which claims priority to U.S. Provisional Application No. 60/488,324 filed Jul. 18, 2003, both of which are incorporated by reference in their entirety.

Particle Size of Ingredients

The particle size of the proton pump inhibitor, antacid and excipients is an important factor which can effect bioavailability, blend uniformity, segregation, and flow properties. In general, smaller particle sizes of a drug increases the bioabsorption rate of the drug with substantially poor water solubility by increasing the surface area. The particle size of the drug and excipients can also affect the suspension properties of the pharmaceutical formulation. For example, smaller particles are less likely to settle and therefore form better suspensions.

In various embodiments, the average particle size of the dry powder (which can be administered directly, as a powder for suspension, or used in a solid dosage form) is less than about 500 microns in diameter, or less than about 450 microns in diameter, or less than about 400 microns in diameter, or less than about 350 microns in diameter, or less than about 300 microns in diameter, or less than about 250 microns in diameter, or less than about 200 microns in diameter, or less than about 150 microns in diameter, or less than about 100 microns in diameter, or less than about 75 microns in diameter, or less than about 50 microns in diameter, or less than about 25 microns in diameter, or less than about 15 microns in diameter. In other embodiments, the average particle size of the aggregates is between about 25 microns in diameter to about 300 microns in diameter. In still other embodiments, the average particle size of the aggregates is between about 25 microns in diameter to about 150 microns in diameter. And, in still further embodiments, the average particle size of the aggregates is between about 25 microns in diameter to about 100 microns in diameter. The term "average particle size" is intended to describe the average diameter of the particles and/or agglomerates used in the pharmaceutical formulation.

In another embodiment, the average particle size of the insoluble excipients is between about 5 µm to about 500 µm, or less than about 400 µm, or less than about 300 µm, or less than about 200 µm, or less than about 150 µm, or less than about 100 µm, or less than about 90 µm, or less than about 80 µm, or less than about 70 µm, or less than about 60 µm, or less than about 50 µm, or less than about 40 µm, or less than about 30 µm, or less than about 25 µm, or less than about 20 µm, or less than about 15 µm, or less than about 10 µm, or less than about 5 µm.

In other embodiments of the present invention, at least about 80% of the particles have a particle size of less than about 300 µm, or less than about 250 µm, or less than about 200 µm, or less than about 150 µm, or less than about 100 µm, or less than about 500 µm. In another embodiment, at least about 85% of the dry powder particles have a particle size of less than about 300 µm, or less than about 250 µm, or less than about 200 µm, or less than about 150 µm, or less than about 100 µm, or less than about 50 µm. In still other embodiments of the present invention, at least about 90% of the dry powder particles have a particle size of less than about 300 µm, or less than about 250 µm, or less than about 200 µm, or less than about 150 µm, or less than about 100 µm, or less than about 50 µm. In yet another embodiment, at least about 95% of the dry powder particles have a particle size of less than about 300 µm, or less than about 250 µm, or less than about 200 µm, or less than about 150 µm, or less than about 100 µm, or less than about 50 µm.

In other embodiments, the average particle size of the insoluble material is between about 5 µm to about 250 µm in diameter. In other embodiments, the average particle size of the insoluble excipients is between about 5 µm to about 100 µm, or between about 5 µm to about 80 µm, or between about 5 µm to about 50 µm in diameter.

In another embodiment, the particle size of other excipients is chosen to be about the same as the particle size of the antacid. In yet another embodiment, the particle size of the insoluable excipients is chosen to be about the same as the particle size of the proton pump inhibitor.

Several factors can be considered in choosing both the proper excipient and its quantity. For example, the excipient should be pharmaceutically acceptable. Also, in some examples, rapid dissolution and neutralization of gastric acid to maintain the gastric pH at about 6.5 for at least one hour. The excipients which will be in contact with the proton pump inhibitor, if any, should also be chemically compatible with the proton pump inhibitor. "Chemically compatible" is intended to mean that the material does not lead to more than 10% degradation of the proton pump inhibitor when stored at room temperature for at least about 1 year.

Parietal cell activators are administered in an amount sufficient to produce the desired stimulatory effect without causing untoward side effects to patients. In one embodiment, the parietal cell activator is administered in an amount of about 5 mg to about 2.5 grams per 20 mg dose of the proton pump inhibitor.

Antacids

The pharmaceutical composition of the invention comprises one or more antacids. A class of antacids useful in the present invention include, but are not limited to, antacids possessing pharmacological activity as a base. In one embodiment, the antacid, when formulated or delivered with an proton pump inhibiting agent, functions to substantially prevent or inhibit the acid degradation of the proton pump inhibitor by gastrointestinal fluid for a period of time, e.g., for a period of time sufficient to preserve the bioavailability of the proton pump inhibitor administered. The antacid can be delivered before, during and/or after delivery of the proton pump inhibitor. In one aspect of the present invention, the antacid includes a salt of a Group IA metal (alkali metal), including, e.g., a bicarbonate salt of a Group IA metal, a carbonate salt of a Group IA metal; an alkaline earth metal antacid (Group IIA metal); an aluminum antacid; a calcium antacid; or a magnesium antacid.

Other antacids suitable for the present invention include, e.g., alkali metal (a Group IA metal including, but not limited to, lithium, sodium, potassium, rubidium, cesium, and francium) or alkaline earth metal (Group IIA metal including, but not limited to, beryllium, magnesium, calcium, strontium, barium, radium) carbonates, phosphates, bicarbonates, citrates, borates, acetates, phthalates, tartrate, succinates and the like, such as sodium or potassium phosphate, citrate, borate, acetate, bicarbonate and carbonate.

In various embodiments, an antacid includes an amino acid, an alkali metal salt of an amino acid, aluminum hydroxide, aluminum hydroxide/magnesium carbonate/calcium carbonate co-precipitate, aluminum magnesium hydroxide, aluminum hydroxide/magnesium hydroxide co-precipitate, aluminum hydroxide/sodium bicarbonate coprecipitate, aluminum glycinate, calcium acetate, calcium bicarbonate, calcium borate, calcium carbonate, calcium citrate, calcium gluconate, calcium glycerophosphate, calcium hydroxide, calcium lactate, calcium phthalate, calcium phosphate, calcium succinate, calcium tartrate, dibasic sodium phosphate, dipotassium hydrogen phosphate, dipotassium phosphate, disodium hydrogen phosphate, disodium succinate, dry aluminum hydroxide gel, L-arginine, magnesium acetate, magnesium aluminate, magnesium borate, magnesium bicarbonate, magnesium carbonate, magnesium citrate, magnesium gluconate, magnesium hydroxide, magnesium lactate, magnesium metasilicate aluminate, magnesium oxide, magnesium phthalate, magnesium phosphate, magnesium silicate, magnesium succinate, magnesium tartrate, potassium acetate, potassium carbonate, potassium bicarbonate, potassium borate, potassium citrate, potassium metaphosphate, potassium phthalate, potassium phosphate, potassium polyphosphate, potassium pyrophosphate, potassium succinate, potassium tartrate, sodium acetate, sodium bicarbonate, sodium borate, sodium carbonate, sodium citrate, sodium gluconate, sodium hydrogen phosphate, sodium hydroxide, sodium lactate, sodium phthalate, sodium phosphate, sodium polyphosphate, sodium pyrophosphate, sodium sesquicarbonate, sodium succinate, sodium tartrate, sodium tripolyphosphate, Effersoda® (mixture of sodium bicarbonate and sodium carbonate), synthetic hydrotalcite, tetrapotassium pyrophosphate, tetrasodium pyrophosphate, tripotassium phosphate, trisodium phosphate, and trometamol. (See, e.g., lists provided in *The Merck Index*, Merck & Co. Rahway, N.J. (2001)). Certain proteins or protein hydrolysates that rapidly neutralize acids can serve as antacids in the present invention. Combinations of the above mentioned antacids may also be used in the pharmaceutical compositions described herein.

The antacids useful in the present invention also include antacids or combinations of antacids that interact with HCl (or other acids in the environment of interest) faster than the proton pump inhibitor interacts with the same acids. When placed in a liquid phase, such as water, these antacids produce and maintain a pH greater than the pKa of the proton pump inhibitor.

In various embodiments, the antacid is selected from sodium bicarbonate, sodium carbonate, calcium carbonate, magnesium oxide, magnesium hydroxide, magnesium carbonate, and mixtures thereof.

The antacids useful in the present invention also include antacids or combinations of antacids that interact with HCl (or other acids in the environment of interest) faster than the proton pump inhibitor interacts with the same acids. When placed in a liquid phase, such as water, these antacids produce and maintain a pH greater than the pKa of the proton pump inhibitor.

In various embodiments, the antacid is selected from sodium bicarbonate, sodium carbonate, calcium carbonate, magnesium oxide, magnesium hydroxide, magnesium carbonate, aluminum hydroxide, and mixtures thereof. In other embodiments, the antacid is present in the pharmaceutical formulations of the present invention in an amount greater than about 5 mEq of antacid. In other embodiments, the antacid is present in the pharmaceutical formulations of the present invention in an amount greater than about 7 mEq of antacid. In other embodiments, the antacid is present in the pharmaceutical formulations of the present invention in an amount greater than about 10 mEq of antacid. In other embodiments, the antacid is present in the pharmaceutical formulations of the present invention in an amount greater than about 15 mEq of antacid. In other embodiments, the antacid is present in the pharmaceutical formulations of the present invention in an amount greater than about 20 mEq of antacid.

In another embodiment, the antacid comprises sodium bicarbonate in about 0.1 mEq/mg proton pump inhibitor to about 5 mEq/mg proton pump inhibitor. In yet another embodiment, the antacid comprises a mixture of sodium bicarbonate and magnesium hydroxide, wherein the sodium bicarbonate and magnesium hydroxide are each present in about 0.1 mEq/mg proton pump inhibitor to about 5 mEq/mg proton pump inhibitor. In still another embodiment, the antacid comprises a mixture of sodium bicarbonate, calcium carbonate, and magnesium hydroxide, wherein the sodium bicarbonate, calcium carbonate, and magnesium hydroxide are each present in about 0.1 mEq/mg proton pump inhibitor to about 5 mEq/mg of the proton pump inhibitor.

In various other embodiments of the present invention, the antacid is present in an amount of about 0.1 mEq/mg to about 5 mEq/mg of the proton pump inhibitor, or about 0.5 mEq/mg to about 3 mEq/mg of the proton pump inhibitor, or about 0.6 mEq/mg to about 2.5 mEq/mg of the proton pump inhibitor, or about 0.7 mEq/mg to about 2.0 mEq/mg of the proton pump inhibitor, or about 0.8 mEq/mg to about 1.8 mEq/mg of the proton pump inhibitor, or about 1.0 mEq/mg to about 1.5 mEq/mg of the proton pump inhibitor, or at least 0.5 mEq/mg of the proton pump inhibitor.

In other embodiments, the antacid is present in the pharmaceutical formulations of the present invention in an from about 5 to about 50 mEq of antacid. In other embodiments, the antacid is present in the pharmaceutical formulations of the present invention in an amount from about 5 to about 40 mEq of antacid. In other embodiments, the antacid is present in the pharmaceutical formulations of the present invention in an amount from about 10 to about 30 mEq of antacid. In other embodiments, the antacid is present in the pharmaceutical formulations of the present invention in an amount from about 10 to about 20 mEq of antacid. In other embodiments, the antacid is present in the pharmaceutical formulations of the present invention in an amount from about 5 to about 15 mEq of antacid.

In another embodiment, the antacid is present in the pharmaceutical formulations of the present invention in an amount of about 0.1 mEq to about 15 mEq/mg of proton pump inhibitor, or about 0.1 mEq/mg of proton pump inhibitor, or about 0.5 mEq/mg of proton pump inhibitor, or about 1 mEq/mg of proton pump inhibitor, or about 2 mEq/mg of proton pump inhibitor, or about 2.5 mEq/mg of proton pump inhibitor, or about 3 mEq/mg of proton pump inhibitor, or about 3.5 mEq/mg of proton pump inhibitor, or about 4 mEq/mg of proton pump inhibitor, or about 4.5 mEq/mg of proton pump inhibitor, or about 5 mEq/mg of proton pump inhibitor, or about 6 mEq/mg of proton pump inhibitor, or about 7 mEq/mg of proton pump inhibitor, or about 8 mEq/mg of proton pump inhibitor, or about 9 mEq/mg of proton pump inhibitor, or about 10 mEq/mg of proton pump inhibitor, or about 11 mEq/mg of proton pump inhibitor, or about 12 mEq/mg of proton pump inhibitor, or about 13 mEq/mg of proton pump inhibitor, or about 14 mEq/mg of proton pump inhibitor, or about 15 mEq/mg of proton pump inhibitor.

In one embodiment, the antacid is present in the pharmaceutical formulations of the present invention in an amount of about 1 mEq to about 160 mEq per dose, or about 1 mEq, or about 5 mEq, or about 10 mEq, or about 15 mEq, or about 20 mEq, or about 25 mEq, or about 30 mEq, or about 35 mEq, or about 40 mEq, or about 45 mEq, or about 50 mEq, or about 60 mEq, or about 70 mEq, or about 80 mEq, or about 90 mEq, or about 100 mEq, or about 110 mEq, or about 120 mEq, or about 130 mEq, or about 140 mEq, or about 150 mEq, or about 160 mEq per dose.

In another embodiment, the antacid is present in an amount of more than about 5 times, or more than about 10 times, or more than about 20 times, or more than about 30 times, or more than about 40 times, or more than about 50 times, or more than about 60 times, or more than about 70 times, or more than about 80 times, or more than about 90 times, or more than about 100 times the amount of the proton pump inhibiting agent on a weight to weight basis in the composition.

In another embodiment, the amount of antacid present in the pharmaceutical formulation is between 200 and 3500 mg. In other embodiments, the amount of antacid present in the pharmaceutical formulation is about 200 mgs, or about 300 mgs, or about 400 mgs, or about 500 mgs, or about 600 mgs, or about 700 mgs, or about 800 mgs, or about 900 mgs, or about 1000 mgs, or about 1100 mgs, or about 1200 mgs, or about 1300 mgs, or about 1400 mgs, or about 1500 mgs, or about 1600 mgs, or about 1700 mgs, or about 1800 mgs, or about 1900 mgs, or about 2000 mgs, or about 2100 mgs, or about 2200 mgs, or about 2300 mgs, or about 2400 mgs, or about 2500 mgs, or about 2600 mgs, or about 2700 mgs, or about 2800 mgs, or about 2900 mgs, or about 3000 mgs, or about 3200 mgs, or about 3500 mgs.

In some embodiments, if the at least one buffering agent is a combination of two or more buffering agents, the combination comprises at least two non-amino acid buffering agents, wherein the combination of at least two non-amino acid buffering agents comprises substantially no aluminum hydroxide-sodium bicarbonate co-precipitate. In other embodiments, if the pharmaceutical composition comprises an amino acid buffering agent, the total amount of buffering agent present in the pharmaceutical composition is less than about 5 mEq, or less than about 4 mEq, or less than about 3 mEq. The phrase "amino acid buffering agent" as used herein includes amino acids, amino acid salts, and amino acid alkali salts. including: glycine, alanine, threonine, isoleucine, valine, phenylalanine, glutamic acid, asparagininic acid, lysine, aluminum glycinate and/or lysine glutamic acid salt, glycine hydrochloride, L-alanine, DL-alanine, L-threonine, DL-threonine, L-isoleucine, L-valine, L-phenylalanine, L-glutamic acid, L-glutamic acid hydrochloride, L-glutamic acid sodium salt, L-asparaginic acid, L-asparaginic acid sodium salt, L-lysine and L-lysine-L-glutamic acid salt. The term "non-amino acid buffering agent" herein includes buffering agents as defined hereinabove but does not include amino acid buffering agents.

In other embodiments, the pharmaceutical composition comprises substantially no or no poly[phosphoryl/sulfon]-ated carbohydrate and is in the form of a solid dosage unit. In still another related embodiment, if such a composition comprises a poly[phosphoryl/sulfon]-ated carbohydrate (e.g. sucralfate or sucrose octasulfate), the weight ratio of poly[phosphoryl/sulfon]-ated carbohydrate to buffering agent is less than 1:5 (0.2), less than 1:10 (0.1) or less than 1:20 (0.05). Alternatively, the poly[phosphoryl/sulfon]-ated carbohydrate is present in the composition, if at all, in an amount less than 50 mg, less than 25 mg, less than 10 mg or less than 5 mg.

Also provided herein are pharmaceutical formulations comprising at least one soluble antacid. For example, in one embodiment, the antacid is sodium bicarbonate and is present in about 0.1 mEq/mg proton pump inhibitor to about 5 mEq/mg proton pump inhibitor. In another embodiment, the antacid is a mixture of sodium bicarbonate and magnesium hydroxide, wherein the sodium bicarbonate and magnesium hydroxide are each present in about 0.1 mEq/mg proton pump inhibitor to about 5 mEq/mg proton pump inhibitor. The term "soluble antacid" as used herein refers to an antacid that has a solubility of at least 500 mg/mL, or 300 mg/mL, or 200 mg/mL, or 100 mL/mL in the gastrointestinal fluid.

In some embodiments of the present invention, the antacid is a specific particle size. For example, the average particle size of the antacid may be no greater than 20 µm, or no greater than 30 µm, or no greater than 40 µm, or no greater than 50 µm, or no greater than 60 µm, or no greater than 70 µm, or no greater than 80 µm, or no greater than 90 µm or no greater than 100 µm in diameter. In various embodiments, at least about 70% of the antacid is no greater than 20 µm, or no greater than 30 µm, or no greater than 40 µm, or no greater than 50 µm, or no greater than 60 µm, or no greater than 70 µm, or no greater than 80 µm, or no greater than 90 µm or no greater than 100 µm in diameter. In other embodiments, at least about 85% of the antacid is no greater than 20 µm, or no greater than 30 µm, or no greater than 40 µm, or no greater than 50 µm, or no greater than 60 µm, or no greater than 70 µm, or no greater than 80 µm, or no greater than 90 µm or no greater than 100 µm in diameter.

Particle size of the buffer, especially that an insoluble buffer can affect the onset of in-vivo neutralization of the stomach acid. Since decreased particle size increases in surface area, the particle size reduction provides an increase in the rate of acid neutralization, leading to superior protection of PPI from gastric acid degradation. On the other hand, extremely fine particle size of buffer will result in the powder mixture that is difficult to manufacture in commercial scale due to their poor flow and difficulties in processing (i.e., compression and encapsulation).

In various embodiments of the present invention, the antacid is micronized. In some embodiments, particle size of at least 90% of antacid ($D_{90}$) is less than about 300 µm, or less than about 250 µm, or less than about 200 µm, or less than about 150 µm, or less than about 100 µm. In other embodiments, at least 75% of the antacid ($D_{75}$) has particle size of less than about 300 µm, or less than about 250 µm, or less than about 200 µm, or less than about 150 µm, or less than about 100 µm. In still other embodiments, at least 50% of the antacid ($D_{50}$) has particle size of less than about 300 µm, or less than about 250 µm, or less than about 200 µm, or less than about 150 µm, or less than about 100 µm.

Spray dried antacid can also facilitate the speed of neutralization by fast reacting with acid upon contact. Sprayed dried antacid typically has spherical particle shape which aids with achieving homogeneous blend during manufacturing process. In one embodiment the antacid is spray dried with at least 15% of coating material such as maltodextrin or starch. In still other embodiment the antacid is spray dried with at least 10% of coating material such as maltodextrin or starch. Yet another embodiment the antacid is spray dried with at least 15% of coating material such as maltodextrin or starch.

Kinetic Stomach Model

The acid neutralizing capacity and pH profile of various antacid combinations can be evaluated by using an in-vitro stomach model. Several of these simulated dynamic models are known in the art. See, e.g., Smyth et al., Correlation of In-Vivo Methodology for Evaluation of Antacids, *J. Pharm. Sci.* Vol. 65, 1045 (1976); Hobert, Fordham et al., In-Vivo Evaluation of Liquid Antacids, *New England Journal of Med.* 288, 923 (1973); Johnson et al., The Chemical Testing of Antacids, *Gut* 5, 585 (1964); Clain et al., In-Vitro Neutralizing Capacity of Commercially Available Antacid Mixtures and Their Role in the Treatment of Peptic Ulcer, *S. Afr. Med. J.*, 57, 158 (1980); Rossett et al., In-Vitro Evaluation of Efficacy of More Frequently Used Antacids with Particular Attention to Tablets, *Gastroentrology*, 26, 490; Decktor et al., Comparative Effects of Liquid Antacids on Esophageal and Gastric pH in Patients with Heartburn, *Am. J. of Therapeutics*, 2, 481 (1995); Charles Fuchs, Antacids: Their Function, Formulation and Evaluation, *Drug and Cosmetic Industry*, 49, 692; Stewart M. Beekman, Preparation and Properties of New Gastric Antacids I, Aluminium Hydroxide-Magnesium Carbonate Dried Gels, *J. Am. Pharm. Assoc.*, 49, 191 (1960). For example, a modified Fuch's model where the continuous influx of 0.5 mEq of acid is added to initial 5.0 mEq of acid to simulate a fasting state of stomach can be used with the present invention.

In various embodiments of the present invention, the antacid increases the gastric pH to at least about 3.5 for no more than about 90 minutes as measured by a simulated stomach model such as Fuch's kinetic in-vitro pH model. In other embodiments, the antacid increases the pH to at least about 3.5 for no more than about 60 minutes. In still other embodiments, the antacid increases the pH to at least about 3.5 for no more than 45 minutes. Depending on the buffer system used (i.e., type of antacid and amount) some embodiments of the present invention, the antacid increases the gastric pH to at least about 3.5 for no more than about 30 minutes as measured by a simulated stomach model such as Fuchs' kinetic in-vitro pH model. In other embodiments, the antacid increases the gastric pH to at least about 3.5 for less than about 25 minutes as measured by a simulated stomach model such as Fuch's kinetic in-vitro pH model. In yet other embodiments, the antacid increases the gastric pH to at least about 3.5 for less than about 20 minutes, or less than about 15 minutes, or less than about 10 minutes as measured by a stimulated stomach model such as Fuch's kinetic in-vitro pH model. In each of these embodiments, the antacid protects at least some of the proton pump inhibitor and a therapeutically effective amount of the proton pump inhibitor is delivered to the subject.

In each of these embodiments, the antacid protects at least some of the proton pump inhibitor and a therapeutically effective amount of the proton pump inhibitor is delivered to the subject.

Disintegrants

Most PPIs are sparingly soluble in water and therefore exhibit a correlation of disintegration time to bioavailability. Thus, it is important to optimize the disintegration time in order to enhance in vivo dissolution of the drug. In order to release the active ingredient from a solid dosage form matrix as efficiently as possible, disintegrant is often used in the formulation, especially when the dosage forms are compressed with binder. Disintegrants help rupturing the dosage form matrix by swelling or capillary action when moisture is absorbed into the dosage form. Starch is the oldest disintegrants and 5-15% level is suggested (Remington, 20th Ed, p 862). Super disintegrants such as Ac-di-Sol or Crospovidones are effective at lower levels (2-4%).

Ac-Di-Sol is effective in both direct compression and wet granulation formulations. The amount of Ac-Di-Sol used in direct compression tableting may vary with typical usage levels between 1 and 3 percent. When added to granulations, generally the same percent is used as with a direct compression formulation. It is often added to both the wet mass and the dried granulations before compression. As with direct compression, the use level typically ranges from 1 to 3 percent with half of the material added to the wet mass and half added to the running powder. This promotes disintegration of both the granules and the tablet.

The amount of Ac-Di-Sol used in capsule formulations generally ranges from 4-6 percent. Reduced interparticle contact within a capsule facilitates the need for elevated levels of disintegrant. Capsules filled on automatic dosater types of equipment, as opposed to semi-automatic or hand-filled machines, are more dense and have a harder structure due to the greater compressional forces needed to form the plug and successfully transfer it into the gelatin shell. Greater plug hardness results in greater effectiveness of Ac-Di-Sol.

Solid Oral Dosage Forms

In some embodiments of the present invention, the pharmaceutical formulation has greater than about 1 wt-% of a disintegrant. In various embodiments of the present invention, the pharmaceutical formulations have between about 1 wt-% to about 11 wt-% or between about 1 wt-% to about 8 wt-%, or about 1 wt-% to about 6 wt-%, or about 1 wt-% to about 4 wt-%, of a disintegrant. In some embodiments the disintegrant is Ac-Di-Sol. In other embodiments the disintegrant is sodium starch glycolated such as Promogel® or Explotab®. In still other embodiments, the pharmaceutical formulations have between about 2 wt-% to about 8 wt-% disintegrant, or between about 2 wt-% to about 6 wt-%, or between about 2 wt-% to about 4 wt-%. In yet other embodiments, the pharmaceutical formulations have greater than about 2 wt-% disintegrant.

Because sodium bicarbonate has effervescent characteristic when mixed with acid such as gastric fluid, some embodiments of the pharmaceutical formulations of the present invention can comprise at least about 400 mgs of sodium bicarbonate and greater than about 1 wt-% of a disintegrant. In some embodiments, the pharmaceutical formulation comprises about 2 wt-% disintegrant, or about 3 wt-% disintegrant, or about 4 wt-% disintegrant. In yet other embodiments, the pharmaceutical formulation comprises less than 8 wt-% disintegrant. In other embodiments, the pharmaceutical formulations have less than about 5 wt-% disintegrant, or less than about 4 wt-% disintegrant, or less than about 3 wt-% disintegrant, or less than about 2 wt-% disintegrant, or less than about 1 wt-% disintegrant. In other embodiments, the sodium bicarbonate helps facilitate the disintegration of the capsule product.

Because sodium bicarbonate has effervescent characteristic when mixed with acid such as gastric fluid, some embodiments of the pharmaceutical formulations of the present invention can comprise at least about 200 mgs of sodium bicarbonate and greater than about 1 wt-% of a disintegrant. In some embodiments, the pharmaceutical formulation comprises about 2 wt-% disintegrant, or about 3 wt-% disintegrant, or about 4 wt-% disintegrant. In yet other embodiments, the pharmaceutical formulation comprises less than 8 wt-% disintegrant. In other embodiments, the pharmaceutical formulations have less than about 5 wt-% disintegrant, or less than about 4 wt-% disintegrant, or less than about 3 wt-% disintegrant, or less than about 2 wt-% disintegrant, or less than about 1 wt-% disintegrant. In other embodiments, the sodium bicarbonate helps facilitate the disintegration of the capsule product.

In some embodiments of the present invention, the wt-% of disintegrant can be decreased and the amount of sodium bicarbonate increased to achieve the desired bioavailability of the proton pump inhibitor. In other embodiments, the wt-% of disintegrant can be increased and the amount of sodium bicarbonate decreased to achieve the desired bioavailability of the proton pump inhibitor.

Binders

Binders impart a cohesiveness to solid oral dosage form formulations: for powder filled capsule formulation, they aid in plug formation that can be filled into a hard sell capsules and for tablet formulation, they ensure the tablet remaining intact after compression. Materials commonly used as binders include starch gelatin, and sugars such as sucrose, glucose, dextrose, molasses, and lactose. The quantity of binder used influences the characteristics of the dosage form and/or manufacturing processes. For example, dosator type encapsulators (e.g. Zanasi machine) normally requires the filling material to be mechanically strong plugs whereas dosing disc type encapsulators (e.g., HK machine) do not require the same degree of high plug breaking force. In general, binder level of 1-10% are used in powder-filled hard gel capsule formulations. Binder usage level in tablet formulations varies whether direct compression, wet granulation, or usage of other excipients such as fillers which itself can act as moderate binder. Formulators skilled in art can determine the binder level for the formulations, but binder usage level of 2-25% in tablet formulations is common.

In some embodiments of the present invention, the wt-% of the disintegrant is at least equivalent to the wt-% of the binder. For example, formulations of the present invention may comprise about 5 wt-% of disintegrant and about 2 wt-% of a binder or about 3 wt-% of a disintegrant and about 3 wt-% of a binder. In other embodiments, the solid oral dosage form does not comprise a binder. In some embodiments, the solid oral dosage form comprises significantly more disintegrant than binder. For example, the binder may be present in an amount of less than 2 wt-% while the disintegrant is present in an amount of greater than 5 wt-%. In other embodiments, the binder and disintegrant are present in the formulation in substantially the same amount. For example, the binder may be present in an amount of about 2 wt-% and the disintegrant may be present in an amount of about 3 wt-%.

Microencapsulation

In accordance with one aspect of the present invention, compositions may include microencapsulation of the proton pump inhibitor or the antacid, in order to enhance the shelf life of the composition and/or enhance the taste of the pharmaceutical composition. See U.S. application Ser. No. 10/893,203, filed Jul. 16, 2004, which claims priority to U.S. Provisional Application No. 60/488,321 filed Jul. 18, 2003, both of which are incorporated by reference in their entirety.

Materials useful for enhancing the shelf life and/or masking the taste of the pharmaceutical compositions of the present invention include materials compatible with the proton pump inhibitor of the pharmaceutical compositions which sufficiently isolate the proton pump inhibitor from other non-compatible excipients. Materials compatible with the proton pump inhibitors of the present invention are those that enhance the shelf life of the proton pump inhibitor, i.e., by slowing or stopping degradation of the proton pump inhibitor.

Exemplary microencapsulation materials useful for enhancing the shelf life of pharmaceutical compositions comprising a proton pump inhibitor include, but are not limited to: hydroxypropyl cellulose ethers (HPC) such as Klucel® or Nisso HPC; low-substituted hydroxypropyl cellulose ethers (L-HPC); hydroxypropyl methyl cellulose ethers (HPMC) such as Seppifilm-LC, Pharmacoat®, Metolose SR, Methocel®-E, Opadry YS, PrimaFlo, Benecel MP824, and Benecel MP843; methylcellulose polymers such as Methocel®-A and Metolose®; Ethylcelluloses (EC) and mixtures thereof such as E461, Ethocel®, Aqualon®-EC, Surelease®; Polyvinyl alcohol (PVA) such as Opadry AMB; hydroxyethylcelluloses such as Natrosol®; carboxymethylcelluloses and salts of carboxymethylcelluloses (CMC) such as Aqualon®-CMC; polyvinyl alcohol and polyethylene glycol co-polymers such as Kollicoat IR®; monoglycerides (Myverol), triglycerides (KLX), polyethylene glycols, modified food starch, acrylic polymers and mixtures of acrylic polymers with cellulose ethers such as Eudragit® EPO, Eudragit® RD100, and Eudragit® E100; cellulose acetate phthalate; sepifilms such as mixtures of HPMC and stearic acid, cyclodextrins; and mixtures of these materials.

In various embodiments, an antacid such as sodium bicarbonate or sodium carbonate is incorporated into the microencapsulation material. In other embodiments, an antioxidant such as BHT is incorporated into the microencapsulation material. In still other embodiments, plasticizers such as polyethylene glycols, e.g., PEG 300, PEG 400, PEG 600, PEG 1450, PEG 3350, and PEG 800, stearic acid, propylene glycol, oleic acid, and triacetin are incorporated into the microencapsulation material. In other embodiments, the microencapsulating material useful for enhancing the shelf life of the pharmaceutical compositions is from the USP or the National Formulary (NF). In yet other embodiments, the microencapsulation material is Klucel. In still other embodiments, the microencapsulation material is methocel.

In further embodiments, one or more other compatible materials are present in the microencapsulation material. Exemplary materials include, but are not limited to, pH modifiers, parietal cell activators, erosion facilitators, diffusion facilitators, anti-adherents, anti-foaming agents, antioxidants, flavoring agents, and carrier materials such as binders, suspending agents, disintegration agents, filling agents, surfactants, solubilizers, stabilizers, lubricants, wetting agents, and diluents.

According to one aspect of the invention, some of the proton pump inhibitor is coated. The coating may be, for example, a gastric resistant coating such as an enteric coating (See, e.g, WO 91/16895 and WO 91/16886), a controlled-release coating, an enzymatic-controlled coating, a film coating, a sustained-release coating, an immediate-release coating, or a delayed-release coating. According to another aspect of the invention, the coating may be useful for enhancing the stability of the pharmaceutical compositions of the present invention.

In addition to microencapsulating the proton pump inhibitors with a material as described herein, the pharmaceutical compositions of the present invention may also comprise one or more flavoring agents. In some embodiments, one or more flavoring agents are mixed with the taste-masking material prior to microencapsulating the proton pump inhibitor and/or antacid. In other embodiments, the flavoring agent is mixed with non-compatible excipients during the formulation process and is therefore not in contact with the proton pump inhibitor and/or antacid, and not part of the microencapsulation material.

"Flavoring agents" or "sweeteners" useful in the pharmaceutical compositions of the present invention include, e.g., acacia syrup, acesulfame K, alitame, anise, apple, aspartame, banana, Bavarian cream, berry, black currant, butterscotch, calcium citrate, camphor, caramel, cherry, cherry cream, chocolate, cinnamon, bubble gum, citrus, citrus punch, citrus cream, cotton candy, cocoa, cola, cool cherry, cool citrus, cyclamate, cylamate, dextrose, eucalyptus, eugenol, fructose, fruit punch, ginger, glycyrrhetinate, glycyrrhiza (licorice) syrup, grape, grapefruit, honey, isomalt, lemon, lime, lemon cream, monoammonium glyrrhizinate (MagnaSweet®), maltol, mannitol, maple, marshmallow, menthol, mint cream, mixed berry, neohesperidine DC, neotame, orange, pear, peach, peppermint, peppermint cream, Prosweet® Powder, raspberry, root beer, rum, saccharin, safrole, sorbitol, spearmint, spearmint cream, strawberry, strawberry cream, stevia, sucralose, sucrose, sodium saccharin, saccharin, aspartame, acesulfame potassium, mannitol, talin, sucralose, sorbitol, swiss cream, tagatose, tangerine, thaumatin, tutti fruitti, vanilla, walnut, watermelon, wild cherry, wintergreen, xylitol, or any combination of these flavoring ingredients, e.g., anise-menthol, cherry-anise, cinnamon-orange, cherry-cinnamon, chocolate-mint, honey-lemon, lemon-lime, lemon-mint, menthol-eucalyptus, orange-cream, vanilla-mint, and mixtures thereof. In other embodiments, sodium chloride is incorporated into the pharmaceutical composition. Based on the proton pump inhibitor, antacid, and excipients, as well as the amounts of each one, one of skill in the art would be able to determine the best combination of flavors to provide the optimally flavored product for consumer demand and compliance. See, e.g., Roy et al., *Modifying Bitterness: Mechanism, Ingredients, and Applications* (1997).

Methods of Microencapsulation

The proton pump inhibitor and/or antacid may be microencapsulated by methods known by one of ordinary skill in the art. Such known methods include, e.g., spray drying processes, spinning disk-solvent processes, hot melt processes, spray chilling methods, fluidized bed, electrostatic deposition, centrifugal extrusion, rotational suspension separation, polymerization at liquid-gas or solid-gas interface, pressure extrusion, or spraying solvent extraction bath. In addition to these, several chemical techniques, e.g., complex coacervation, solvent evaporation, polymer-polymer incompatibility, interfacial polymerization in liquid media, in situ polymerization, in-liquid drying, and desolvation in liquid media could also be used.

The spinning disk method allows for: 1) an increased production rate due to higher feed rates and use of higher solids loading in feed solution, 2) the production of more spherical particles, 3) the production of a more even coating, and 4) limited clogging of the spray nozzle during the process.

Spray drying is often more readily available for scale-up. In various embodiments, the material used in the spray-dry encapsulation process is emulsified or dispersed into the core material in a concentrated form, e.g., 10-60% solids. The microencapsulation material is, in one embodiment, emulsified until about 1 to 3 μm droplets are obtained. Once a dispersion of proton pump inhibitor and encapsulation material are obtained, the emulsion is fed as droplets into the heated chamber of the spray drier. In some embodiments, the droplets are sprayed into the chamber or spun off a rotating disk. The microspheres are then dried in the heated chamber and fall to the bottom of the spray drying chamber where they are harvested.

In some embodiments of the present invention, the microspheres have irregular geometries. In other embodiments, the microspheres are aggregates of smaller particles.

In various embodiments, the proton pump inhibitor and/or antacid are present in the microspheres in an amount greater than 1%, greater than 2.5%, greater than 5%, greater than 10%, greater than 15%, greater than 20%, greater than 25%, greater than 30%, greater than 35%, greater than 40%, greater than 45%, greater than 50%, greater than 55%, greater than 60%, greater than 65%, greater than 70%, greater than 75%, greater than 80%, greater than 85%, greater than 90% greater than 95% or greater than 98% weight percent of the proton pump inhibitor to the microencapsulation material used to enhance the stability of the pharmaceutical composition or the taste-masking material.

Stability

A pharmaceutical formulation of the present invention is stable if, e.g., the proton pump inhibitor has less than about 0.5% degradation after one month of storage at room temperature, or less than about 1% degradation after one month at room temperature, or less than about 1.5% degradation after one month of storage at room temperature, or less than about 2% degradation after one month storage at room temperature, or less than about 2.5% degradation after one month of storage at room temperature, or less than about 3% degradation after one month of storage at room temperature.

In other embodiments, a pharmaceutical formulation of the present invention may have stable if the pharmaceutical formulation contains less than about 5% total impurities after about 3 years of storage, or after about 2.5 years of storage, or about 2 years of storage, or about 1.5 years of storage, or about 1 year of storage, or after 11 months of storage, or after 10 months of storage, or after 9 months of storage, or after 8 months of storage, or after 7 months of storage, or after 6 months of storage, or after 5 months of storage, or after 4 months of storage, or after 3 months of storage, or after 2 months of storage, or after 1 month of storage.

In further embodiments, pharmaceutical formulations of the present invention may contain microencapsulated omeprazole and have enhanced shelf life stability if the pharmaceutical formulation contains less degradation of the proton pump inhibitor than proton pump inhibitor in the same formulation which is not microencapsulated, or "bare". For example, if bare proton pump inhibitor in the pharmaceutical formulation degrades at room temperature by more than about 2% after one month of storage and the microencapsulated material degrades at room temperature by less than about 2% after one month of storage, then the proton pump inhibitor has been microencapsulated with a compatible material that enhances the shelf life of the pharmaceutical formulation.

Dosage

The proton pump inhibiting agent is administered and dosed in accordance with good medical practice, taking into account the clinical condition of the individual patient, the site and method of administration, scheduling of administration, and other factors known to medical practitioners. In human therapy, it is important to provide a dosage form that delivers the required therapeutic amount of the therapeutic agent in vivo, and renders therapeutic agent bioavailable in a rapid manner. In addition to the dosage forms described herein, the dosage forms described by Phillips et al. in U.S. Pat. Nos. 5,840,737, 6,489,346, 6,699,885 and 6,645,988 are incorporated herein by reference.

The percent of intact drug that is absorbed into the bloodstream is not narrowly critical, as long as a therapeutically effective amount, e.g., a gastrointestinal-disorder-effective amount of a proton pump inhibiting agent, is absorbed following administration of the pharmaceutical composition to a subject. Gastrointestinal-disorder-effective amounts may be found in U.S. Pat. No. 5,622,719. It is understood that the amount of proton pump inhibiting agent and/or antacid that is administered to a subject is dependent on a number of factors, e.g., the sex, general health, diet, and/or body weight of the subject.

Illustratively, administration of a substituted bicyclic arylimidazole to a young child or a small animal, such as a dog, a relatively low amount of the proton pump inhibitor, e.g., about 1 mg to about 30 mg, will often provide blood serum concentrations consistent with therapeutic effectiveness. Where the subject is an adult human or a large animal, such as a horse, achievement of a therapeutically effective blood serum concentration will require larger dosage units, e.g., about 10 mg, about 15 mg, about 20 mg, about 30 mg, about 40 mg, about 80 mg, or about 120 mg dose for an adult human, or about 150 mg, or about 200 mg, or about 400 mg, or about 800 mg, or about 1000 mg dose, or about 1500 mg dose, or about 2000 mg dose, or about 2500 mg dose, or about 3000 mg dose or about 3200 mg dose or about 3500 mg dose for an adult horse.

In various other embodiments of the present invention, the amount of proton pump inhibitor administered to a subject is, e.g., about 0.5-2 mg/Kg of body weight, or about 0.5 mg/Kg of body weight, or about 1 mg/Kg of body weight, or about 1.5 mg/Kg of body weight, or about 2 mg/Kg of body weight.

Treatment dosages generally may be titrated to optimize safety and efficacy. Typically, dosage-effect relationships from in vitro and/or in vivo tests initially can provide useful guidance on the proper doses for subject administration. In terms of treatment protocols, it should be appreciated that the dosage to be administered will depend on several factors, including the particular agent that is administered, the route chosen for administration, and the condition of the particular subject.

In various embodiments, unit dosage forms for humans contain about 1 mg to about 120 mg, or about 1 mg, or about 5 mg, or about 10 mg, or about 15 mg, or about 20 mg, or about 30 mg, or about 40 mg, or about 50 mg, or about 60 mg, or about 70 mg, or about 80 mg, or about 90 mg, or about 100 mg, or about 110 mg, or about 120 mg of a proton pump inhibitor.

In a further embodiment of the present invention, the pharmaceutical composition is administered in an amount to achieve a measurable serum concentration of a non-acid degraded proton pump inhibiting agent greater than about 100 ng/ml within about 30 minutes after administration of the pharmaceutical composition. In another embodiment of the present invention, the pharmaceutical composition is administered to the subject in an amount to achieve a measurable serum concentration of a non-acid degraded or non-acid reacted proton pump inhibiting agent greater than about 100 ng/ml within about 15 minutes after administration of the pharmaceutical composition. In yet another embodiment, the pharmaceutical composition is administered to the subject in an amount to achieve a measurable serum concentration of a non-acid degraded or non-acid reacted proton pump inhibiting agent greater than about 100 ng/ml within about 10 minutes after administration of the pharmaceutical composition.

In another embodiment of the present invention, the composition is administered to the subject in an amount to achieve a measurable serum concentration of the proton pump inhibiting agent greater than about 150 ng/ml within about 15 minutes and to maintain a serum concentration of the proton pump inhibiting agent of greater than about 150 ng/ml from about 15 minutes to about 1 hour after administration of the composition. In yet another embodiment of the present invention, the composition is administered to the subject in an amount to achieve a measurable serum concentration of the proton pump inhibiting agent greater than about 250 ng/ml within about 15 minutes and to maintain a serum concentration of the proton pump inhibiting agent of greater than about 250 ng/ml from about 15 minutes to about 1 hour after administration of the composition. In another embodiment of the present invention, the composition is administered to the subject in an amount to achieve a measurable serum concentration of the proton pump inhibiting agent greater than about 350 ng/ml within about 15 minutes and to maintain a serum concentration of the proton pump inhibiting agent of greater than about 350 ng/ml from about 15 minutes to about 1 hour after administration of the composition. In another embodiment of the present invention, the composition is administered to the subject in an amount to achieve a measurable serum concentration of the proton pump inhibiting agent greater than about 450 ng/ml within about 15 minutes and to maintain a serum concentration of the proton pump inhibiting agent of greater than about 450 ng/ml from about 15 minutes to about 1 hour after administration of the composition.

In another embodiment of the present invention, the composition is administered to the subject in an amount to achieve a measurable serum concentration of the proton pump inhibiting agent greater than about 150 ng/ml within about 30 minutes and to maintain a serum concentration of the proton pump inhibiting agent of greater than about 150 ng/ml from about 30 minutes to about 1 hour after administration of the composition. In yet another embodiment of the present invention, the composition is administered to the subject in an amount to achieve a measurable serum concentration of the proton pump inhibiting agent greater than about 250 ng/ml within about 30 minutes and to maintain a serum concentration of the proton pump inhibiting agent of greater than about 250 ng/ml from about 30 minutes to about 1 hour after administration of the composition. In another embodiment of the present invention, the composition is administered to the subject in an amount to achieve a measurable serum concentration of the proton pump inhibiting agent greater than about 350 ng/ml within about 30 minutes and to maintain a serum concentration of the proton pump inhibiting agent of greater than about 350 ng/ml from about 30 minutes to about 1 hour after administration of the composition. In another embodiment of the present invention, the composition is administered to the subject in an amount to achieve a measurable serum concentration of the proton pump inhibiting agent greater than about 450 ng/ml within about 30 minutes and to maintain a serum concentration of the proton pump inhibiting agent of greater than about 450 ng/ml from about 30 minutes to about 1 hour after administration of the composition.

In still another embodiment of the present invention, the composition is administered to the subject in an amount to achieve a measurable serum concentration of a non-acid degraded or non-acid reacted proton pump inhibiting agent greater than about 500 ng/ml within about 1 hour after administration of the composition. In yet another embodiment of the present invention, the composition is administered to the subject in an amount to achieve a measurable serum concentration of a non-acid degraded or non-acid reacted proton pump inhibiting agent greater than about 300 ng/ml within about 45 minutes after administration of the composition.

In another embodiment of the present invention, the composition is administered to the subject in an amount sufficient to achieve a maximum serum concentration (Cmax) at a time (Tmax) that is within about 90, 70, 60, 50, 40, 30 or 20 minutes after administration of the composition according to the present invention.

In still another embodiment of the invention, the composition is administered to the subject in an amount sufficient to achieve a maximum serum concentration (Cmax) at a time (Tmax) that is between about 10 and about 90 minutes, between about 10 to about 60 minutes, between about 15 to about 60 minutes or between about 20 to about 60 minutes after administration of the composition according to the present invention. In some specific embodiments, the values of Cmax and Tmax are averages over a test population. In other specific embodiments, the values of Cmax and Tmax are the values for an individual.

In still another embodiment, the composition is administered in an amount sufficient to achieve a maximum serum concentration (Cmax) of from about 400 to about 2000 ng/mL, from about 400 to about 1500 ng/mL, from about 1000 to about 1500 ng/mL, from about 400 to about 1000 ng/mL or from about 400 to about 700 ng/mL. In some specific embodiments, the values of Cmax and Tmax are averages over a test population. In other specific embodiments, the values of Cmax and Tmax are the values for an individual.

In a further embodiment, the composition is administered in an amount sufficient to achieve a maximum serum concentration (Cmax) of greater than 400 ng/mL, greater than 600 ng/mL, greater than 1000 ng/mL. In some specific embodiments, the values of Cmax and Tmax are averages over a test population. In other specific embodiments, the values of Cmax and Tmax are the values for an individual.

In one embodiment of the present invention, the composition is administered to a subject in a gastrointestinal-disorder-effective amount, that is, the composition is administered in an amount that achieves a therapeutically-effective dose of a proton pump inhibiting agent in the blood serum of a subject for a period of time to elicit a desired therapeutic effect. Illustratively, in a fasting adult human (fasting for generally at least 10 hours) the composition is administered to achieve a therapeutically-effective dose of a proton pump inhibiting agent in the blood serum of a subject within about 45 minutes after administration of the composition. In another embodiment of the present invention, a therapeutically-effective dose of the proton pump inhibiting agent is achieved in the blood serum of a subject within about 30 minutes from the time of administration of the composition to the subject. In yet another embodiment, a therapeutically-effective dose of the proton pump inhibiting agent is achieved in the blood serum of a subject within about 20 minutes from the time of administration to the subject. In still another embodiment of the present invention, a therapeutically-effective dose of the proton pump inhibiting agent is achieved in the blood serum of a subject at about 15 minutes from the time of administration of the composition to the subject.

In further embodiments, the oral bioavailability of the proton pump inhibitor is at least about 25%. In other embodiments, the oral bioavailability of the proton pump inhibitor is at least about 30%. In still other embodiments, the oral bioavailability of the proton pump inhibitor is at least 35%, or at least 40%, or at least 45%, or at least 50%, or at least 55% bioavailable, or at least 60%.

In alternative embodiments, the pharmaceutical composition comprises at least about 5 mEq of antacid and is bioequivalent to a proton pump inhibitor product such as Priolosec®, Nexium®, Prevacid®, Protonic®, or Aciphex®. In other embodiments, the pharmaceutical composition comprises between about 5 mEq to about 30 mEq of antacid and is bioequivalent to a proton pump inhibitor product such as Priolosec®, Nexium®, Prevacid®, Protonic®, or Aciphex®. In still other embodiments, the pharmaceutical composition comprises between about mEq to about 30 mEq, or about 5 mEq, or about 7 mEq, or about 10 mEq, or about 13 mEq, or about 15 mEq, or about 17 mEq, or about 20 mEq, or about 22 mEq, or about 25 mEq, or about 27 mEq, or about 30 mEq of antacid and is bioequivalent to a proton pump inhibitor product such as Priolosec®, Nexium®, Prevacid®, Protonic®, or Aciphex®. "Bioequivalent" is intended to mean that the area under the serum concentration time curve (AUC) and the peak serum concentration ($C_{max}$) are each within 80% and 120%.

In alternative embodiments, the pharmaceutical composition comprises at least about 5 mEq of antacid and is bioequivalent to a proton pump inhibitor product such as Priolosec®, Nexium®, Prevacid®, Protonic®, or Aciphex®. In other embodiments, the pharmaceutical composition comprises between about 5 mEq to about 11 mEq of antacid and is bioequivalent to a proton pump inhibitor product such as Priolosec®, Nexium®, Prevacid®, Protonic®, or Aciphex®. In still other embodiments, the pharmaceutical composition comprises between about 5 mEq to about 11 mEq, or about 5 mEq, or about 6 mEq, or about 7 mEq, or about 8 mEq, or about 9 mEq, or about 10 mEq, or about 11 mEq of antacid and is bioequivalent to a proton pump inhibitor product such as Priolosec®, Nexium®, Prevacid®, Protonic®, or Aciphex®.

In other embodiments, when administered to a subject, the pharmaceutical composition has an area under the serum concentration time curve (AUC) for the proton pump inhibitor that is equivalent to the area under the serum concentration time curve (AUC) for the proton pump inhibitor when the enteric form of the proton pump inhibitor is delivered without antacid. "Equivalent" is intended to mean that the area under the serum concentration time curve (AUC) for the proton pump inhibitor is within ±30% of the area under the serum concentration time curve (AUC) when the same dosage amount of the proton pump inhibitor is enterically coated and delivered to the subject with less than 1 mEq of antacid. The "enteric form of the proton pump inhibitor" is intended to mean that some or most of the proton pump inhibitor has been enterically coated to ensure that at least some of the drug is released in the proximal region of the small intestine (duodenum), rather than the acidic environment of the stomach.

In yet other embodiments, the pharmaceutical compositions provide a release profile of the proton pump inhibitor, using USP dissolution methods, whereby greater than about 50% of the proton pump inhibitor is released from the composition within about 2 hours; or greater than 50% of the proton pump inhibitor is released from the composition within about 1.5 hours; or greater than 50% of the proton pump inhibitor is released from the composition within about 1 hour after exposure to gastrointestinal fluid. In another embodiment, greater than about 60% of the proton pump inhibitor is released from the composition within about 2 hours; or greater than 60% of the proton pump inhibitor is released from the composition within about 1.5 hours; or greater than 60% of the proton pump inhibitor is released from the composition within about 1 hour after exposure to gastrointestinal fluid. In yet another embodiment, greater than about 70% of the proton pump inhibitor is released from the composition within about 2 hours; or greater than 70% of the proton pump inhibitor is released from the composition within about 1.5 hours; or greater than 70% of the proton pump inhibitor is released from the composition within about 1 hour after exposure to gastrointestinal fluid.

Compositions contemplated by the present invention provide a therapeutic effect as proton pump inhibiting agent medications over an interval of about 5 minutes to about 24 hours after administration, enabling, for example, once-a-day, twice-a-day, or three times a day administration if desired. Generally speaking, one will desire to administer an amount of the compound that is effective to achieve a serum level commensurate with the concentrations found to be effective in vivo for a period of time effective to elicit a therapeutic effect. Determination of these parameters is well within the skill of the art.

Dosage Forms

The pharmaceutical compositions of the present invention contain desired amounts of proton pump inhibitor and antacid and can be in the form of: a tablet, (including a suspension tablet, a chewable tablet, a fast-melt tablet, a bite-disintegration tablet, a rapid-disintegration tablet, an effervescent tablet, or a caplet), a pill, a powder (including a sterile packaged powder, a dispensable powder, or an effervescent powder) a capsule (including both soft or hard capsules, e.g., capsules made from animal-derived gelatin or plant-derived HPMC) a lozenge, a sachet, a troche, pellets, granules, or an aerosol. The pharmaceutical compositions of the present invention can be manufactured by conventional pharmacological techniques.

In some embodiments, the pharmaceutical compositions of the present invention contain desired amounts of proton pump inhibiting inhibitor and antacid and are in a solid dosage form. In other embodiments, the pharmaceutical compositions of the present invention contain desired amounts of proton pump inhibitor and antacid and are administered in the form of a capsule (including both soft or hard capsules, e.g., capsules made from animal-derived gelatineor plant-derived HPMC). The pharmaceutical compositions of the present invention can be manufactured by conventional pharmacological techniques.

Conventional pharmacological techniques include, e.g., one or a combination of methods: (1) dry mixing, (2) direct compression, (3) milling, (4) dry or non-aqueous granulation, (5) wet granulation, or (6) fusion. See, e.g., Lachman et al., *The Theory and Practice of Industrial Pharmacy* (1986). Other methods include, e.g., prilling, spray drying, pan coating, melt granulation, granulation, wurster coating, tangential coating, top spraying, extruding, coacervation and the like.

In one embodiment, the proton pump inhibitor is microencapsulated prior to being formulated into one of the above forms. In another embodiment, some of the proton pump inhibitor is microencapsulated prior to being formulated. In another embodiment, some or all of the antacid is microencapsulated prior to being formulated. In still another embodiment, some or most of the proton pump inhibitor is coated prior to being further formulated by using standard coating procedures, such as those described in *Remington's Pharmaceutical Sciences,* 20th Edition (2000). In yet other embodiments contemplated by the present invention, a film coating is provided around the pharmaceutical composition.

In other embodiments, the pharmaceutical compositions further comprise one or more additional materials such as a pharmaceutically compatible carrier, binder, filling agent, suspending agent, flavoring agent, sweetening agent, disintegrating agent, surfactant, preservative, lubricant, colorant, diluent, solubilizer, moistening agent, stabilizer, wetting agent, anti-adherent, parietal cell activator, anti-foaming agent, antioxidant, chelating agent, antifungal agent, antibacterial agent, or one or more combination thereof.

In other embodiments, one or more layers of the pharmaceutical formulation are plasticized. Illustratively, a plasticizer is generally a high boiling point solid or liquid. Suitable plasticizers can be added from about 0.01% to about 50% by weight (w/w) of the coating composition. Plasticizers include, e.g., diethyl phthalate, citrate esters, polyethylene glycol, glycerol, acetylated glycerides, triacetin, polypropylene glycol, polyethylene glycol, triethyl citrate, dibutyl sebacate, stearic acid, stearol, stearate, and castor oil.

Exemplary Solid Oral Dosage Compositions

Solid oral dosage compositions, e.g., tablets, chewable tablets, effervescent tablets, caplets, and capsules, can be prepared, for example, by mixing the proton pump inhibitor, one or more antacid, and pharmaceutical excipients to form a bulk blend composition. When referring to these bulk blend compositions as homogeneous, it is meant that the proton pump inhibitor and antacid are dispersed evenly throughout the composition so that the composition may be readily subdivided into equally effective unit dosage forms, such as tablets, pills, and capsules. The individual unit dosages may also comprise film coatings, which disintegrate upon oral ingestion or upon contact with diluent.

Compressed tablets are solid dosage forms prepared by compacting the bulk blend compositions described above. In various embodiments, compressed tablets of the present invention will comprise one or more functional excipients such as binding agents and/or disintegrants. In other embodiments, the compressed tablets will comprise a film surrounding the final compressed tablet. In other embodiments, the compressed tablets comprise one or more excipients and/or flavoring agents.

A chewable tablet may be prepared by compacting bulk blend compositions, described above. In one embodiment, the chewable tablet comprises a material useful for enhancing the shelf life of the pharmaceutical composition. In another embodiment, the microencapsulated material has taste-masking properties. In various other embodiments, the chewable tablet comprises one or more flavoring agents and one or more taste-masking materials. In yet other embodiments the chewable tablet comprised both a material useful for enhancing the shelf life of the pharmaceutical formulation and one or more flavoring agents.

In various embodiments, the proton pump inhibitor, antacid, and optionally one or more excipients, are dry blended and compressed into a mass, such as a tablet or caplet, having a hardness sufficient to provide a pharmaceutical composition that substantially disintegrates within less than about 30 minutes, less than about 35 minutes, less than about 40 minutes, less than about 45 minutes, less than about 50 minutes, less than about 55 minutes, or less than about 60 minutes, after oral administration, thereby releasing the antacid and the proton pump inhibitor into the gastrointestinal fluid. When at least 50% of the pharmaceutical composition has disintegrated, the compressed mass has substantially disintegrated.

A capsule may be prepared by placing any of the bulk blend compositions described above, into a capsule. In some embodiments of the present invention, the therapeutic dose is split into multiple (e.g., two, three, or four) capsules. In some embodiments, the entire dose of the proton pump inhibitor and antacid are delivered in a capsule form. For example, the capsule may comprise between about 10 mg to about 120 mg of a proton pump inhibitor and between about 5 mEq to about 30 mEq of antacid. In some embodiments, the antacid may be selected from sodium bicarbonate, magnesium hydroxide, calcium carbonate, magnesium oxide, and mixtures thereof. In alternative embodiments the capsule comprises 5 mEq to about 30 mEq of sodium bicarbonate.

Exemplary Powder Compositions

A powder for suspension may be prepared by combining at least one acid labile proton pump inhibitor and between about 5 mEq to about 11 mEq of antacid. In various embodiments, the powder may comprise one or more pharmaceutical excipients and flavors. A powder for suspension may be prepared, for example, by mixing the proton pump inhibitor, one or more antacids, and optional pharmaceutical excipients to form a bulk blend composition. This bulk blend is uniformly subdivided into unit dosage packaging or multi-dosage packaging units. The term "uniform" means the homogeneity of the bulk blend is substantially maintained during the packaging process.

In some embodiments, some or all of the proton pump inhibitor is micronized. Additional embodiments of the present invention also comprise a suspending agent and/or a wetting agent.

Effervescent powders are also prepared in accordance with the present invention. Effervescent salts have been used to disperse medicines in water for oral administration. Effervescent salts are granules or coarse powders containing a medicinal agent in a dry mixture, usually composed of sodium bicarbonate, citric acid and/or tartaric acid. When salts of the present invention are added to water, the acids and the base react to liberate carbon dioxide gas, thereby causing "effervescence." Examples of effervescent salts include, e.g., the following ingredients: sodium bicarbonate or a mixture of sodium bicarbonate and sodium carbonate, citric acid and/or tartaric acid. Any acid-base combination that results in the liberation of carbon dioxide can be used in place of the combination of sodium bicarbonate and citric and tartaric acids, as long as the ingredients were suitable for pharmaceutical use and result in a pH of about 6.0 or higher.

The method of preparation of the effervescent granules of the present invention employs three basic processes: wet granulation, dry granulation and fusion. The fusion method is used for the preparation of most commercial effervescent powders. It should be noted that, although these methods are intended for the preparation of granules, the formulations of effervescent salts of the present invention could also be prepared as tablets, according to known technology for tablet preparation.

Powder for Suspension

In some embodiments, compositions are provided comprising a pharmaceutical at least one proton pump inhibitor, about 5 mEq to about 11 mEq of an antacid, and at least one suspending agent for oral administration to a subject. The composition may be a powder for suspension, and upon admixture with water, a substantially uniform suspension is obtained. See U.S. patent application Ser. No. 10/893,092, filed Jul. 16, 2004, which claims priority to U.S. Provisional Application No. 60/488,324 filed Jul. 18, 2003, both of which are herein incorporated by reference in their entirety.

A suspension is "substantially uniform" when it is mostly homogenous, that is, when the suspension is composed of approximately the same concentration of proton pump inhibitor at any point throughout the suspension. A suspension is determined to be composed of approximately the same concentration of proton pump inhibitor throughout the suspension when there is less than about 20%, less than about 15%, less than about 13%, less than about 11%, less than about 10%, less than about 8%, less than about 5%, or less than about 3% variation in concentration among samples taken from various points in the suspension.

The concentration at various points throughout the suspension can be determined by any suitable means known in the art. For example, one suitable method of determining concentration at various points involves dividing the suspension into three substantially equal sections: top, middle and bottom. The layers are divided starting at the top of the suspension and ending at the bottom of the suspension. Any number of sections suitable for determining the uniformity of the suspension can be used, such as for example, two sections, three sections, four sections, five sections, or six or more sections.

In one embodiment, the composition comprises at least one proton pump inhibitor, between about 5 mEq to about 11 mEq of antacid, and a gum suspending agent, wherein the average particle size of the insoluble material is less than about 200 µm. In some embodiments, the average particle size of the insoluble material is less than about 100 µm. In other embodiments, the average particle size of the insoluble material is less than about 50 µm. The composition is a powder for suspension, and upon admixture with water, a first suspension is obtained that is substantially more uniform when compared to a second suspension comprising the proton pump inhibitor, the antacid, and suspending agent, wherein the suspending agent is not xanthan gum.

In another embodiment, the composition comprises omeprazole, sodium bicarbonate and xanthan gum. The composition is a powder for suspension, and upon admixture with water, a substantially uniform suspension is obtained. In yet another embodiment, the composition is a powder for suspension and comprises omeprazole, about 5 mEq to about 11 mEq sodium bicarbonate, xanthan gum, and at least one sweetener or flavoring agent.

Combination Therapy

The compositions and methods described herein may also be used in conjunction with other well known therapeutic reagents that are selected for their particular usefulness against the condition that is being treated. In general, the compositions described herein and, in embodiments where combinational therapy is employed, other agents do not have to be administered in the same pharmaceutical composition, and may, because of different physical and chemical characteristics, have to be administered by different routes. The determination of the mode of administration and the advisability of administration, where possible, in the same pharmaceutical composition, is well within the knowledge of the skilled clinician. The initial administration can be made according to established protocols known in the art, and then, based upon the observed effects, the dosage, modes of administration and times of administration can be modified by the skilled clinician.

The particular choice of compounds used will depend upon the diagnosis of the attending physicians and their judgment of the condition of the patient and the appropriate treatment protocol. The compounds may be administered concurrently (e.g., simultaneously, essentially simultaneously or within the same treatment protocol) or sequentially, depending upon the nature of the proliferative disease, the condition of the patient, and the actual choice of compounds used. The determination of the order of administration, and the number of repetitions of administration of each therapeutic agent during a treatment protocol, is well within the knowledge of the skilled physician after evaluation of the disease being treated and the condition of the patient.

It is understood that the dosage regimen to treat, prevent, or ameliorate the condition(s) for which relief is sought, can be modified in accordance with a variety of factors. These factors include the type of gastric acid disorder from which the subject suffers, the proton pump inhibitor being administered, as well as the age, weight, sex, diet, and medical condition of the subject. Thus, the dosage regimen actually employed can vary widely and therefore can deviate from the dosage regimens set forth herein. For example, proton pump inhibitors can be formulated to deliver rapid relief as well as sustained relief of a gastric acid related disorder.

The pharmaceutical agents which make up the combination therapy disclosed herein may be a combined dosage form or in separate dosage forms intended for substantially simultaneous administration. The pharmaceutical agents that make up the combination therapy may also be administered sequentially, with either therapeutic compound being administered by a regimen calling for two-step administration. The two-step administration regimen may call for sequential administration of the active agents or spaced-apart administration of the separate active agents. The time period between the multiple administration steps may range from, a few minutes to several hours, depending upon the properties of each pharmaceutical agent, such as potency, solubility, bioavailability, plasma half-life and kinetic profile of the pharmaceutical agent. Circadian variation of the target molecule concentration may also determine the optimal dose interval.

In some embodiments, the present methods, kits, and compositions can be used in combination with another pharmaceutical agent that is indicated for treating or preventing a gastrointestinal disorder, such as, for example, an anti-bacterial agent, an alginate, a prokinetic agent, or an $H_2$-antagonist which are commonly administered to minimize the pain and/or complications related to this disorder. These drugs have certain disadvantages associated with their use. Some of these drugs are not completely effective in the treatment of the aforementioned conditions and/or produce adverse side effects, such as mental confusion, constipation, diarrhea, and thrombocytopenia.

In other embodiments, the present methods, kits, and compositions can be used in combination with other pharmaceutical agents, including but not limited to: NSAIDs including but not limited to aminoarylcarboxylic acid derivatives such as enfenamic acid, etofenamate, flufenamic acid, isonixin, meclofenamic acid, mefenamic acid, niflumic acid, talniflumate, terofenamate, and tolfenamic acid; arylacetic acid derivatives such as aceclofenac, acemetacin, alclofenac, amfenac, amtolmetin guacil, bromfenac, bufexamac, cinmetacin, clopirac, diclofenac sodium, etodolac, felbinac, fenclozic acid, fentiazac, glucametacin, ibufenac, indomethacin, isofezolac isoxepac, lonazolac, metiazinic acid, mofezolac, oxametacine, pirazolac, proglumetacin, sulindac, tiaramide, tolmetin, tropesin, and zomepirac; arylbutyric acid derivatives such as bumadizon, butibufen, fenbufen, xenbucin; arylcarboxylic acids such as clidanac, ketorolac, tinoridine; arylpropionic acid derivatives such as alminoprofen, benoxaprofin, bermoprofen, bucloxic acid, carprofen, fenoprofen, flunoxaprofen, flurbiprofen, ibuprofen, ibuproxam, indoprofen, ketoprofen, loxoprofen, naproxen, oxaprozin, piketoprofin, pirprofen, pranoprofen, protizinic acid, suprofen, tiaprofenic acid, ximoprofen, and zaltoprofen; pyrazoles such as difenamizole, and epirozole; pyrazolones such as apazone, benzpiperylon, feprazone, mofebutazone, morazone, oxyphenbutazone, phenylbutazone, pipebuzone, propyphenazone, prostaglandins, ramifenazone, suxibuzone, and thiazolinobutazone; salicylic acid derivatives such as acetaminosalol, aspirin, benorylate, bromosaligenin, calcium acetylsalicylate, diflunisal, etersalate, fendosal, gentisic acid, glycol salicylate, imidazole salicylate, lysine acetylsalicylate, mesalamine, morpholine salicylate, 1-naphtyl salicylate, olsalazine, parsalmide, phenyl acetylsalicylate, phenyl salicylate, salacetamide, salicylamide o-acetic acid, salicylsulfinuric acid, salsalate, sulfasalazine; thiazinecarboxamides such as ampiroxicam, droxicam, isoxicam, lomoxicam, piroxicam, and tenoxicam; cyclooxygenase-II inhibitors ("COX-II") such as Celebrex (Celecoxib), Vioxx, Relafen, Lodine, and Voltaren and others, such as epsilon-acetamidocaproic acid, s-adenosylmethionine, 3-amino-4-hydroxybutytic acid, amixetrine, bendazac, benzydamine, α-bisabolol, bucololome, difenpiramide, ditazol, emorfazone, fepradinol, guaiazulene, nabumetone, nimesulide, oxaceprol, paranyline, perisoxal, proquazone, tenidap and zilenton; sleep aids including but not limited to a benzodiazepine hypnotic, non-benzodiazepine hypnotic, antihistamine hypnotic, antidepressant hypnotic, herbal extract, barbiturate, peptide hypnotic, triazolam, brotizolam, loprazolam, lormetazepam, flunitrazepam, flurazepam, nitrazepam, quazepam, estazolam, temazepam, lorazepam, oxazepam, diazepam, halazepam, prazepam, alprazolam, chlordiazepoxide, clorazepate, an imidazopyridine or pyrazolopyrimidine hypnotic, zolpidem or zolpidem tartarate, zopiclone, eszopiclone, zaleplon, indiplone, diphenhydramine, doxylamine, phenyltoloxamine, pyrilamine, doxepin, amtriptyline, trimipramine, trazodon, nefazodone, buproprion, bupramityiptyline, an herbal extract such as valerian extract or amentoflavone, a hormone such as melatonin, or gabapeptin; motility agents, including but not limited to 5-HT inhibitors such as cisapride, domperidone, and metoclopramide, and agents useful for treating irritable bowel syndrome.

For the sake of brevity, all patents and other references cited herein are incorporated by reference in their entirety.

EXAMPLES

The present invention is further illustrated by the following examples, which should not be construed as limiting in any way. The experimental procedures to generate the data shown are discussed in more detail below. For all formulations herein, multiple doses may be proportionally compounded as is known in the art. The coatings, layers and encapsulations are applied in conventional ways using equipment customary for these purposes.

The invention has been described in an illustrative manner, and it is to be understood that the terminology used is intended to be in the nature of description rather than of limitation.

Example 1

Modified Fuchs Model for Antacid Selection

Samples were prepared and analyzed using a method that is a variation of the Fuchs' procedure described in the literature. The procedure described simulates a gastric environment with continuous acid influx. A description of experimental set-up and sample analysis is provided below. Changes may be made to these instructions after initial sample evaluation to optimize sample analysis and collection of relevant information.

Set-Up:
1. A glass sample vessel (~150 mL capacity) containing 50 mL of a standardized solution of 0.1 N HCl was placed into a water bath set at 37° C. (±2° C.).
2. A second glass vessel containing >70 mL of a standardized solution of 1.0 N HCl was placed into the same water bath.
3. The stir paddle was then placed into the sample vessel and set at an appropriate speed. The speed of the stir paddle was recorded and used for all samples analyzed. The speed of the paddle should be adequate to dissolve the sample and added acid without causing interference with the pH measurement or splashing of the solution.
4. Prior to the start of each sample analysis, the tubing was primed and it was verified that the flow rate with 1.0 N HCl was 0.5 mL/min and the temperature was 37° C. (+2° C.). The pump and tubing were then set-up to allow the transfer of 1.0 N HCl acid into the sample vessel.
5. The pH meter was calibrated to accurately measure pH between 1 and 10 and it was verified that the electronic storage device was ready to collect pH and/or temperature data at a pre-defined rate.
6. When necessary, the sample was crushed into a fine powder using a mortar and pestle and then transferred to a suitable container and weighed.
7. The pH probe was placed into the glass sample vessel containing 50 mL of 0.1 N HCl at 37° C. (±2° C.).
8. The timer and pH data collection was then started. The sample was then transferred into the vessel and the exact time that the sample was introduced into the acid was recorded. The sample container was then re-weighed to determine the exact weight added.
9. The sample was then stirred for approximately 6 minutes and the flow of the 1.0 N HCl at a rate of 0.5 mL/min was started. The exact start time of the acid flow was recorded.

10. For samples with not more than (≤) 30 mEq ANC the sample continued to stir and the pH was monitored for 1 hour in 15 second intervals.

11. The duration of the test was recorded and the total volume of 0.1 N HCl added was calculated based on the flow rate.

Various buffer combinations were screened using this modified Fuchs in-vitro dynamic stomach model, described above, and it was discovered that the correlation of the theoretical ANC of a given buffer to the actual neutralization capacity and the speed depended on several factors such as solubility, particle size, presence and level of binders and/or disintegrants. For example, it was determined that the smaller the particle size of the buffer the closer the theoretical value was to the actual ANC of a given buffer. This particle size effect was especially noticeable for the insoluble or sparingly soluble antacids such as calcium carbonate or magnesium hydroxide. Contrastingly, the larger the particles size of the antacids, the lower the actual ANC was (e.g., sub-100 US mesh size, sub-80 US mesh size, and sub-60 mesh size of Magnesium Hydroxide).

It was also determined that spray dried magnesium hydroxide with 5% starch such as MS-90@ from SPI Pharma performed better than the USP grade manufactured by precipitation (USP grade Magnesium Hydroxide) in the on set speed of neutralization. In similar pattern, It spray dried calcium carbonate with 5% starch such as Destab® Calcium carbonate-95S from Particle Dynamics performed better than the USP grade calcium carbonate manufactured by precipitation in the on set speed of neutralization as well as the actual neutralization capacity measured by the area under curve (AUC) of the dynamic pH profile.

Example 2

Disintegrant Optimization Trials: Mixed Buffer System

Most proton pump inhibitors are sparingly soluble in water. These sparingly soluble drugs have a strong correlation of disintegration time to bioavailability, and it is important to optimize the disintegration time, which enhances in vivo dissolution of the drug. This trial used a sub-80 mesh US mesh size magnesium hydroxide based formulation as shown in Table 2.A.1 and tested levels between 3% and 11% levels of disintegrant (Croscarmellose Sodium, Ac-di-Sol) for the capsule dosage form performance. Disintegration test outlined by USP (United State Pharmacopia) was chosen as the test method to determine the optimal level of disintegrant. All capsule products containing between 5% to 11% Ac-Di-Sol performed similarly in terms of their physical characteristic, flow properties, and encapsulation characteristics. Disintegration testing of samples with mixed buffer systems indicated that capsule disintegration time is reduced when the level of disintegrant is increased from 3% to 5%. Increasing the level of disintegrant beyond 5% did not lower the disintegration time significantly.

Capsules were filled on a Pharm Op Zansi® LZ-64 dosator encapsulator using the compositions set forth in Table 2.A.1, below. The results of the disintegration study are shown in Table 2.A.2, below.

TABLE 2.A.1

| | Disintegrant Optimization Trials | | | | | | | |
|---|---|---|---|---|---|---|---|---|
| | SAN-10D1 3% Disintegrant | | SAN-10D2 5% Disintegrant | | SAN-10D3 8% Disintegrant | | SAN-10D4 11% Disintegrant | |
| Ingredients | Mg/cap | % | Mg/cap | % | Mg/cap | % | Mg/cap | % |
| OMEPRAZOLE USP | 40.8 | 4.1 | 40.8 | 4.1 | 40.8 | 3.9 | 40.8 | 3.8 |
| Sodium Bicarbonate #2 USP | 420 | 43.4 | 420 | 42.6 | 420 | 41.2 | 420 | 39.9 |
| Magnesium Hydroxide (sieved) sub 80 mesh | 470 | 48.6 | 470 | 47.7 | 470 | 46.2 | 470 | 44.6 |
| Croscarmellose Sodium NF | 30 | 3.1 | 49 | 5.0 | 81 | 8.0 | 116 | 11.0 |
| Magnesium Stearate NF | 7 | 0.7 | 7 | 0.7 | 7 | 0.7 | 7 | 0.7 |
| Totals: | 967 | 100.0 | 986 | 100.0 | 1018 | 100.0 | 1053 | 100.0 |

TABLE 2.A.2

| | Disintegrant Optimization Trials | | |
|---|---|---|---|
| Trial Number/ | Disintegration Times | | |
| Description | First | Last | Comments/Observations |
| SAN-10D1 (3% Ac-Di-Sol) | 9'10" | 11'20" | Virtually all disintegrated at 9 mins. |
| SAN-10D2 (5% Ac-Di-Sol) | 7'30" | 12' | Virtually all disintegrated at 7 mins 30 secs. |
| SAN-10D3 (8% Ac-Di-Sol) | 8' | 11' | Virtually all disintegrated at 7 mins. |
| SAN-10D4 (11% Ac-Di-Sol) | 7'30" | 10'30" | Virtually all disintegrated at 7 mins. |

Example 2B

Disintegrant Optimization Trials—Sodium Bicarbonate Buffer

Sodium bicarbonate has effervescent characteristic when mixed with acid such as gastric fluid. This facilitates the disintegration time of a capsule product, and the disintegration requirement would be less than that of the mixed buffer system when sodium bicarbonate is used as a single buffer. This trial used a USP#2 grade sodium bicarbonate based formulation as shown in table 2.B.1. and tested levels between 1% and 5% levels of disintegrant (Croscarmellose Sodium, Ac-di-Sol) for the capsule dosage form performance. Disintegration test outlined by USP (United State Pharmacopia) was chosen as the test method to determine the optimal level of disintegrant. All capsule products containing between 1% to 5% Ac-Di-Sol performed similarly in terms of their physical characteristic, flow properties, and encapsulation characteristics. However, disintegration testing of samples indicated that capsule disintegration time is reduced when the level of disintegrant is increased from 1% to 2%. Increasing the level of disintegrant beyond 3% did not lower the disintegration time significantly.

TABLE 2.B.1

Disintegrant Optimization Trials

| Ingredients | SAN-10BB1 1% Disintegrant | | SAN-10BB2 2% Disintegrant | | SAN-10BB3 3% Disintegrant | | SAN-10BB4 5% Disintegrant | |
|---|---|---|---|---|---|---|---|---|
| | Mg/cap | % | Mg/cap | % | Mg/cap | % | Mg/cap | % |
| OMEPRAZOLE USP | 40 | 3.5 | 40 | 3.4 | 40 | 3.4 | 40 | 3.3 |
| Sodium Bicarbonate #2 USP | 1100 | 94.9 | 1100 | 94.0 | 1100 | 93.1 | 1100 | 91.1 |
| Croscarmellose Sodium NF | 12 | 1.0 | 23 | 20. | 35 | 3.0 | 60 | 5.0 |
| Magnesium Stearate NF | 7 | 0.6 | 7 | 0.6 | 7 | 0.6 | 7 | 0.6 |
| Totals: | 967 | 100.0 | 986 | 100.0 | 1018 | 100.0 | 1053 | 100.0 |

TABLE 2.B.2

Disintegrant Optimization Trials: Sodium Bicarbonate Buffer

| Trial Number/ Description | Disintegration Times | | Comments/Observations |
|---|---|---|---|
| | First | Last | |
| SAN-10BB1 (1% Ac-Di-Sol) | 6'40" | 8'20" | Virtually all disintegrated at 7 mins. |
| SAN-10BB2 (2% Ac-Di-Sol) | 4'30" | 6' | Virtually all disintegrated at 5 mins 30 secs. |
| SAN-10BB3 (3% Ac-Di-Sol) | 4' | 5'30" | Virtually all disintegrated at 5 mins. |
| SAN-10BB4 (5% Ac-Di-Sol) | 4' | 5'30" | Virtually all disintegrated at 5 mins. |

Example 3

Binder Optimization Trials

A low level of binder 3-8% is commonly used in capsule product manufacturing to make a plug before encapsulation. The use of the binder such as Klucel®-EXP (hydroxypropyl cellulose) or microcrystalline cellulose (Avicel® PH-102, PH-200) was evaluated with the presence of 0-5% of disintegrant in the powder for the performance using the dynamic stomach model (modified Fuchs model). In general use of the binder had a negative impact on the actual ANC and the speed of neutralization in the pH profiling tests, unless used in combination with a disintegrant.

TABLE 3.A.1

Binder Optimization Trials

| Ingredients | SAN-10F1 | | SAN-10F2 | | SAN-10F3 | | SAN-10F4 | | SAN-10F5 | |
|---|---|---|---|---|---|---|---|---|---|---|
| | Mg/cap | % | Mg/cap | % | Mg/cap | % | Mg/cap | % | Mg/cap | % |
| Omeprazole USP | 40.0 | 4.5 | 40.0 | 4.0 | 40.0 | 3.8 | 40.0 | 3.6 | 40.0 | 3.6 |
| Sodium Bicarbonate #2 USP | 250 | 27.9 | 250 | 25.1 | 350 | 33.4 | 350 | 31.9 | 350 | 31.9 |
| Magnesium Hydroxide | 600.0 | 66.9 | 600.0 | 60.2 | 600.0 | 57.3 | 600.0 | 54.7 | 600.0 | 54.7 |
| Klucel-EXP | 0 | 0.0 | 100 | 10.0 | 50 | 4.8 | 100 | 9.1 | 50 | 4.6 |
| Croscarmellose Sodium NF | 0 | 0.0 | 0 | 0.0 | 0 | 0.0 | 0 | 0.0 | 50 | 4.6 |
| Magnesium Stearate NF | 7 | 0.8 | 7 | 0.7 | 7 | 0.7 | 7 | 0.6 | 7 | 0.6 |
| Totals: | 897.0 | 100.0 | 997.0 | 100.0 | 997.0 | 100.0 | 1,097.0 | 100.0 | 1,097.0 | 100.0 |

TABLE 3.A.2

Binder Optimization Trials

| Ingredients | TR2001 | | TR2002 | | TR2003 | | TR2004 | | TR2005 | |
|---|---|---|---|---|---|---|---|---|---|---|
| | Mg/cap | % | Mg/cap | % | Mg/cap | % | Mg/cap | % | Mg/cap | % |
| Omeprazole USP | 40 | 4.5 | 40 | 4.0 | 40 | 4.0 | 40 | 3.6 | 40 | 3.6 |
| Sodium Bicarbonate #2 USP | 450 | 50.2 | 450 | 45.1 | 450 | 45.1 | 450 | 41.0 | 450 | 41.0 |
| Magnesium Hydroxide | 500 | 55.7 | 500 | 50.2 | 500 | 50.2 | 500 | 45.6 | 500 | 45.6 |
| Klucel-EXP | 20 | 2.2 | 20 | 2.0 | 50 | 5.0 | 50 | 4.6 | 0 | 0.0 |
| Croscarmellose |  |  |  |  |  |  |  |  |  |  |

TABLE 3.A.2-continued

Binder Optimization Trials

| Ingredients | TR2001 Mg/cap | % | TR2002 Mg/cap | % | TR2003 Mg/cap | % | TR2004 Mg/cap | % | TR2005 Mg/cap | % |
|---|---|---|---|---|---|---|---|---|---|---|
| Sodium NF | 20 | 2.2 | 50 | 5.0 | 50 | 5.0 | 20 | 1.8 | 20 | 1.8 |
| Magnesium Stearate NF | 7 | 0.8 | 7 | 0.7 | 7 | 0.7 | 7 | 0.6 | 7 | 0.6 |
| Totals: | 897 | 100.0 | 997 | 100.0 | 997 | 100.0 | 1,097.0 | 100.0 | 1,097.0 | 100.0 |

The pH test results (table 3.A.1. and table 3.A.2.) shows that hand-filled capsules with the binders at 5-10% level had a very slow neutralization speed while the capsule with binder and disintegrant had an adequate speed of neutralization. The capsules with no binder and no disintegrant showed a medium neutralization speed. Table 3BB showed the similar findings that the presence of binder slows down the neutralization speed while use of disintegrant mitigate the negative impact of binder in the formulation.

TABLE 3.B.1

Neutralization Speed of Capsules with Various Level of Binder and Disintegrant

| Sample | Binder Level (%) | Disintegrant Level (%) | Total ANC (mEq) | Total Time Above pH (min) 3.5 | 5.0 | 6.0 | 6.5 |
|---|---|---|---|---|---|---|---|
| SAN-10F1 | 0 | 0 | 23.6 | 14.75 | 11.25 | 5.75 | 1.50 |
| SAN-10F2 | 10 | 0 | 23.6 | 0 | 0 | 0 | 0 |
| SAN-10F3 | 0 | 4.8 | 24.7 | 19.5 | 18.25 | 12.2 | 6.50 |
| SAN-10F4 | 9.1 | 4.8 | 24.7 | 15.45 | 11.30 | 9.50 | 7.45 |
| SAN-10F5 | 4.6 | 4.6 | 24.7 | 34.25 | 30.00 | 22.50 | 15.25 |

TABLE 3.B.2

Neutralization Speed of Capsules with Various Level of Binder and Disintegrant

| Sample | Binder Level (%) | Disintegrant Level (%) | Total ANC (mEq) | Total Time Above pH (min) 3.5 | 5.0 | 6.0 | 6.5 |
|---|---|---|---|---|---|---|---|
| TR2001 | 2.2 | 2.2 | 22.5 | 8.5 | 7.00 | 0.25 | 0 |
| TR2002 | 2.0 | 5.0 | 22.5 | 0.25 | 0 | 0 | 0 |
| TR2003 | 5.0 | 5.0 | 22.5 | 7.25 | 6.00 | 0.25 | 0 |
| TR2004 | 4.6 | 1.8 | 22.5 | 0 | 0 | 0 | 0 |
| TR2005 | 0.0 | 1.8 | 22.5 | 0 | 0 | 0 | 0 |

Example 4

Capsule Formulations

The following formulations were prepared by the following process: The sodium bicarbonate and omeprazole were combined in a mixer and blended for 5 minutes. To that mixture, the magnesium hydroxide (if any) and croscarmellose sodium were added and mixed for 5 minutes. The blend was then passed through a #20 mesh s/s screen and then mixed for 10 minutes. Magnesium stearate was then added to the mixture and blended for 3 minutes. The material was then encapsulated into hard gelatin capsule shells using a Profill® manual capsule filler.

| Ingredients | SAN-10A Mg/caps | SAN-10B Mg/caps | SAN-10BB Mg/caps | SAN-10C Mg/caps |
|---|---|---|---|---|
| OMEPRAZOLE USP | 40 | 40 | 40 | 20 |
| Sodium Bicarbonate #2 USP | 420 | 420 | 1100 | 800 |
| Magnesium Hydroxide (sieved) 100 mesh | 470 | 0 | 0 | 0 |
| Magnesium Hydroxide (sieved) 60 mesh | 0 | 470 | 0 | 0 |
| Croscarmellose Sodium NF | 30 | 30 | 20 | 20 |
| Magnesium Stearate NF | 10 | 10 | 10 | 8 |
| Totals: | 970 | 970 | 1170 | 848 |

| Ingredients | SAN-10D Mg/caps | SAN-10E Mg/caps | SAN-10F Mg/caps | SAN-10G Mg/caps | SAN-10H Mg/caps |
|---|---|---|---|---|---|
| OMEPRAZOLE USP | 40 | 40 | 40 | 40 | 40 |
| Sodium Bicarbonate #2 USP | 420 | 378 | 335 | 378 | 420 |
| Magnesium Hydroxide (sieved) 80 mesh | 470 | 0 | 0 | 0 | 0 |
| Magnesium Hydroxide (sieved) 60 mesh | 0 | 0 | 375 | 0 | 375 |
| Magnesium Hydroxide 95-MS | 0 | 447.4 | 0 | 447.4 | 0 |
| Croscarmellose Sodium NF | 30 | 27 | 24 | 56 | 82 |
| Magnesium Stearate NF | 7 | 6 | 5 | 6 | 5 |
| Totals: | 967 | 898.4 | 779.8 | 928 | 922 |

Example 5

Capsule Formulations with Sodium Bicarbonate and Less than 3% Disintegrant

The following specific formulations are provided by way of reference only and are not intended to limit the scope of the invention. Each formulation contains therapeutically effective doses of PPI as well as sufficient buffering agent to prevent acid degradation of at least some of the PPI by raising the pH of gastric fluid. Amounts of buffer are expressed in weight as well as in molar equivalents (mEq). The capsules are prepared by blending the PPI with one or more buffering agents, and homogeneously blending with excipients. The appropriate weight of bulk blend composition is filled into a hard gelatine capsule (e.g., size 00) using an automatic encapsulator. The PPI can be in a micronized form.

| PPI | Buffering Agent | Excipient |
|---|---|---|
| 40 mg omeprazole | 11.3 mEq or 950 mg NaHCO$_3$ | 50 mg Klucel<br>30 mg Ac-di-Sol<br>10 mg magnesium stearate<br>2.8% disintegrant |

| PPI | Buffering Agent | Excipient |
|---|---|---|
| 40 mg omeprazole | 10.5 mEq or 880 mg NaHCO$_3$ | 30 mg Klucel<br>20 mg Crospovidone<br>10 mg magnesium stearate<br>2.0% disintegrant |

| PPI | Buffering Agent | Excipient |
|---|---|---|
| 60 mg omeprazole per capsule | 11.4 mEq or 960 mg NaHCO$_3$ | 20 mg MCC<br>25 mg Ac-Di-Sol<br>10 mg magnesium stearate<br>1.9% disintegrant |

Example 6

Capsule Formulations with Mixed Buffer Systems and 3-11% Disintegrant

The following specific formulations are provided by way of reference only and are not intended to limit the scope of the invention. Each formulation contains therapeutically effective doses of PPI as well as sufficient buffering agent to prevent acid degradation of at least some of the PPI by raising the pH of gastric fluid. Amounts of buffer are expressed in weight as well as in molar equivalents (mEq). The capsules are prepared by blending the PPI with one or more buffering agents, and homogeneously blending with excipients. The appropriate weight of bulk blend composition is filled into a hard gelatinecapsule (e.g., size 00) using an automatic encapsulator. The PPI can be in a micronized form.

| PPI | Buffering Agent | Excipient |
|---|---|---|
| 40 mg omeprazole | 20.6 mEq or 600 mg Mg(OH)$_2$<br>3 mEq or 250 mg NaHCO$_3$<br>23.6 mEq or 950 mgs total buffer | 20 mg MCC<br>50 mg Ac-di-Sol<br>10 mg magnesium stearate<br>5.2% disintegrant |

| PPI | Buffering Agent | Excipient |
|---|---|---|
| 40 mg omeprazole | 20.6 mEq or 600 mg Mg(OH)$_2$<br>3 mEq or 250 mg NaHCO$_3$<br>23.6 mEq or 950 mgs total buffer | 100 mg MCC<br>50 mg Ac-di-Sol<br>10 mg magnesium stearate<br>4.8% disintegrant |

| PPI | Buffering Agent | Excipient |
|---|---|---|
| 40 mg omeprazole | 20.6 mEq or 600 mg Mg(OH)$_2$<br>3 mEq or 250 mg NaHCO$_3$<br>23.6 mEq or 950 mgs total buffer | 30 mg MCC<br>100 mg sodium starch glycolate (Primojel ®)<br>10 mg magnesium stearate<br>9.7% disintegrant |

| PPI | Buffering Agent | Excipient |
|---|---|---|
| 40 mg omeprazole | 20.6 mEq or 600 mg Mg(OH)$_2$<br>3 mEq or 250 mg NaHCO$_3$<br>23.6 mEq or 850 mgs total buffer | 50 mg Klucel<br>50 mg Ac-di-Sol<br>10 mg magnesium stearate<br>5.0% disintegrant |

| PPI | Buffering Agent | Excipient |
|---|---|---|
| 40 mg omeprazole | 20.6 mEq or 600 mg Mg(OH)$_2$<br>3 mEq or 250 mg NaHCO$_3$<br>23.6 mEq or 850 mgs total buffer | 30 mg Klucel<br>30 mg Ac-di-Sol<br>10 mg magnesium stearate<br>3.1% disintegrant |

| PPI | Buffering Agent | Excipient |
|---|---|---|
| 20 mg omeprazole | 20.6 mEq or 600 mg Mg(OH)$_2$<br>3 mEq or 250 mg NaHCO$_3$<br>23.6 mEq or 850 mgs total buffer | 100 mg Klucel<br>30 mg Ac-di-Sol<br>10 mg magnesium stearate<br>3.0% disintegrant |

| PPI | Buffering Agent | Excipient |
|---|---|---|
| 20 mg omeprazole | 20.6 mEq or 600 mg Mg(OH)$_2$<br>3.0 mEq or 250 mg NaHCO$_3$<br>23.6 mEq or 850 mgs total buffer | 30 mg Klucel<br>70 mg Crospovidone<br>10 mg magnesium stearate<br>7.1% disintegrant |

| PPI | Buffering Agent | Excipient |
|---|---|---|
| 10 mg omeprazole per capsule | 17.1 mEq or 500 mg Mg(OH)$_2$<br>3.0 mEq or 250 mg NaHCO$_3$<br>20.1 mEq or 750 mg total buffer | 30 mg sodium starch glycolate (Explotab ®)<br>15 mg Klucel<br>7 mg magnesium stearate<br>3.7% disintegrant |

| PPI | Buffering Agent | Excipient |
|---|---|---|
| 20 mg omeprazole per capsule | 20.6 mEq or 600 mg Mg(OH)$_2$<br>3.0 mEq or 250 mg NaHCO$_3$<br>23.6 mEq or 850 mgs total buffer | 50 mg Ac-Di-Sol<br>30 mg Klucel<br>10 mg magnesium stearate<br>5.2% disintegrant |

| PPI | Buffering Agent | Excipient |
|---|---|---|
| 20 mg microencapsulated omeprazole per capsule | 20.6 mEq or 600 mg Mg(OH)$_2$<br>3.0 mEq or 250 mg NaHCO$_3$<br>23.6 mEq or 850 mg total buffer | 50 mg Ac-Di-Sol<br>50 mg Klucel<br>10 mg magnesium stearate<br>5.1% disintegrant |

| PPI | Buffering Agent | Excipient |
|---|---|---|
| 20 mg omeprazole per capsule | 20.6 mEq or 600 mg Mg(OH)$_2$<br>4.2 mEq or 350 mg NaHCO$_3$<br>24.7 mEq or 950 mg total buffer | 40 mg Ac-Di-Sol<br>35 mg Klucel<br>10 mg magnesium stearate<br>4.1% disintegrant |

| PPI | Buffering Agent | Excipient |
|---|---|---|
| 40 mg omeprazole per capsule | 17.1 mEq or 500 mg Mg(OH)$_2$<br>4.2 mEq or 350 mg NaHCO$_3$<br>21.3 mEq or 850 mg total buffer | 40 mg Ac-Di-Sol<br>45 mg Klucel<br>10 mg magnesium stearate<br>4.1% disintegrant |

| PPI | Buffering Agent | Excipient |
|---|---|---|
| 15 mg microencapsulated lansoprazole per capsule | 17.1 mEq or 500 mg Mg(OH)$_2$<br>3.0 mEq or 250 mg NaHCO$_3$<br>20.71 mEq or 750 mg total buffer | 50 mg Ac-Di-Sol<br>15 mg Klucel<br>7 mg magnesium stearate<br>6.0% disintegrant |

| PPI | Buffering Agent | Excipient |
|---|---|---|
| 15 mg lansoprazole per capsule | 17.1 mEq or 500 mg Mg(OH)$_2$<br>3.0 mEq or 250 mg NaHCO$_3$<br>20.1 mEq or 750 mg total buffer | 30 mg Crospovidone<br>15 mg Klucel<br>7 mg magnesium stearate<br>3.7% disintegrant |

| PPI | Buffering Agent | Excipient |
|---|---|---|
| 30 mg lansoprazole per capsule | 17.1 mEq or 500 mg Mg(OH)$_2$<br>4.2 mEq or 350 mg NaHCO$_3$<br>21.3 mEq or 850 mg total buffer | 40 mg Ac-Di-Sol<br>30 mg Klucel<br>10 mg magnesium stearate<br>4.2% disintegrant |

| PPI | Buffering Agent | Excipient |
|---|---|---|
| 20 mg omeprazole per capsule | 17.1 mEq or 500 mg Mg(OH)$_2$<br>3.0 mEq or 250 mg NaHCO$_3$<br>20.1 mEq or 750 mg total buffer | 50 mg Ac-Di-Sol<br>30 mg Klucel<br>10 mg magnesium stearate<br>5.8% disintegrant |

| PPI | Buffering Agent | Excipient |
|---|---|---|
| 60 mg omeprazole per capsule | 17.1 mEq or 500 mg Mg(OH)$_2$<br>3.0 mEq or 250 mg NaHCO$_3$<br>20.1 mEq or 750 mg total buffer | 30 mg Crospovidone<br>15 mg Klucel<br>7 mg magnesium stearate<br>3.5% disintegrant |

| PPI | Buffering Agent | Excipient |
|---|---|---|
| 40 mg omeprazole per capsule | 20.6 mEq or 600 mg Mg(OH)$_2$<br>4.2 mEq or 350 mg NaHCO$_3$<br>24.8 mEq or 950 mg total buffer | 40 mg Ac-Di-Sol<br>35 mg Klucel<br>10 mg magnesium stearate<br>3.7% disintegrant |

| PPI | Buffering Agent | Excipient |
|---|---|---|
| 15 mg microencapsulated lansoprazole per capsule | 17.1 mEq or 500 mg Mg(OH)$_2$ 3.0 mEq or 250 mg NaHCO$_3$ 20.1 mEq or 750 mg total buffer | 60 mg Ac-Di-Sol 15 mg Klucel 7 mg magnesium stearate 7.1% disintegrant |

| PPI | Buffering Agent | Excipient |
|---|---|---|
| 60 mg ompeprazole per capsule | 17.1 mEq or 500 mg Mg(OH)$_2$ 3.0 mEq or 250 mg NaHCO$_3$ 20.1 mEq or 750 mg total buffer | 30 mg Ac-Di-Sol 15 mg Klucel 7 mg magnesium stearate 3.5% disintegrant |

| PPI | Buffering Agent | Excipient |
|---|---|---|
| 20 mg omeprazole per capsule Size 0 capsule | 6.9 mEq or 200 mg Mg(OH)$_2$ 3.9 mEq or 330 mg NaHCO$_3$ 10.8 mEq or 530 mg total buffer | 30 mg Ac-Di-Sol 35 mg Klucel 6 mg magnesium stearate 4.8% disintegrant |

| PPI | Buffering Agent | Excipient |
|---|---|---|
| 15 mg micro-encapsulated lansoprazole per capsule Size 1 capsule | 6.9 mEq or 200 mg Mg(OH)$_2$ 2.6 mEq or 220 mg NaHCO$_3$ 8.5 mEq or 420 mg total buffer | 35 mg Ac-Di-Sol 20 mg Klucel 6 mg magnesium stearate 7.1% disintegrant |

| PPI | Buffering Agent | Excipient |
|---|---|---|
| 30 mg lansoprazole per capsule Size 1 capsule | 3.4 mEq or 100 mg Mg(OH)$_2$ 3.8 mEq or 315 mg NaHCO$_3$ 7.2 mEq or 415 mg total buffer | 20 mg Ac-Di-Sol 30 mg Klucel 5 mg magnesium stearate 4.0% disintegrant |

| PPI | Buffering Agent | Excipient |
|---|---|---|
| 60 mg ompeprazole per capsule Size 2 capsule | 5.1 mEq or 150 mg Mg(OH)$_2$ 3.0 mEq or 250 mg NaHCO$_3$ 8.1 mEq or 400 mg total buffer | 20 mg Ac-Di-Sol 10 mg Klucel 4 mg magnesium stearate 4.1% disintegrant |

| PPI | Buffering Agent | Excipient |
|---|---|---|
| 120 mg ompeprazole per capsule Size 1 capsule | 8.6 mEq or 250 mg Mg(OH)$_2$ 2.4 mEq or 200 mg NaHCO$_3$ 11.0 mEq or 450 mg total buffer | 30 mg Ac-Di-Sol 30 mg Klucel 8 mg magnesium stearate 4.7% disintegrant |

| PPI | Buffering Agent | Excipient |
|---|---|---|
| 10 mg omeprazole per capsule Size 2 capsule | 3.4 mEq or 100 mg Mg(OH)$_2$ 3.0 mEq or 250 mg NaHCO$_3$ 6.4 mEq or 350 mg total buffer | 18 mg Ac-Di-Sol 15 mg Klucel 7 mg magnesium stearate 4.5% disintegrant |

Example 7A

Capsule Formulations without Binder

The following specific formulations are provided by way of reference only and are not intended to limit the scope of the invention. Each formulation contains therapeutically effective doses of PPI as well as sufficient buffering agent to prevent acid degradation of at least some of the PPI by raising the pH of gastric fluid. Amounts of buffer are expressed in weight as well as in molar equivalents (mEq). The capsules are prepared by blending the PPI with one or more buffering agents, and homogeneously blending with excipients. The appropriate weight of bulk blend composition is filled into a hard gelatine capsule (e.g., size 00) using an automatic encapsualtor. The PPI can be in a micronized form.

TABLE 7A

| PPI | Buffering Agent | Excipient |
|---|---|---|
| 40 mg omeprazole | 20.6 mEq or 600 mg Mg(OH)$_2$ 3.0 mEq or 250 mg NaHCO$_3$ 23.6 mEq or 950 mgs total buffer | 50 mg Ac-di-Sol 10 mg magnesium stearate |

TABLE 7B

| PPI | Buffering Agent | Excipient |
|---|---|---|
| 40 mg microencapsulated omeprazole per capsule | 15.4 mEq or 450 mg Mg(OH)$_2$ 2.4 mEq or 200 mg NaHCO$_3$ 17.8 mEq or 650 mg total buffer | 30 mg Ac-Di-Sol 7 mg magnesium stearate |

TABLE 7C

| PPI | Buffering Agent | Excipient |
|---|---|---|
| 40 mg omeprazole per capsule | 10.5 mEq or 880 mg NaHCO$_3$ 10.5 mEq or 880 mg total buffer | 20 mg Ac-Di-Sol 9 mg magnesium stearate Size 0 Elongated capsule |

TABLE 7D

| PPI | Buffering Agent | Excipient |
|---|---|---|
| 40 mg microencapsulated ompeprazole per capsule | 3.4 mEq or 100 mg Mg(OH)$_2$ 2.4 mEq or 200 mg NaHCO$_3$ 5.8 mEq or 300 mg total buffer | 20 mg Ac-Di-Sol 5 mg magnesium stearate Size 2 capsule |

Example 7B

40 mg Omeprazole (SAN-7E)

The following specific formulations are provided by way of illustrating the present invention and are not intended to be limiting. The capsules were prepared by blending the indicated amount of micronized omeprazole USP (purchased from Union Quimico Farmaceutica, "UQUIFA") about half the indicated amount of sodium bicarbonate USP #2. After blending the omeprazole and sodium bicarbonate, the remaining sodium bicarbonate USP #2 was added along with the indicated amount of croscarmellose sodium and magnesium stearate. Once the omeprazole was homogeneously blended with the excipients, the appropriate weight of composition was filled into hard gelatin capsules, size 00, using a dosing disc/tampling pin-type automatic encapsulator.

In particular, a 110 kg blend for manufacturing 40 mg/capsule omeprazole immediate release capsules according to the present invention was manufactured by the following procedure: First, about half of the sodium bicarbonate was blended with omeprazole in a 5 cubic foot V-blender. First, about one quarter of the total sodium bicarbonate (i.e. about 25% of 102.47 kg (the total amount of sodium bicarbonate USP #2) was passed through a 16/20 mesh screen and charged into the V-blender. Next, 3.80 kg of omeprazole USP were passed through a 16/20 mesh screen and charged into the V-blender. Then, about one quarter of the total sodium bicarbonate were passed through the 16/20 mesh screen and charged into the V-blender. Once the sodium bicarbonate (about half the total) and omeprazole were charged into the V-blender, they were mixed for 5 minutes to form a pre-blend.

Next, about half of the sodium bicarbonate and the crocarmellose was added to the pre-blend. Approximately one quarter of the of the total sodium bicarbonate was passed through a 16/20 mesh screen and charged into the V-blender. Then 2.79 kg of crocarmellose sodium NF, EP was passed through the 16/20 mesh screen and charged into the V-blender. Finally, the remaining one quarter of the sodium bicarbonate was passed through the screen and charged into the V-blender. The resulting mixture was 5 minutes, sampled for BU, mixed again for 5 minutes, sampled for BU, mixed again for 5 minutes, and sampled again for BU.

Last, magnesium stearate was added to the mixture. The magnesium stearate, 0.93 Kg, was passed through a 30 mesh screen and charged into the V-blender. The mixture was mixed for 3 minutes then discharged into a drum. The mixture was then sampled for BU and then encapsulated in size 00 hard gelatin capsules on a H&K tamping pin encapsulator.

The amounts of omeprazole and excipients used in this example are set forth in the following table:

TABLE 7E

| Ingredient | % | mg/capsule | Amount Required for 110 Kg: | Acid Neutralizing Content (meq per capsule) |
|---|---|---|---|---|
| Omeprazole USP | 3.5% | 40.8* mg/caps | 3.80 Kg | — |
| Sodium Bicarbonate USP #2 | 93.2 | 1100 | 102.47 | 13.1 meq |
| Croscarmellose Sodium NF, EP | 2.5 | 30 | 2.79 | — |
| Magnesium Stearate | 0.8 | 10 | 0.93 | — |
| Total: | 100.0 | 1180.8 | 110.00 | 13.1 |

*An overage of 2% of omeprazole was used to ensure at least 100% indicated omeprazole per capsule.

Example 7C

20 mg Omeprazole (SAN-7F)

In another particular example, a 1300 Kg blend of 20 mg omeprazole per capsule was manufactured by the following procedure:

First, about half of the sodium bicarbonate was blended with omeprazole in a 60 cubic foot V-blender. About one quarter of the total sodium bicarbonate (i.e. about 25% of 1232.33 kg (the total amount of sodium bicarbonate USP #2) was passed through a 16/20 mesh screen and charged into the V-blender. Next, 22.85 Kg of omeprazole USP were passed through the 16/20 mesh screen and charged into the V-blender. Then, about one quarter of the total sodium bicarbonate were passed through the 16/20 mesh screen and charged into the V-blender. Once the sodium bicarbonate (about half the total) and omeprazole were charged into the V-blender, they were mixed for 5 minutes to form a pre-blend.

Next, about half of the sodium bicarbonate and the croscarmellose was added to the pre-blend. Approximately one quarter of the of the total sodium bicarbonate was passed through a 16/20 mesh screen and charged into the V-blender. Then 33.61 Kg of Croscarmellose sodium NF, EP was passed through the 16/20 mesh screen and charged into the V-blender. Finally, the remaining one quarter of the sodium bicarbonate was passed through the screen and charged into the V-blender. The resulting mixture was mixed 5 minutes, sampled for batch uniformity (BU), mixed again for 5 minutes, sampled for BU, mixed again for 5 minutes, and sampled again for BU.

Last, magnesium stearate was added to the mixture. The magnesium stearate, 11.20 Kg, was passed through a 30 mesh screen and charged into the V-blender. The mixture was mixed for 3 minutes then discharged into a drum. The mixture was then sampled for BU and encapsulated in size 00 hard gelatin capsules on a H&K tamping pin encapsulator.

The amounts of omeprazole and excipients used in this example are set forth in the following table:

TABLE 7F

| Ingredient | % | mg/capsule | Amount Required for 110 Kg: | Acid Neutralizing Content (meq per capsule) |
|---|---|---|---|---|
| Omeprazole USP | 1.8% | 20.4* mg/capsule | 22.85 Kg | — |
| Sodium Bicarbonate USP #2 | 94.8 | 1100.0 | 1232.33 | 13.1 meq |
| Croscarmellose Sodium NF, EP | 2.6 | 30.0 | 33.61 | — |
| Magnesium Stearate | 0.9 | 10.0 | 11.20 | — |
| Total: | 100.1 | 1160.4 | 1300.00 | 13.1 |

*An overage of 2% omeprazole was used to ensure that each capsule contained at least 100% of the indicated dose of 20 mg/capsule.

Example 8

Capsule Formulations

The following specific formulations are provided by way of reference only and are not intended to limit the scope of the invention. Each formulation contains therapeutically effective doses of PPI as well as sufficient antacid to prevent acid degradation of at least some of the PPI by raising the pH of gastric fluid. Amounts of antacid are expressed in weight as well as in molar equivalents (mEq). The capsules are prepared by blending the PPI with antacids, and homogeneously blending with excipients as shown in Tables 8.A. to 8.H. below. The appropriate weight of bulk blend composition is filled into a hard gelatine capsule (e.g., size 00) using an automatic encapsualtor (H & K 1500 or MG2 G60). The PPI can be in a micronized form.

TABLE 8.A

Omeprazole (20 mg) Capsule

| PPI | Antacid | Excipient |
|---|---|---|
| 20 mg omeprazole | 6.9 mEq or 200 mg Mg(OH)$_2$ | 30 mg Ac-Di-Sol |
|  | 3.9 mEq or 330 mg NaHCO$_3$ | 35 mg Klucel |
| per capsule | 10.8 mEq or 530 mg total antacid | 6 mg magnesium stearate |
|  |  | Size 0 capsule |

TABLE 8.B

Omeprazole (40 mg) Capsule

| PPI | Antacid | Excipient |
|---|---|---|
| 40 mg omeprazole per capsule | 10.5 mEq or 880 mg NaHCO$_3$ | 40 mg Ac-Di-Sol |
|  | 10.5 mEq or 880 mg total antacid | 9 mg magnesium stearate |
|  |  | Size 0 Elongated capsule |

TABLE 8.C

Lansoprazole (15 mg) Capsule

| PPI | Antacid | Excipient |
|---|---|---|
| 15 mg microencapsulated lansoprazole per capsule | 6.9 mEq or 200 mg Mg(OH)$_2$ | 35 mg Ac-Di-Sol |
|  | 2.6 mEq or 220 mg NaHCO$_3$ | 20 mg Klucel |
|  | 9.5 mEq or 420 mg total antacid | 6 mg magnesium stearate |
|  |  | Size 1 capsule |

TABLE 8.D

Lansoprazole (30 mg) Capsule

| PPI | Antacid | Excipient |
|---|---|---|
| 30 mg lansoprazole per capsule | 3.4 mEq or 100 mg Mg(OH)$_2$ | 20 mg Ac-Di-Sol |
|  | 3.8 mEq or 315 mg NaHCO$_3$ | 30 mg Klucel |
|  | 7.2 mEq or 415 mg total antacid | 5 mg magnesium stearate |
|  |  | Size 1 capsule |

TABLE 8.E

Omeprazole (60 mg) Capsule

| PPI | Antacid | Excipient |
|---|---|---|
| 60 mg omeprazole per capsule | 5.1 mEq or 150 mg Mg(OH)$_2$ | 20 mg Ac-Di-Sol |
|  | 3.0 mEq or 250 mg NaHCO$_3$ | 10 mg Klucel |
|  | 8.1 mEq or 400 mg total antacid | 4 mg magnesium stearate |
|  |  | Size 2 capsule |

TABLE 8.F

Omeprazole (60 mg) Capsule

| PPI | Antacid | Excipient |
|---|---|---|
| 120 mg omeprazole per capsule | 8.6 mEq or 250 mg Mg(OH)$_2$ | 30 mg Ac-Di-Sol |
|  | 2.4 mEq or 200 mg NaHCO$_3$ | 30 mg Klucel |
|  | 11.0 mEq or 450 mg total antacid | 8 mg magnesium stearate |
|  |  | Size 1 capsule |

TABLE 8.G

Omeprazole (10 mg) Capsule

| PPI | Antacid | Excipient |
|---|---|---|
| 10 mg microencapsulated omeprazole per capsule | 3.4 mEq or 100 mg Mg(OH)$_2$ | 18 mg Ac-Di-Sol |
|  | 3.0 mEq or 250 mg NaHCO$_3$ | 15 mg |
|  | 6.4 mEq or 350 mg total antacid | Microcrystalline) Cellulose (MCC, PH102  7 mg magnesium stearate |
|  |  | Size 2 capsule |

TABLE 8.H

Omeprazole (40 mg) Capsule

| PPI | Antacid | Excipient |
|---|---|---|
| 40 mg microencapsulated | 3.4 mEq or 100 mg Mg(OH)$_2$ 2.4 mEq or 200 mg NaHCO$_3$ | 20 mg Ac-Di-Sol 5 mg magnesium |
| omeprazole per capsule | 5.8 mEq or 300 mg total antacid | stearate Size 2 capsule |

Example 9

Tablet Formulations

The following specific formulations are provided by way of reference only and are not intended to limit the scope of the invention. Each formulation contains therapeutically effective doses of PPI and sufficient antacid to prevent acid degradation of at least some of the PPI by raising the pH of gastric fluid. Amounts of antacid are expressed in weight as well as in molar equivalents (mEq). The tablets are prepared by blending the PPI and antacids, and homogeneously blending with excipients as shown in Tables 9.A. to 9.H. below. The appropriate weight of bulk blended composition is compressed using oval shaped toolings in a rotary press (Manesty Express) to achieve a hardness of 15-20 kPa. The PPI can be in a micronized form.

TABLE 9.A

Omeprazole (20 mg) Tablet

| PPI | Antacid | Excipient |
|---|---|---|
| 20 mg omeprazole per | 5.1 mEq or 150 mg Mg(OH)$_2$ 4.8 mEq or 400 mg NaHCO$_3$ | 30 mg Ac-Di-Sol 65 mg Klucel |
| tablet | 9.9 mEq or 550 mg total antacid | 10 mg magnesium stearate |

TABLE 9.B

Omeprazole (40 mg) Tablet

| PPI | Antacid | Excipient |
|---|---|---|
| 40 mg microencapsulated | 5.1 mEq or 150 mg Mg(OH)$_2$ 3.0 mEq or 250 mg NaHCO$_3$ | 20 mg Ac-Di-Sol 40 mg |
| omeprazole per tablet | 8.1 mEq or 350 mg total antacid | Microcrystalline cellulose (MCC, PH102) 7 mg magnesium stearate |

TABLE 9.C

Lansoprazole (15 mg) Tablet

| PPI | Antacid | Excipient |
|---|---|---|
| 15 mg microencapsulated | 8.6 mEq or 250 mg Mg(OH)$_2$ 2.4 mEq or 200 mg NaHCO$_3$ | 30 mg Ac-Di-Sol 55 mg Plasdone |
| lansoprazole per tablet | 11.0 mEq or 450 mg total antacid | 8 mg magnesium stearate |

TABLE 9.D

Lansoprazole (30 mg) Tablet

| PPI | Antacid | Excipient |
|---|---|---|
| 30 mg lansoprazole | 6.2 mEq or 180 mg Mg(OH)$_2$ 4.2 mEq or 350 mg NaHCO$_3$ | 25 mg Ac-Di-Sol 55 mg Klucel |
| per tablet | 10.4 mEq or 430 mg total antacid | 8 mg magnesium stearate |

TABLE 9.E

Omeprazole (60 mg) Tablet

| PPI | Antacid | Excipient |
|---|---|---|
| 60 mg omeprazole | 7.5 mEq or 220 mg Mg(OH)$_2$ 3.0 mEq or 250 mg NaHCO$_3$ | 20 mg Ac-Di-Sol 60 mg Klucel |
| per tablet | 10.5 mEq or 470 mg total antacid | 10 mg magnesium stearate |

TABLE 9.F

Omeprazole (20 mg) Tablet

| PPI | Antacid | Excipient |
|---|---|---|
| 20 mg omeprazole | 7.5 mEq or 220 mg Mg(OH)$_2$ 2.4 mEq or 200 mg NaHCO$_3$ | 20 mg Ac-Di-Sol 60 mg Klucel |
| per tablet | 9.9 mEq or 420 mg total antacid | 8 mg magnesium stearate |

TABLE 9.G

Omeprazole (10 mg) Tablet

| PPI | Antacid | Excipient |
|---|---|---|
| 10 mg microencapsulated | 3.4 mEq or 100 mg Mg(OH)$_2$ 3.0 mEq or 250 mg NaHCO$_3$ | 15 mg Ac-Di-Sol 40 mg Klucel |
| omeprazole per tablet | 6.4 mEq or 350 mg total antacid | 6 mg magnesium stearate |

TABLE 9.H

Omeprazole (40 mg) Tablet

| PPI | Antacid | Excipient |
|---|---|---|
| 40 mg micro- | 5.1 mEq or 150 mg Mg(OH)$_2$ 3.8 mEq or 315 mg NaHCO$_3$ | 20 mg Ac-Di-Sol 50 mg Microcrystalline |
| encapsulated omeprazole per tablet | 8.9 mEq or 465 mg total antacid | Cellulose (MCC, PH102) 10 mg magnesium stearate |

Example 10

Chewable Tablet Formulations

The following specific formulations are provided by way of reference only and are not intended to limit the scope of the invention. Each formulation contains therapeutically effective doses of PPI and sufficient antacid to prevent acid degradation of at least some of the PPI by raising the pH of gastric fluid. Amounts of antacid are expressed in weight as well as in molar equivalents (mEq). The tablets are prepared by blending the PPI and antacids, and homogeneously blending with excipients as shown in Tables 10.A to 10.H. below. The appropriate weight of bulk blended composition is compressed using 17 mm FFBE toolings in a rotary press (Manesty Express) to achieve a hardness of 10-14 kPa. The PPI can be in a micronized form.

TABLE 10.A

Omeprazole (20 mg) Chewable Tablet

| PPI | Antacid | Excipient |
|---|---|---|
| 20 mg micro-encapsulated omeprazole per tablet | 5.1 mEq or 150 mg Mg(OH)$_2$<br>3.8 mEq or 315 mg NaHCO$_3$<br>8.9 mEq or 465 mg total antacid | 100 mg Xylitab<br>30 mg Ac-Di-Sol<br>80 mg Klucel<br>20 mg Sucralose<br>10 mg cherry flavor<br>10 mg magnesium stearate<br>1 mg Red #40 Lake |

TABLE 10.B

Omeprazole (40 mg) Chewable Tablet

| PPI | Antacid | Excipient |
|---|---|---|
| 40 mg micro-encapsulated omeprazole per tablet | 7.5 mEq or 220 mg Mg(OH)$_2$<br>2.4 mEq or 200 mg NaHCO$_3$<br>9.9 mEq or 420 mg total antacid | 100 mg Dipac sugar<br>20 mg Ac-Di-Sol<br>80 mg Klucel<br>17 mg grape flavor<br>11 mg magnesium stearate<br>1 mg Red #40 Lake<br>1 mg Blue #2 Lake |

TABLE 10.C

Lansoprazole (15 mg) Chewable Tablet

| PPI | Antacid | Excipient |
|---|---|---|
| 15 mg lansoprazole per tablet | 5.1 mEq or 150 mg Mg(OH)$_2$<br>2.4 mEq or 200 mg NaHCO$_3$<br>7.5 mEq or 350 mg total antacid | 80 mg Xylitab<br>25 mg Ac-Di-Sol<br>70 mg Microcrystalline Cellulose<br>50 mg Asulfame-K<br>15 mg grape flavor<br>10 mg magnesium stearate<br>1 mg red #40 lake<br>1 mg blue #2 lake |

TABLE 10.D

Lansoprazole (30 mg) Chewable Tablet

| PPI | Antacid | Excipient |
|---|---|---|
| 30 mg micro-encapsulated lansoprazole per tablet | 5.1 mEq or 150 mg Mg(OH)$_2$<br>3.8 mEq or 315 mg NaHCO$_3$<br>8.9 mEq or 465 mg total antacid | 70 mg Destab Sugar<br>30 mg Ac-Di-Sol<br>100 mg Klucel<br>20 mg Asulfame-K<br>15 mg cherry flavor<br>9 mg magnesium stearate<br>1 mg Red #40 Lake |

TABLE 10.E

Omeprazole (60 mg) Chewable Tablet

| PPI | Antacid | Excipient |
|---|---|---|
| 60 mg micro-encapsulated omeprazole per tablet | 4.4 mEq or 220 mg Ca(OH)$_2$<br>3.6 mEq or 300 mg NaHCO$_3$<br>8.0 mEq or 520 mg total antacid | 80 mg Xylitab<br>30 mg Ac-Di-Sol<br>100 mg Klucel<br>35 mg Sucralose<br>10 mg cherry flavor<br>9 mg magnesium stearate<br>2 mg Red #40 Lake |

TABLE 10.F

Omeprazole (60 mg) Chewable Tablet

| PPI | Antacid | Excipient |
|---|---|---|
| 60 mg omeprazole per tablet | 3.0 mEq or 150 mg Ca(OH)$_2$<br>3.0 mEq or 250 mg NaHCO$_3$<br>6.0 mEq or 400 mg total antacid | 70 mg Xylitab<br>25 mg Ac-Di-Sol<br>90 mg Microcrystalline Cellulose (PH 102)<br>8 mg mint flavor<br>10 mg magnesium stearate |

TABLE 10.G

Omeprazole (10 mg) Chewable Tablet

| PPI | Antacid | Excipient |
|---|---|---|
| 10 mg omeprazole per tablet | 8.0 mEq or 400 mg Ca(OH)$_2$<br>3.6 mEq or 300 mg NaHCO$_3$<br>11.6 mEq or 700 mg total antacid | 110 mg Ditab Sugar<br>30 mg Ac-Di-Sol<br>20 mg Sucralose<br>100 mg Klucel<br>15 mg mint flavor<br>15 mg magnesium stearate |

TABLE 10.H

Omeprazole (40 mg) Chewable Tablet

| PPI | Antacid | Excipient |
|---|---|---|
| 40 mg microencapsulated omeprazole per tablet | 7.5 mEq or 350 mg Ca(OH)$_2$<br>3.0 mEq or 250 mg NaHCO$_3$<br>10.5 mEq or 600 mg total antacid | 70 mg Xylitab<br>30 mg Ac-Di-Sol<br>10 mg Sucralose<br>80 mg Klucel<br>10 mg mint flavor<br>8 mg magnesium stearate |

Example 11

Bite-Disintegration Chewable Tablet Formulations

The following specific formulations are provided by way of reference only and are not intended to limit the scope of the invention. Each formulation contains therapeutically effective doses of PPI and sufficient antacid to prevent acid degradation of at least some of the PPI by raising the pH of gastric fluid. Amounts of antacid are expressed in weight as well as in molar equivalents (mEq). The tablets are prepared by blending the PPI with antacids, and homogeneously blending with excipients as shown in Tables 11.A to 11.H. below. The appropriate weight of bulk blended composition is compressed using 10 mm FFBE toolings in a rotary press (Manesty Express) to achieve a hardness of 5-9 kPa. The PPI can be in a micronized form.

TABLE 11.A

Omeprazole (20 mg) Bite-Disintegration Chewable Tablet

| PPI | Antacid | Excipient |
|---|---|---|
| 20 mg per tablet | 7.5 mEq or 350 mg $Ca(OH)_2$<br>3.0 mEq or 250 mg $NaHCO_3$ | 20 mg sucralose<br>40 mg Ac-Di-Sol |
| | 10.5 mEq or 600 mg total antacid | 30 mg pregelatinized starch<br>30 mg Klucel<br>15 mg cherry flavor<br>8 mg magnesium stearate<br>1 mg Red #40 Lake |

TABLE 11.B

Omeprazole (40 mg) Bite-Disintegration Chewable Tablet

| PPI | Antacid | Excipient |
|---|---|---|
| 40 mg microencapsulated omeprazole per tablet | 8.0 mEq or 400 mg $Ca(OH)_2$<br>3.6 mEq or 300 mg $NaHCO_3$ | 20 mg sucralose<br>40 mg Ac-Di-Sol |
| | 11.6 mEq or 700 mg total | 35 mg pregelatinized starch<br>25 mg Klucel<br>15 mg cherry flavor<br>8 mg magnesium stearate<br>1 mg Red #40 Lake |

TABLE 11.C

Lansoprazole (15 mg) Bite-Disintegration Chewable Tablet

| PPI | Antacid | Excipient |
|---|---|---|
| 15 mg lansoprazole per tablet | 7.9 mEq or 230 mg $Mg(OH)_2$<br>3.6 mEq or 300 mg $NaHCO_3$ | 20 mg sucralose<br>35 mg Ac-Di-Sol |
| | 11.5 mEq or 530 mg total | 35 mg pregelatinized starch<br>25 mg Klucel<br>17 mg grape flavor<br>8 mg magnesium stearate<br>1 mg Red #40 Lake<br>1 mg Blue #2 lake |

TABLE 11.D

Lansoprazole (30 mg) Bite-Disintegration Chewable Tablet

| PPI | Antacid | Excipient |
|---|---|---|
| 30 mg microencapsulated lansoprazole per tablet | 5.1 mEq or 150 mg $Mg(OH)_2$<br>3.8 mEq or 315 mg $NaHCO_3$ | 27 mg sucralose<br>40 mg Ac-Di-Sol |
| | 8.9 mEq or 465 mg total antacid | 35 mg pregelatinized starch<br>30 mg Microcrystalline Cellulose (PH101)<br>20 mg cherry flavor<br>10 mg magnesium stearate<br>2 mg Red #40 Lake |

TABLE 11.E

Omeprazole (60 mg) Bite-Disintegration Chewable Tablet

| PPI | Antacid | Excipient |
|---|---|---|
| 60 mg micro-encapsulated omeprazole per tablet | 7.9 mEq or 230 mg $Mg(OH)_2$<br>3.0 mEq or 250 mg $NaHCO_3$ | 34 mg sucralose<br>30 mg Ac-Di-Sol |
| | 10.9 mEq or 480 mg total antacid | 35 mg pregelatinized starch<br>30 mg Klucel<br>25 mg cherry flavor<br>10 mg magnesium stearate<br>2 mg Red #40 Lake |

TABLE 11.F

Omeprazole (60 mg) Bite-Disintegration Chewable Tablet

| PPI | Antacid | Excipient |
|---|---|---|
| 60 mg omeprazole per tablet | 7.0 mEq or 350 mg $Ca(OH)_2$<br>3.0 mEq or 250 mg $NaHCO_3$ | 30 mg sucralose<br>40 mg Ac-Di-Sol |
| | 10.0 mEq or 600 mg total antacid | 30 mg pregelatinized starch<br>30 mg Klucel<br>40 mg Xylitab<br>7 mg mint flavor<br>10 mg magnesium stearate |

TABLE 11.G

Omeprazole (10 mg) Bite-Disintegration Chewable Tablet

| PPI | Antacid | Excipient |
|---|---|---|
| 10 mg omeprazole per tablet | 5.0 mEq or 250 mg $Ca(OH)_2$<br>2.9 mEq or 240 mg $NaHCO_3$ | 20 mg sucralose<br>40 mg Ac-Di-Sol |
| | 7.9 mEq or 490 mg total antacid | 30 mg pregelatinized starch<br>30 mg Klucel<br>15 mg cherry flavor<br>8 mg magnesium stearate<br>1 mg Red #40 Lake |

TABLE 11.H

Omeprazole (40 mg) Bite-Disintegration Chewable Tablet

| PPI | Antacid | Excipient |
|---|---|---|
| 40 mg micro-encapsulated omeprazole per tablet | 8.0 mEq or 400 mg Ca(OH)$_2$<br>2.9 mEq or 240 mg NaHCO$_3$<br>10.9 mEq or 1590 mg total antacid | 30 mg sucralose<br>40 mg Ac-Di-Sol<br>30 mg pregelatinized starch<br>30 mg Klucel<br>40 mg Xylitab<br>7 mg mint flavor<br>10 mg magnesium stearate |

Example 12

Powder for Suspension Formulations

The following specific formulations are provided by way of reference only and are not intended to limit the scope of the invention. Each formulation contains therapeutically effective doses of PPI and sufficient antacid to prevent acid degradation of at least some of the PPI by raising the pH of gastric fluid. The PPI can be in a micronized form.

TABLE 12.A

Microencapsulated Omeprazole (20/40/60/120 mg) Powder for Suspension

| | 1 | 2 | 3 | 4 | 5 | 6 | 7 | 8 | 9 | 10 |
|---|---|---|---|---|---|---|---|---|---|---|
| Microencapsulated Omeprazole | 20 | 20 | 20 | 40 | 40 | 40 | 60 | 60 | 120 | 120 |
| Sodium Bicarbonate | 200 | 220 | 300 | 140 | 160 | 200 | 300 | 280 | 150 | 200 |
| Magnesium Hydroxide | 250 | 170 | 150 | 250 | 170 | 150 | 170 | 150 | 100 | 150 |
| Calcium Carbonate | 0 | 0 | 0 | 0 | 100 | 150 | 0 | 100 | 0 | 150 |
| Xylitol 300 (sweetener) | 1000 | 1000 | 1000 | 1000 | 1000 | 1000 | 1000 | 1000 | 1000 | 1000 |
| Sucrose-powder (sweetener) | 1000 | 1000 | 1000 | 1000 | 1000 | 1000 | 1000 | 1000 | 1000 | 1000 |
| Sucralose (sweetener) | 60 | 100 | 150 | 75 | 100 | 70 | 80 | 130 | 125 | 80 |
| Xanthan Gum | 10 | 55 | 31 | 80 | 39 | 48 | 72 | 25 | 64 | 68 |
| Peach Flavor | 33 | 15 | 75 | 32 | 60 | 50 | 77 | 38 | 35 | 62 |
| Peppermint | 13 | 10 | 29 | 28 | 36 | 42 | 56 | 17 | 16 | 50 |
| Total Weight | 2586 | 2590 | 2755 | 2645 | 2705 | 2750 | 2815 | 2800 | 2610 | 2880 |
| Total ANC | 11.0 | 8.4 | 8.7 | 10.2 | 9.7 | 10.5 | 9.4 | 10.5 | 5.2 | 10.5 |

TABLE 12.B

Omeprazole (20 mg) Powder for Suspension

| | 1 | 2 | 3 | 4 | 5 | 6 | 7 | 8 | 9 | 10 |
|---|---|---|---|---|---|---|---|---|---|---|
| Omeprazole | 20 | 20 | 20 | 20 | 20 | 20 | 20 | 20 | 20 | 20 |
| Sodium Bicarbonate | 200 | 220 | 300 | 140 | 160 | 200 | 300 | 280 | 150 | 200 |
| Magnesium Hydroxide | 250 | 170 | 150 | 250 | 170 | 150 | 170 | 150 | 100 | 150 |
| Calcium Carbonate | 0 | 0 | 0 | 0 | 100 | 150 | 0 | 100 | 0 | 150 |
| Xylitol 300 (sweetener) | 1000 | 1000 | 1000 | 1000 | 1000 | 1000 | 1000 | 1000 | 1000 | 1000 |
| Sucrose-powder (sweetener) | 1000 | 1000 | 1000 | 1000 | 1000 | 1000 | 1000 | 1000 | 1000 | 1000 |
| Sucralose (sweetener) | 60 | 100 | 150 | 75 | 100 | 70 | 80 | 130 | 125 | 80 |
| Xanthan Gum | 10 | 55 | 31 | 80 | 39 | 48 | 72 | 25 | 64 | 68 |
| Peach Flavor | 33 | 15 | 75 | 32 | 60 | 50 | 77 | 38 | 35 | 62 |
| Peppermint | 13 | 10 | 29 | 28 | 36 | 42 | 56 | 17 | 16 | 50 |
| Total Weight | 2586 | 2590 | 2755 | 2625 | 2685 | 2730 | 2775 | 2760 | 2510 | 2780 |
| Total ANC | 11.0 | 8.4 | 8.7 | 10.2 | 9.7 | 10.5 | 9.4 | 10.5 | 5.2 | 10.5 |

TABLE 12.C

Omeprazole (40 mg) Powder for Suspension

| | 1 | 2 | 3 | 4 | 5 | 6 | 7 | 8 | 9 | 10 |
|---|---|---|---|---|---|---|---|---|---|---|
| Omeprazole | 40 | 40 | 40 | 40 | 40 | 40 | 40 | 40 | 40 | 40 |
| Sodium Bicarbonate | 200 | 220 | 300 | 140 | 160 | 200 | 300 | 280 | 150 | 200 |
| Magnesium Hydroxide | 250 | 170 | 150 | 250 | 170 | 150 | 170 | 150 | 100 | 150 |
| Calcium Carbonate | 0 | 0 | 0 | 0 | 100 | 150 | 0 | 100 | 0 | 150 |
| Xylitol 300 (sweetener) | 1000 | 1000 | 1000 | 1000 | 1000 | 1000 | 1000 | 1000 | 1000 | 1000 |
| Sucrose-powder (sweetener) | 1000 | 1000 | 1000 | 1000 | 1000 | 1000 | 1000 | 1000 | 1000 | 1000 |
| Sucralose (sweetener) | 60 | 100 | 150 | 75 | 100 | 70 | 80 | 130 | 125 | 80 |

TABLE 12.C-continued

| Omeprazole (40 mg) Powder for Suspension | | | | | | | | | | |
|---|---|---|---|---|---|---|---|---|---|---|
| | 1 | 2 | 3 | 4 | 5 | 6 | 7 | 8 | 9 | 10 |
| Xanthan Gum 75 | 10 | 55 | 31 | 80 | 39 | 48 | 72 | 25 | 64 | 68 |
| Peach Flavor | 33 | 15 | 75 | 32 | 60 | 50 | 77 | 38 | 35 | 62 |
| Peppermint | 13 | 10 | 29 | 28 | 36 | 42 | 56 | 17 | 16 | 50 |
| Total Weight | 2606 | 2610 | 2775 | 2645 | 2705 | 2750 | 2795 | 2780 | 2530 | 2800 |
| Total ANC | 11.0 | 8.4 | 8.7 | 10.2 | 9.7 | 10.5 | 9.4 | 10.5 | 5.2 | 10.5 |

TABLE 12.D

| Omeprazole (60 mg) Powder for Suspension | | | | | | | | | | |
|---|---|---|---|---|---|---|---|---|---|---|
| | 1 | 2 | 3 | 4 | 5 | 6 | 7 | 8 | 9 | 10 |
| Omeprazole | 60 | 60 | 60 | 60 | 60 | 60 | 60 | 60 | 60 | 60 |
| Sodium Bicarbonate | 200 | 220 | 300 | 140 | 160 | 200 | 300 | 280 | 150 | 200 |
| Magnesium Hydroxide | 250 | 170 | 150 | 250 | 170 | 150 | 170 | 150 | 100 | 150 |
| Calcium Carbonate | 0 | 0 | 0 | 0 | 100 | 150 | 0 | 100 | 0 | 150 |
| Xylitol 300 (sweetener) | 1000 | 1000 | 1000 | 1000 | 1000 | 1000 | 1000 | 1000 | 1000 | 1000 |
| Sucrose-powder (sweetener) | 1000 | 1000 | 1000 | 1000 | 1000 | 1000 | 1000 | 1000 | 1000 | 1000 |
| Sucralose (sweetener) | 60 | 100 | 150 | 75 | 100 | 70 | 80 | 130 | 125 | 80 |
| Xanthan Gum 75 | 10 | 55 | 31 | 80 | 39 | 48 | 72 | 25 | 64 | 68 |
| Peach Flavor | 33 | 15 | 75 | 32 | 60 | 50 | 77 | 38 | 35 | 62 |
| Peppermint | 13 | 10 | 29 | 28 | 36 | 42 | 56 | 17 | 16 | 50 |
| Total Weight | 2626 | 2630 | 2795 | 2665 | 2725 | 2770 | 2815 | 2800 | 2550 | 2820 |
| Total ANC | 11.0 | 8.4 | 8.7 | 10.2 | 9.7 | 10.5 | 9.4 | 10.5 | 5.2 | 10.5 |

Example 13

Naked or Microencapsulated Omeprazole 40 mg Chewable Tablets, Capsules, and Caplets are Pharmacokinetically Bioequivalent to Prilosec® Delayed-Release Capsules 40 mg with Respect to Area Under the Curve (AUC)

This trial was conducted as an open-label, single-dose, crossover trial, with each subject receiving up to twelve different oral omeprazole formulations, one in each of the twelve treatment periods. Each dose was followed by a minimum 7-day washout. Omeprazole was administered at a dose of 40 mg. The amount of antacid used in the formulations varied as set forth in Table 13A. All formulations were administered with about 120 ml (4 oz) of water after an overnight fast and 1 hour prior to a standardized, high-fat breakfast. Within a given treatment period, the same treatment was administered to all subjects.

The omeprazole was delivered as either Prilosec® or as an immediate-release formulation according to the invention (i.e. without an enteric coating). Omeprazole was formulated as uncoated or microencapsulated granules a powder in a capsule, a caplet or in a compressed chewable tablet.

Selection of the exact formulation for each treatment period is set forth in Table 13A, below.

TABLE 13A

The pharmacokinetic release trial periods 1–12 with the tested omeprazole dosage forms. (All dosage forms contained 40 mg omeprazole as follows: Prilosec ® 40 mg, or a capsule, tablet, or caplet form, 40 mg).

| Period | Study Material |
|---|---|
| 1 (Prilosec ®) | Prilosec ® (40 mg omeprazole) |
| 2 (SAN - 10A) | SAN - 10A Capsule, 21.1 mEq (420 mg SB & 470 mg MH) Utilizes <100 mesh MH |

TABLE 13A-continued

The pharmacokinetic release trial periods 1–12 with the tested omeprazole dosage forms. (All dosage forms contained 40 mg omeprazole as follows: Prilosec ® 40 mg, or a capsule, tablet, or caplet form, 40 mg).

| Period | Study Material |
|---|---|
| 3 (SAN - 15A) | Period 3 Tablet, 30.7 mEq (850 mg SB & 600 mg MH) "Naked" OME & MS95 MH |
| 4 (SAN - 10B) | SAN - 10B Capsule, 21.1 mEq (420 mg SB & 470 mg MH) Utilizes <60 mesh MH |
| 5 (SAN - 15B) | Period 5 Tablet, 30.7 mEq (850 mg SB & 600 mg MH) with Klucel eAPI & MS95 MH |
| 6 (SAN - 10J) | SAN - 10J Capsule, 19.1 mEq (378 mg SB & 425 mg MH) Utilizes MS95 MH |
| 7 (SAN - 15C) | Period 7 Tablet, 30.7 mEq (850 mg SB & 600 mg MH) with Methocel eAPI & MS95 MH |
| 8 (SAN - 10H) | SAN - 10H Capsule, 17.9 mEq (420 mg SB & 375 mg MH) Utilizes <60 mesh MH |
| 9 (SAN - 10BB) | SAN - 10BB Capsule, 13.1 mEq (1100 mg SB) |
| 10 (SAN - 15D) | Period 10 Caplet, 18.8 mEq (280 mg SB & 450 mg MH) eAPI, MS95 MH & 4.9% disintegrant |
| 11 (SAN - 10C) | SAN - 10C Capsule, 10.5 mEq (880 mg SB) |
| 12 (SAN - 15E) | Period 12 Caplet, 18.8 mEq (280 mg SB & 450 mg MH) eAPI, MS95 MH & 7.9% disintegrant |

Volunteers were screened for up to 14 days before baseline measurements of blood plasma levels of omeprazole. In each period, a standardized high-fat breakfast was given in the clinic 1 hour after dosing of omeprazole. Blood samples for determination of plasma omeprazole concentrations were collected for 12 hours post treatment.

Duration of Treatment

Including screening, subjects participated in this trial for up to 170 days.

Design Rationale

This trial was designed to assess the pharmacokinetics of immediate-release omeprazole chewable tablets, oral capsule and caplets versus the Prilosec® 40 mg delayed-release formulation. The duration of the trial for each subject was approximately 24 weeks, including up to 14 days for screening and a minimum 7 day wash-out period between omeprazole doses.

Data from 12 healthy male subjects were expected to provide adequate power to assess pharmacokinetics and safety using descriptive statistics. The descriptive statistics were assessed using the pharmacokinetic parameters: Tmax, Cmax, AUC(0-t), AUC(0-inf), T½ and kel. Safety evaluations were based on the occurrence (vel non) of adverse events, blood chemistry and hematology, use of concomitant medications and change from baseline in physical examination findings and vital signs.

As the study employed a single dose of omeprazole for each period of dosing, the analysis focused on Day 1 of dosing.

The time of drug administration (after an overnight fast and 1 hour prior to a meal) meets the regulatory guidance for bioequivalence (fasting) and anticipates actual use.

Treatments Administered:

The treatments administered to subjects in this trial are listed in Table 13A, above. In general, the treatment protocol entailed a 14 day assessment period, followed by a first period (Period 1) in which Prilosec® 40 mg delayed release capsule was administered to the subjects, after an overnight fast, and 1 hour prior to a standardized high-fat breakfast. Plasma sampling was conducted for 6 hour post-dose. Period 1 was followed by a 7-14 day washout period, during which the plasma levels of omeprazole were expected to decrease to a steady baseline. The second through twelfth periods (Periods 2-12) were conducted in a similar manner to Period 1, in each period substituting a dosage form according to the invention for the delayed-release formulation used in Period 1. The specific dosage forms used in the study are set forth in Table 13A, above. Each of the 12 healthy male volunteers received the same course of treatment without randomization.

Pharmacokinetic Sampling, Analytical Methods, and Parameters

Blood samples (3 mL) were obtained by venipuncture within 30 minutes before each dose and at 0, 5, 10, 15, 20, 30, 45, 60, 90, 120, 180, 240, 300, 360 minutes (6 hours) after delivery of each dose during each trial period. Zero time was the time that the subject swallowed a capsule, caplet or chewable tablet of trial drug.

Plasma omeprazole concentrations were measured using a previously validated liquid chromatography mass spectrometry (LC-MSIMS) assay (MDS Pharma Services, Lincoln, Nebr.). The linear assay range was 5.0 to 750 ng/mL.

The following pharmacokinetic parameters were measured for each subject:

Plasma omeprazole concentration at each sampling time

Peak omeprazole plasma concentration (Cmax) and the time at which Cmax is observed (Tmax) obtained directly from the data without interpolation Terminal elimination rate constant (Kel) determined from a log-linear regression analysis of the terminal plasma omeprazole concentrations Half-life of drug elimination (T½) calculated as 0.693/Kel Area under the plasma drug time-concentration curve calculated from 0 time to last time point evaluated [AUC(0-t)] calculated using the trapezoidal rule with the plasma concentration at time t being the last measurable concentration Area under the plasma drug time-concentration curve calculated from 0 time and extrapolated to infinity [AUC(0-inf)] calculated as AUC(0-t)+Ct/Kel, where Ct is the last measurable plasma concentration (at time t) and Kel is the terminal elimination rate constant defined above Primary Endpoint The primary pharmacokinetic endpoint was the bioavailability of omeprazole [AUC(0-inf)].

Pharmacokinetic Analysis

For the analysis of data collected on Day 1 of each period (pre-meal dosing), an analysis of variance (ANOVA) model was used to test the bioequivalence of each of the tested drug formulations. The model included the following factors: treatment, period, sequence, and subject nested within sequence. Ninety percent confidence intervals (CIs) for treatment differences were calculated; the endpoints of these CIs were then reverse transformed to represent CIs about the percent mean ratios on the original scale. With respect to AUC(0-inf) and Cmax, equivalence was declared for each parameter if the bounds of the 90% CIs for the percent mean ratio, comparing a composition according to the invention (Periods 2-12) with Prilosec, were between 80% and 125%.

Determination of Sample Size

A sample size of 12 initial healthy male subjects was considered sufficient to ensure that at least 5 subjects finished the entire trial.

Pharmacokinetic Results

Figure 14:
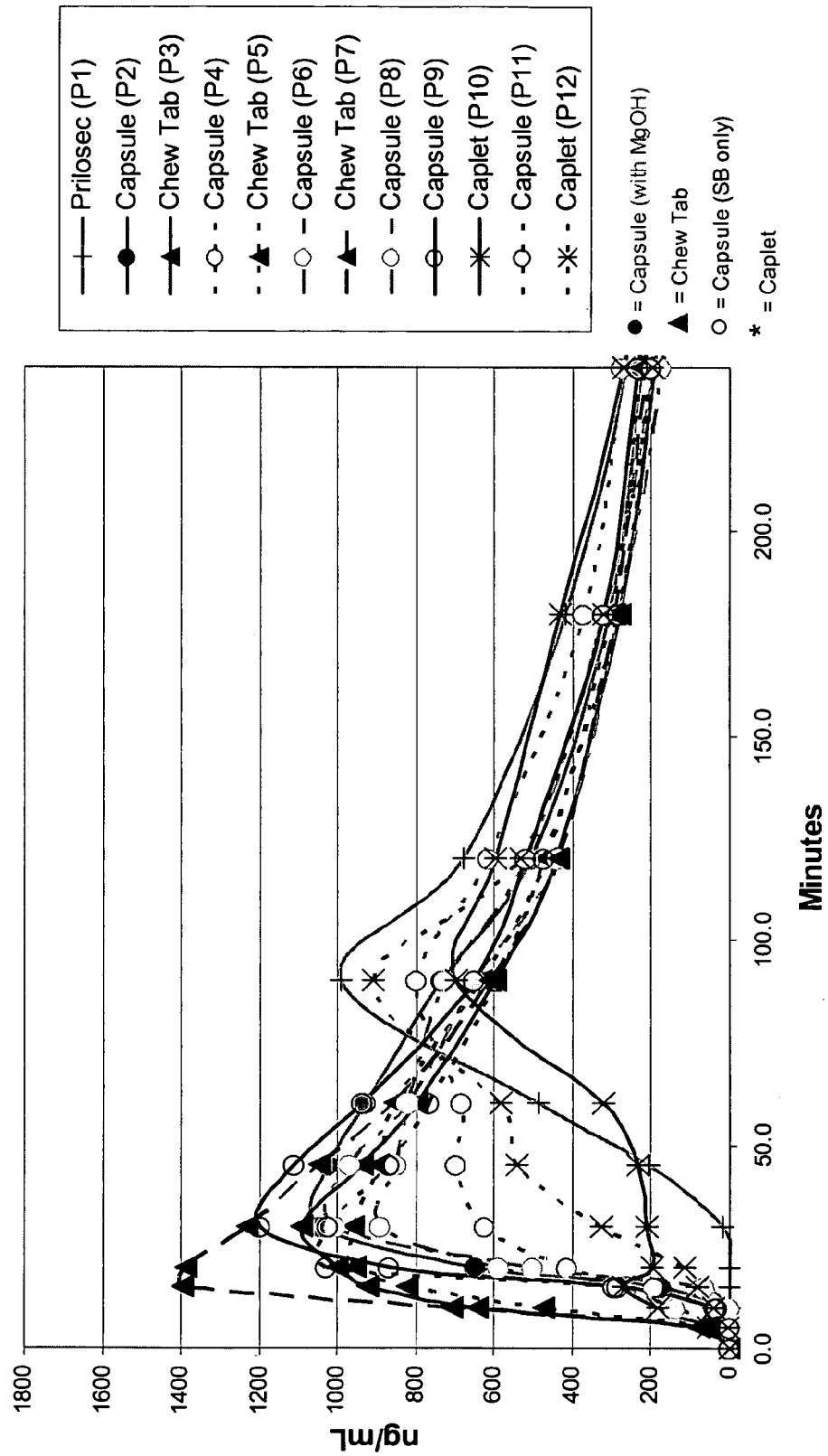
FIG. 14 is a graph comparing the average pharmacokinetic release profiles of immediate release omeprazole chewable tablets (SAN-15A, SAN-15B and SAN-15C), capsules (SAN-10A, SAN-10B, SAN-10C, SAN-10E, SAN-10H, SAN-10BB), and a caplets (SAN-15D and SAN-15E) according to the present invention as compared to Priolosec® enteric coated omeprazole 40 mg. The compositions according to the present invention are all set forth in Table 13A, below.
Figure 15:
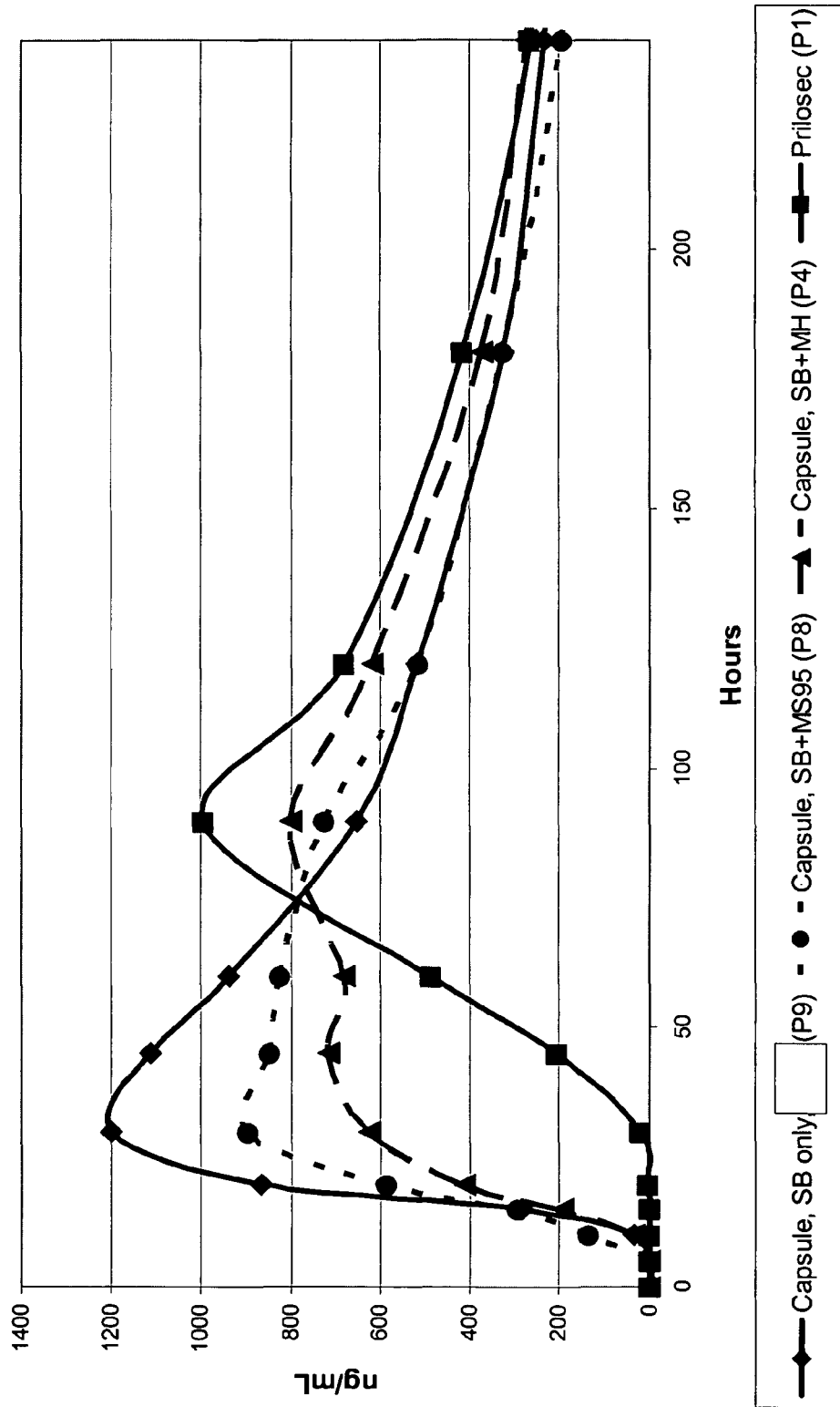
FIG. 15 is a graph comparing the average pharmacokinetic release profiles of SAN-10BB (P9), SAN-10H (P8) and SAN-10B (P4) omeprazole capsules, 40 mg per dose. The formulations are described in detail in Example 13.
Figure 16:
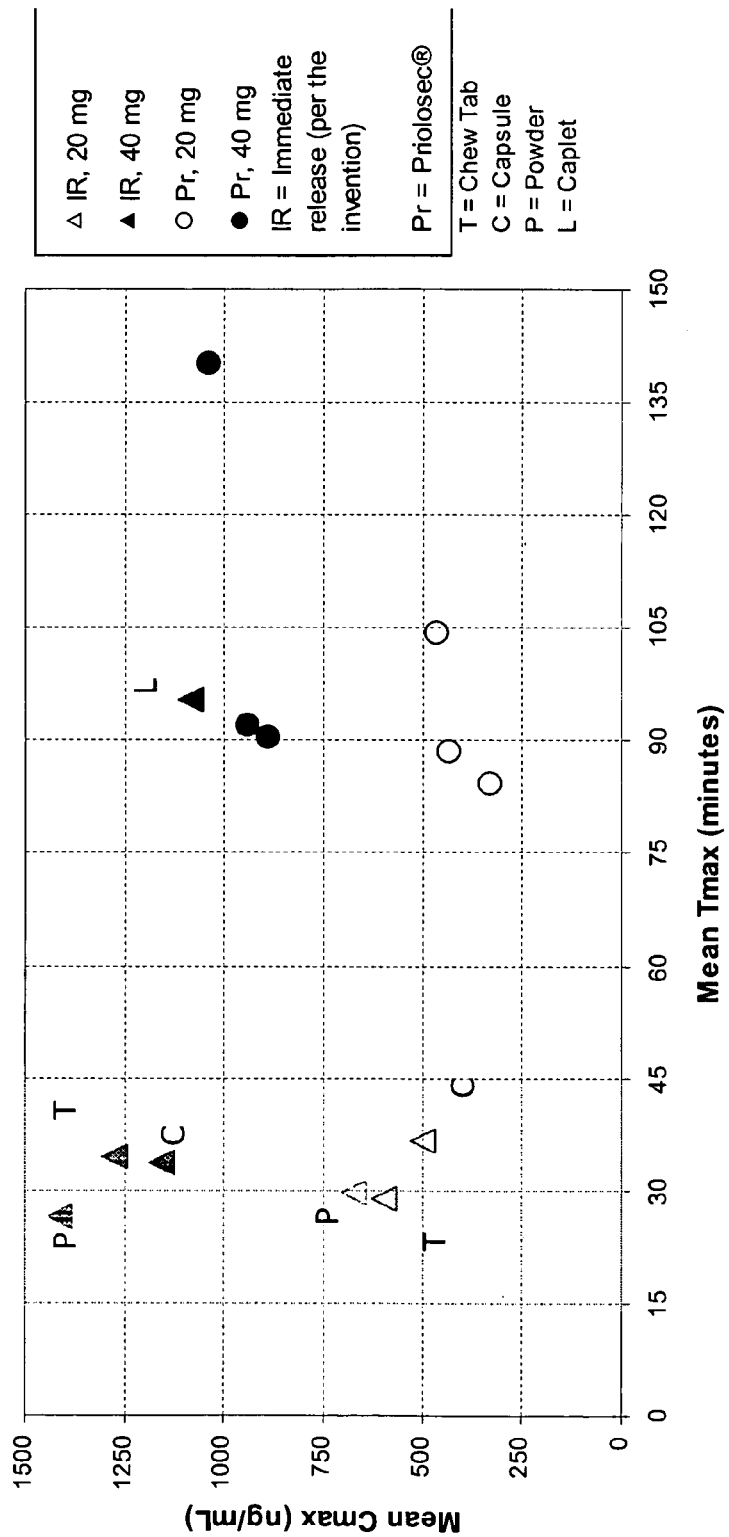
FIG. 16 is a graph comparing the Cmax and Tmax values for immediate release omeprazole powder, capsule, chew tab and caplet formulations according to the present invention with those of Prilosec® brand enteric coated omeprazole. The omeprazole powder is immediate release omeprazole powder for suspension, 20 or 40 mg micronized omeprazole and 1680 mg (20 mEq) of sodium bicarbonate, described in Example 16; the chewable tablets are 20 or 40 mg SAN-38 chewable tablets, as described herein; the capsules are SAN-7E (40 mg) or SAN-7F (20 mg) capsules as decribed in Examples 7, 14 and 15, below.
Figure 18:
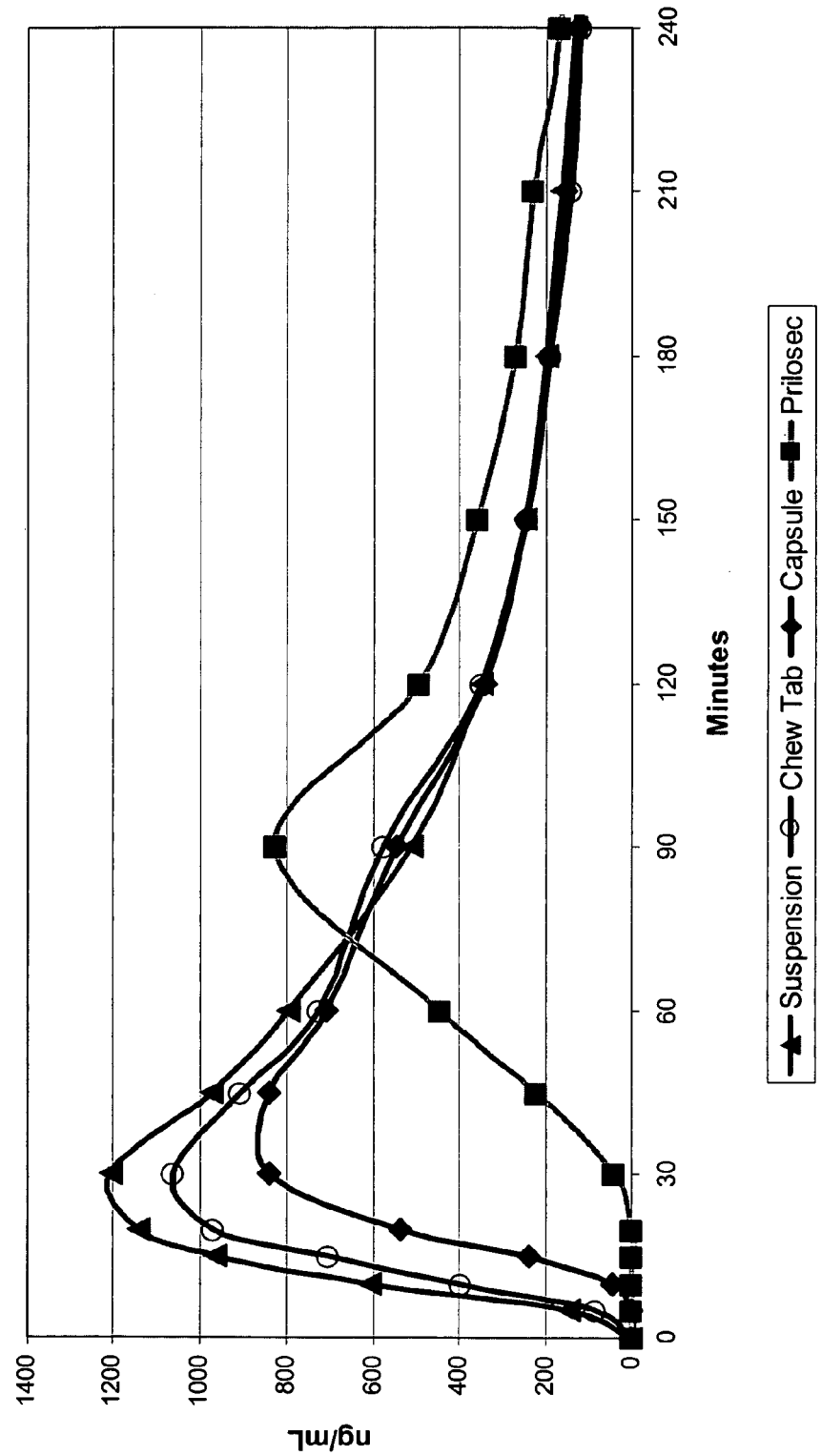
FIG. 18 is a graph comparing the average pharmacokinetic release profiles of immediate release omeprazole suspension (40 mg)(Example 16), chewable tablets (40 mg), capsule (40 mg)(Example 7E), and Prilosec® enteric coated omeprazole (40 mg) from the human clinical trial described in Example 15B, Day 1.
Figure 19:
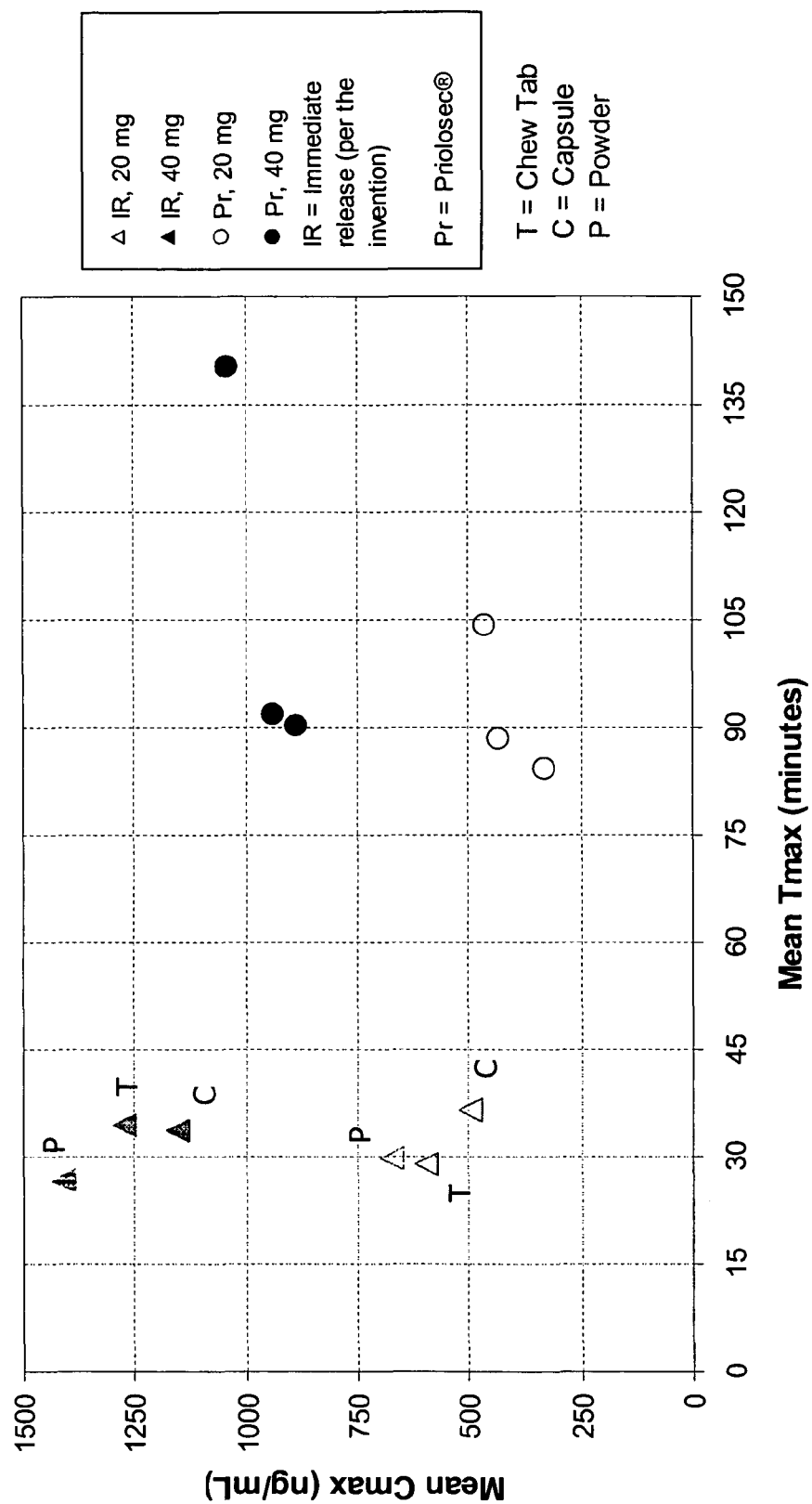
FIG. 19 is a graph comparing the mean peak plasma concentration (Cmax) verses the time at which Cmax is observed (Tmax) for 20 mg and 40 mg immediate release chewable tablets, capsules (SAN-7F, SAN-7E, respectively), and immediate release omeprazole suspension according to the present invention and 20 and 40 mg Prilosec® enteric coated omeprazole. The data are from the human clinical trial in Examples 14B and 15 B, Day 1.
Figure 21:
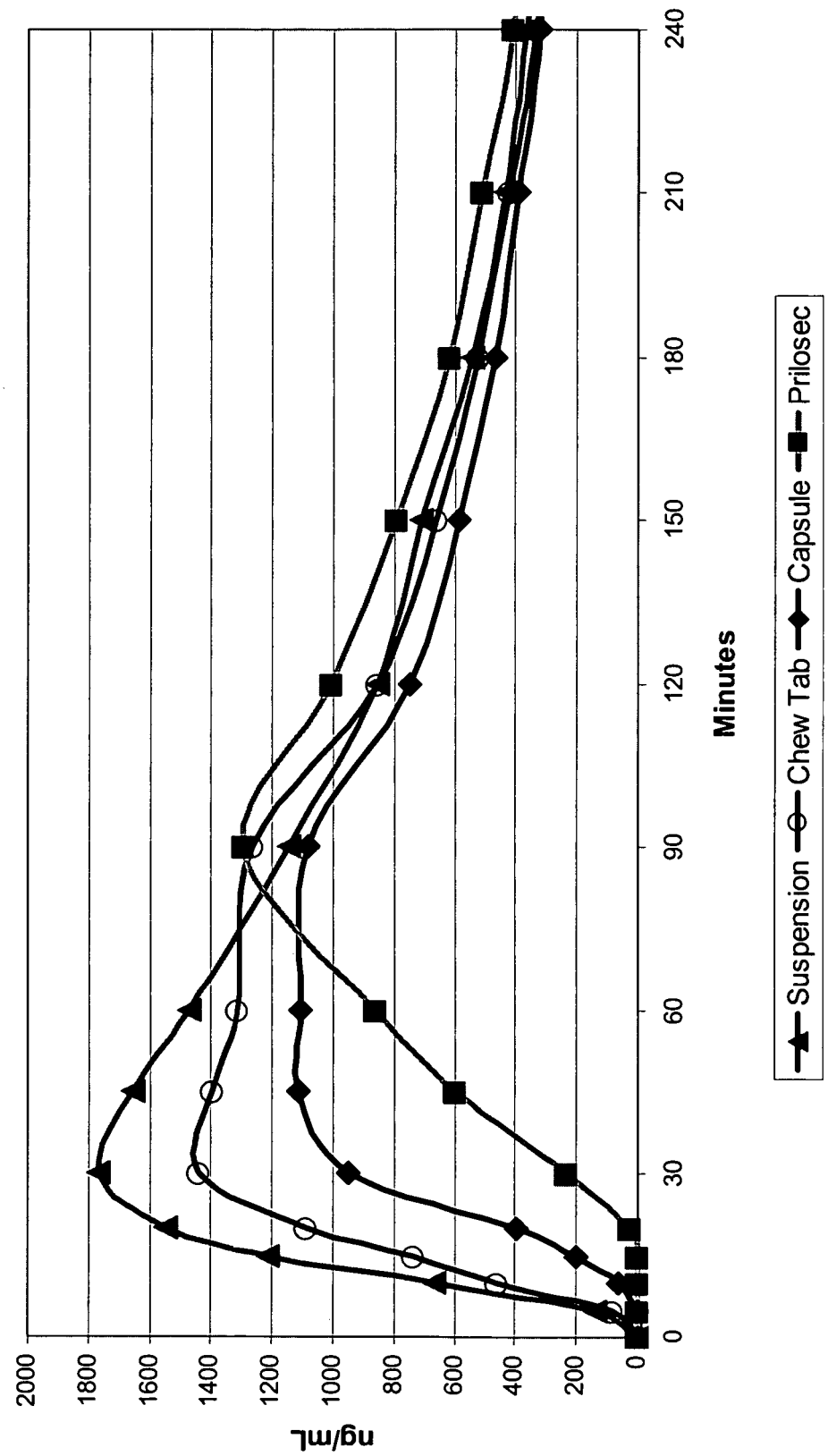
FIG. 21 is a graph comparing the average pharmacokinetic release profiles of immediate release omeprazole suspension (40 mg), chewable tablets (40 mg), capsule (40 mg) (SAN-7E) according to the present invention with Prilosec® brand enteric coated omeprazole (40 mg) from the human clinical trial in Example 15B, Day 7.
Figure 22:
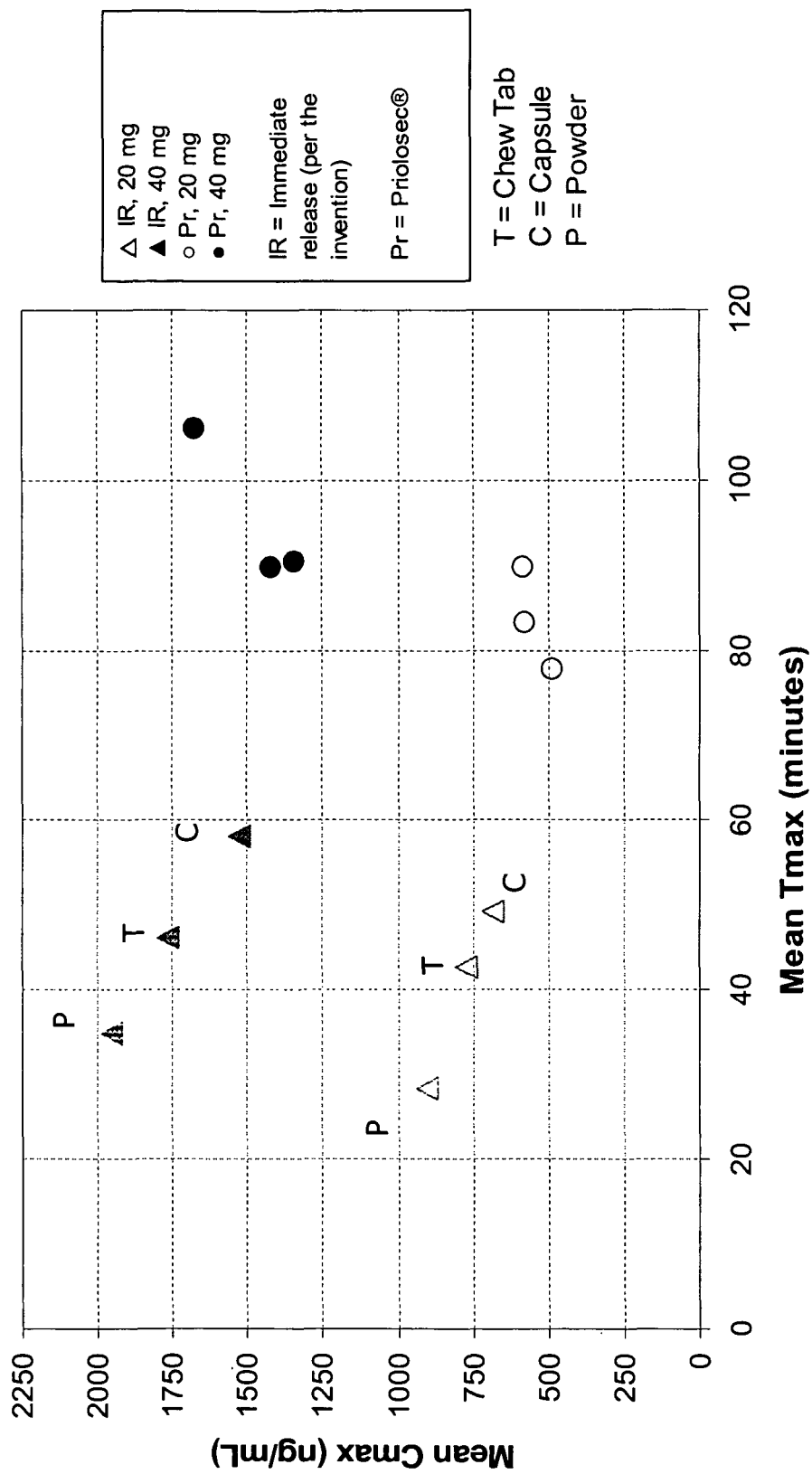
FIG. 22 is a graph comparing the mean peak plasma concentration (Cmax) verses the time at which Cmax is observed (Tmax) for immediate release omeprazole chewable tablets, capsules, and suspension according to the present invention (20 and 40 mg) and Prilosec® brand enteric coated omeprazole (20 and 40 mg) from the human clinical trial set forth in 14B, 15B Day 7.
Figure 23:
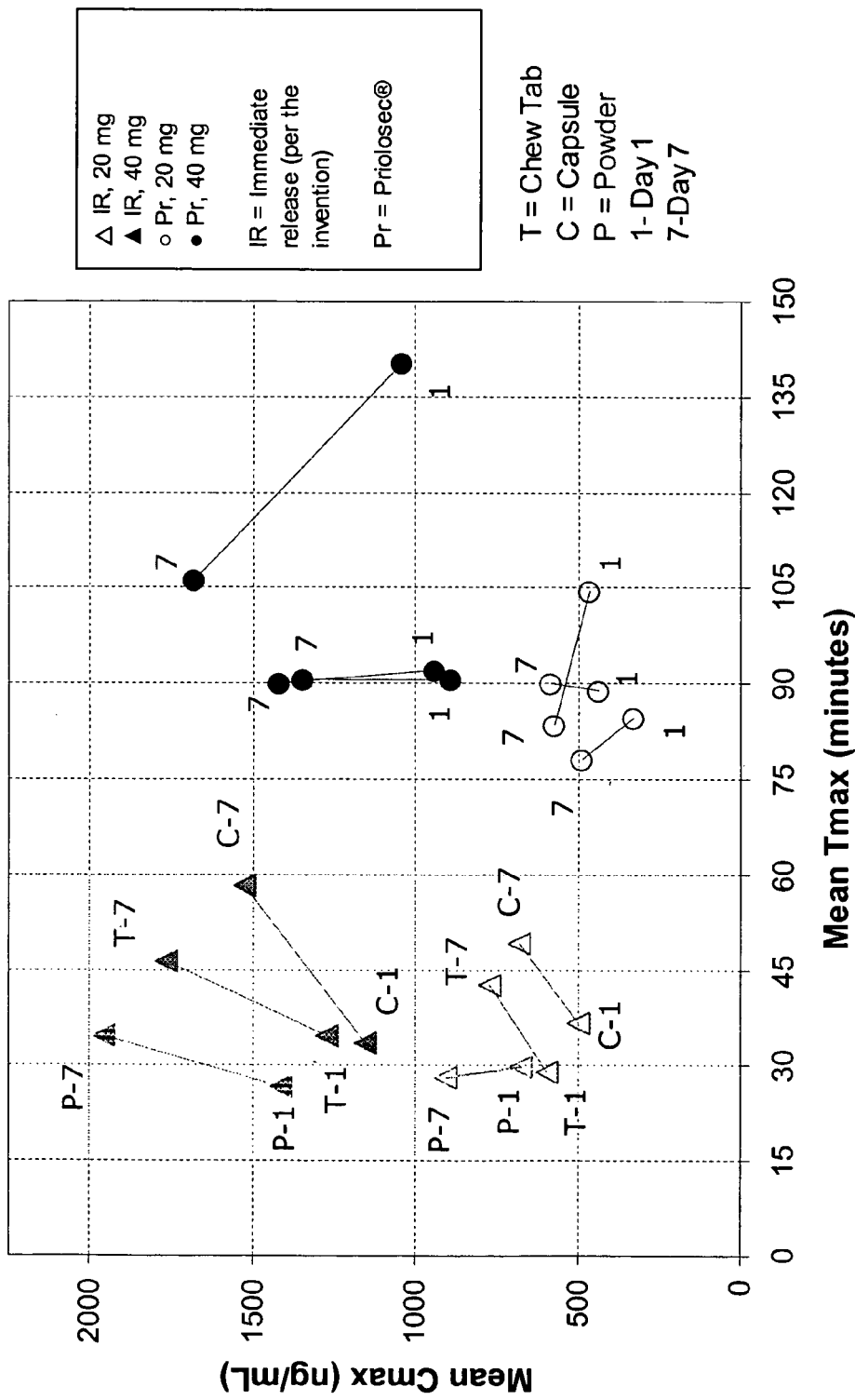
FIG. 23 is a graph comparing the Cmax versus Tmax of immediate release omeprazole chewable tablets, capsules, and suspension according to the present invention and Prilosec® brand enteric coated omeprazole. The data for both 20 mg and 40 mg doses are from the clinical trial set forth in Examples 14B, 15B, Days 1 and 7.
Figure 24:
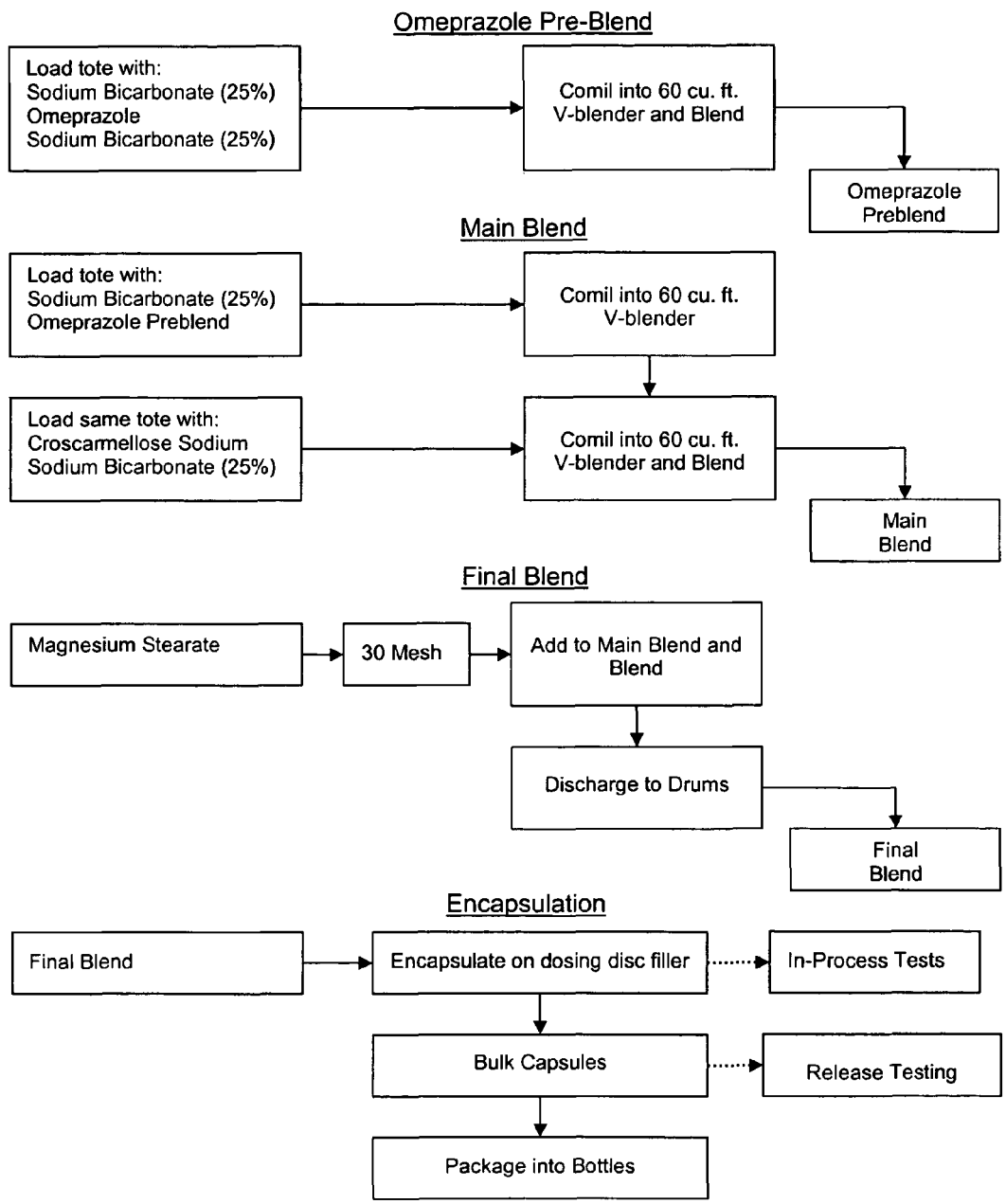
FIG. 24 is a flow chart depicting Manufacturing Process of immediate release capsules according to the present invention.

Pharmacokinetic results are presented in Table 13 B. and FIGS. 14-16, 18, 19, 21, 22, 23.

TABLE 13.B

Pharmacokinetic Release Profiles of Formulated OME and Prilosec 40 mg Study of Periods 1–12

| ng/mL | Period/Test Dosage | Day | Intervals (Minutes) | | | | | | | |
|---|---|---|---|---|---|---|---|---|---|---|
| | | | 0 | 5 | 10 | 15 | 20 | 30 | 45 | 60 |
| Mean | Prilosec (P1) | 1 | 0 | 0 | 0 | 0 | 0 | 2 | 20 | 205 | 485 |
| Min | Prilosec (P1) | 1 | 0 | 0 | 0 | 0 | 0 | 0 | 0 | 37 | 104 |
| Max | Prilosec (P1) | 1 | 0 | 0 | 0 | 0 | 0 | 15 | 80 | 543 | 1474 |
| Mean | Capsule (P2) (SAN-10A) | 1 | 0 | 0 | 0 | 29 | 176 | 647 | 1043 | 1022 | 929 |
| Min | Capsule (P2) (SAN-10A) | 1 | 0 | 0 | 0 | 0 | 0 | 11 | 26 | 152 | 158 |
| Max | Capsule (P2) (SAN-15A) | 1 | 0 | 0 | 0 | 340 | 888 | 1600 | 2351 | 2696 | 2295 |
| Mean | Chew Tab (P3) (SAN-15A) | 1 | 0 | 80 | 642 | 921 | 1001 | 1092 | 939 | 800 |
| Min | Chew Tab (P3) (SAN-15A) | 1 | 0 | 0 | 73 | 149 | 188 | 177 | 145 | 132 |
| Max | Chew Tab (P3) (SAN-15A) | 1 | 0 | 352 | 1321 | 1779 | 2073 | 2705 | 2571 | 2311 |
| Mean | Capsule (P4) (SAN-10B) | 1 | 0 | 0 | 36 | 192 | 413 | 623 | 698 | 682 |
| Min | Capsule (P4) (SAN-10B) | 1 | 0 | 0 | 0 | 8 | 19 | 94 | 128 | 175 |
| Max | Capsule (P4) (SAN-10B) | 1 | 0 | 0 | 373 | 966 | 1403 | 1727 | 1801 | 1792 |
| Mean | Chew Tab (P5) (SAN-15B) | 1 | 0 | 53 | 473 | 820 | 956 | 958 | 897 | 856 |
| Min | Chew Tab (P5) (SAN-15B) | 1 | 0 | 0 | 36 | 330 | 428 | 379 | 227 | 167 |
| Max | Chew Tab (P5) (SAN-15B) | 1 | 0 | 150 | 1073 | 1770 | 2110 | 2327 | 2848 | 3097 |
| Mean | Capsule (P6) (SAN-10E) | 1 | 0 | 0 | 0 | 1 | 65 | 502 | 1007 | 969 | 818 |

TABLE 13.B-continued

Pharmacokinetic Release Profiles of Formulated OME and Prilosec 40 mg Study of Periods 1–12

| | | | | | | | | | |
|---|---|---|---|---|---|---|---|---|---|
| Min | Capsule (P6) (SAN-10E) | 1 | 0 | 0 | 0 | 0 | 14 | 47 | 156 | 170 |
| Max | Capsule (P6) (SAN-10E) | 1 | 0 | 0 | 10 | 173 | 1126 | 2323 | 2721 | 2474 |
| Mean | Chew Tab (P7) (SAN-15C) | 1 | 0 | 65 | 706 | 1396 | 1386 | 1230 | 1048 | 852 |
| Min | Chew Tab (P7) (SAN-15C) | 1 | 0 | 0 | 191 | 473 | 711 | 515 | 321 | 226 |
| Max | Chew Tab (P7) (SAN-15C) | 1 | 0 | 382 | 1172 | 2807 | 2306 | 2580 | 2358 | 2117 |
| Mean | Capsule (P8) (SAN-10H) | 1 | 0 | 0 | 136 | 293 | 586 | 893 | 848 | 823 |
| Min | Capsule (P8) (SAN-10H) | 1 | 0 | 0 | 0 | 11 | 57 | 266 | 196 | 197 |
| Max | Capsule (P8) (SAN-10H) | 1 | 0 | 0 | 451 | 1100 | 1428 | 1697 | 1627 | 1871 |
| Mean | Capsule (P9) (SAN-10BB) | 1 | 0 | 0 | 37 | 286 | 867 | 1198 | 1111 | 936 |
| Min | Capsule (P9) (SAN-10BB) | 1 | 0 | 0 | 0 | 24 | 120 | 299 | 275 | 204 |
| Max | Capsule (P9) (SAN-10BB) | 1 | 0 | 0 | 172 | 809 | 1624 | 2305 | 1957 | 2222 |
| Mean | Caplet (P10) (SAN-15D) | 1 | 0 | 56 | 184 | 269 | 199 | 213 | 235 | 322 |
| Min | Caplet (P10) (SAN-15D) | 1 | 0 | 0 | 5 | 23 | 28 | 49 | 48 | 56 |
| Max | Caplet (P10) (SAN-15D) | 1 | 0 | 440 | 1256 | 1518 | 744 | 595 | 469 | 1013 |
| Mean | Capsule (P11) (SAN-10C) | 1 | 0 | 1 | 33 | 292 | 1027 | 1026 | 868 | 767 |
| Min | Capsule (P11) (SAN-10C) | 1 | 0 | 0 | 0 | 26 | 52 | 267 | 337 | 237 |
| Max | Capsule (P11) (SAN-10C) | 1 | 0 | 7 | 196 | 827 | 2024 | 2056 | 1729 | 1992 |
| Mean | Caplet (P12) (SAN-15E) | 1 | 0 | 5 | 43 | 81 | 116 | 327 | 540 | 583 |

| ng/mL | Period/Test Dosage | Day | 90 | 120 | 180 | 240 | 300 | 360 | N | Cmax (ng/mL) | Tmax (hr) |
|---|---|---|---|---|---|---|---|---|---|---|---|
| Mean | Prilosec (P1) | 1 | 991 | 679 | 417 | 265 | 203 | 143 | 12 | 1061 | 1.38 |
| Min | Prilosec (P1) | 1 | 241 | 127 | 37 | 8 | 8 | 0 | 12 | 273 | 1.00 |
| Max | Prilosec (P1) | 1 | 2994 | 2146 | 1596 | 1093 | 1081 | 707 | 12 | 2994 | 1.50 |
| Mean | Capsule (P2) (SAN-10A) | 1 | 733 | 504 | 309 | 226 | 149 | 107 | 12 | 1155 | 0.76 |
| Min | Capsule (P2) (SAN-10A) | 1 | 96 | 51 | 19 | 6 | 0 | 0 | 12 | 285 | 0.63 |
| Max | Capsule (P2) (SAN-15A) | 1 | 2133 | 1670 | 1362 | 1215 | 835 | 676 | 12 | 2696 | 1.50 |
| Mean | Chew Tab (P3) (SAN-15A) | 1 | 597 | 441 | 280 | 193 | 129 | 95 | 12 | 1201 | 0.54 |
| Min | Chew Tab (P3) (SAN-15A) | 1 | 71 | 42 | 9 | 0 | 0 | 0 | 12 | 196 | 0.50 |
| Max | Chew Tab (P3) (SAN-15A) | 1 | 2133 | 1701 | 1322 | 999 | 709 | 587 | 12 | 2705 | 1.50 |
| Mean | Capsule (P4) (SAN-10B) | 1 | 799 | 616 | 371 | 274 | 182 | 147 | 12 | 990 | 1.22 |
| Min | Capsule (P4) (SAN-10B) | 1 | 120 | 44 | 9 | 0 | 0 | 0 | 12 | 222 | 0.33 |
| Max | Capsule (P4) (SAN-10B) | 1 | 2358 | 2168 | 1691 | 1491 | 983 | 900 | 12 | 2358 | 2.00 |
| Mean | Chew Tab (P3) (SAN-15C) | 1 | 633 | 467 | 305 | 226 | 148 | 122 | 12 | 1192 | 0.50 |
| Min | Chew Tab (P3) (SAN-15C) | 1 | 70 | 29 | 14 | 7 | 0 | 0 | 12 | 428 | 0.17 |
| Max | Chew Tab (P3) (SAN-15C) | 1 | 2586 | 2058 | 1532 | 1279 | 788 | 744 | 12 | 3097 | 1.00 |
| Mean | Capsule (P6) (SAN-10E) | 1 | 648 | 436 | 284 | 175 | 137 | 89 | 12 | 1130 | 0.78 |
| Min | Capsule (P6) (SAN-10E) | 1 | 92 | 51 | 20 | 0 | 0 | 0 | 12 | 399 | 0.33 |
| Max | Capsule (P6) (SAN-10E) | 1 | 2415 | 1879 | 1323 | 994 | 858 | 590 | 12 | 2721 | 1.50 |
| Mean | Chew Tab (P7) | 1 | 610 | 436 | 295 | 217 | 161 | 112 | 11 | 1550 | 0.33 |
| Min | Chew Tab (P7) | 1 | 67 | 31 | 7 | 0 | 0 | 0 | 11 | 711 | 0.25 |
| Max | Chew Tab (P7) | 1 | 2244 | 1538 | 1279 | 1069 | 760 | 596 | 11 | 2807 | 0.50 |
| Mean | Capsule (P8) (SAN-10H) | 1 | 724 | 516 | 323 | 192 | 135 | 102 | 8 | 1128 | 0.78 |
| Min | Capsule (P8) (SAN-10H) | 1 | 87 | 48 | 14 | 0 | 0 | 0 | 8 | 362 | 0.25 |
| Max | Capsule (P8) (SAN-10H) | 1 | 2196 | 1848 | 1426 | 882 | 685 | 556 | 8 | 2196 | 1.50 |
| Mean | Capsule (P9) (SAN-10BB) | 1 | 652 | 519 | 323 | 234 | 161 | 118 | 8 | 1364 | 0.55 |
| Min | Capsule (P9) (SAN-10BB) | 1 | 120 | 82 | 20 | 0 | 0 | 0 | 8 | 535 | 0.33 |
| Max | Capsule (P9) (SAN-10BB) | 1 | 1806 | 1755 | 1269 | 1074 | 824 | 637 | 8 | 2305 | 0.75 |
| Mean | Caplet (P10) | 1 | 699 | 598 | 430 | 271 | 178 | 136 | 8 | 111 | 1.59 |
| Min | Caplet (P10) | 1 | 143 | 97 | 42 | 21 | 10 | 6 | 8 | 531 | 0.25 |
| Max | Caplet (P10) | 1 | 1440 | 1850 | 1404 | 1036 | 749 | 633 | 8 | 1850 | 3.00 |

TABLE 13.B-continued

Pharmacokinetic Release Profiles of Formulated OME and Prilosec 40 mg Study of Periods 1–12

| Mean | Capsule (P11) (SAN-10C) | 1 | 591 | 473 | 286 | 204 | 133 | 111 | 7 | 1378 | 0.57 |
| Min | Capsule (P11) (SAN-10C) | 1 | 74 | 41 | 16 | 0 | 0 | 0 | 7 | 414 | 0.33 |
| Max | Capsule (P11) (SAN-10C) | 1 | 1842 | 1826 | 1214 | 1004 | 657 | 592 | 7 | 2056 | 1.00 |
| Mean | Caplet (P12) | 1 | 909 | 531 | 320 | 196 | 143 | 110 | 8 | 1083 | 1.59 |

Formulations in Tables 13A and 13B were prepared according to the following protocols:

Preparation of Capsules

SAN-10A, SAN-10B, SAN-10BB and SAN-10K capsules were prepared on a 1.5 kg batch size in a 6 quart planetary mixer. The grade of each ingredient is shown in Table 13C below. Omeprazole USP is micronized omeprazole obtained from UQUIFA, holder of the Type II DMF for micronized omeprazole.

About half the sodium bicarbonate (#2 USP) was blended together with omeprazole and then with the other half of the sodium bicarbonate. Magnesium hydroxide was screened through a 100 or 60 US mesh screen and then charged into the planetary mixer. Then the entire blend was passed through a #20 mesh s/s screen and reintroduced into the Planetary Mixer and mixed for 10 minutes. Magnesium stearate was screened through a #40 mesh s/s screen directly into the Planetary Mixer and blended for 3 minutes. The mixture was then encapsulated in hard gelatin capsules, size #00, using a Profill® manual encapsulator. The amount of each ingredient used in SAN-10A, SAN-10B, SAN-10BB and SAN-10K capsules is set forth in Table 13C.

TABLE 13C

| Ingredients | SAN-10A | | SAN-10B | | SAN-10BB | | SAN-10K | |
|---|---|---|---|---|---|---|---|---|
| | mg/caps | % | mg/caps | % | mg/caps | % | mg/caps | % |
| Omeprazole USP | 40.8 | 4.2 | 40.8 | 4.2 | 40.8 | 3.5 | 40.8 | 4.3 |
| Sodium Bicarbonate #2 USP | 420 | 43.3 | 420 | 43.3 | 1100 | 94.0 | 882 | 93 |
| Magnesium Hydroxide (screened) 100 mesh | 470 | 48.4 | 0 | 0 | 0 | 0 | 0 | 0 |
| Magnesium Hydroxide (screened) 60 mesh | 0 | 0 | 470 | 48.4 | 0 | 0 | 0 | 0 |
| Croscarmellose Sodium NF | 30 | 3.1 | 30 | 3.1 | 20 | 1.7 | 20 | 2.1 |
| Magnesium Stearate NF | 10 | 1.0 | 10 | 1.0 | 10 | 0.9 | 10 | 1.0 |
| Totals | 970.8 | 100.0 | 970.8 | 100 | mg/caps | % | mg/caps | % |

SAN-10E and SAN-10H were prepared in a manner similar to that described for SAN-10A, etc., above, except that SAN-10E used a special grade of magnesium hydroxide (MS-95), which is a spray-dried magnesium hydroxide containing 95% magnesium hydroxide and 5% pre-gelatinized starch. SAN-10H is a blend fortified with croscarmellose sodium, which was developed for encapsulation on a Zanasi LZ64 dosator-type encapsulator. The amount of each ingredient is set forth in Table 13C. Both SAN-10E and SAN-10H were encapsulated in hard gelatin capsules, size #00. SAN-10E capsules were encapsulated using the Profill® hand encapsulator. SAN-10H capsules were encapsulated using the Zansi LZ64 dosator type encapsulator. The amount of each ingredient per capsule is set forth in Table 13C below.

TABLE 13D

| Ingredients | SAN-10E | | SAN-10H | |
|---|---|---|---|---|
| | mg/caps | % | mg/caps | % |
| Omeprazole USP | 40.8 | 4.5 | 40.8 | 4.4 |
| Sodium Bicarbonate #2 USP | 378 | 42.0 | 420 | 45.6 |
| Magnesium Hydroxide (screened) 100 mesh | 0 | 0 | 0 | 0 |
| Magnesium Hydroxide (screened) 60 mesh | 0 | 0 | 375 | 40.6 |
| Magnesium Hydroxide MS-95 | 447.4 | 49.8 | 0 | 0 |
| Croscarmellose Sodium NF | 27 | 3.0 | 82 | 8.9 |
| Magnesium Stearate NF | 6 | 0.7 | 5 | 0.5 |
| Totals | 899.2 | 100.0 | 922.8 | 100.0 |

Preparation of Chewable Tablets

Micronized omeprazole USP (UQUIFA) was microencapsulated with hydroxypropylcellulose (HPC) using a spray drying process. The grade of HPC was Klucel®, EF. The amount of each excipient used is set forth in Table 13E.

TABLE 13E

| Excipient | Weight (%) Feed Suspension | Weigh (%) Dry Product | Function |
|---|---|---|---|
| Omeprazole USP | 6.00% | 37.00% | API |
| HPC Klucel ® EF, NF | 10.0 | 61.6 | Coating Material |
| Sodium Bicarbonate, USP | 0.23 | 1.4 | pH Adjuster |
| Purified Water, USP | 83.8 | N/A | Suspension |
| Totals | 100.00% | 100.00% | Medium |

HPC was added slowly to purified water and mixed until dissolved. Sodium bicarbonate and omeprazole were then added slowly to prevent agglomeration. The spray composition was then screened prior to introducing it into the spray drier. The spray composition was then spray dried using a Niro® spray drier, which is equipped with a rotary spray atomizer. The final omeprazole content of the microencapsulated formulation is 37%.

Microencapsulated omeprazole was combined with about half the antacid excipient were blended to homogeneity to form an omeprazole pre-blend. The flavor components were next mixed with one another to form a flavor pre-blend. The omeprazole pre-blend and the flavor pre-blend were combined to form a main blend. Finally, a lubricant, magnesium stearate was added to the main blend to form the final blend. Tablets were formed on a commercial Fette press. The amount of the active ingredient and excipients used are set forth in Table 13A, above.

Conclusion

Naked or microencapsulated omeprazole 40 mg in Tablet, Capsule and Caplet forms (Periods 2-12) were bioequivalent to Prilosec® Capsules 40 mg with regard to AUC(0-inf). See FIGS. 14 and 15. The two treatments were not equivalent with regard to peak plasma concentration, Cmax. This difference in Cmax had no apparent effect on the pharmacodynamics or safety of the 40 mg formulation in this trial. The two treatments were also not equivalent with regard to pharmacokinetic release profiles.

Example 14A

Formulation of SAN-7F (20 mg Omeprazole Capsules)

A 1300 kg lot of 20 mg omeprazole capsules was manufactured under cGMP conditions. The formulation is set forth in Table 14A, below:

TABLE 14A

| Ingredient | % Weight | mg/Capsule | Amount Required for 1300 kg Batch (kg) |
|---|---|---|---|
| Omeprazole, USP | 1.8% | 20.4 mg/cap | 22.9 kg |
| Sodium Bicarbonate, USP #2 | 94.8 | 1100 | 1232 |

TABLE 14A-continued

| Ingredient | % Weight | mg/Capsule | Amount Required for 1300 kg Batch (kg) |
|---|---|---|---|
| Croscarmellose Sodium, NF | 2.6 | 30 | 33.6 |
| Magnesium Stearate, NF | 0.9 | 10 | 11.2 |
| Totals | 100 | 1160.4 | 1300 |

The following ingredients were added to a tote (tote #1) in the following order: Sodium bicarbonate (about 25% of total), omeprazole USP, sodium bicarbonate (about 25% of total). The contents of tote #1 were then charged into a 60 ft$^3$ V-blender through a Comil® powder mill equipped with a 16 mesh equivalent screen, operating the powder screen at a speed setting of high (800 rpm). The contents were mixed for 5 minutes at 8 rpm. About 25% of the total amount of sodium bicarbonate was then charged into a tote (tote #2). Then the contents of the V-blender were charged into tote #2. The contents of tote #2 were then passed through a Comil® powder mill equipped with a 16 mesh equivalent screen at a speed setting of high (800 rpm).

Next, croscarmellose sodium and the remaining amount of sodium bicarbonate were charged into tote #1. The contents of tote #1 were then passed through a Comil® powder mill equipped with a 16 mesh equivalent screen at a speed setting of high (800 rpm) and charged into the V-blender. The mixture was then blended for 15 minutes a 8 rpm. Then magnesium stearate was screened through a #30 mesh hand screen and charged into the V-blender. The resulting mixture was then blended for 3 minutes at 8 rpm. The contents of the V-blender were then discharged into labeled containers lined with inner clear polyethylene bag overwrapped with an outer black polyethylene bag. The resulting mixture was encapsulated on a H&K 1200® dosing disc/tamping pin-type encapsulator using hard gelatin capsules size #00.

Critical Encapsulation Process Parameters
  Encapsulator powder bed depth
  Dosing disc size
  Tamping pin settings The encapsulator powder bed depth, dosing disc size, and tamping pin settings are all controlling factors in achieving target capsule weights and maintaining the consistency of those weights throughout the encapsulation process. The encapsulator powder bed depth is maintained at a uniform level above the dosing disc. The dosing disc size is fixed by the dosing disc thickness, which is 24 mm for the SAN-7F Capsules 20 mg process. Tamping pin settings are adjusted to achieve the desired target weight and maintain consistent weight uniformity.

Example 14B

Clinical Trial with SAN-7F 20 mg Capsule

Trial Objectives
Primary Objective

The primary objective was to test the hypothesis that SAN-7F Capsules 20 mg (omeprazole 20 mg/dose) are pharmacokinetically bioequivalent to Prilosec 20 mg with respect to area under the curve (AUC).

Secondary Objectives:
  The secondary objectives were:
  1. To assess whether SAN-7F Capsules 20 mg are pharmacodynamically bioequivalent to Prilosec 20 mg with respect to percent decrease from Baseline in integrated gastric acidity; and 2. To compare the pharmacokinetics of SAN-7F Capsules 20 mg administered post-meal to the pharmacokinetics of SAN-7F Capsules 20 mg administered pre-meal.

Design:

This was an open-label, randomized, 2-period crossover trial to evaluate the pharmacokinetics, pharmacodynamics, and safety of 7 consecutive daily doses of SAN-7F. Capsules containing 20 mg omeprazole were compared to 7 consecutive daily doses of Prilosec 20 mg in healthy subjects. A comparison of pharmacokinetic parameters for SAN-7F administered before versus after a meal was conducted.

Volunteers were screened within 21 days before baseline measurements (gastric pH, vital signs). Gastric pH was recorded for 24 hours before the first dose of trial drug. In Period 1, subjects received SAN-7F 20 mg or Prilosec 20 mg, as randomized, 1 hour before breakfast for 7 consecutive days. A standardized high-fat breakfast was given in the clinic 1 hour after dosing on Days 1 and 7, or 1 hour after water for baseline assessment. Standardized lunch and dinner were also given 5 and 10 hours post-dose at baseline and on Days 1 and 7 in the clinic. Blood samples for determination of plasma omeprazole concentrations were collected for 12 hours, and gastric pH was measured for 24 hours after the doses on Days 1 and 7. Subjects who had received SAN-7F 20 mg (omeprazole) in Period 1 were given an eighth dose (Day 8) 1 hour after the start of the standardized high-fat breakfast. Blood samples were collected for 12 hours after the eighth dose (see Section 9.8 regarding the Dose 8 deviation). After a 10- to 14-day washout period, subjects returned for Period 2 and received an alternate treatment from that received in Period 1. Procedures in Period 2 were identical to those in Period 1, except that there was no eighth dose of SAN-7F 20 mg.

Number of Subjects (Planned and Analyzed)

Thirty-six subjects were dosed and 30 subjects complete 7 days of dosing in each period of the trial. Thirty subjects were included in the pharmacokinetic analysis and 25 subjects were included in the pharmacodynamic analysis for Doses 1 and 7. Because of an error in post-meal administration of SAN-7F Capsules 20 mg on Day 8 (Period 1), pharmacokinetic analyses for post-meal administration of SAN-7F Capsules 20 mg were not completed.

Duration of Treatment

Including screening, subjects participated in this trial for up to 40 days.

Design Rationale:

A 2-period crossover design is consistent with FDA guidance for the assessment of comparative pharmacokinetics in healthy volunteers.

Data from 24 subjects were expected to provide adequate power to show bioequivalence between the 2 formulations evaluated in this trial, based on the intersubject variability with regard to the pharmacokinetics [AUC(0-inf)] and pharmacodynamics of omeprazole in previous trials.

The 20-mg dose was studied in support of using a SAN-7F Capsules 20 mg omeprazole dose for short-term treatment of active duodenal ulcer, treatment of heartburn and other symptoms associated with gastroesophageal reflux disease (GERD), short-term treatment of erosive esophagitis, and maintenance of healing of erosive esophagitis.

The primary analysis focused on Day 7 of dosing, since the pharmacokinetics of omeprazole are known to change with repeated dosing and the pharmacodynamic effects are maximal by the seventh day of consecutive daily dosing (steady state).

The time of drug administration (after an overnight fast and 1 hour prior to a meal) meets the regulatory guidance for bioequivalence (fasting) and anticipates actual use.

In Period 1 at steady state (Day 8), the pharmacokinetics of SAN-7F Capsules 20 mg given post-meal were compared to those of SAN-7F 20 mg given pre-meal (Day 7). This comparison was conducted to evaluate the effect of food on the bioavailability of SAN-7F Capsules 20 mg. This portion of the protocol was not conducted correctly during this period.

Treatments Administered:

The treatments administered to subjects in this trial are listed in the table below.

TABLE 14B

| Treatment | Treatment Description |
| --- | --- |
| SAN-7F | SAN-7F Capsules (omeprazole immediate-release capsules) 20 mg administered orally with 120 mL water each morning after an overnight fast, 1 hour before starting a standardized high fat breakfast. |
| Prilosec | Prilosec Capsules (omeprazole delayed-release capsules) 20 mg administered orally with 120 mL water each morning after an overnight fast, 1 hour before starting a standardized high-fat breakfast. |
| SAN-7F Dose 8 | SAN-7F Capsules (omeprazole immediate-release capsules) 20 mg, administered orally with 120 mL water on Day 8 in Period 1, 1 hour after starting a standardized high-fat breakfast. |

The description below represents the schedule of events:

Events:

1. Period 1—SAN-7F Capsules 20 mg or Prilosec 20 mg (by randomization).

Location of the lower esophageal sphincter (LES) on the day the subject checked into the clinic (Day minus 2).

Seven consecutive single daily AM doses pre-meal (plus Dose 8 on Day 8 post-meal only for subjects receiving SAN-7F Capsules 20 mg). Twelve-hour PK sampling after Doses 1, 7, and 8 (SAN-7F Capsules 20 mg only). Twenty-four-hour gastric pH monitoring during Baseline starting on Day minus 1, and during treatment starting on Day 1 (Dose 1) and Day 7 (Dose 7).

2. 10-14 Day Washout

3. Period 2—SAN-7F Capsules 20 mg or Prilosec 20 mg—Alternative formulation to that in Period 1. Seven consecutive single daily AM doses pre-meal. Twelve-hour PK sampling after Doses 1 and 7. Twenty-four-hour gastric pH monitoring during Baseline starting on Day minus 1, and during treatment starting on Day 1 (Dose 1) and Day 7 (Dose 7).

Pharmacokinetic Sampling, Analytical Methods, and Parameters

Blood samples (3 mL) were obtained by venipuncture within 30 minutes before each dose and at 5, 10, 15, 20, 30, 45, 60, 90, 120, 150, 180, 210, 240, 300, 360, 420, 480, 540, 600, 660, and 720 minutes (12 hours) after each dose on Days 1 and 7 of both periods and Day 8 of Period 1 (for SAN-7F Capsules 20 mg). Zero time was the time that the subject swallowed a capsule of trial drug.

Plasma omeprazole concentrations were measured using a validated liquid chromatography mass spectrometry (LC-MSIMS) assay (MDS Pharma Services, Lincoln, Nebr.). The linear assay range was 5.0 to 750 ng/mL.

The following pharmacokinetic parameters were measured for each subject:

Plasma omeprazole concentration at each sampling time

Peak omeprazole plasma concentration (Cmax) and the time at which Cmax is observed (Tmax) obtained directly from the data without interpolation Terminal elimination rate constant (Kel) determined from a log-linear regression analysis of the terminal plasma omeprazole concentrations Half-life of drug elimination (T%) calculated as 0.693/Kel Area under the plasma drug time-concentration curve calculated from 0 time to last time point evaluated [AUC (0-t)] calculated using the trapezoidal rule with the plasma concentration at time t being the last measurable concentration Area under the plasma drug time-concentration curve calculated from 0 time and extrapolated to infinity [AUC (0-inf)] calculated as AUC(0-t)+Ct/Kel, where Ct is the last measurable plasma concentration and Kel is the terminal elimination rate constant defined above Measurement of Gastric pH Subjects remained propped up in bed (about 45 degrees) from the time of initial gastric pH recording, through 5 hours post dose. Subjects were then allowed restricted physical activity until bedtime, at which time they were again propped up in bed (approximately 45 degrees) and remained in this position for the remainder of the pH monitoring period. Gastric pH data were collected every 4 seconds (this measured value was then imputed for each of the following 3 seconds by the software) using an ambulatory pH recording system (Digitrapper@ 400, Medtronic Functional Diagnostics, Inc, Shoreview, Minn. USA) with a disposable antimony electrode and an internal standard (Medtronic Zinetics 24@ Single-Use pH Catheter with or without the lower esophageal [LES] locator). At the Period 1 check-in (Day minus 2), the LES was located manometrically (Medtronic Polygram '98 for Windows v. 2.20) and the distance from the upper border of the LES to the nares was recorded on the CRF.

For all measurements of gastric pH, the electrode was placed in the stomach 10 cm below the upper border of the LES using measurements determined at Day minus 2 of Period 1. The probe was inserted approximately 1 hour prior to dosing and the proximal end was taped to the side of the face to prevent shifting of the probe. Prior to insertion, the electrode was calibrated at room temperature to pH 1 and 7 using standard commercial polyelectrolyte solutions (Medtronic, Toronto). The software used to process the pH data corrected for the difference between electrode calibration temperature (approximately 25° C.) and recording temperature (37° C.). Recordings continued from approximately 1 minute before until 24 hours after dosing (trial drug or water during Baseline). Times for the following events were indicated electronically on the pH record using the following event markers: beginning of pH recording, dosing of trial drugs, initiation of each meal, and the end of the pH recording.

Readjustment of the gastric pH probe for any potential migration of the pH probe out of the stomach during evening hours was achieved using the following procedures: During baseline periods before dosing, the Digitrappers were checked every hour from 16 hours to 24 hours after administering 120 mL water. If a pH value was >2.5 (1-minute observation), the subject was repositioned and asked to take 1 or more sips of water (≤60 mL total). If the pH did not decrease to ≤2.5 within 5 minutes, the probe was partially withdrawn and then advanced to 10 cm below the upper border of the LES (the administration of ≤60 mL water per hour was permitted to facilitate this procedure). If after repositioning the probe, the pH was not ≤2.5, no further adjustments were made during that hour. These procedures were repeated as necessary during the subsequent hours to ensure that the probe was properly placed. The number of times that the probe was adjusted (water administered or probe repositioned) was recorded on the CRF.

For all dosing periods, the Digitrappers were checked every hour from 16 hours to 24 hours after administering the dose. If the pH was >5 (1-minute observation), the subject was repositioned. If the pH did not decrease to ≤5 within the next 5 minutes, the subject was administered ≤60 ml of water. If the pH did not decrease to ≤5 within the next 1 minute, the probe was partially withdrawn and then advanced to 10 cm below the upper border of the LES (≤60 mL of water may have been administered to facilitate this procedure). If after repositioning the probe, the pH was still >5, no further adjustments were made during that hour. These procedures were repeated, as needed, during the subsequent hour(s) to assure that the probe was properly placed. The hourly assessments and actions taken were recorded on the CRF.

Pharmacodynamic Parameters and Methodology

The following pharmacodynamic parameters were measured for each 24-hour period in 15-minute intervals:

Integrated gastric acidity (mmol*hr/L), calculated for each 15-minute interval during the 24-hour recording period, as follows:

Acid concentration (mmol/L)=$1000 \times 10^{-pH}$

Acidity (mmol*hr/L)=(acid concentration at time "t"+acid concentration at time "$t_1$")/2×(t−$t_1$), where t and $t_1$ are the times of 2 consecutive pH measurements Integrated gastric acidity (mmol*hr/L) calculated as the sum of acidity over each 15-minute interval Mean gastric acid concentration (mmol/t), calculated as integrated gastric acidity for each 15-minute interval/ 0.25 hour Median gastric pH, calculated for each 15-minute interval Percent time gastric pH was ≤4, calculated for each 15-minute interval Values for gastric pH were recorded once every 4 seconds. The software used to process the record filled in the same value for the following 3 seconds. Each record was divided into 15-minute intervals beginning with zero time as the recording interval prior to dosing. All pH values outside the acceptable range of 0.5 to 7.5, inclusive, were excluded prior to analysis.

Missing (or excluded) values for gastric pH were handled as follows:

If pH values were missing in a 15-minute interval, integrated gastric acidity and mean gastric acid concentration were calculated by integrating across the missing data; however, only the available values were used to calculate the percentage of time gastric pH was ≤4 and the median gastric pH.

If all of the pH values were missing in an entire 15 minute interval, integrated gastric acidity, mean gastric acid concentration, and percentage of time gastric pH was ≤4 were calculated as the mean of the values from the interval immediately preceding and immediately following the interval for which all pH values were missing. For an interval with all missing pH values, the median of all values from the interval immediately preceding and immediately following were assigned to the interval with all missing values.

Primary Endpoint

The primary pharmacokinetic endpoint was the bioavailability of omeprazole [AUC(0-inf)] after the seventh dose of each omeprazole formulation.

Secondary Endpoints
  The secondary endpoints were:
    Peak plasma concentration (Cmax) after the seventh dose of each omeprazole formulation.
    AUC(0-inf) and Cmax after the first dose of each omeprazole formulation.
    All other pharmacokinetic parameters after the first and seventh doses of each omeprazole formulation: Tmax, Kel, $T_{1/2}$, AUC(0-t).
    All pharmacokinetic parameters obtained with SAN-7F Capsules 20 mg administered post-meal.
Pharmacokinetic Analysis
  For the analysis of data collected on Days 1 and 7 of each period (pre-meal dosing), an analysis of variance (ANOVA) model was used to test the bioequivalence of SAN-7F Capsules 20 mg and Prilosec, using the natural logarithmic transformation of AUC(0-inf) and Cmax. The model included the following factors: treatment, period, sequence, and subject nested within sequence. Ninety percent confidence intervals (CIs) for treatment differences were calculated; the endpoints of these CIs were then reverse transformed to represent CIs about the percent mean ratios on the original scale. With respect to AUC(0-inf) and Cmax, equivalence was declared for each parameter, if the bounds of the 90% CIs for the percent mean ratio, SAN-7F to Prilosec, were between 80% and 125%.
Pharmacodynamic Statistical and Analytical Plan
Pharmacodynamic Endpoints
Primary Endpoint
  The primary pharmacodynamic endpoint was the percent decrease from Baseline in integrated gastric acidity for the 24-hour interval after the seventh dose of each omeprazole formulation.
Secondary Endpoint
  The secondary pharmacodynamic endpoint was the percent decrease from Baseline in integrated gastric acidity for the 24-hour interval after the first dose of each omeprazole formulation.
Other Pharmacodynamic Parameters (24-Hour Post-Dose Intervals)
    Mean gastric acid concentration (mM)
    Median gastric pH
    Percent time gastric pH≤4
Pharmacodynamic Analysis
  The pharmacodynamic effects of SAN-7F Capsules 20 mg and Prilosec 20 mg during the 24-hour post-dose recording period were assessed after the first and seventh doses by evaluating the following parameters: integrated gastric acidity, mean gastric acid concentration, median gastric pH, and the percentage of time gastric pH was ≤4 for the 24-hour period.
Evaluation of Period Effect
  Prior to evaluating the pharmacodynamic effects of SAN-7F Capsules and Prilosec with respect to integrated gastric acidity, the possibility of a period effect was assessed using an ANOVA model that included factors for period and subject, fit to the 24-hour baseline values for integrated gastric acidity for each of the 2 periods. If no statistically significant difference was found between the 2 baseline values, it was concluded that there was no period effect. In this case, the mean of the 2 baseline values was used as the baseline value for each subject. If a statistically significant difference was found between the baseline values, it would be concluded that there was a period effect. In this case, integrated gastric acidity was adjusted for the period effect in the statistical analysis by analyzing the percent decrease from the corresponding baseline value for each subject.

Analysis of Pharmacodynamic Endpoints
  The analysis of integrated gastric acidity for the 24-hour period following dosing was conducted on the percent decrease from Baseline on Days 1 and 7 calculated for each subject as 100×[Baseline−Day 1 (or Day 7)]/Baseline.
  An ANOVA model was used to test the pharmacodynamic equivalence of SAN-7F. Capsules and Prilosec, using the natural logarithmic transformation of percent decrease from Baseline in integrated gastric acidity. The model included the following factors: treatment, period, sequence, and subject nested within sequence. Ninety percent confidence intervals (CIs) for treatment differences were calculated; the endpoints of these CIs were then reverse transformed to represent CIs about the percent mean ratios on the original scale. Pharmacodynamic equivalence was declared if the bounds of the 90% CIs for the percent mean ratio of percent decrease from Baseline in integrated gastric acidity, SAN-7F to Prilosec, were between 80% and 125%.
Descriptive Analyses
  The ratio of the percent decrease from Baseline for integrated gastric acidity for the 24-hour period following the first and seventh doses with SAN-7F Capsules and Prilosec was calculated for each subject as: percent decrease from Baseline for SAN-7F/percent decrease from Baseline for Prilosec using the appropriate baseline value. The medians and boundaries of the inter-quartile range (25th and 75th percentiles) of the ratios for all subjects were tabulated.
Analyses of Other Pharmacodynamic Parameters
  The ratio of the percent decrease from Baseline for mean gastric acid concentration and for the percentage of time gastric pH was ≤4 for the 24 hour period following dosing with SAN-7F Capsules and Prilosec was calculated for each subject as: percent decrease from Baseline for SAN-7F/percent decrease from Baseline for Prilosec (using the appropriate baseline value). For median gastric pH, the ratio of the increase from Baseline for SAN-7F and Prilosec was calculated for each subject (using the appropriate baseline value) as: increase from Baseline for SAN-7F/increase from Baseline for Prilosec. The medians and boundaries of the inter-quartile range (25th and 75th percentiles) of the ratios for all subjects were tabulated.
Disposition of Subjects
  Thirty-six subjects entered the trial and received at least one dose of trial drug; 30 subjects completed the trial.

TABLE 14.C

Summary of Subject Disposition

|  | n | % |
|---|---|---|
| Subjects who received at least one dose of either trial drug | 36 | 100.0 |
| Subjects who completed both 7-day treatment periods | 30 | 83.3 |
| Subjects who received 8 doses of SAN-7F 20 mg* | 22 | 61.1 |
| Subjects who withdrew | 6 | 16.7 |

*Includes 15 subjects who received an eighth dose of SAN-7F 20 mg on Day 9 but no dose on Day 8 in Period 1 and 7 other subjects who received 8 consecutive daily dose of SAN-7F 20 mg in Period 2.

Figure 17:
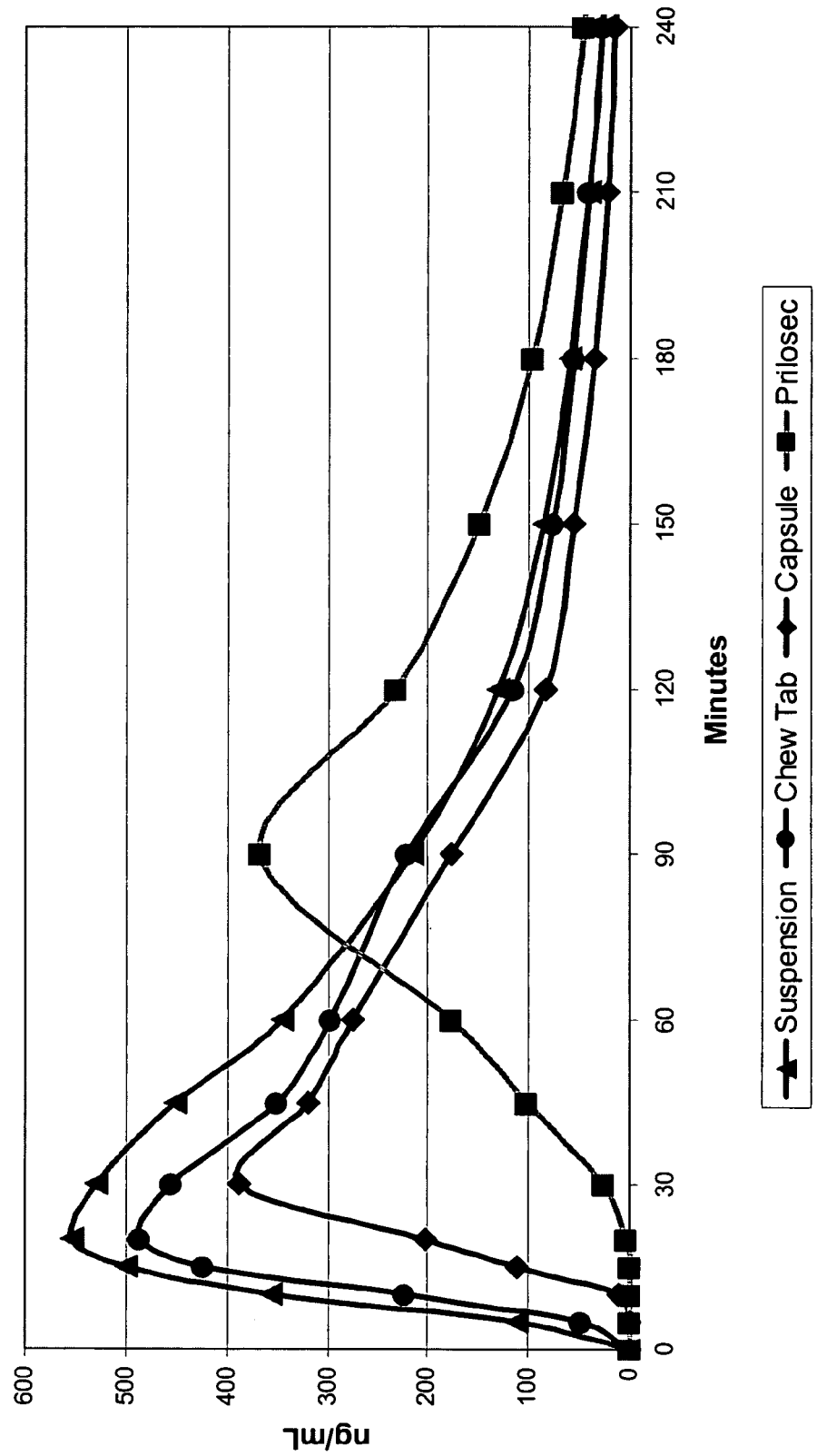
FIG. 17 is a graph comparing the average pharmacokinetic release profiles of immediate release omeprazole suspension (20 mg)(Example 16), chewable tablets (20 mg), capsule (20 mg)(Example 7F), and Prilosec® brand enteric coated omeprazole (20) mg from the human clinical trial described in Example 14B, Day 1.
Figure 20:
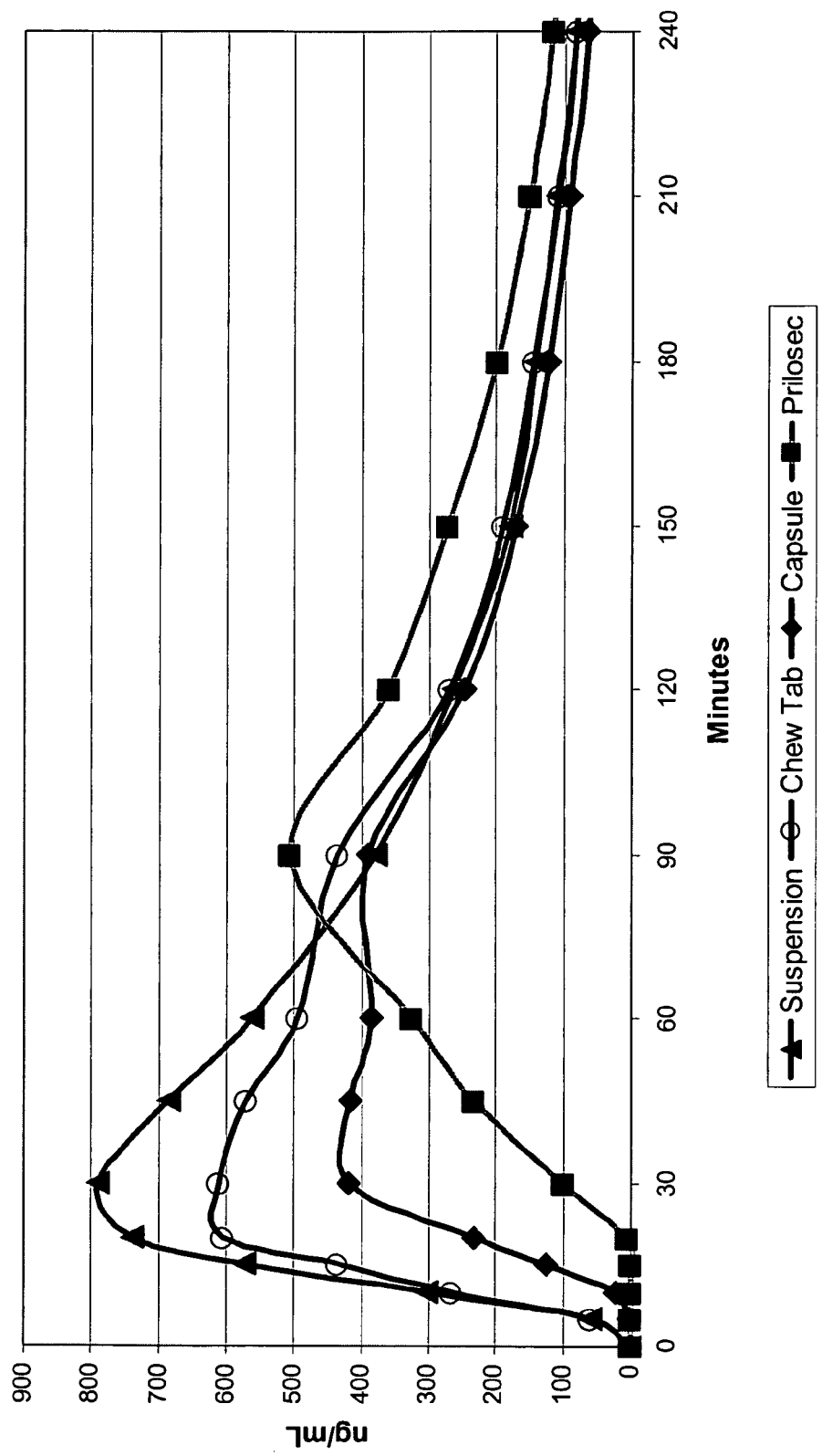
FIG. 20 is a graph comparing the average pharmacokinetic release profiles of immediate release omeprazole suspension (20 mg), chewable tablets (20 mg), capsule (20 mg) (SAN-7F) according to the present invention with Prilosec (20 mg) from the human clinical trial in Example 14B, Day 7.

Pharmacokinetic Results
  Pharmacokinetic results are presented the in Table 14.D. and FIGS. 16, 17, 19, 20, 22 and 23.
  After one dose, SAN-7F Capsules 20 mg and Prilosec 20 mg were bioequivalent with respect to AUC. The percent mean ratio of SAN-7F 20 mg to Prilosec 20 mg was 105.31% for AUC(0-inf) with the bounds of the 90% CI between 80% and 125% (98.94% and 112.09%). As expected for the immediate-release product, the Cmax for SAN-7F 20 mg was higher than for Prilosec 20 mg (percent mean ratio of 148.49%, 90% CI of 129.16% to 170.72%). The Tmax for SAN-7F was shorter than the Tmax for Prilosec (p<0.001; ANOVA).

Pharmacokinetic Conclusions

After the first dose and at steady state (Day 7), SAN-7F Capsules 20 mg were equivalent to Prilosec 20 mg with respect to [AUC(0-inf)] (the primary pharmacokinetic endpoint). The 2 treatments were not equivalent with respect to Cmax on Days 1 and 7 with the percent mean ratio of 148% on Day 1 and 145% on Day 7. The Tmax was shorter for the immediate-release product on Days 1 and 7 (p<0.001).

Pharmacodynamic Conclusions

On Day 7 of dosing, SAN-7F Capsules 20 mg were found equivalent to Prilosec 20 mg with regard to the primary pharmacodynamic endpoint, percent decrease from Baseline in integrated gastric acidity over 24 hours. SAN-7F 20 mg and Prilosec 20 mg both decreased integrated gastric acidity by approximately 70% from Baseline at Day 7.

Trial Conclusion

Since comparisons in this trial involved a delayed-release formulation (Prilosec 20 mg) and an immediate-release formulation (SAN-7F Capsules 20 mg), it was anticipated that the Tmax would occur earlier and the Cmax would be higher for SAN-7F 20 mg than for Prilosec 20 mg. It was also expected that the 2 products would be equivalent with regard to AUC and, therefore, also with regard to their pharmacodynamic effects.

As anticipated, SAN-7F 20 mg was found equivalent to Prilosec 20 mg on Day 7 (and Day 1) of dosing with regard to AUC (0-inf) and equivalent at Day 7 with regard to percent decrease from Baseline in integrated gastric acidity over 24 hours. For Cmax, the upper bound of the 90% confidence interval for the percent mean ratio exceeded 125% on Days 1 and 7. The pharmacodynamic data show that SAN-7F 20 mg and Prilosec 20 mg were equally effective in decreasing integrated gastric acidity at steady state (Day 7).

Both SAN-7F Capsules 20 mg and Prilosec 20 mg were well tolerated during the 7-day to 9-day dosing periods in this trial. No meaningful differences between the treatments were observed with respect to safety.

TABLE 14.D 20 mg PK Summary for Day 1 and 7 (S7F = SAN-7F; Pr = Prilosec ®)

| Drug | ng mL | Day | 0 | 5 | 10 | 15 | 20 | 30 | 45 | 60 | 90 | 120 | 150 | 180 |
|---|---|---|---|---|---|---|---|---|---|---|---|---|---|---|
| S7F | Mean | 1 | 0 | 0 | 11 | 111 | 202 | 388 | 320 | 274 | 177 | 83 | 55 | 35 |
| S7F | Min | 1 | 0 | 0 | 0 | 0 | 0 | 0 | 0 | 94 | 36 | 0 | 9 | 0 |
| S7F | Max | 1 | 0 | 0 | 110 | 1090 | 927 | 1090 | 958 | 775 | 466 | 246 | 181 | 120 |
| S7F | Mean | 7 | 0 | 4 | 23 | 125 | 231 | 418 | 417 | 384 | 391 | 245 | 169 | 123 |
| S7F | Min | 7 | 0 | 0 | 0 | 0 | 0 | 0 | 0 | 7 | 22 | 53 | 28 | 15 |
| S7F | Max | 7 | 0 | 120 | 257 | 721 | 1130 | 1530 | 1240 | 1080 | 1270 | 735 | 576 | 473 |
| Pr | Mean | 1 | 0 | 0 | 0 | 0 | 1 | 17 | 87 | 171 | 309 | 160 | 96 | 68 |
| Pr | Min | 1 | 0 | 0 | 0 | 0 | 0 | 0 | 0 | 0 | 81 | 50 | 23 | 13 |
| Pr | Max | 1 | 0 | 0 | 0 | 0 | 27 | 205 | 319 | 441 | 794 | 622 | 394 | 301 |
| Pr | Mean | 7 | 0 | 0 | 0 | 1 | 8 | 76 | 222 | 292 | 380 | 277 | 194 | 145 |
| Pr | Min | 7 | 0 | 0 | 0 | 0 | 0 | 0 | 0 | 0 | 0 | 62 | 43 | 25 |
| Pr | Max | 7 | 12 | 8 | 8 | 12 | 88 | 333 | 994 | 988 | 1220 | 775 | 560 | 420 |

20 mg PK Summary for Day 1 and 7 (Continued) (S7F = SAN-7F; Pr = Prilosec ®, 40 mg).

| Drug | ng/mL | Day | 210 | 240 | 300 | 360 | 420 | 480 | 540 | 600 | 660 | 720 | N | Cmax (ng/mL) | Tmax (hr) |
|---|---|---|---|---|---|---|---|---|---|---|---|---|---|---|---|
| S7F | Mean | 1 | 22 | 14 | 6 | 3 | 1 | 0 | 0 | 0 | 0 | 0 | 30 | 498 | 0.61 |
| S7F | Min | 1 | 0 | 0 | 0 | 0 | 0 | 0 | 0 | 0 | 0 | 0 | 30 | 140 | 0.25 |
| S7F | Max | 1 | 76 | 46 | 23 | 18 | 10 | 14 | 0 | 5 | 7 | 6 | 30 | 1090 | 1.50 |
| S7F | Mean | 7 | 90 | 65 | 38 | 22 | 13 | 7 | 4 | 3 | 1 | 1 | 30 | 680 | 0.82 |
| S7F | Min | 7 | 10 | 6 | 0 | 0 | 0 | 0 | 0 | 0 | 0 | 0 | 30 | 228 | 0.25 |
| S7F | Max | 7 | 362 | 297 | 196 | 143 | 91 | 61 | 42 | 28 | 18 | 13 | 30 | 1530 | 1.50 |
| Pr | Mean | 1 | 44 | 28 | 12 | 6 | 3 | 1 | 0 | 0 | 0 | 0 | 30 | 328 | 1.41 |
| Pr | Min | 1 | 8 | 0 | 0 | 0 | 0 | 0 | 0 | 0 | 0 | 0 | 30 | 101 | 0.75 |
| Pr | Max | 1 | 163 | 105 | 51 | 25 | 13 | 8 | 0 | 0 | 6 | 5 | 30 | 794 | 3.00 |
| Pr | Mean | 7 | 104 | 86 | 47 | 26 | 15 | 8 | 5 | 3 | 1 | 1 | 30 | 487 | 1.30 |
| Pr | Min | 7 | 14 | 0 | 0 | 0 | 0 | 0 | 0 | 0 | 0 | 0 | 30 | 170 | 0.50 |
| Pr | Max | 7 | 308 | 456 | 167 | 122 | 73 | 65 | 39 | 25 | 18 | 11 | 30 | 1220 | 2.50 |

Example 15A

Formulation of SAN-7E (40 mg Omeprazole Capsules)

A 1300 kg lot of 40 mg omeprazole capsules was manufactured under cGMP conditions. The formulation is set forth in Table 15A, below:

TABLE 15A

| Ingredient | % Weight | mg/Capsule | Amount Required for 1300 kg Batch (kg) |
|---|---|---|---|
| Omeprazole, USP | 3.5% | 40.8 mg/cap | 45.7 kg |
| Sodium Bicarbonate, USP #2 | 93.2 | 1100 | 1232 |
| Croscarmellose Sodium, NF | 1.5 | 30 | 33.6 |
| Magnesium Stearate, NF | 0.8 | 10 | 11.2 |
| Totals | 100 | 1160.4 | 1300 |

The following ingredients were added to a tote (tote #1) in the following order: Sodium bicarbonate (about 25% of total), omeprazole USP, sodium bicarbonate (about 25% of total). The contents of tote #1 were then charged into a 60 ft³ V-blender through a Comil® powder mill equipped with a 16 mesh equivalent screen, operating the powder screen at a speed setting of high (800 rpm). The contents were mixed for 5 minutes at 8 rpm. About 25% of the total amount of sodium bicarbonate was then charged into a tote (tote #2). Then the contents of the V-blender were charged into tote #2. The contents of tote #2 were then passed through a Comil® powder mill equipped with a 16 mesh equivalent screen at a speed setting of high (800 rpm).

Next, croscarmellose sodium and the remaining amount of sodium bicarbonate were charged into tote #1. The contents of tote #1 were then passed through a Comil® powder mill equipped with a 16 mesh equivalent screen at a speed setting of high (800 rpm) and charged into the V-blender. The mixture was then blended for 15 minutes a 8 rpm. Then magnesium stearate was screened through a #30 mesh hand screen and charged into the V-blender. The resulting mixture was then blended for 3 minutes at 8 rpm. The contents of the V-blender were then discharged into labeled containers lined with inner clear polyethylene bag overwrapped with an outer black polyethylene bag. The resulting mixture was encapsulated on a H&K 1200® dosing disc/tamping pin-type encapsulator using hard gelatin capsules size #00.

Example 15B

Clinical Trial

A clinical trial was conducted in order to compare the pharmacokinetic profile of a 40 mg omeprazole capsule according to the present invention with Prilosec® 40 mg delayed release capsules. SAN-7E 40 mg capsules according to the invention were formulated as in Example 7B, above. The results of these clinical trials are discussed below and are depicted graphically in FIGS. 16, 18, 19, 21, 22 and 23.

Trial objectives, design, pharmacokinetic and pharmacodynamic endpoints, design rationale, treatments administered, schedule of events, pharmacokinetic sampling, analytical methods and parameters, measurement of gastric pH, pharmacodynamic parameters and methodology, pharmacokinetic statistical and analytical plan are the same as in Example 14 above with the exception of use with SAN-7E Capsules 40 mg and Prilosec 40 mg instead of 20 mg of each drug. The capsules are prepared by blending the PPI and homogeneously blending with other components shown in Table 15A.

Number of Subjects (Planned and Analyzed):

Thirty-six subjects were dosed and 30 subjects complete 7 days of dosing in each period of the trial. Thirty-five subjects were included in the pharmacokinetic analysis and 34 subjects were included in the pharmacodynamic analysis for Doses 1 and 7. Eighteen subjects were included in the post-meal (Day 8) versus pre-meal (Day 7) analysis.

Duration of Treatment:

Including screening, subjects participated in this trial for up to 41 days.

Pharmacokinetic Results

Pharmacokinetic results are presented in the Table 15.B. and FIGS. 16, 18, 19, 21, 22 and 23.

Pharmacokinetic Conclusions

After the first dose and at steady state (Day 7), SAN-7E Capsules 40 mg were equivalent to Prilosec 40 mg with respect to [AUC(0-inf)] (the primary pharmacokinetic endpoint). The 2 treatments were not equivalent with respect to Cmax on Days 1 and 7 with the percent mean ratio of 149% on Day 1 and 117% on Day 7. The Tmax was shorter for the immediate-release product on Days 1 and 7 (p<0.001).

Pharmacodynamic Conclusions

On Day 7 of dosing, SAN-7E Capsules 40 mg were found equivalent to Prilosec 40 mg with regard to the primary pharmacodynamic endpoint, percent decrease from baseline in integrated gastric acidity over 24 hours. SAN-7E 40 mg and Prilosec 40 mg both decreased integrated gastric acidity by 74% and 80%, respectively, from Baseline at Day 7.

TABLE 15.A

| SAN-7E Capsules Composition, 40 mg Omeprazole | |
|---|---|
| Ingredient | Quantity (40 mg) |
| Omeprazole | 40.8 mg* |
| Sodium Bicarbonate | 1100 mg |
| CROSCARMELLOSE SODIUM | 30 mg |
| Magnesium Stearate | 10 mg |
| Gelatin Capsule | 1 shell |
| Total Weight/Unit | 1180 mg |

*Includes a 2% omeprazole overage in the blend manufacture that assures label claim amount of omeprazole in the final product.

TABLE 15.B 40 mg PK Summary for Day 1 and 7. (Drug: S7E = SAN-7E; Pr = Prilosec ® 40 mg.)

| Drug | ng/mL | Day | Interval (minutes) | | | | | | | | | | | |
|------|-------|-----|---|---|----|----|----|----|----|----|----|-----|-----|-----|
| | | | 0 | 5 | 10 | 15 | 20 | 30 | 45 | 60 | 90 | 120 | 150 | 180 |
| S7E | Mean | 1 | 0 | 0 | 46 | 237 | 535 | 842 | 840 | 709 | 545 | 338 | 248 | 193 |
| S7E | Min | 1 | 0 | 0 | 0 | 0 | 0 | 24 | 116 | 127 | 0 | 19 | 14 | 7 |
| S7E | Max | 1 | 0 | 12 | 703 | 1730 | 2310 | 2420 | 2420 | 2120 | 2000 | 1570 | 1450 | 1210 |
| S7E | Mean | 7 | 3 | 3 | 63 | 202 | 398 | 949 | 1115 | 1104 | 1083 | 747 | 585 | 463 |
| S7E | Min | 7 | 0 | 0 | 0 | 0 | 0 | 13 | 32 | 37 | 262 | 0 | 74 | 42 |
| S7E | Max | 7 | 96 | 82 | 1900 | 3420 | 2960 | 3020 | 2420 | 2380 | 2350 | 1980 | 1850 | 1620 |
| Pr | Mean | 1 | 0 | 0 | 0 | 0 | 3 | 71 | 195 | 408 | 793 | 546 | 369 | 259 |
| Pr | Min | 1 | 0 | 0 | 0 | 0 | 0 | 0 | 0 | 0 | 111 | 59 | 23 | 10 |
| Pr | Max | 1 | 0 | 0 | 0 | 0 | 58 | 1800 | 1140 | 1580 | 2650 | 2100 | 1650 | 1350 |
| Pr | Mean | 7 | 1 | 1 | 1 | 2 | 20 | 171 | 456 | 639 | 1217 | 969 | 725 | 606 |
| Pr | Min | 7 | 0 | 0 | 0 | 0 | 0 | 0 | 0 | 0 | 12 | 119 | 116 | 67 |
| Pr | Max | 7 | 16 | 14 | 14 | 19 | 392 | 1420 | 2110 | 2230 | 2950 | 2370 | 1770 | 1620 |

TABLE 15.B-continued 40 mg PK Summary for Day 1 and 7. (Drug: S7E = SAN-7E; Pr = Prilosec ® 40 mg.)

| Drug | ng/mL | Day | 210 | 240 | 300 | 360 | 420 | 480 | 540 | 600 | 660 | 720 | N | Cmax (ng/mL) | Tmax (hr) |
|---|---|---|---|---|---|---|---|---|---|---|---|---|---|---|---|
| S7E | Mean | 1 | 152 | 125 | 86 | 60 | 41 | 30 | 22 | 16 | 12 | 9 | 35 | 1154 | 0.56 |
| S7E | Min | 1 | 5 | 0 | 0 | 0 | 0 | 0 | 0 | 0 | 0 | 0 | 35 | 255 | 0.25 |
| S7E | Max | 1 | 1140 | 1080 | 871 | 707 | 520 | 457 | 362 | 294 | 230 | 186 | 35 | 2420 | 1.50 |
| S7E | Mean | 7 | 393 | 323 | 249 | 183 | 131 | 94 | 74 | 53 | 37 | 28 | 35 | 1526 | 0.97 |
| S7E | Min | 7 | 27 | 14 | 0 | 0 | 0 | 0 | 0 | 0 | 0 | 0 | 35 | 437 | 0.25 |
| S7E | Max | 7 | 1570 | 1570 | 1350 | 1190 | 1060 | 736 | 636 | 572 | 418 | 386 | 35 | 3420 | 3.50 |
| Pr | Mean | 1 | 208 | 164 | 114 | 77 | 45 | 38 | 27 | 20 | 17 | 12 | 35 | 888 | 1.51 |
| Pr | Min | 1 | 0 | 6 | 0 | 0 | 0 | 0 | 0 | 0 | 0 | 0 | 35 | 119 | 0.50 |
| Pr | Max | 1 | 1250 | 1140 | 919 | 592 | 295 | 422 | 310 | 270 | 217 | 174 | 35 | 2650 | 2.50 |
| Pr | Mean | 7 | 466 | 397 | 264 | 188 | 131 | 95 | 65 | 46 | 34 | 22 | 35 | 1344 | 1.51 |
| Pr | Min | 7 | 30 | 20 | 7 | 0 | 0 | 00 | 0 | 0 | 0 | 0 | 35 | 234 | 0.50 |
| Pr | Max | 7 | 1420 | 1260 | 1000 | 801 | 549 | 435 | 310 | 240 | 199 | 133 | 35 | 2950 | 2.50 |

The number of patients who completed the post-meal portion of the study was 18. The following table summarizes the pharmacokinetic parameters for the pre- and post-meal dosing of 40 mg omeprazole immediate release capsules.

TABLE 15.C

Summary of Post-meal (Day 8) and Pre-meal (Day 7) Plasma Omeprazole Pharmacokinetic Parameters for Immediate Release Capsules (SAN-7E) Plasma Omeprazole

| Parameter | SAN-7E (Post-meal) | | | SAN-7E (Pre-meal) | | |
|---|---|---|---|---|---|---|
| | n | Mean | S.D. | n | Mean | S.D. |
| Cmax (ng/mL) | 18 | 1026 | 645.6 | 18 | 1646 | 771.4 |
| Tmax (hr) | 18 | 1.74 | 1.27 | 18 | 0.93 | 0.74 |
| AUC (0–t)(ng * hr/mL) | 18 | 3221 | 2349 | 18 | 3976 | 2592 |
| AUC(0–inf)(ng * hr/mL) | 18 | 3221 | 2488 | 18 | 4071 | 2721 |
| T½ (hr) | 18 | 1.38 | 0.66 | 18 | 1.38 | 0.66 |
| kel (1/hr) | 18 | 0.61 | 0.26 | 18 | 0.61 | 0.27 |
| ln (Cmax) | 18 | 6.70 | 0.79 | 18 | 7.28 | 0.54 |
| ln[AUC(0–t)] | 18 | 7.76 | 0.90 | 18 | 8.01 | 0.84 |
| IN[AUC(0–inf)] | 18 | 7.78 | 0.91 | 18 | 8.03 | 0.85 |

Example 16

Powder for Suspension

Following procedures similar to those set forth in Examples 14 and 15, above, 20 and 40 mg omeprazole immediate release powders for suspension were prepared and tested in subjects. The powder compositions tested are set forth in the following tables 16A and 16B.

TABLE 16A

Omeprazole Powder for Suspension 20 mg per dose

| Ingredient | Omeprazole Immediate Release Powder 20 mg per dose |
|---|---|
| Omeprazole, Micronized USP | 0.021 |
| Sodium Bicarbonate | 1.680 |
| Xanthan Gum | 0.039 |
| Sucrose | 2.000 |
| Xylitol | 2.000 |

TABLE 16A-continued

Omeprazole Powder for Suspension 20 mg per dose

| Ingredient | Omeprazole Immediate Release Powder 20 mg per dose |
|---|---|
| Crystalline Sucralose | 0.080 |
| Peppermint Flavor, Mane F94249 | 0.011 |
| Peach flavor #57.695/AP 05.51 | 0.030 |
| Totals | 5.861 |

TABLE 16B

Omeprazole Powder for Suspension 40 mg per dose

| Ingredient | Omeprazole Immediate Release Powder 40 mg per dose |
|---|---|
| Omeprazole, Micronized USP | 0.042 |
| Sodium Bicarbonate | 1.680 |
| Xanthan Gum | 0.039 |
| Sucrose | 2.000 |
| Xylitol | 2.000 |
| Crystalline Sucralose | 0.080 |
| Peppermint Flavor, Mane F94249 | 0.011 |
| Peach flavor #57.695/AP 05.51 | 0.030 |
| Totals | 5.882 |

The results of these clinical trials are set forth in FIGS. 16-23.

Many modifications, equivalents, and variations of the present invention are possible in light of the above teachings, therefore, it is to be understood that within the scope of the appended claims, the invention may be practiced other than as specifically described.

What is claimed is:

1. A pharmaceutical formulation in a single capsule dosage form consisting of:
   (a) about 10 mgs to about 100 mgs of at least one micronized bicyclic aryl-imidazole acid-labile proton pump inhibitor;
   (b) at least one antacid, wherein the antacid comprises about 400 mgs to about 1400 mgs of sodium bicarbonate;
   (c) about 2 wt-% to about 5 wt-% of a disintegrant; and
   (d) about 0.5 wt-% to about 3 wt-% of Magnesium Stearate wherein upon oral administration of the capsule to a fasted human subject, a $T_{max}$ of the proton pump inhibitor is obtained within 60 minutes after administration on day 1; and an initial serum concentration of the proton pump inhibitor is greater than 300 ng/ml within 45 minutes after administration.

2. The pharmaceutical formulation according to claim 1, wherein the proton pump inhibitor is omeprazole, esomeprazole or lansoprazole, or a salt thereof.

3. The pharmaceutical formulation according to claim 1, wherein the antacid further comprises potassium bicarbonate, sodium carbonate, calcium carbonate, magnesium oxide, magnesium hydroxide, magnesium carbonate, aluminum hydroxide, or mixtures thereof; and the total amount of antacid present in the capsule is about 10 mEq.

4. The pharmaceutical formulation according to claim 1, wherein the sodium bicarbonate is present in an amount of at least 800 mgs.

5. The pharmaceutical formulation according to claim 1, wherein the disintegrant is croscarmellose sodium and is present in an amount of about 3 wt-%.

6. The pharmaceutical formulation according to claim 1, wherein the disintegrant is present in an amount of about 3 wt-% to about 5 wt-%.

7. The pharmaceutical formulation of claim 1, wherein $T_{max}$ of the proton pump inhibitor on day 7 is obtained within 60 minutes after oral administration of the capsule to the subject.

8. The pharmaceutical formulation according to claim 1, wherein the average $C_{max}$ of the proton pump inhibiting agent is less than 1250 ng/ml after oral administration of the capsule to the subject.

9. A pharmaceutical formulation in a single capsule oral dosage form consisting of:
  (a) micronized omeprazole or a salt thereof in an amount of about 20 mgs or about 40 mgs;
  (b) about 800 mgs to about 1400 mgs of sodium bicarbonate ($NaHCO_3$);
  (c) about 2 wt-% to about 8 wt-% of a disintegrant; and
  (d) about 0.5 wt-% to about 3 wt-% of Magnesium Stearate.

10. The pharmaceutical composition of claim 9, wherein:
  (a) the $NaHCO_3$ is present in an amount of between 1000 mgs and 1300 mgs; and
  (b) the disintegrant is croscarmellose sodium and is present in an amount of about 3 wt-% to about 5 wt-%;
wherein upon oral administration of the capsule to a fasted human subject, a $T_{max}$ of the proton pump inhibitor is obtained within 60 minutes after administration on day 1.

11. A method of inhibiting a gastric acid related gastrointestinal disorder in a subject comprising administering one or more capsules of a single capsule oral dosage form to a human subject in need thereof, the single capsule oral dosage form consisting of:
  (a) about 10 mgs to about 100 mgs of at least one micronized bicyclic aryl-imidazole acid-labile proton pump inhibitor;
  (b) an antacid, wherein the antacid comprises about 400 mgs to about 1400 mgs of sodium bicarbonate ($NaHCO_3$);
  (c) about 2 wt-% to about 5 wt-% of a disintegrant; and
  (d) about 0.5 wt-% to about 3 wt-% of Magnesium Stearate
wherein upon oral administration of the capsule to a fasted human subject, a Tmax of the proton pump inhibitor is obtained within 60 minutes after administration on day 1.

* * * * *